United States Patent
Nakamura et al.

(10) Patent No.: US 11,760,797 B2
(45) Date of Patent: Sep. 19, 2023

(54) ANTI-INTERLEUKIN-33 ANTIBODIES AND USES THEREOF

(71) Applicant: Genentech, Inc., South San Francisco, CA (US)

(72) Inventors: Gerald R. Nakamura, San Francisco, CA (US); Dhaya Seshasayee, Cupertino, CA (US); Menno Van Lookeren Campagne, San Francisco, CA (US); Tiffany Wong, South San Francisco, CA (US); Jia Wu, Foster City, CA (US); Hongkang Xi, South San Francisco, CA (US); Jack Bevers, III, San Francisco, CA (US); Hiu Nam Chan, South San Francisco, CA (US); Laetitia Comps-Agrar, Foster City, CA (US); Racquel Corpuz, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 102 days.

(21) Appl. No.: 17/199,810

(22) Filed: Mar. 12, 2021

(65) Prior Publication Data

US 2021/0284725 A1 Sep. 16, 2021

Related U.S. Application Data

(60) Provisional application No. 63/022,080, filed on May 8, 2020, provisional application No. 62/989,526, filed on Mar. 13, 2020.

(51) Int. Cl.
*C07K 16/24* (2006.01)
*A61K 39/395* (2006.01)
*A61K 39/00* (2006.01)
*A61K 45/06* (2006.01)

(52) U.S. Cl.
CPC ........ *C07K 16/244* (2013.01); *A61K 39/3955* (2013.01); *A61K 45/06* (2013.01); *A61K 2039/505* (2013.01); *C07K 2317/24* (2013.01); *C07K 2317/31* (2013.01); *C07K 2317/55* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 5,500,362 A | 3/1996 | Robinson et al. |
| 6,054,297 A | 4/2000 | Carter et al. |
| 6,084,083 A | 7/2000 | Levinson |
| 6,156,887 A | 12/2000 | Levinson |
| 6,204,371 B1 | 3/2001 | Levinson |
| 6,288,218 B1 | 9/2001 | Levinson |
| 6,414,117 B1 | 7/2002 | Levinson |
| 6,562,343 B1 | 5/2003 | Levinson |
| 6,582,959 B2 | 6/2003 | Kim |
| 6,703,020 B1 | 3/2004 | Thorpe et al. |
| 6,884,879 B1 | 4/2005 | Baca et al. |
| 7,060,269 B1 | 6/2006 | Baca et al. |
| 7,172,750 B2 | 2/2007 | Levinson |
| 7,560,530 B1 | 7/2009 | Chackerian et al. |
| 7,674,459 B2 | 3/2010 | Fung et al. |
| 8,067,199 B2 | 11/2011 | Fung et al. |
| 8,088,618 B2 | 1/2012 | Fung et al. |
| 8,187,569 B2 | 5/2012 | Mertens et al. |
| 8,187,596 B1 | 5/2012 | Chackerian et al. |
| 8,318,160 B2 | 11/2012 | Fung et al. |
| 8,734,797 B2 | 5/2014 | Fung et al. |
| 9,090,694 B2 | 7/2015 | Duffy et al. |
| 9,212,227 B2 | 12/2015 | Duffy et al. |
| 9,309,319 B2 | 4/2016 | Fertig et al. |
| 9,453,072 B2 | 9/2016 | Murphy et al. |
| 9,523,696 B2 | 12/2016 | Snider |
| 9,738,727 B2 | 8/2017 | Wu et al. |
| 9,758,578 B2 | 9/2017 | Fujino et al. |
| 9,970,944 B2 | 5/2018 | Schmitz et al. |
| 10,000,564 B2 | 6/2018 | Murphy et al. |
| 10,059,764 B2 | 8/2018 | Horlick et al. |
| 10,093,730 B2 | 10/2018 | Hass et al. |
| 10,421,822 B2 | 9/2019 | Kelley et al. |
| 10,723,795 B2 | 7/2020 | Hass et al. |
| 10,836,820 B2 | 11/2020 | Horlick et al. |
| 2002/0081293 A1 | 6/2002 | Fung et al. |
| 2003/0158399 A1 | 8/2003 | Levinson |
| 2003/0190317 A1 | 10/2003 | Baca et al. |

(Continued)

FOREIGN PATENT DOCUMENTS

| | | |
|---|---|---|
| EP | 0666868 B1 | 4/2002 |
| EP | 1725261 B1 | 1/2011 |

(Continued)

OTHER PUBLICATIONS

Clare et al., Eye (2022) 36:266-272; https://doi.org/10.1038/s41433-021-01725-5.*
Wechsler et al., N Engl J Med 2021;385:1656-68. DOI: 10.1056/NEJMoa2024257, updated Oct. 28, 2021.*
Sanofi Jun. 21, 2019 Press Release "Sanofi and Regeneron announce positive topline Phase 2 results for IL-33 antibody in asthma" [downloaded Dec. 10, 2019].*
Adamko et al., "The rise of the phoenix: the expanding role of the eosinophil in health and disease," Allergy. 60(1):13-22 (2005).

(Continued)

*Primary Examiner* — Marianne P Allen
(74) *Attorney, Agent, or Firm* — Clark & Elbing LLP; Thomas J. Takara

(57) ABSTRACT

The invention provides interleukin-33 (IL-33) antibodies and methods of making and using the same, e.g., for treatment of IL-33 mediated disorders (e.g., ocular disorders such as AMD (e.g., geographic atrophy (GA)).

27 Claims, 12 Drawing Sheets

Specification includes a Sequence Listing.

(56) References Cited

U.S. PATENT DOCUMENTS

| | | |
|---|---|---|
| 2003/0206899 A1 | 11/2003 | Ferrara et al. |
| 2005/0112126 A1 | 5/2005 | Baca et al. |
| 2005/0186208 A1 | 8/2005 | Fyfe et al. |
| 2006/0009360 A1 | 1/2006 | Pifer et al. |
| 2007/0042978 A1 | 2/2007 | Girard et al. |
| 2010/0260770 A1 | 10/2010 | Coyle |
| 2011/0045501 A1 | 2/2011 | Bosch et al. |
| 2011/0165063 A1 | 7/2011 | Hsieh et al. |
| 2011/0236388 A1 | 9/2011 | Baehner et al. |
| 2012/0207752 A1 | 8/2012 | Chackerian et al. |
| 2013/0287777 A1 | 10/2013 | Duffy et al. |
| 2013/0336980 A1 | 12/2013 | Duffy et al. |
| 2014/0017244 A1 | 1/2014 | Duerr et al. |
| 2014/0105887 A1 | 4/2014 | Chackerian et al. |
| 2016/0145344 A1 | 5/2016 | Akbari |
| 2016/0168640 A1 | 6/2016 | Khosla et al. |
| 2016/0235838 A1 | 8/2016 | Weiner et al. |
| 2017/0066831 A1 | 3/2017 | Duffy et al. |
| 2017/0096483 A1 | 4/2017 | Orengo et al. |
| 2017/0283494 A1 | 10/2017 | Fujino et al. |
| 2018/0171405 A1 | 6/2018 | Khosla et al. |
| 2018/0251542 A1 | 9/2018 | Murphy et al. |
| 2021/0002361 A1 | 1/2021 | Hass et al. |

FOREIGN PATENT DOCUMENTS

| | | | |
|---|---|---|---|
| EP | 2271672 B1 | 11/2015 | |
| EP | 2734222 B1 | 10/2016 | |
| EP | 3088517 A1 | 11/2016 | |
| EP | 2475388 B1 | 11/2017 | |
| EP | 2970460 B1 | 4/2020 | |
| EP | 3092253 B1 | 3/2021 | |
| JP | 2014-506321 A | 3/2014 | |
| JP | 2014-523746 A | 9/2014 | |
| WO | WO-89/06692 A1 | 7/1989 | |
| WO | WO-92/19579 A1 | 11/1992 | |
| WO | WO-94/10202 A1 | 5/1994 | |
| WO | WO-95/27062 A1 | 10/1995 | |
| WO | WO-96/27603 A1 | 9/1996 | |
| WO | WO-96/30046 A1 | 10/1996 | |
| WO | WO-98/45331 A2 | 10/1998 | |
| WO | WO-98/45332 A2 | 10/1998 | |
| WO | WO-01/21641 A1 | 3/2001 | |
| WO | WO-01/70817 A1 | 9/2001 | |
| WO | WO-01/70818 A1 | 9/2001 | |
| WO | WO-2005/012359 A2 | 2/2005 | |
| WO | WO-2005/044853 A2 | 5/2005 | |
| WO | WO-2005/062967 A2 | 7/2005 | |
| WO | WO-2005/079844 A2 | 9/2005 | |
| WO | WO-2007/056227 A2 | 5/2007 | |
| WO | WO-2007/127749 A2 | 11/2007 | |
| WO | WO-2007/130627 A2 | 11/2007 | |
| WO | WO-2007/131031 A2 | 11/2007 | |
| WO | WO-2007/140205 A2 | 12/2007 | |
| WO | WO-2007/143295 A2 | 12/2007 | |
| WO | WO-2008/066443 A1 | 6/2008 | |
| WO | WO-2008/132709 A1 | 11/2008 | |
| WO | WO-2008/144610 A1 | 11/2008 | |
| WO | WO-2009/053098 A1 | 4/2009 | |
| WO | WO-2009/120899 A2 | 10/2009 | |
| WO | WO-2009/155724 A2 | 12/2009 | |
| WO | WO-2009/120903 A9 | 2/2010 | |
| WO | WO-2010/069532 A1 | 6/2010 | |
| WO | WO-2010/087972 A2 | 8/2010 | |
| WO | WO-2010/102251 A2 | 9/2010 | |
| WO | WO-2011/031600 A1 | 3/2011 | |
| WO | WO-2011/047266 A1 | 4/2011 | |
| WO | WO-2011/143562 A2 | 11/2011 | |
| WO | WO-2012/055891 A1 | 5/2012 | |
| WO | WO-2012/083132 A2 | 6/2012 | |
| WO | WO-2012/088094 A2 | 6/2012 | |
| WO | WO-2012/103240 A2 | 8/2012 | |
| WO | WO-2012/113927 A1 | 8/2012 | |
| WO | WO-2012/145209 A2 | 10/2012 | |
| WO | WO-2013/014208 A2 | 1/2013 | |
| WO | WO-2013/165894 A2 | 11/2013 | |
| WO | WO-2013/165894 A3 | 11/2013 | |
| WO | WO-2013/173761 A2 | 11/2013 | |
| WO | WO-2014/062621 A1 | 4/2014 | |
| WO | WO-2014/072446 A1 | 5/2014 | |
| WO | WO-2014/090800 A1 | 6/2014 | |
| WO | WO-2014/126277 A1 | 8/2014 | |
| WO | WO-2014/128254 A1 | 8/2014 | |
| WO | WO-2014/152195 A1 | 9/2014 | |
| WO | WO-2014/164959 A2 | 10/2014 | |
| WO | WO-2014/178392 A1 | 11/2014 | |
| WO | WO-2015/042521 A1 | 3/2015 | |
| WO | WO-2015/054012 A1 | 4/2015 | |
| WO | WO-2015/061441 A1 | 4/2015 | |
| WO | WO-2015/077888 A1 | 6/2015 | |
| WO | WO-2015/099175 A1 | 7/2015 | |
| WO | WO-2015/106080 A2 | 7/2015 | |
| WO | WO-2015/132602 A1 | 9/2015 | |
| WO | WO-2015/143343 A2 | 9/2015 | |
| WO | WO-2015/164354 A1 | 10/2015 | |
| WO | WO-2015/179918 A1 | 12/2015 | |
| WO | WO-2016/020502 A1 | 2/2016 | |
| WO | WO-2016/073157 A1 | 5/2016 | |
| WO | WO-2016/073890 A1 | 5/2016 | |
| WO | WO-2016/077366 A1 | 5/2016 | |
| WO | WO-2016/077381 A1 | 5/2016 | |
| WO | WO-2016/085832 A1 | 6/2016 | |
| WO | WO-2016/090250 A1 | 6/2016 | |
| WO | WO-2016/122865 A1 | 8/2016 | |
| WO | WO-2016/138590 A1 | 9/2016 | |
| WO | WO-2016/140921 A1 | 9/2016 | |
| WO | WO-2016/149276 A1 | 9/2016 | |
| WO | WO-2016/156440 A1 | 10/2016 | |
| WO | WO-2016/207304 A2 | 12/2016 | |
| WO | WO-2017/009750 A1 | 1/2017 | |
| WO | WO-2017/021814 A1 | 2/2017 | |
| WO | WO-2017/187307 A1 | 11/2017 | |
| WO | WO-2018/081075 A1 | 5/2018 | |
| WO | WO 2021/183849 | * | 9/2021 |

OTHER PUBLICATIONS

Akhabir et al., "Lung expression quantitative trait loci data set identifies important functional polymorphisms in the asthma-associated IL1RL1 region," J Allergy Clin Immunol. 134(3):729-31 (2014).

Alves-Filho et al., "Interleukin-33 attenuates sepsis by enhancing neutrphil influx to the site of infection," Nat Med. 16(6):708-12 (2010) (6 pages).

Askmyr et al., "Selective killing of candidate AML stem cells by antibody targeting of IL1RAP," Blood. 121(18):3709-13 (2013).

Baekkevold et al., "Molecular characterization of NF-HEV, a nuclear factor preferentially expressed in human high endothelial venules," Am J Pathol. 163(1):69-79 (2003).

Bonilla et al., "The Alarmin Interleukin-33 Drives Protective Antiviral CD8+ T Cell Responses," Science. 335(6071):984-9 (2012) (7 pages).

Bousquet et al., "Uniform definition of asthma severity, control, and exacerbations: document presented for the World Health Organization Consultation on Severe Asthma," J Allergy Clin Immunol. 126(5):926-38 (2010).

Brown et al., "Tolerance of single, but not multiple, amino acid replacements in antibody VH CDR2: a means of minimizing B cell wastage from somatic hypermutation?" J Immunol. 156(9):3285-91 (1996).

Cairns, "Inhibitors of mast cell tryptase beta as therapeutics for the treatment of asthma and inflammatory disorders," Pulm Pharmacol Ther. 18(1):55-66 (2005).

Carmeliet et al., "Angiogenesis in cancer and other diseases," Nature. 407(6801):249-57 (2000).

Casset et al., "A peptide mimetic of an anti-CD4 monoclonal antibody by rational design," Biochem Biophys Res Commun. 307(1):198-205 (2003).

Chen et al., "Selection and analysis of an optimized anti-VEGF antibody: crystal structure of an affinity-matured Fab in complex with antigen," J Mol Biol. 293(4):865-81 (1999).

(56) References Cited

OTHER PUBLICATIONS

Ferrara et al., "Binding to the extracellular matrix and proteolytic processing: two key mechanisms regulating vascular endothelial growth factor action," Mol Biol Cell. 21(5):687-90 (2010).
Fournié et al., "The Pro-tumorigenic IL-33 Involved in Antitumor Immunity: A Yin and Yang Cytokine," Front Immunol. 9:2506 (2018) (9 pages).
Hamzaoui et al., "Induced sputum levels of IL-33 and soluble ST2 in young asthmatic children," J Asthma. 50(8):803-9 (2013).
Ho et al., "Common genetic variation at the IL1RL1 locus regulates IL-33/ST2 signaling," J Clin Invest. 123(10):4208-18 (2013).
Hong et al., "Identification of constitutively active interleukin 33 (IL-33) splice variant," J Biol Chem. 286(22):20078-86 (2011).
Houck et al., "The Vascular Endothelial Growth Factor Family: Identification of a Fourth Molecular Species and Characterization of Alternative Splicing of RNA," Mol Endocrinol. 5(12):1806-14 (1991).
Ito et al., "ST2: the biomarker at the heart of GVHD severity," Blood. 125(1):10-1 (2015).
Jang et al., "Interleukin-33 and Mast Cells Bridge Innate and Adaptive Immunity: From the Allergologist's Perspective," Int Neurourol J. 19(3):142-50 (2015).
Ji et al., "Methionine, tryptophan, and histidine oxidation in a model protein, PTH: mechanisms and stabilization," J Pharm Sci. 98(12):4485-500 (2009).
Kakkar et al., "The IL-33/ST2 pathway: therapeutic target and novel biomarker," Nat Rev Drug Discov. 7(10):827-40 (2008).
Kim et al., "Anti-IL-33 antibody has a therapeutic effect in a murine model of allergic rhinitis," Allergy. 67(2):183-90 (2012).
Lefrançais et al., "IL-33 is processed into mature bioactive forms by neutrophil elastase and cathepsin G," Proc Natl Acad Sci U S A. 109(5):1673-8 (2012).
Leung et al., "Vascular endothelial growth factor is a secreted angiogenic mitogen," Science. 246(4935):1306-9 (1989).
Li et al., "IL-33 neutralization suppresses lupus disease inlupus-prone mice," Inflammation. 37(3):824-32 (2014).
Liew et al., "Disease-associated functions of IL-33: the new kid in the IL-1 family," Nat Rev Immunol. 10(2):103-10 (2010).
Liew et al., "Interleukin-33 in health and disease," Nat Rev Immunol. 16(11):676-89 (2016).
Lingel et al., "The structure of interleukin-33 and its interaction with the ST2 and IL-1RAcP receptors—insight into heterotrimeric interleukin-1 signaling complexes," available in PMC Oct. 14, 2010, published in final edited form as: Structure. 17(10):1398-410 (2009) (24 pages).
Liu et al., "Anti-IL-33 antibody treatment inhibits airway inflammation in a murine model of allergic asthma," Biochem Biophys Res Commun. 386(1):181-5 (2009).
Liu et al., "Structural insights into the interaction of IL-33 with its receptors," Proc Natl Acad Sci U S A. 110(37):14918-23 (2013).
Lu et al., "Interleukin-33 prevents the development of autoimmune diabetes in NOD mice," Int Immunopharmacol. 70:9-15 (2019).
Mali et al., "RNA-Guided Human Genome Engineering via Cas9," available in PMC Aug. 15, 2013, published in final edited form as: Science. 339(6121):823-6 (2013) (8 pages).
Martin et al., "Special aspects of interleukin-33 and the IL-33 receptor complex," Semin Immunol. 25(6):449-57 (2013).
Matsumoto, "Serum periostin: a novel biomarker for asthma management," Allergol Int. 63(2):153-60 (2014).
Munitz et al., "Eosinophils: 'new' roles for 'old' cells," Allergy. 59(3):268-75 (2004).
Nabe, "Interleukin (IL)-33: new therapeutic target for atopic diseases," J Pharmacol Sci. 126(2):85-91 (2014).
O'Donnell et al., "An antitumorigenic role for the IL-33 receptor, ST2L, in colon cancer," Br J Cancer. 114(1):37-43 (2016).
Oldhoff et al., "Anti-IL-5 recombinant humanized monoclonal antibody (mepolizumab) for the treatment of atopic dermatitis," Allergy. 60(5):693-6 (2005).
Paul, Chapter 9: Structure and Function of Immunoglobulins, *Fundamental Immunology, Third Edition*. Raven Press Ltd., 292-295 (1993) (6 pages).
Popkov et al., "Human/mouse cross-reactive anti-VEGF receptor 2 recombinant antibodies selected from an immune b9 allotype rabbit antibody library," J Immunol Methods. 288(1-2):149-64 (2004).
Presta et al., "Humanization of an anti-vascular endothelial growth factor monoclonal antibody for the therapy of solid tumors and other disorders," Cancer Res. 57(20):4593-9 (1997).
Qiu et al., "Anti-interleukin-33 inhibits cigarette smoke-induced lung inflammation in mice," Immunology. 138(1):76-82 (2013).
Ramirez-Carrozzi et al., "Functional analysis of protective IL1RL1 variants associated with asthma risk," J Allergy Clin Immunol. 135(4):1080-3.e3 (2015) (7 pages).
Sakai et al., "Interleukin-33 Is Hepatoprotective During Liver Ischemia/Reperfusion in Mice," Hepatology. 56(4):1468-78 (2012).
Sedhom et al., "Neutralisation of the interleukin-33/ST2 pathway ameliorates experimental colitis through enhancement of mucosal healing in mice," Gut. 62(12):1714-23 (2013) (11 pages).
Sotos et al., "The transitivity misconception of Pearson's correlation coefficient," Statistics Education Research Journal 8(2):33-55 (2009).
Vo et al., "Comparison study of IL-33 gene expression in haplogroup H, J, L, and K cybrids," Invest Ophthalmol Vis Sci. 54(15):4988 (2013) (Abstract only) (2 pages).
Xi et al., "IL-33 amplifies an innate immune response in the degenerating retina," J Exp Med. 213(2):189-207 (2016).
Xia et al., "Increased IL-33 expression in chronic obstructive pulmonary disease," Am J Physiol Lung Cell Mol Physiol. 308(7):L619-L627 (2015).
Yuan et al., "Construction of human nonimmune library and selection of scFvs against IL-33," Appl Biochem Biotechnol. 167(3):498-509 (2012).
Zhang et al., "Improving pH gradient cation-exchange chromatography of monoclonal antibodies by controlling ionic strength," J Chromatogr A. 1272:56-64 (2013).
International Preliminary Report on Patentability for International Patent Application No. PCT/US2021/022057, dated Sep. 6, 2022 (7 pages).
International Search Report and Written Opinion for International Patent Application No. PCT/US2021/022057, dated Jun. 16, 2021 (16 pages).

\* cited by examiner

FIG. 1A

Heavy chain variable region

| Kabat number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 1E1 hybridoma | E | V | Q | L | V | E | S | G | G | G | L | V | Q | P | G | G | S | L | K | L | S | C | A | A | S | G | F | T | F | N | N | Y | W | M | T | W | I | R | Q | A | P | G |
| 1E1v8 | E | V | Q | L | V | E | S | G | G | G | L | V | Q | P | G | G | S | L | R | L | S | C | A | A | S | G | F | T | F | N | N | Y | W | M | T | W | I | R | Q | A | P | G |

CDR H1 - Contact
CDR H1 - Kabat

| Kabat number | 44 | 45 | 46 | 47 | 48 | 49 | 50 | 51 | 52 | 52a | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 |
|---|---|---|---|---|---|---|---|---|---|---|---|---|---|---|---|---|---|---|---|---|---|---|---|---|---|---|---|---|---|---|---|---|---|---|---|---|---|---|---|---|
| 1E1 hybridoma | K | G | L | E | W | I | A | S | I | T | Y | T | G | G | T | Y | Y | P | D | S | V | K | G | R | F | T | I | S | R | D | D | A | K | S | T | L | Y | L | Q | M |
| 1E1v8 | K | G | L | E | W | V | A | S | I | T | Y | T | G | G | T | Y | Y | P | D | S | V | K | G | R | F | T | I | S | R | D | D | A | K | S | S | L | Y | L | Q | M |

CDR H2 - Contact
CDR H2 - Kabat

| Kabat number | 82a | 82b | 83 | 84 | 85 | 86 | 87 | 88 | 89 | 90 | 91 | 92 | 93 | 94 | 95 | 96 | 97 | 98 | 99 | 100 | 100a | 100b | 100c | 100d | 100e | 101 | 102 | 103 | 104 | 105 | 106 | 107 | 108 | 109 | 110 | 111 | 112 | 113 | |
|---|---|---|---|---|---|---|---|---|---|---|---|---|---|---|---|---|---|---|---|---|---|---|---|---|---|---|---|---|---|---|---|---|---|---|---|---|---|---|---|
| 1E1 hybridoma | S | L | R | S | E | D | T | A | T | Y | Y | C | T | R | A | N | Y | Y | N | T | Y | G | G | F | P | Y | W | G | Q | G | T | L | V | T | V | S | S | | SEQ ID NO:35 |
| 1E1v8 | S | L | R | A | E | D | T | A | V | Y | Y | C | T | R | A | N | Y | Y | N | T | Y | G | G | F | P | Y | W | G | Q | G | T | L | V | T | V | S | S | | SEQ ID NO:7 |

CDR H3 - Contact
CDR H3 - Kabat

FIG. 1B

Light chain variable region

| Kabat number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 1E1 hybridoma | D | I | Q | M | T | Q | S | P | S | S | L | S | A | S | L | G | E | T | V | S | I | E | C | L | A | S | E | G | F | S | N | D | L | A | W | Y | Q | Q | K | S | G | K |
| 1E1v8 | D | I | Q | M | T | Q | S | P | S | S | L | S | A | S | V | G | D | R | V | T | I | T | C | L | A | S | E | G | F | S | N | D | L | A | W | Y | Q | Q | K | P | G | K |

CDR L1 – Contact: positions 30–36
CDR L1 – Kabat: positions 24–34

| Kabat number | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 1E1 hybridoma | S | P | Q | L | L | I | Y | A | A | S | R | L | Q | D | G | V | P | S | R | F | S | G | S | G | S | G | T | R | F | S | L | K | I | S | G | M | Q | P | E | D | E | A |
| 1E1v8 | S | P | K | L | L | I | Y | A | A | S | R | L | Q | D | G | V | P | S | R | F | S | G | S | G | S | G | T | D | F | T | L | T | I | S | S | L | Q | P | E | D | F | A |

CDR L2 – Contact: positions 46–52
CDR L2 – Kabat: positions 50–56

| Kabat number | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | | |
|---|---|---|---|---|---|---|---|---|---|---|---|---|---|---|---|---|---|---|---|---|---|---|---|---|---|
| 1E1 hybridoma | D | Y | F | C | Q | Q | G | S | K | Y | P | L | T | F | G | G | G | T | K | L | E | I | K | | SEQ ID NO:36 |
| 1E1v8 | T | Y | F | C | Q | Q | G | S | K | Y | P | L | T | F | G | G | G | T | K | V | E | I | K | | SEQ ID NO:8 |

CDR L3 – Contact: positions 89–96
CDR L3 – Kabat: positions 89–97

| Kabat number | 82a | 82b | 82c | 83 | 84 | 85 | 86 | 87 | 88 | 89 | 90 | 91 | 92 | 93 | 94 | 95 | 96 | 97 | 98 | 99 | 100 | 100a | 100b | 100c | 100d | 100e | 101 | 102 | 103 | 104 | 105 | 106 | 107 | 108 | 109 | 110 | 111 | 112 | 113 | VH SEQ ID NO. |
|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | | | | | | | | | | | | | | |
| | | | | | | | | | | | | | | | | CDR H3 - Contact | | | | | | | | | | | | | | | | | | | | | | | |
| | | | | | | | | | | | | | | | | | | | | | | CDR H3 - Kabat | | | | | | | | | | | | | | | | |
| 1E1.chimera | S | L | L | R | S | E | D | T | A | T | Y | Y | C | T | R | A | N | Y | Y | Y | N | T | Y | G | G | F | P | Y | W | G | Q | G | T | L | V | T | V | S | S | 35 |
| 1E1v1 | S | L | L | R | A | E | D | T | A | V | Y | Y | C | T | R | A | N | Y | Y | Y | N | T | Y | G | G | F | P | Y | W | G | Q | G | T | L | V | T | V | S | S | 41 |
| 1E1v2 | S | L | L | R | A | E | D | T | A | V | Y | Y | C | T | R | A | N | Y | Y | Y | N | T | Y | G | G | F | P | Y | W | G | Q | G | T | L | V | T | V | S | S | 43 |
| 1E1v3 | S | L | L | R | A | E | D | T | A | V | Y | Y | C | T | R | A | N | Y | Y | Y | N | T | Y | G | G | F | P | Y | W | G | Q | G | T | L | V | T | V | S | S | 41 |
| 1E1v4 | S | L | L | R | A | E | D | T | A | V | Y | Y | C | T | R | A | N | Y | Y | Y | N | T | Y | G | G | F | P | Y | W | G | Q | G | T | L | V | T | V | S | S | 43 |
| 1E1v5 | S | L | L | R | A | E | D | T | A | V | Y | Y | C | T | R | A | N | Y | Y | Y | N | T | Y | G | G | F | P | Y | W | G | Q | G | T | L | V | T | V | S | S | 44 |
| 1E1v6 | S | L | L | R | A | E | D | T | A | V | Y | Y | C | T | R | A | N | Y | Y | Y | N | T | Y | G | G | F | P | Y | W | G | Q | G | T | L | V | T | V | S | S | 46 |
| 1E1v7 | S | L | L | R | A | E | D | T | A | V | Y | Y | C | T | R | A | N | Y | Y | Y | N | T | Y | G | G | F | P | Y | W | G | Q | G | T | L | V | T | V | S | S | 48 |
| 1E1v8 | S | L | L | R | A | E | D | T | A | V | Y | Y | C | T | R | A | N | Y | Y | Y | N | T | Y | G | G | F | P | Y | W | G | Q | G | T | L | V | T | V | S | S | 7 |
| 1E1v9 | S | L | L | R | A | E | D | T | A | V | Y | Y | C | T | R | A | N | Y | Y | Y | N | T | Y | G | G | F | P | Y | W | G | Q | G | T | L | V | T | V | S | S | 43 |
| 1E1v10 | S | L | L | R | A | E | D | T | A | V | Y | Y | C | T | R | A | N | Y | Y | Y | N | T | Y | G | G | F | P | Y | W | G | Q | G | T | L | V | T | V | S | S | 44 |
| 1E1v11 | S | L | L | R | A | E | D | T | A | V | Y | Y | C | T | R | A | N | Y | Y | Y | N | T | Y | G | G | F | P | Y | W | G | Q | G | T | L | V | T | V | S | S | 46 |
| 1E1v12 | S | L | L | R | A | E | D | T | A | V | Y | Y | C | T | R | A | N | Y | Y | Y | N | T | Y | G | G | F | P | Y | W | G | Q | G | T | L | V | T | V | S | S | 48 |
| 1E1v13 | S | L | L | R | A | E | D | T | A | V | Y | Y | C | T | R | A | N | Y | Y | Y | N | T | Y | G | G | F | P | Y | W | G | Q | G | T | L | V | T | V | S | S | 50 |
| 1E1v14 | S | L | L | R | A | E | D | T | A | V | Y | Y | C | T | R | A | N | Y | Y | Y | N | T | Y | G | G | F | P | Y | W | G | Q | G | T | L | V | T | V | S | S | 43 |
| 1E1v15 | S | L | L | R | A | E | D | T | A | V | Y | Y | C | T | R | A | N | Y | Y | Y | N | T | Y | G | G | F | P | Y | W | G | Q | G | T | L | V | T | V | S | S | 44 |
| 1E1v16 | S | L | L | R | A | E | D | T | A | V | Y | Y | C | T | R | A | N | Y | Y | Y | N | T | Y | G | G | F | P | Y | W | G | Q | G | T | L | V | T | V | S | S | 46 |
| 1E1v17 | S | L | L | R | A | E | D | T | A | V | Y | Y | C | T | R | A | N | Y | Y | Y | N | T | Y | G | G | F | P | Y | W | G | Q | G | T | L | V | T | V | S | S | 48 |
| 1E1v18 | S | L | L | R | A | E | D | T | A | V | Y | Y | C | T | R | A | N | Y | Y | Y | N | T | Y | G | G | F | P | Y | W | G | Q | G | T | L | V | T | V | S | S | 50 |
| 1E1v19 | S | L | L | R | A | E | D | T | A | V | Y | Y | C | T | R | A | N | Y | Y | Y | N | T | Y | G | G | F | P | Y | W | G | Q | G | T | L | V | T | V | S | S | 43 |
| 1E1v20 | S | L | L | R | A | E | D | T | A | V | Y | Y | C | T | R | A | N | Y | Y | Y | N | T | Y | G | G | F | P | Y | W | G | Q | G | T | L | V | T | V | S | S | 44 |
| 1E1v21 | S | L | L | R | A | E | D | T | A | V | Y | Y | C | T | R | A | N | Y | Y | Y | N | T | Y | G | G | F | P | Y | W | G | Q | G | T | L | V | T | V | S | S | 46 |
| 1E1v22 | S | L | L | R | A | E | D | T | A | V | Y | Y | C | T | R | A | N | Y | Y | Y | N | T | Y | G | G | F | P | Y | W | G | Q | G | T | L | V | T | V | S | S | 48 |
| 1E1v23 | S | L | L | R | A | E | D | T | A | V | Y | Y | C | T | R | A | N | Y | Y | Y | N | T | Y | G | G | F | P | Y | W | G | Q | G | T | L | V | T | V | S | S | 50 |
| 1E1.K3-11VH1-46 | S | L | R | R | S | E | D | T | A | V | Y | Y | C | T | R | A | N | Y | Y | Y | N | T | Y | G | G | F | P | Y | W | G | Q | G | T | L | V | T | V | S | S | 65 |
| 1E1.K1-27.VH3-66 | S | L | R | R | A | E | D | T | A | V | Y | Y | C | T | R | A | N | Y | Y | Y | N | T | Y | G | G | F | P | Y | W | G | Q | G | T | L | V | T | V | S | S | 52 |

| Kabat number | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | VL SEQ ID NO. |
|---|---|---|---|---|---|---|---|---|---|---|---|---|---|---|---|---|---|---|---|---|---|---|---|---|
| 1E1.chimera | D | Y | F | C | Q | Q | G | S | K | Y | P | L | T | F | G | S | G | T | K | L | E | I | K | 36 |
| 1E1v1 | T | Y | Y | C | Q | Q | G | S | K | Y | P | L | T | F | G | G | G | T | K | V | E | I | K | 55 |
| 1E1v2 | T | Y | Y | C | Q | Q | G | S | K | Y | P | L | T | F | G | G | G | T | K | V | E | I | K | 55 |
| 1E1v3 | T | Y | F | C | Q | Q | G | S | K | Y | P | L | T | F | G | G | G | T | K | V | E | I | K | 8 |
| 1E1v4 | T | Y | F | C | Q | Q | G | S | K | Y | P | L | T | F | G | G | G | T | K | V | E | I | K | 8 |
| 1E1v5 | T | Y | F | C | Q | Q | G | S | K | Y | P | L | T | F | G | G | G | T | K | V | E | I | K | 8 |
| 1E1v6 | T | Y | F | C | Q | Q | G | S | K | Y | P | L | T | F | G | G | G | T | K | V | E | I | K | 8 |
| 1E1v7 | T | Y | F | C | Q | Q | G | S | K | Y | P | L | T | F | G | G | G | T | K | V | E | I | K | 8 |
| 1E1v8 | T | Y | F | C | Q | Q | G | S | K | Y | P | L | T | F | G | G | G | T | K | V | E | I | K | 8 |
| 1E1v9 | T | Y | F | C | Q | Q | G | S | K | Y | P | L | T | F | G | G | G | T | K | V | E | I | K | 57 |
| 1E1v10 | T | Y | F | C | Q | Q | G | S | K | Y | P | L | T | F | G | G | G | T | K | V | E | I | K | 57 |
| 1E1v11 | T | Y | F | C | Q | Q | G | S | K | Y | P | L | T | F | G | G | G | T | K | V | E | I | K | 57 |
| 1E1v12 | T | Y | F | C | Q | Q | G | S | K | Y | P | L | T | F | G | G | G | T | K | V | E | I | K | 57 |
| 1E1v13 | T | Y | F | C | Q | Q | G | S | K | Y | P | L | T | F | G | G | G | T | K | V | E | I | K | 57 |
| 1E1v14 | T | Y | F | C | Q | Q | G | S | K | Y | P | L | T | F | G | G | G | T | K | V | E | I | K | 58 |
| 1E1v15 | T | Y | F | C | Q | Q | G | S | K | Y | P | L | T | F | G | G | G | T | K | V | E | I | K | 58 |
| 1E1v16 | T | Y | F | C | Q | Q | G | S | K | Y | P | L | T | F | G | G | G | T | K | V | E | I | K | 58 |
| 1E1v17 | T | Y | F | C | Q | Q | G | S | K | Y | P | L | T | F | G | G | G | T | K | V | E | I | K | 58 |
| 1E1v18 | T | Y | F | C | Q | Q | G | S | K | Y | P | L | T | F | G | G | G | T | K | V | E | I | K | 58 |
| 1E1v19 | T | Y | Y | C | Q | Q | G | S | K | Y | P | L | T | F | G | G | G | T | K | V | E | I | K | 59 |
| 1E1v20 | T | Y | Y | C | Q | Q | G | S | K | Y | P | L | T | F | G | G | G | T | K | V | E | I | K | 59 |
| 1E1v21 | T | Y | Y | C | Q | Q | G | S | K | Y | P | L | T | F | G | G | G | T | K | V | E | I | K | 59 |
| 1E1v22 | T | Y | Y | C | Q | Q | G | S | K | Y | P | L | T | F | G | G | G | T | K | V | E | I | K | 59 |
| 1E1v23 | T | Y | Y | C | Q | Q | G | S | K | Y | P | L | T | F | G | G | G | T | K | V | E | I | K | 59 |
| 1E1.K3-11.VH1-46 | V | Y | Y | C | Q | Q | G | S | K | Y | P | L | T | F | G | G | G | T | K | V | E | I | K | 69 |
| 1E1.K1-27.VH3-66 | T | Y | Y | C | Q | Q | G | S | K | Y | P | L | T | F | G | G | G | T | K | V | E | I | K | 61 |

CDR L3 – Contact
CDR L3 – Kabat

SEQUENCE LISTING

```
<160> NUMBER OF SEQ ID NOS: 81

<210> SEQ ID NO 1
<211> LENGTH: 5
<212> TYPE: PRT
<213> ORGANISM: Artificial Sequence
<220> FEATURE:
<223> OTHER INFORMATION: Synthetic Construct

<400> SEQUENCE: 1

Asn Tyr Trp Met Thr
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic Construct

<400> SEQUENCE: 2

Ser Ile Thr Tyr Thr Gly Gly Gly Thr Tyr Tyr Pro Asp Ser Val Lys
1               5                   10                  15

Gly

<210> SEQ ID NO 3
<211> LENGTH: 13
<212> TYPE: PRT
<213> ORGANISM: Artificial Sequence
<220> FEATURE:
<223> OTHER INFORMATION: Synthetic Construct

<400> SEQUENCE: 3

Ala Asn Tyr Tyr Tyr Asn Thr Tyr Gly Gly Phe Pro Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic Construct

<400> SEQUENCE: 4

Leu Ala Ser Glu Gly Phe Ser Asn Asp Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic Construct

<400> SEQUENCE: 5

Ala Ala Ser Arg Leu Gln Asp
```

```
<210> SEQ ID NO 6
<211> LENGTH: 9
<212> TYPE: PRT
<213> ORGANISM: Artificial Sequence
<220> FEATURE:
<223> OTHER INFORMATION: Synthetic Construct

<400> SEQUENCE: 6

Gln Gln Gly Ser Lys Tyr Pro Leu Thr
1               5

<210> SEQ ID NO 7
<211> LENGTH: 122
<212> TYPE: PRT
<213> ORGANISM: Artificial Sequence
<220> FEATURE:
<223> OTHER INFORMATION: Synthetic Construct

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Trp Met Thr Trp Ile Arg Gln Ala Pro Gly Lys Gly Leu Glu Trp Val
        35                  40                  45

Ala Ser Ile Thr Tyr Thr Gly Gly Thr Tyr Tyr Pro Asp Ser Val
    50                  55                  60

Lys Gly Arg Phe Thr Ile Ser Arg Asp Asp Ala Lys Ser Ser Leu Tyr
65                  70                  75                  80

Leu Gln Met Asn Ser Leu Arg Ala Glu Asp Thr Ala Val Tyr Tyr Cys
                85                  90                  95

Thr Arg Ala Asn Tyr Tyr Tyr Asn Thr Tyr Gly Gly Phe Pro Tyr Trp
            100                 105                 110

Gly Gln Gly Thr Leu Val Thr Val Ser Ser
        115                 120

<210> SEQ ID NO 8
<211> LENGTH: 107
<212> TYPE: PRT
<213> ORGANISM: Artificial Sequence
<220> FEATURE:
<223> OTHER INFORMATION: Synthetic Construct

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Leu Ala Ser Glu Gly Phe Ser Asn Asp
            20                  25                  30

Leu Ala Trp Tyr Gln Gln Lys Pro Gly Lys Ser Pro Lys Leu Leu Ile
        35                  40                  45

Tyr Ala Ala Ser Arg Leu Gln Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Gly Ser Lys Tyr Pro Leu
                85                  90                  95

Thr Phe Gly Gly Gly Thr Lys Val Glu Ile Lys
            100                 105
```

```
<210> SEQ ID NO 9
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (6)..(6)
<223> OTHER INFORMATION: Xaa is Glu or Gln
<220> FEATURE:
<221> NAME/KEY: MISC_FEATURE
<222> LOCATION: (9)..(9)
<223> OTHER INFORMATION: Xaa is Gly or Ala
<220> FEATURE:
<221> NAME/KEY: MISC_FEATURE
<222> LOCATION: (10)..(10)
<223> OTHER INFORMATION: Xaa is Gly or Glu
<220> FEATURE:
<221> NAME/KEY: MISC_FEATURE
<222> LOCATION: (11)..(11)
<223> OTHER INFORMATION: Xaa is Leu or Val
<220> FEATURE:
<221> NAME/KEY: MISC_FEATURE
<222> LOCATION: (12)..(12)
<223> OTHER INFORMATION: Xaa is Val or Lys
<220> FEATURE:
<221> NAME/KEY: MISC_FEATURE
<222> LOCATION: (13)..(13)
<223> OTHER INFORMATION: Xaa is Gln or Lys
<220> FEATURE:
<221> NAME/KEY: MISC_FEATURE
<222> LOCATION: (16)..(16)
<223> OTHER INFORMATION: Xaa is Gly, Ala, or Thr
<220> FEATURE:
<221> NAME/KEY: MISC_FEATURE
<222> LOCATION: (18)..(18)
<223> OTHER INFORMATION: Xaa is Leu or Val
<220> FEATURE:
<221> NAME/KEY: MISC_FEATURE
<222> LOCATION: (19)..(19)
<223> OTHER INFORMATION: Xaa is Arg or Lys
<220> FEATURE:
<221> NAME/KEY: MISC_FEATURE
<222> LOCATION: (20)..(20)
<223> OTHER INFORMATION: Xaa is Leu or Val
<220> FEATURE:
<221> NAME/KEY: MISC_FEATURE
<222> LOCATION: (23)..(23)
<223> OTHER INFORMATION: Xaa is Ala, Lys, or Leu

<400> SEQUENCE: 9

Glu Val Gln Leu Val Xaa Ser Gly Xaa Xaa Xaa Xaa Xaa Pro Gly Xaa
1               5                   10                  15

Ser Xaa Xaa Xaa Ser Cys Xaa Ala Ser Gly Phe Thr Phe Asn
            20                  25                  30

<210> SEQ ID NO 10
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is Ile or Val
<220> FEATURE:
<221> NAME/KEY: MISC_FEATURE
<222> LOCATION: (8)..(8)
<223> OTHER INFORMATION: Xaa is Lys or Gln
<220> FEATURE:
<221> NAME/KEY: MISC_FEATURE
<222> LOCATION: (13)..(13)
```

```
<223> OTHER INFORMATION: Xaa is Val, Met, or Ile
<220> FEATURE:
<221> NAME/KEY: MISC_FEATURE
<222> LOCATION: (14)..(14)
<223> OTHER INFORMATION: Xaa is Ala or Gly

<400> SEQUENCE: 10

Trp Xaa Arg Gln Ala Pro Gly Xaa Gly Leu Glu Trp Xaa Xaa
1               5                   10

<210> SEQ ID NO 11
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is Phe or Val
<220> FEATURE:
<221> NAME/KEY: MISC_FEATURE
<222> LOCATION: (4)..(4)
<223> OTHER INFORMATION: Xaa is Ile or Met
<220> FEATURE:
<221> NAME/KEY: MISC_FEATURE
<222> LOCATION: (5)..(5)
<223> OTHER INFORMATION: Xaa is Ser or Thr
<220> FEATURE:
<221> NAME/KEY: MISC_FEATURE
<222> LOCATION: (8)..(8)
<223> OTHER INFORMATION: Xaa is Asp, Asn, or Thr
<220> FEATURE:
<221> NAME/KEY: MISC_FEATURE
<222> LOCATION: (9)..(9)
<223> OTHER INFORMATION: Xaa is Ala or Ser
<220> FEATURE:
<221> NAME/KEY: MISC_FEATURE
<222> LOCATION: (10)..(10)
<223> OTHER INFORMATION: Xaa is Lys or Thr
<220> FEATURE:
<221> NAME/KEY: MISC_FEATURE
<222> LOCATION: (11)..(11)
<223> OTHER INFORMATION: Xaa is Ser or Asn
<220> FEATURE:
<221> NAME/KEY: MISC_FEATURE
<222> LOCATION: (12)..(12)
<223> OTHER INFORMATION: Xaa is Ser or Thr
<220> FEATURE:
<221> NAME/KEY: MISC_FEATURE
<222> LOCATION: (13)..(13)
<223> OTHER INFORMATION: Xaa is Leu or Val
<220> FEATURE:
<221> NAME/KEY: MISC_FEATURE
<222> LOCATION: (15)..(15)
<223> OTHER INFORMATION: Xaa is Leu or Met
<220> FEATURE:
<221> NAME/KEY: MISC_FEATURE
<222> LOCATION: (16)..(16)
<223> OTHER INFORMATION: Xaa is Gln or Glu
<220> FEATURE:
<221> NAME/KEY: MISC_FEATURE
<222> LOCATION: (17)..(17)
<223> OTHER INFORMATION: Xaa is Met or Leu
<220> FEATURE:
<221> NAME/KEY: MISC_FEATURE
<222> LOCATION: (18)..(18)
<223> OTHER INFORMATION: Xaa is Asn or Ser
<220> FEATURE:
<221> NAME/KEY: MISC_FEATURE
<222> LOCATION: (22)..(22)
<223> OTHER INFORMATION: Xaa is Ala or Ser
<220> FEATURE:
<221> NAME/KEY: MISC_FEATURE
<222> LOCATION: (27)..(27)
<223> OTHER INFORMATION: Xaa is Val or Thr
```

<400> SEQUENCE: 11

Arg Xaa Thr Xaa Xaa Arg Asp Xaa Xaa Xaa Xaa Xaa Xaa Tyr Xaa Xaa
1               5                   10                  15

Xaa Xaa Ser Leu Arg Xaa Glu Asp Thr Ala Xaa Tyr Tyr Cys Thr Arg
            20                  25                  30

<210> SEQ ID NO 12
<211> LENGTH: 11
<212> TYPE: PRT
<213> ORGANISM: Artificial Sequence
<220> FEATURE:
<223> OTHER INFORMATION: Synthetic Construct

<400> SEQUENCE: 12

Trp Gly Gln Gly Thr Leu Val Thr Val Ser Ser
1               5                   10

<210> SEQ ID NO 13
<211> LENGTH: 23
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is Asp or Glu
<220> FEATURE:
<221> NAME/KEY: MISC_FEATURE
<222> LOCATION: (3)..(3)
<223> OTHER INFORMATION: Xaa is Gln or Val
<220> FEATURE:
<221> NAME/KEY: MISC_FEATURE
<222> LOCATION: (4)..(4)
<223> OTHER INFORMATION: Xaa is Met or Leu
<220> FEATURE:
<221> NAME/KEY: MISC_FEATURE
<222> LOCATION: (9)..(9)
<223> OTHER INFORMATION: Xaa is Ser or Ala
<220> FEATURE:
<221> NAME/KEY: MISC_FEATURE
<222> LOCATION: (10)..(10)
<223> OTHER INFORMATION: Xaa is Ser or Thr
<220> FEATURE:
<221> NAME/KEY: MISC_FEATURE
<222> LOCATION: (13)..(13)
<223> OTHER INFORMATION: Xaa is Ala or Leu
<220> FEATURE:
<221> NAME/KEY: MISC_FEATURE
<222> LOCATION: (15)..(15)
<223> OTHER INFORMATION: Xaa is Val, Pro, or Leu
<220> FEATURE:
<221> NAME/KEY: MISC_FEATURE
<222> LOCATION: (17)..(17)
<223> OTHER INFORMATION: Xaa is Asp or Glu
<220> FEATURE:
<221> NAME/KEY: MISC_FEATURE
<222> LOCATION: (18)..(18)
<223> OTHER INFORMATION: Xaa is Arg or Thr
<220> FEATURE:
<221> NAME/KEY: MISC_FEATURE
<222> LOCATION: (19)..(19)
<223> OTHER INFORMATION: Xaa is Val or Ala
<220> FEATURE:
<221> NAME/KEY: MISC_FEATURE
<222> LOCATION: (20)..(20)
<223> OTHER INFORMATION: Xaa is Thr or Ser
<220> FEATURE:
<221> NAME/KEY: MISC_FEATURE
<222> LOCATION: (21)..(21)
<223> OTHER INFORMATION: Xaa is Ile or Leu
<220> FEATURE:
<221> NAME/KEY: MISC_FEATURE
<222> LOCATION: (22)..(22)

<223> OTHER INFORMATION: Xaa is Thr, Ser, or Glu

<400> SEQUENCE: 13

Xaa Ile Xaa Xaa Thr Gln Ser Pro Xaa Xaa Leu Ser Xaa Ser Xaa Gly
1               5                   10                  15

Xaa Xaa Xaa Xaa Xaa Xaa Cys
            20

<210> SEQ ID NO 14
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is Tyr or Phe
<220> FEATURE:
<221> NAME/KEY: MISC_FEATURE
<222> LOCATION: (6)..(6)
<223> OTHER INFORMATION: Xaa is Pro or Ser
<220> FEATURE:
<221> NAME/KEY: MISC_FEATURE
<222> LOCATION: (8)..(8)
<223> OTHER INFORMATION: Xaa is Lys or Gln
<220> FEATURE:
<221> NAME/KEY: MISC_FEATURE
<222> LOCATION: (9)..(9)
<223> OTHER INFORMATION: Xaa is Ser or Ala
<220> FEATURE:
<221> NAME/KEY: MISC_FEATURE
<222> LOCATION: (11)..(11)
<223> OTHER INFORMATION: Xaa is Lys, Arg, or Gln
<220> FEATURE:
<221> NAME/KEY: MISC_FEATURE
<222> LOCATION: (12)..(12)
<223> OTHER INFORMATION: Xaa is Leu or Ser

<400> SEQUENCE: 14

Trp Xaa Gln Gln Lys Xaa Gly Xaa Xaa Pro Xaa Xaa Leu Ile Tyr
1               5                   10                  15

<210> SEQ ID NO 15
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is Val or Ile
<220> FEATURE:
<221> NAME/KEY: MISC_FEATURE
<222> LOCATION: (4)..(4)
<223> OTHER INFORMATION: Xaa is Ser or Ala
<220> FEATURE:
<221> NAME/KEY: MISC_FEATURE
<222> LOCATION: (14)..(14)
<223> OTHER INFORMATION: Xaa is Asp or Arg
<220> FEATURE:
<221> NAME/KEY: MISC_FEATURE
<222> LOCATION: (16)..(16)
<223> OTHER INFORMATION: Xaa is Thr or Ser
<220> FEATURE:
<221> NAME/KEY: MISC_FEATURE
<222> LOCATION: (18)..(18)
<223> OTHER INFORMATION: Xaa is Thr or Lys
<220> FEATURE:
<221> NAME/KEY: MISC_FEATURE
<222> LOCATION: (21)..(21)
<223> OTHER INFORMATION: Xaa is Ser or Gly
<220> FEATURE:

```
<221> NAME/KEY: MISC_FEATURE
<222> LOCATION: (22)..(22)
<223> OTHER INFORMATION: Xaa is Leu or Met
<220> FEATURE:
<221> NAME/KEY: MISC_FEATURE
<222> LOCATION: (23)..(23)
<223> OTHER INFORMATION: Xaa is Gln or Glu
<220> FEATURE:
<221> NAME/KEY: MISC_FEATURE
<222> LOCATION: (27)..(27)
<223> OTHER INFORMATION: Xaa is Phe, Val, or Glu
<220> FEATURE:
<221> NAME/KEY: MISC_FEATURE
<222> LOCATION: (29)..(29)
<223> OTHER INFORMATION: Xaa is Thr, Val, or Asp
<220> FEATURE:
<221> NAME/KEY: MISC_FEATURE
<222> LOCATION: (31)..(31)
<223> OTHER INFORMATION: Xaa is Phe or Tyr

<400> SEQUENCE: 15

Gly Xaa Pro Xaa Arg Phe Ser Gly Ser Gly Ser Gly Thr Xaa Phe Xaa
1               5                   10                  15

Leu Xaa Ile Ser Xaa Xaa Xaa Pro Glu Asp Xaa Ala Xaa Tyr Xaa Cys
            20                  25                  30

<210> SEQ ID NO 16
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is Gly or Ser
<220> FEATURE:
<221> NAME/KEY: MISC_FEATURE
<222> LOCATION: (7)..(7)
<223> OTHER INFORMATION: Xaa is Val or Leu

<400> SEQUENCE: 16

Phe Gly Xaa Gly Thr Lys Xaa Glu Ile Lys
1               5                   10

<210> SEQ ID NO 17
<211> LENGTH: 30
<212> TYPE: PRT
<213> ORGANISM: Artificial Sequence
<220> FEATURE:
<223> OTHER INFORMATION: Synthetic Construct

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn
            20                  25                  30

<210> SEQ ID NO 18
<211> LENGTH: 14
<212> TYPE: PRT
<213> ORGANISM: Artificial Sequence
<220> FEATURE:
<223> OTHER INFORMATION: Synthetic Construct

<400> SEQUENCE: 18

Trp Ile Arg Gln Ala Pro Gly Lys Gly Leu Glu Trp Val Ala
1               5                   10
```

<210> SEQ ID NO 19
<211> LENGTH: 32
<212> TYPE: PRT
<213> ORGANISM: Artificial Sequence
<220> FEATURE:
<223> OTHER INFORMATION: Synthetic Construct

<400> SEQUENCE: 19

Arg Phe Thr Ile Ser Arg Asp Asp Ala Lys Ser Ser Leu Tyr Leu Gln
1               5                   10                  15

Met Asn Ser Leu Arg Ala Glu Asp Thr Ala Val Tyr Tyr Cys Thr Arg
            20                  25                  30

<210> SEQ ID NO 20
<211> LENGTH: 11
<212> TYPE: PRT
<213> ORGANISM: Artificial Sequence
<220> FEATURE:
<223> OTHER INFORMATION: Synthetic Construct

<400> SEQUENCE: 20

Trp Gly Gln Gly Thr Leu Val Thr Val Ser Ser
1               5                   10

<210> SEQ ID NO 21
<211> LENGTH: 23
<212> TYPE: PRT
<213> ORGANISM: Artificial Sequence
<220> FEATURE:
<223> OTHER INFORMATION: Synthetic Construct

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 22
<211> LENGTH: 15
<212> TYPE: PRT
<213> ORGANISM: Artificial Sequence
<220> FEATURE:
<223> OTHER INFORMATION: Synthetic Construct

<400> SEQUENCE: 22

Trp Tyr Gln Gln Lys Pro Gly Lys Ser Pro Lys Leu Leu Ile Tyr
1               5                   10                  15

<210> SEQ ID NO 23
<211> LENGTH: 32
<212> TYPE: PRT
<213> ORGANISM: Artificial Sequence
<220> FEATURE:
<223> OTHER INFORMATION: Synthetic Construct

<400> SEQUENCE: 23

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Phe Cys
            20                  25                  30

<210> SEQ ID NO 24
<211> LENGTH: 10
<212> TYPE: PRT
<213> ORGANISM: Artificial Sequence
<220> FEATURE:

<223> OTHER INFORMATION: Synthetic Construct

<400> SEQUENCE: 24

Phe Gly Gly Gly Thr Lys Val Glu Ile Lys
1               5                   10

<210> SEQ ID NO 25
<211> LENGTH: 226
<212> TYPE: PRT
<213> ORGANISM: Artificial Sequence
<220> FEATURE:
<223> OTHER INFORMATION: Synthetic Construct

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Trp Met Thr Trp Ile Arg Gln Ala Pro Gly Lys Gly Leu Glu Trp Val
        35                  40                  45

Ala Ser Ile Thr Tyr Thr Gly Gly Thr Tyr Tyr Pro Asp Ser Val
    50                  55                  60

Lys Gly Arg Phe Thr Ile Ser Arg Asp Asp Ala Lys Ser Ser Leu Tyr
65                  70                  75                  80

Leu Gln Met Asn Ser Leu Arg Ala Glu Asp Thr Ala Val Tyr Tyr Cys
                85                  90                  95

Thr Arg Ala Asn Tyr Tyr Tyr Asn Thr Tyr Gly Gly Phe Pro Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp
225

<210> SEQ ID NO 26
<211> LENGTH: 214
<212> TYPE: PRT
<213> ORGANISM: Artificial Sequence
<220> FEATURE:
<223> OTHER INFORMATION: Synthetic Construct

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Leu Ala Ser Glu Gly Phe Ser Asn Asp
            20                  25                  30

Leu Ala Trp Tyr Gln Gln Lys Pro Gly Lys Ser Pro Lys Leu Leu Ile

```
            35                  40                  45
Tyr Ala Ala Ser Arg Leu Gln Asp Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Phe Cys Gln Gln Gly Ser Lys Tyr Pro Leu
             85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 27
<211> LENGTH: 30
<212> TYPE: PRT
<213> ORGANISM: Artificial Sequence
<220> FEATURE:
<223> OTHER INFORMATION: Synthetic Construct

<400> SEQUENCE: 27

Glu Val Gln Leu Val Glu Ser Gly Gly Gly Leu Val Gln Pro Gly Thr
  1               5                  10                  15

Ser Leu Lys Leu Ser Cys Leu Ala Ser Gly Phe Thr Phe Asn
             20                  25                  30

<210> SEQ ID NO 28
<211> LENGTH: 14
<212> TYPE: PRT
<213> ORGANISM: Artificial Sequence
<220> FEATURE:
<223> OTHER INFORMATION: Synthetic Construct

<400> SEQUENCE: 28

Trp Ile Arg Gln Ala Pro Gly Lys Gly Leu Glu Trp Ile Ala
  1               5                  10

<210> SEQ ID NO 29
<211> LENGTH: 32
<212> TYPE: PRT
<213> ORGANISM: Artificial Sequence
<220> FEATURE:
<223> OTHER INFORMATION: Synthetic Construct

<400> SEQUENCE: 29

Arg Phe Thr Ile Ser Arg Asp Asp Ala Lys Ser Thr Leu Tyr Leu Gln
  1               5                  10                  15

Met Asn Ser Leu Arg Ser Glu Asp Thr Ala Thr Tyr Tyr Cys Thr Arg
             20                  25                  30
```

<210> SEQ ID NO 30
<211> LENGTH: 11
<212> TYPE: PRT
<213> ORGANISM: Artificial Sequence
<220> FEATURE:
<223> OTHER INFORMATION: Synthetic Construct

<400> SEQUENCE: 30

Trp Gly Gln Gly Thr Leu Val Thr Val Ser Ser
1               5                   10

<210> SEQ ID NO 31
<211> LENGTH: 23
<212> TYPE: PRT
<213> ORGANISM: Artificial Sequence
<220> FEATURE:
<223> OTHER INFORMATION: Synthetic Construct

<400> SEQUENCE: 31

Asp Ile Gln Met Thr Gln Ser Pro Ala Ser Leu Ser Ala Ser Leu Gly
1               5                   10                  15

Glu Thr Val Ser Ile Glu Cys
            20

<210> SEQ ID NO 32
<211> LENGTH: 15
<212> TYPE: PRT
<213> ORGANISM: Artificial Sequence
<220> FEATURE:
<223> OTHER INFORMATION: Synthetic Construct

<400> SEQUENCE: 32

Trp Tyr Gln Gln Lys Ser Gly Lys Ser Pro Gln Leu Leu Ile Tyr
1               5                   10                  15

<210> SEQ ID NO 33
<211> LENGTH: 32
<212> TYPE: PRT
<213> ORGANISM: Artificial Sequence
<220> FEATURE:
<223> OTHER INFORMATION: Synthetic Construct

<400> SEQUENCE: 33

Gly Val Pro Ser Arg Phe Ser Gly Ser Gly Ser Gly Thr Arg Phe Ser
1               5                   10                  15

Leu Lys Ile Ser Gly Met Gln Pro Glu Asp Glu Ala Asp Tyr Phe Cys
            20                  25                  30

<210> SEQ ID NO 34
<211> LENGTH: 10
<212> TYPE: PRT
<213> ORGANISM: Artificial Sequence
<220> FEATURE:
<223> OTHER INFORMATION: Synthetic Construct

<400> SEQUENCE: 34

Phe Gly Ser Gly Thr Lys Leu Glu Ile Lys
1               5                   10

<210> SEQ ID NO 35
<211> LENGTH: 122
<212> TYPE: PRT
<213> ORGANISM: Artificial Sequence
<220> FEATURE:
<223> OTHER INFORMATION: Synthetic Construct

<400> SEQUENCE: 35

Glu Val Gln Leu Val Glu Ser Gly Gly Gly Leu Val Gln Pro Gly Thr
1               5                   10                  15

Ser Leu Lys Leu Ser Cys Leu Ala Ser Gly Phe Thr Phe Asn Asn Tyr
            20                  25                  30

Trp Met Thr Trp Ile Arg Gln Ala Pro Gly Lys Gly Leu Glu Trp Ile
        35                  40                  45

Ala Ser Ile Thr Tyr Thr Gly Gly Thr Tyr Tyr Pro Asp Ser Val
    50                  55                  60

Lys Gly Arg Phe Thr Ile Ser Arg Asp Asp Ala Lys Ser Thr Leu Tyr
65                  70                  75                  80

Leu Gln Met Asn Ser Leu Arg Ser Glu Asp Thr Ala Thr Tyr Tyr Cys
                85                  90                  95

Thr Arg Ala Asn Tyr Tyr Asn Thr Tyr Gly Gly Phe Pro Tyr Trp
            100                 105                 110

Gly Gln Gly Thr Leu Val Thr Val Ser Ser
        115                 120

<210> SEQ ID NO 36
<211> LENGTH: 107
<212> TYPE: PRT
<213> ORGANISM: Artificial Sequence
<220> FEATURE:
<223> OTHER INFORMATION: Synthetic Construct

<400> SEQUENCE: 36

Asp Ile Gln Met Thr Gln Ser Pro Ala Ser Leu Ser Ala Ser Leu Gly
1               5                   10                  15

Glu Thr Val Ser Ile Glu Cys Leu Ala Ser Glu Gly Phe Ser Asn Asp
            20                  25                  30

Leu Ala Trp Tyr Gln Gln Lys Ser Gly Lys Ser Pro Gln Leu Leu Ile
        35                  40                  45

Tyr Ala Ala Ser Arg Leu Gln Asp Gly Val Pro Ser Arg Phe Ser Gly
    50                  55                  60

Ser Gly Ser Gly Thr Arg Phe Ser Leu Lys Ile Ser Gly Met Gln Pro
65                  70                  75                  80

Glu Asp Glu Ala Asp Tyr Phe Cys Gln Gln Gly Ser Lys Tyr Pro Leu
                85                  90                  95

Thr Phe Gly Ser Gly Thr Lys Leu Glu Ile Lys
            100                 105

<210> SEQ ID NO 37
<211> LENGTH: 452
<212> TYPE: PRT
<213> ORGANISM: Artificial Sequence
<220> FEATURE:
<223> OTHER INFORMATION: Synthetic Construct

<400> SEQUENCE: 37

Glu Val Gln Leu Val Glu Ser Gly Gly Gly Leu Val Gln Pro Gly Thr
1               5                   10                  15

Ser Leu Lys Leu Ser Cys Leu Ala Ser Gly Phe Thr Phe Asn Asn Tyr
            20                  25                  30

Trp Met Thr Trp Ile Arg Gln Ala Pro Gly Lys Gly Leu Glu Trp Ile
        35                  40                  45

Ala Ser Ile Thr Tyr Thr Gly Gly Thr Tyr Tyr Pro Asp Ser Val
    50                  55                  60

Lys Gly Arg Phe Thr Ile Ser Arg Asp Asp Ala Lys Ser Thr Leu Tyr
65                  70                  75                  80

Leu Gln Met Asn Ser Leu Arg Ser Glu Asp Thr Ala Thr Tyr Tyr Cys
            85                  90                  95

Thr Arg Ala Asn Tyr Tyr Tyr Asn Thr Tyr Gly Gly Phe Pro Tyr Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 38
<211> LENGTH: 214

```
<212> TYPE: PRT
<213> ORGANISM: Artificial Sequence
<220> FEATURE:
<223> OTHER INFORMATION: Synthetic Construct

<400> SEQUENCE: 38

Asp Ile Gln Met Thr Gln Ser Pro Ala Ser Leu Ser Ala Ser Leu Gly
1               5                   10                  15

Glu Thr Val Ser Ile Glu Cys Leu Ala Ser Glu Gly Phe Ser Asn Asp
            20                  25                  30

Leu Ala Trp Tyr Gln Gln Lys Ser Gly Lys Ser Pro Gln Leu Leu Ile
        35                  40                  45

Tyr Ala Ala Ser Arg Leu Gln Asp Gly Val Pro Ser Arg Phe Ser Gly
    50                  55                  60

Ser Gly Ser Gly Thr Arg Phe Ser Leu Lys Ile Ser Gly Met Gln Pro
65                  70                  75                  80

Glu Asp Glu Ala Asp Tyr Phe Cys Gln Gln Gly Ser Lys Tyr Pro Leu
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 39
<211> LENGTH: 14
<212> TYPE: PRT
<213> ORGANISM: Artificial Sequence
<220> FEATURE:
<223> OTHER INFORMATION: Synthetic Construct

<400> SEQUENCE: 39

Trp Val Arg Gln Ala Pro Gly Lys Gly Leu Glu Trp Val Ala
1               5                   10

<210> SEQ ID NO 40
<211> LENGTH: 32
<212> TYPE: PRT
<213> ORGANISM: Artificial Sequence
<220> FEATURE:
<223> OTHER INFORMATION: Synthetic Construct

<400> SEQUENCE: 40

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Thr Arg
            20                  25                  30
```

```
<210> SEQ ID NO 41
<211> LENGTH: 122
<212> TYPE: PRT
<213> ORGANISM: Artificial Sequence
<220> FEATURE:
<223> OTHER INFORMATION: Synthetic Construct

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Trp Met Thr Trp Val Arg Gln Ala Pro Gly Lys Gly Leu Glu Trp Val
        35                  40                  45

Ala Ser Ile Thr Tyr Thr Gly Gly Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Arg Ala Asn Tyr Tyr Tyr Asn Thr Tyr Gly Gly Phe Pro Tyr Trp
            100                 105                 110

Gly Gln Gly Thr Leu Val Thr Val Ser Ser
        115                 120

<210> SEQ ID NO 42
<211> LENGTH: 14
<212> TYPE: PRT
<213> ORGANISM: Artificial Sequence
<220> FEATURE:
<223> OTHER INFORMATION: Synthetic Construct

<400> SEQUENCE: 42

Trp Ile Arg Gln Ala Pro Gly Lys Gly Leu Glu Trp Ile Ala
1               5                   10

<210> SEQ ID NO 43
<211> LENGTH: 122
<212> TYPE: PRT
<213> ORGANISM: Artificial Sequence
<220> FEATURE:
<223> OTHER INFORMATION: Synthetic Construct

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Trp Met Thr Trp Ile Arg Gln Ala Pro Gly Lys Gly Leu Glu Trp Ile
        35                  40                  45

Ala Ser Ile Thr Tyr Thr Gly Gly Thr Tyr Tyr Pro Asp Ser Val
    50                  55                  60

Lys Gly Arg Phe Thr Ile Ser Arg Asp Asp Ala Lys Ser Ser Leu Tyr
65                  70                  75                  80

Leu Gln Met Asn Ser Leu Arg Ala Glu Asp Thr Ala Val Tyr Tyr Cys
                85                  90                  95

Thr Arg Ala Asn Tyr Tyr Tyr Asn Thr Tyr Gly Gly Phe Pro Tyr Trp
            100                 105                 110

Gly Gln Gly Thr Leu Val Thr Val Ser Ser
        115                 120
```

<210> SEQ ID NO 44
<211> LENGTH: 122
<212> TYPE: PRT
<213> ORGANISM: Artificial Sequence
<220> FEATURE:
<223> OTHER INFORMATION: Synthetic Construct

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Trp Met Thr Trp Val Arg Gln Ala Pro Gly Lys Gly Leu Glu Trp Val
        35                  40                  45

Ala Ser Ile Thr Tyr Thr Gly Gly Thr Tyr Tyr Pro Asp Ser Val
    50                  55                  60

Lys Gly Arg Phe Thr Ile Ser Arg Asp Asp Ala Lys Ser Ser Leu Tyr
65                  70                  75                  80

Leu Gln Met Asn Ser Leu Arg Ala Glu Asp Thr Ala Val Tyr Tyr Cys
                85                  90                  95

Thr Arg Ala Asn Tyr Tyr Tyr Asn Thr Tyr Gly Gly Phe Pro Tyr Trp
            100                 105                 110

Gly Gln Gly Thr Leu Val Thr Val Ser Ser
        115                 120

<210> SEQ ID NO 45
<211> LENGTH: 32
<212> TYPE: PRT
<213> ORGANISM: Artificial Sequence
<220> FEATURE:
<223> OTHER INFORMATION: Synthetic Construct

<400> SEQUENCE: 45

Arg Phe Thr Ile Ser Arg Asp Asp Ala Lys Asn Ser Leu Tyr Leu Gln
1               5                   10                  15

Met Asn Ser Leu Arg Ala Glu Asp Thr Ala Val Tyr Tyr Cys Thr Arg
            20                  25                  30

<210> SEQ ID NO 46
<211> LENGTH: 122
<212> TYPE: PRT
<213> ORGANISM: Artificial Sequence
<220> FEATURE:
<223> OTHER INFORMATION: Synthetic Construct

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Trp Met Thr Trp Val Arg Gln Ala Pro Gly Lys Gly Leu Glu Trp Val
        35                  40                  45

Ala Ser Ile Thr Tyr Thr Gly Gly Thr Tyr Tyr Pro Asp Ser Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Arg Ala Asn Tyr Tyr Asn Thr Tyr Gly Gly Phe Pro Tyr Trp
            100                 105                 110

Gly Gln Gly Thr Leu Val Thr Val Ser Ser
        115                 120

<210> SEQ ID NO 47
<211> LENGTH: 32
<212> TYPE: PRT
<213> ORGANISM: Artificial Sequence
<220> FEATURE:
<223> OTHER INFORMATION: Synthetic Construct

<400> SEQUENCE: 47

Arg Phe Thr Ile Ser Arg Asp Asn Ala Lys Ser Ser Leu Tyr Leu Gln
1               5                   10                  15

Met Asn Ser Leu Arg Ala Glu Asp Thr Ala Val Tyr Tyr Cys Thr Arg
            20                  25                  30

<210> SEQ ID NO 48
<211> LENGTH: 122
<212> TYPE: PRT
<213> ORGANISM: Artificial Sequence
<220> FEATURE:
<223> OTHER INFORMATION: Synthetic Construct

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Trp Met Thr Trp Val Arg Gln Ala Pro Gly Lys Gly Leu Glu Trp Val
        35                  40                  45

Ala Ser Ile Thr Tyr Thr Gly Gly Thr Tyr Tyr Pro Asp Ser Val
    50                  55                  60

Lys Gly Arg Phe Thr Ile Ser Arg Asp Asn Ala Lys Ser Ser Leu Tyr
65                  70                  75                  80

Leu Gln Met Asn Ser Leu Arg Ala Glu Asp Thr Ala Val Tyr Tyr Cys
                85                  90                  95

Thr Arg Ala Asn Tyr Tyr Asn Thr Tyr Gly Gly Phe Pro Tyr Trp
            100                 105                 110

Gly Gln Gly Thr Leu Val Thr Val Ser Ser
        115                 120

<210> SEQ ID NO 49
<211> LENGTH: 14
<212> TYPE: PRT
<213> ORGANISM: Artificial Sequence
<220> FEATURE:
<223> OTHER INFORMATION: Synthetic Construct

<400> SEQUENCE: 49

Trp Val Arg Gln Ala Pro Gly Lys Gly Leu Glu Trp Ile Ala
1               5                   10

<210> SEQ ID NO 50
<211> LENGTH: 122
<212> TYPE: PRT
<213> ORGANISM: Artificial Sequence
<220> FEATURE:
<223> OTHER INFORMATION: Synthetic Construct

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Trp Met Thr Trp Val Arg Gln Ala Pro Gly Lys Gly Leu Glu Trp Ile
            35                  40                  45

Ala Ser Ile Thr Tyr Thr Gly Gly Thr Tyr Tyr Pro Asp Ser Val
        50                  55                  60

Lys Gly Arg Phe Thr Ile Ser Arg Asp Asp Ala Lys Ser Ser Leu Tyr
65                      70                  75                  80

Leu Gln Met Asn Ser Leu Arg Ala Glu Asp Thr Ala Val Tyr Tyr Cys
                85                  90                  95

Thr Arg Ala Asn Tyr Tyr Tyr Asn Thr Tyr Gly Gly Phe Pro Tyr Trp
            100                 105                 110

Gly Gln Gly Thr Leu Val Thr Val Ser Ser
            115                 120

<210> SEQ ID NO 51
<211> LENGTH: 32
<212> TYPE: PRT
<213> ORGANISM: Artificial Sequence
<220> FEATURE:
<223> OTHER INFORMATION: Synthetic Construct

<400> SEQUENCE: 51

Arg Phe Thr Ile Ser Arg Asp Asp Ser Lys Ser Thr Leu Tyr Leu Gln
1               5                   10                  15

Met Asn Ser Leu Arg Ala Glu Asp Thr Ala Val Tyr Tyr Cys Thr Arg
            20                  25                  30

<210> SEQ ID NO 52
<211> LENGTH: 122
<212> TYPE: PRT
<213> ORGANISM: Artificial Sequence
<220> FEATURE:
<223> OTHER INFORMATION: Synthetic Construct

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Trp Met Thr Trp Val Arg Gln Ala Pro Gly Lys Gly Leu Glu Trp Ile
            35                  40                  45

Ala Ser Ile Thr Tyr Thr Gly Gly Thr Tyr Tyr Pro Asp Ser Val
        50                  55                  60

Lys Gly Arg Phe Thr Ile Ser Arg Asp Asp Ser Lys Ser Thr Leu Tyr
65                      70                  75                  80

Leu Gln Met Asn Ser Leu Arg Ala Glu Asp Thr Ala Val Tyr Tyr Cys
                85                  90                  95

Thr Arg Ala Asn Tyr Tyr Tyr Asn Thr Tyr Gly Gly Phe Pro Tyr Trp
            100                 105                 110

Gly Gln Gly Thr Leu Val Thr Val Ser Ser
            115                 120

<210> SEQ ID NO 53
<211> LENGTH: 15
<212> TYPE: PRT
<213> ORGANISM: Artificial Sequence

```
<220> FEATURE:
<223> OTHER INFORMATION: Synthetic Construct

<400> SEQUENCE: 53

Trp Phe Gln Gln Lys Pro Gly Lys Ala Pro Lys Ser Leu Ile Tyr
1               5                   10                  15

<210> SEQ ID NO 54
<211> LENGTH: 32
<212> TYPE: PRT
<213> ORGANISM: Artificial Sequence
<220> FEATURE:
<223> OTHER INFORMATION: Synthetic Construct

<400> SEQUENCE: 54

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 55
<211> LENGTH: 107
<212> TYPE: PRT
<213> ORGANISM: Artificial Sequence
<220> FEATURE:
<223> OTHER INFORMATION: Synthetic Construct

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Leu Ala Ser Glu Gly Phe Ser Asn Asp
            20                  25                  30

Leu Ala Trp Phe Gln Gln Lys Pro Gly Lys Ala Pro Lys Ser Leu Ile
        35                  40                  45

Tyr Ala Ala Ser Arg Leu Gln Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Lys Tyr Pro Leu
                85                  90                  95

Thr Phe Gly Gly Gly Thr Lys Val Glu Ile Lys
            100                 105

<210> SEQ ID NO 56
<211> LENGTH: 15
<212> TYPE: PRT
<213> ORGANISM: Artificial Sequence
<220> FEATURE:
<223> OTHER INFORMATION: Synthetic Construct

<400> SEQUENCE: 56

Trp Tyr Gln Gln Lys Pro Gly Lys Ala Pro Lys Ser Leu Ile Tyr
1               5                   10                  15

<210> SEQ ID NO 57
<211> LENGTH: 107
<212> TYPE: PRT
<213> ORGANISM: Artificial Sequence
<220> FEATURE:
<223> OTHER INFORMATION: Synthetic Construct

<400> SEQUENCE: 57

Asp Ile Gln Met Thr Gln Ser Pro Ser Ser Leu Ser Ala Ser Val Gly
```

```
                1               5                   10                  15
Asp Arg Val Thr Ile Thr Cys Leu Ala Ser Glu Gly Phe Ser Asn Asp
                20                  25                  30

Leu Ala Trp Tyr Gln Gln Lys Pro Gly Lys Ala Pro Lys Ser Leu Ile
            35                  40                  45

Tyr Ala Ala Ser Arg Leu Gln Asp Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Gly Ser Lys Tyr Pro Leu
                85                  90                  95

Thr Phe Gly Gly Gly Thr Lys Val Glu Ile Lys
                100                 105

<210> SEQ ID NO 58
<211> LENGTH: 107
<212> TYPE: PRT
<213> ORGANISM: Artificial Sequence
<220> FEATURE:
<223> OTHER INFORMATION: Synthetic Construct

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Leu Ala Ser Glu Gly Phe Ser Asn Asp
                20                  25                  30

Leu Ala Trp Phe Gln Gln Lys Pro Gly Lys Ala Pro Lys Ser Leu Ile
            35                  40                  45

Tyr Ala Ala Ser Arg Leu Gln Asp Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Gly Ser Lys Tyr Pro Leu
                85                  90                  95

Thr Phe Gly Gly Gly Thr Lys Val Glu Ile Lys
                100                 105

<210> SEQ ID NO 59
<211> LENGTH: 107
<212> TYPE: PRT
<213> ORGANISM: Artificial Sequence
<220> FEATURE:
<223> OTHER INFORMATION: Synthetic Construct

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Leu Ala Ser Glu Gly Phe Ser Asn Asp
                20                  25                  30

Leu Ala Trp Tyr Gln Gln Lys Pro Gly Lys Ala Pro Lys Ser Leu Ile
            35                  40                  45

Tyr Ala Ala Ser Arg Leu Gln Asp Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Ser Lys Tyr Pro Leu
                85                  90                  95
```

Thr Phe Gly Gly Gly Thr Lys Val Glu Ile Lys
            100                 105

<210> SEQ ID NO 60
<211> LENGTH: 32
<212> TYPE: PRT
<213> ORGANISM: Artificial Sequence
<220> FEATURE:
<223> OTHER INFORMATION: Synthetic Construct

<400> SEQUENCE: 60

Gly Val Pro Ser Arg Phe Ser Gly Ser Gly Thr Asp Phe Thr
1               5                   10                  15

Leu Thr Ile Ser Ser Leu Gln Pro Glu Asp Val Ala Thr Tyr Tyr Cys
            20                  25                  30

<210> SEQ ID NO 61
<211> LENGTH: 107
<212> TYPE: PRT
<213> ORGANISM: Artificial Sequence
<220> FEATURE:
<223> OTHER INFORMATION: Synthetic Construct

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Leu Ala Ser Glu Gly Phe Ser Asn Asp
            20                  25                  30

Leu Ala Trp Tyr Gln Gln Lys Pro Gly Lys Ser Pro Lys Leu Leu Ile
        35                  40                  45

Tyr Ala Ala Ser Arg Leu Gln Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Gly Ser Lys Tyr Pro Leu
                85                  90                  95

Thr Phe Gly Gly Gly Thr Lys Val Glu Ile Lys
            100                 105

<210> SEQ ID NO 62
<211> LENGTH: 30
<212> TYPE: PRT
<213> ORGANISM: Artificial Sequence
<220> FEATURE:
<223> OTHER INFORMATION: Synthetic Construct

<400> SEQUENCE: 62

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Asn
            20                  25                  30

<210> SEQ ID NO 63
<211> LENGTH: 14
<212> TYPE: PRT
<213> ORGANISM: Artificial Sequence
<220> FEATURE:
<223> OTHER INFORMATION: Synthetic Construct

<400> SEQUENCE: 63

Trp Val Arg Gln Ala Pro Gly Gln Gly Leu Glu Trp Met Gly
1               5                   10

<210> SEQ ID NO 64
<211> LENGTH: 32
<212> TYPE: PRT
<213> ORGANISM: Artificial Sequence
<220> FEATURE:
<223> OTHER INFORMATION: Synthetic Construct

<400> SEQUENCE: 64

Arg Val Thr Met Thr Arg Asp Thr Ser Thr Ser Thr Val Tyr Met Glu
1               5                   10                  15

Leu Ser Ser Leu Arg Ser Glu Asp Thr Ala Val Tyr Tyr Cys Thr Arg
            20                  25                  30

<210> SEQ ID NO 65
<211> LENGTH: 122
<212> TYPE: PRT
<213> ORGANISM: Artificial Sequence
<220> FEATURE:
<223> OTHER INFORMATION: Synthetic Construct

<400> SEQUENCE: 65

Glu Val Gln Leu Val Gln Ser Gly Ala Glu Val Lys Lys Pro Gly Ala
1               5                   10                  15

Ser Val Lys Val Ser Cys Lys Ala Ser Gly Phe Thr Phe Asn Asn Tyr
            20                  25                  30

Trp Met Thr Trp Val Arg Gln Ala Pro Gly Gln Gly Leu Glu Trp Met
        35                  40                  45

Gly Ser Ile Thr Tyr Thr Gly Gly Thr Tyr Tyr Pro Asp Ser Val
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Ala Asn Tyr Tyr Tyr Asn Thr Tyr Gly Gly Phe Pro Tyr Trp
            100                 105                 110

Gly Gln Gly Thr Leu Val Thr Val Ser Ser
        115                 120

<210> SEQ ID NO 66
<211> LENGTH: 23
<212> TYPE: PRT
<213> ORGANISM: Artificial Sequence
<220> FEATURE:
<223> OTHER INFORMATION: Synthetic Construct

<400> SEQUENCE: 66

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 67
<211> LENGTH: 15
<212> TYPE: PRT
<213> ORGANISM: Artificial Sequence
<220> FEATURE:
<223> OTHER INFORMATION: Synthetic Construct

<400> SEQUENCE: 67

Trp Tyr Gln Gln Lys Pro Gly Gln Ala Pro Arg Leu Leu Ile Tyr
1               5                   10                  15

-continued

<210> SEQ ID NO 68
<211> LENGTH: 32
<212> TYPE: PRT
<213> ORGANISM: Artificial Sequence
<220> FEATURE:
<223> OTHER INFORMATION: Synthetic Construct

<400> SEQUENCE: 68

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
                20                  25                  30

<210> SEQ ID NO 69
<211> LENGTH: 107
<212> TYPE: PRT
<213> ORGANISM: Artificial Sequence
<220> FEATURE:
<223> OTHER INFORMATION: Synthetic Construct

<400> SEQUENCE: 69

Glu Ile Val Leu Thr Gln Ser Pro Ala Thr Leu Ser Leu Ser Pro Gly
1               5                   10                  15

Glu Arg Ala Thr Leu Ser Cys Leu Ala Ser Glu Gly Phe Ser Asn Asp
                20                  25                  30

Leu Ala Trp Tyr Gln Gln Lys Pro Gly Gln Ala Pro Arg Leu Leu Ile
            35                  40                  45

Tyr Ala Ala Ser Arg Leu Gln Asp Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Lys Ser Tyr Pro Leu
                85                  90                  95

Thr Phe Gly Gly Gly Thr Lys Val Glu Ile Lys
            100                 105

<210> SEQ ID NO 70
<211> LENGTH: 450
<212> TYPE: PRT
<213> ORGANISM: Artificial Sequence
<220> FEATURE:
<223> OTHER INFORMATION: Synthetic Construct

<400> SEQUENCE: 70

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Trp Met Tyr Trp Val Arg Gln Ala Pro Gly Lys Gly Leu Glu Trp Val
            35                  40                  45

Ala Ala Ile Thr Pro Asn Ala Gly Glu Asp Tyr Tyr Pro Glu Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly His Tyr Tyr Tyr Thr Ser Tyr Ser Leu Gly Tyr Trp Gly
            100                 105                 110

Gln Gly Thr Leu Val Thr Val Ser Ser Ala Ser Thr Lys Gly Pro Ser

```
            115                 120                 125
Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Ala Ala Gly
225                 230                 235                 240

Ala Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Leu
            420                 425                 430

His Glu Ala Leu His Ser His Tyr Thr Gln Lys Ser Leu Ser Leu Ser
        435                 440                 445

Pro Gly
    450

<210> SEQ ID NO 71
<211> LENGTH: 213
<212> TYPE: PRT
<213> ORGANISM: Artificial Sequence
<220> FEATURE:
<223> OTHER INFORMATION: Synthetic Construct

<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asn Lys His
```

```
                20                  25                  30
Leu Asp Trp Tyr Gln Gln Lys Pro Gly Lys Ala Pro Lys Leu Leu Ile
            35                  40                  45

Tyr Phe Thr Asn Asn Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Phe Gln Tyr Asn Gln Gly Trp Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 72
<211> LENGTH: 449
<212> TYPE: PRT
<213> ORGANISM: Artificial Sequence
<220> FEATURE:
<223> OTHER INFORMATION: Synthetic Construct

<400> SEQUENCE: 72

Glu Val Gln Leu Val Glu Thr Gly Gly Gly Leu Ile Gln Pro Gly Gly
1               5                   10                  15

Ser Leu Arg Leu Ser Cys Ala Ala Ser Gly Phe Thr Phe Ser Phe Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Ile His Gly Ile Arg Ala Ala Tyr Asp Ala Phe Ile Ile
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
```

```
                165                 170                 175
Pro Ala Val Leu Gln Ser Ser Gly Leu Tyr Ser Leu Ser Ser Val Val
                180                 185                 190

Thr Val Pro Ser Ser Leu Gly Thr Lys Thr Tyr Thr Cys Asn Val
                195                 200             205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
                260                 265                 270

Asp Pro Glu Val Gln Phe Asn Trp Tyr Val Asp Gly Val Glu Val His
                275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Gln Glu Glu Met Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
                420                 425                 430

Glu Ala Leu His Asn His Tyr Thr Gln Lys Ser Leu Ser Leu Ser Leu
                435                 440                 445

Gly

<210> SEQ ID NO 73
<211> LENGTH: 215
<212> TYPE: PRT
<213> ORGANISM: Artificial Sequence
<220> FEATURE:
<223> OTHER INFORMATION: Synthetic Construct

<400> SEQUENCE: 73

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ile Asn
                20                  25                  30

Leu Ser Trp Tyr Gln Gln Lys Pro Gly Gln Ala Pro Arg Leu Leu Ile
            35                  40                  45

Tyr Gly Ala Ser His Arg Leu Thr Gly Ile Pro Asp Arg Phe Ser Gly
        50                  55                  60

Ser Gly Ser Gly Thr Asp Phe Thr Leu Thr Ile Ser Arg Leu Glu Pro
65                  70                  75                  80
```

```
Glu Asp Phe Ala Val Tyr Tyr Cys His Gln Tyr Ser Gln Pro Pro
                85                  90                  95

Phe Thr Phe Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 74
<211> LENGTH: 117
<212> TYPE: PRT
<213> ORGANISM: Artificial Sequence
<220> FEATURE:
<223> OTHER INFORMATION: Synthetic Construct

<400> SEQUENCE: 74

Gln Val Leu Leu Val Gln Ser Gly Ala Glu Val Lys Lys Pro Gly Ala
1               5                   10                  15

Thr Val Lys Val Ser Cys Lys Ala Ser Gly Ser Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Asn Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Leu Arg Tyr Asn Trp Lys Ser Trp Gly Gln Gly Thr Leu
            100                 105                 110

Val Thr Val Ser Ser
        115

<210> SEQ ID NO 75
<211> LENGTH: 108
<212> TYPE: PRT
<213> ORGANISM: Artificial Sequence
<220> FEATURE:
<223> OTHER INFORMATION: Synthetic Construct

<400> SEQUENCE: 75

Glu Ile Val Leu Thr Gln Ser Pro Gly Thr Leu Ser Leu Ser Pro Gly
1               5                   10                  15

Glu Arg Val Thr Leu Ser Cys Arg Ala Ser Gln Ser Val Gly Arg Pro
            20                  25                  30

Tyr Leu Ala Trp Tyr Gln Gln Ile Pro Gly Gln Ala Pro Arg Leu Leu
```

```
                35                  40                  45
Ile Tyr Gly Ala Ser Ser Arg Ala Thr Asp Ile Pro Asp Arg Phe Ser
         50                  55                  60

Gly Asn Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Asp Asn Ser Pro
                 85                  90                  95

Tyr Thr Phe Gly Gln Gly Thr Arg Leu Glu Ile Lys
            100                 105

<210> SEQ ID NO 76
<211> LENGTH: 122
<212> TYPE: PRT
<213> ORGANISM: Artificial Sequence
<220> FEATURE:
<223> OTHER INFORMATION: Synthetic Construct

<400> SEQUENCE: 76

Glu Val Gln Leu Val Glu Ser Gly Gly Asn Leu Glu Gln Pro Gly Gly
 1               5                  10                  15

Ser Leu Arg Leu Ser Cys Thr Ala Ser Gly Phe Thr Phe Ser Arg Ser
             20                  25                  30

Ala Met Asn Trp Val Arg Ala Pro Gly Lys Gly Leu Glu Trp Val
         35                  40                  45

Ser Gly Ile Ser Gly Ser Gly Arg Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Ser Ala Glu Asp Thr Ala Ala Tyr Tyr Cys
                 85                  90                  95

Ala Lys Asp Ser Tyr Thr Thr Ser Trp Tyr Gly Gly Met Asp Val Trp
            100                 105                 110

Gly His Gly Thr Thr Val Thr Val Ser Ser
            115                 120

<210> SEQ ID NO 77
<211> LENGTH: 107
<212> TYPE: PRT
<213> ORGANISM: Artificial Sequence
<220> FEATURE:
<223> OTHER INFORMATION: Synthetic Construct

<400> SEQUENCE: 77

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Phe Ser Trp
             20                  25                  30

Leu Ala Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Ile Tyr Tyr Cys Gln Gln Ala Asn Ser Val Pro Ile
                 85                  90                  95

Thr Phe Gly Gln Gly Thr Arg Leu Glu Ile Lys
            100                 105
```

<210> SEQ ID NO 78
<211> LENGTH: 126
<212> TYPE: PRT
<213> ORGANISM: Artificial Sequence
<220> FEATURE:
<223> OTHER INFORMATION: Synthetic Construct

<400> SEQUENCE: 78

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Ala Ile Asp Gln Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Lys Phe Met Gln Leu Trp Gly Gly Gly Leu Arg Tyr Pro
            100                 105                 110

Phe Gly Tyr Trp Gly Gln Gly Thr Met Val Thr Val Ser Ser
        115                 120                 125
```

<210> SEQ ID NO 79
<211> LENGTH: 106
<212> TYPE: PRT
<213> ORGANISM: Artificial Sequence
<220> FEATURE:
<223> OTHER INFORMATION: Synthetic Construct

<400> SEQUENCE: 79

```
Ser Tyr Val Leu Thr Gln Pro Pro Ser Val Ser Val Ser Pro Gly Gln
1               5                   10                  15

Thr Ala Ser Ile Thr Cys Ser Gly Glu Arg Met Gly Asp Lys Tyr Ala
            20                  25                  30

Ala Trp Tyr Gln Gln Lys Pro Gly Gln Ser Pro Val Leu Val Ile Tyr
        35                  40                  45

Arg Asp Thr Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gly Val Leu Lys Gln Asp Thr Gly Val
                85                  90                  95

Phe Gly Gly Gly Thr Lys Leu Thr Val Leu
            100                 105
```

<210> SEQ ID NO 80
<211> LENGTH: 120
<212> TYPE: PRT
<213> ORGANISM: Artificial Sequence
<220> FEATURE:
<223> OTHER INFORMATION: Synthetic Construct

<400> SEQUENCE: 80

```
Gln Val Gln Leu Glu Glu Ser Gly Pro Gly Leu Val Gln Pro Ser Gln
1               5                   10                  15

Thr Leu Ser Leu Thr Cys Thr Val Ser Gly Phe Ser Leu Thr Ser Gln
```

```
                         20                  25                  30
Asn Val His Trp Val Arg Gln Pro Pro Gly Lys Gly Leu Glu Trp Met
            35                  40                  45

Gly Arg Met Arg Phe Asn Gly Asp Thr Ser Tyr Asn Ser Thr Leu Lys
        50                  55                  60

Ser Arg Leu Ser Ile Ser Arg Asp Thr Ser Lys Asn Gln Val Phe Leu
65                  70                  75                  80

Arg Leu Asn Ser Leu Gln Thr Asp Asp Thr Gly Thr Tyr Tyr Cys Ala
                85                  90                  95

Arg Gln Arg Asp Asn Tyr Gly Ser Tyr Tyr Phe Asp Asp Trp Gly Gln
            100                 105                 110

Gly Ile Met Val Thr Val Ser Ser
        115                 120

<210> SEQ ID NO 81
<211> LENGTH: 106
<212> TYPE: PRT
<213> ORGANISM: Artificial Sequence
<220> FEATURE:
<223> OTHER INFORMATION: Synthetic Construct

<400> SEQUENCE: 81

Asp Thr Val Leu Thr Gln Ser Pro Ala Leu Ala Val Ser Pro Gly Glu
1               5                   10                  15

Arg Val Thr Ile Ser Cys Arg Ala Ser Glu Ser Val Leu Thr Leu Leu
            20                  25                  30

Asn Trp Tyr Gln Gln Lys Pro Gly Gln His Pro Lys Leu Leu Ile Tyr
        35                  40                  45

Leu Ala Ser His Leu Glu Ser Gly Val Pro Ala Arg Phe Ser Gly Arg
    50                  55                  60

Gly Ser Gly Thr Asp Phe Thr Leu Thr Ile Asp Pro Val Glu Ala Asp
65                  70                  75                  80

Asp Thr Ala Ser Tyr Tyr Cys Gln Gln Ser Trp Ile Asp Pro Trp Thr
                85                  90                  95

Phe Gly Gly Gly Thr Thr Leu Glu Leu Lys
            100                 105
```

ANTI-INTERLEUKIN-33 ANTIBODIES AND USES THEREOF

SEQUENCE LISTING

The instant application contains a Sequence Listing which has been submitted electronically in ASCII format and is hereby incorporated by reference in its entirety. Said ASCII copy, created on Mar. 11, 2021, is named 50474-219003_Sequence_Listing_03.11.21_ST25 and is 68,754 bytes in size.

FIELD OF THE INVENTION

The invention relates to anti-interleukin-33 (IL-33) antibodies, and methods of making and using the same, including for treatment of IL-33-mediated disorders.

BACKGROUND

Age-related macular degeneration (AMD) is the leading cause of irreversible blindness in people aged 50 years or older in the developed world. The majority of the visual loss occurs in the advanced stage of AMD, which has two clinical forms: a non-exudative form, geographic atrophy (GA), which is characterized by loss of photoreceptors, retinal pigment epithelium (RPE), and choriocapillaris, and an exudative or wet form, which is characterized by choroidal neovascularization (CNV). In the early stages of GA, patients typically show minimal changes in central visual acuity (VA). However, while central VA may not yet be affected, patients often still experience significant symptoms from visual dysfunction, such as dense parafoveal scotomas (e.g., leading to difficulties with face recognition), delayed dark adaptation, reduced contrast sensitivity, and a decrease in reading rate. In the later stages, as the GA lesion expands into the fovea, a profound decrease in central VA occurs with a decline in activities of daily living. Moreover, GA is bilateral in most patients with advanced AMD. As such, GA is a significant cause of both moderate and severe central visual loss. At present, there are no approved treatments for GA, and there is a high unmet need with more than five million patients worldwide.

Interleukin-33 (IL-33) is a member of the interleukin-1 (IL-1) cytokine family that is encoded by the IL33 gene, and is expressed in structural cells, such as smooth muscle, epithelial (e.g., retinal pigment epithelium (RPE) cells), endothelial cells (e.g., choroidal endothelial cells), Muller cells, and astrocytes. IL-33 can be induced by inflammatory factors in macrophages and dendritic cells. Cellular stress caused by environmental triggers, such as allergens, toxins, and pathogens, can lead to IL-33 release. For example, IL-33 is released from Muller cells upon phototoxic stress, and induces $CCL_2$ and monocyte-dependent retinal degeneration in preclinical models. Bioavailable IL-33 associates with a heterodimeric IL-33 receptor complex composed of suppression of tumorigenicity 2 (ST2) protein and interleukin-1 receptor accessory protein (IL-1RAcP) to activate the AP-1 and NF-κB pathways through the adaptor protein myeloid differentiation primary response 88 (MyD88) and possibly MyD88-adapter-like (Mal) protein. IL-33 stimulates a number of cell types, including innate type II (ILC2) cells, mast cells, basophils, eosinophils, and dendritic cells, to promote Type 2 immunity.

The IL-33 pathway has been suggested to be involved in various diseases, including ocular diseases (e.g, GA) for which there remains a need to develop improved compositions, and methods for treatment.

SUMMARY

The present invention relates, inter alia, to anti-IL-33 antibodies and methods of making and using the same.

In one aspect, provided herein is an isolated antibody that specifically binds IL-33, or an antigen-binding fragment thereof, wherein the antibody comprises a binding domain comprising a heavy chain variable (VH) domain and a light chain variable (VL) domain, the binding domain comprising the following six complementarity-determining regions (CDRs): (a) a CDR-H1 comprising the amino acid sequence of NYWMT (SEQ ID NO: 1); (b) a CDR-H2 comprising the amino acid sequence of SITYTGGGTYYPDSVKG (SEQ ID NO: 2); (c) a CDR-H3 comprising the amino acid sequence of ANYYYNTYGGFPY (SEQ ID NO: 3); (d) a CDR-L1 comprising the amino acid sequence of LASEGFSNDLA (SEQ ID NO: 4); (e) a CDR-L2 comprising the amino acid sequence of AASRLQD (SEQ ID NO: 5); and (f) a CDR-L3 comprising the amino acid sequence of QQGSKYPLT (SEQ ID NO: 6).

In another aspect, provided herein is an isolated antibody that specifically binds IL-33, or an antigen-binding fragment thereof, wherein the antibody comprises a binding domain comprising (a) a VH domain comprising an amino acid sequence having at least 95% sequence identity to the amino acid sequence of SEQ ID NO: 7; (b) a VL domain comprising an amino acid sequence having at least 95% sequence identity to the amino acid sequence of SEQ ID NO: 8; or (c) a VH domain as in (a) and a VL domain as in (b).

In some aspects, the VH domain comprises: (a) an FR-H1 comprising the amino acid sequence of EVQLVX$_1$SGX$_2$X$_3$X$_4$X$_5$X$_6$PGX$_7$SX$_8$X$_9$X$_{10}$SCX$_{11}$ASGFTFN (SEQ ID NO: 9), wherein X$_1$ is E or Q; X$_2$ is G or A; X$_3$ is G or E; X$_4$ is L or V; X$_5$ is V or K; X$_6$ is Q or K; X$_7$ is G, A, or T; X$_8$ is L or V; X$_9$ is R or K; X$_{10}$ is L or V; and X$_{11}$ is A, K, or L; (b) an FR-H2 comprising the amino acid sequence of WX$_1$RQAPGX$_2$GLEWX$_3$X$_4$(SEQ ID NO: 10), wherein X$_1$ is I or V; X$_2$ is K or Q; X$_3$ is V, M, or I; and X$_4$ is A or G; (c) an FR-H3 comprising the amino acid sequence of RX$_1$TX$_2$X$_3$RDX$_4$X$_5$X$_6$X$_7$X$_8$X$_9$YX$_{10}$X$_{11}$X$_{12}$X$_{13}$SLRX$_{14}$EDTAX$_{15}$YYCTR (SEQ ID NO: 11), wherein X$_1$ is F or V; X$_2$ is I or M; X$_3$ is S or T; X$_4$ is D, N, or T; X$_5$ is A or S; X$_6$ is K or T; X$_7$ is S or N; X$_8$ is S or T; X$_9$ is L or V; X$_{10}$ is L or M; X$_{11}$ is Q or E; X$_{12}$ is M or L; X$_{13}$ is N or S; X$_{14}$ is A or S; and X$_{15}$ is V or T; and (d) an FR-H4 comprising the amino acid sequence of WGQGTLVTVSS (SEQ ID NO: 12).

In some aspects, the VH domain comprises: (a) an FR-H1 comprising the amino acid sequence of EVQLVESGGGLVQPGGSLRLSCAASGFTFN (SEQ ID NO: 17); (b) an FR-H2 comprising the amino acid sequence of WIRQAPGKGLEWVA (SEQ ID NO: 18); (c) an FR-H3 comprising the amino acid sequence of RFTISRDDAKSSLYLQMNSLRAEDTAVYYCTR (SEQ ID NO: 19); and (d) an FR-H4 comprising the amino acid sequence of WGQGTLVTVSS (SEQ ID NO: 12).

In some aspects, the VH domain comprises the amino acid sequence of SEQ ID NO: 7.

In some aspects, the VH domain comprises: (a) an FR-H1 comprising the amino acid sequence of EVQLVESGGGLVQPGGSLRLSCAASGFTFN (SEQ ID NO: 17); (b) an FR-H2 comprising the amino acid sequence of WVRQAPGKGLEWVA (SEQ ID NO: 39); (c) an FR-H3 comprising the amino acid sequence of RFTISRDNAKNS- LYLQMNSLRAEDTAVYYCTR (SEQ ID NO: 40); and (d) an FR-H4 comprising the amino acid sequence of WGQGTLVTVSS (SEQ ID NO: 12).

In some aspects, the VH domain comprises the amino acid sequence of SEQ ID NO: 41.

In some aspects, the VH domain comprises: (a) an FR-H1 comprising the amino acid sequence of EVQLVESGG-GLVQPGGSLRLSCAASGFTFN (SEQ ID NO: 17); (b) an FR-H2 comprising the amino acid sequence of WIRQAPGKGLEWIA (SEQ ID NO: 42); (c) an FR-H3 comprising the amino acid sequence of RFTISRDDAKSS-LYLQMNSLRAEDTAVYYCTR (SEQ ID NO: 19); and (d) an FR-H4 comprising the amino acid sequence of WGQGTLVTVSS (SEQ ID NO: 12).

In some aspects, the VH domain comprises the amino acid sequence of SEQ ID NO: 43.

In some aspects, the VH domain comprises: (a) an FR-H1 comprising the amino acid sequence of EVQLVESGG-GLVQPGGSLRLSCAASGFTFN (SEQ ID NO: 17); (b) an FR-H2 comprising the amino acid sequence of WVRQAPGKGLEWVA (SEQ ID NO: 39); (c) an FR-H3 comprising the amino acid sequence of RFTISRDDAKSS-LYLQMNSLRAEDTAVYYCTR (SEQ ID NO: 19); and (d) an FR-H4 comprising the amino acid sequence of WGQGTLVTVSS (SEQ ID NO: 12).

In some aspects, the VH domain comprises the amino acid sequence of SEQ ID NO: 44.

In some aspects, the VH domain comprises: (a) an FR-H1 comprising the amino acid sequence of EVQLVESGG-GLVQPGGSLRLSCAASGFTFN (SEQ ID NO: 17); (b) an FR-H2 comprising the amino acid sequence of WVRQAPGKGLEWVA (SEQ ID NO: 39); (c) an FR-H3 comprising the amino acid sequence of RFTISRDDAKNS-LYLQMNSLRAEDTAVYYCTR (SEQ ID NO: 45); and (d) an FR-H4 comprising the amino acid sequence of WGQGTLVTVSS (SEQ ID NO: 12).

In some aspects, the VH domain comprises the amino acid sequence of SEQ ID NO: 46.

In some aspects, the VH domain comprises: (a) an FR-H1 comprising the amino acid sequence of EVQLVESGG-GLVQPGGSLRLSCAASGFTFN (SEQ ID NO: 17); (b) an FR-H2 comprising the amino acid sequence of WVRQAPGKGLEWVA (SEQ ID NO: 39); (c) an FR-H3 comprising the amino acid sequence of RFTISRDNAKSS-LYLQMNSLRAEDTAVYYCTR (SEQ ID NO: 47); and (d) an FR-H4 comprising the amino acid sequence of WGQGTLVTVSS (SEQ ID NO: 12).

In some aspects, the VH domain comprises the amino acid sequence of SEQ ID NO: 48.

In some aspects, the VH domain comprises: (a) an FR-H1 comprising the amino acid sequence of EVQLVESGG-GLVQPGGSLRLSCAASGFTFN (SEQ ID NO: 17); (b) an FR-H2 comprising the amino acid sequence of WVRQAPGKGLEWIA (SEQ ID NO: 49); (c) an FR-H3 comprising the amino acid sequence of RFTISRDDAKSS-LYLQMNSLRAEDTAVYYCTR (SEQ ID NO: 19); and (d) an FR-H4 comprising the amino acid sequence of WGQGTLVTVSS (SEQ ID NO: 12).

In some aspects, the VH domain comprises the amino acid sequence of SEQ ID NO: 50.

In some aspects, the VH domain comprises: (a) an FR-H1 comprising the amino acid sequence of EVQLVESGG-GLVQPGGSLRLSCAASGFTFN (SEQ ID NO: 17); (b) an FR-H2 comprising the amino acid sequence of WVRQAPGKGLEWIA (SEQ ID NO: 49); (c) an FR-H3 comprising the amino acid sequence of RFTISRDDSKST-LYLQMNSLRAEDTAVYYCTR (SEQ ID NO: 51); and (d) an FR-H4 comprising the amino acid sequence of WGQGTLVTVSS (SEQ ID NO: 12).

In some aspects, the VH domain comprises the amino acid sequence of SEQ ID NO: 52.

In some aspects, the VL domain comprises: (a) an FR-L1 comprising the amino acid sequence of $X_1IX_2X_3TQSPX_4X_5LSX_6SX_7GX_8X_9X_{10}X_{11}X_{12}X_{13}C$ (SEQ ID NO: 13), wherein $X_1$ is D or E; $X_2$ is Q or V; $X_3$ is M or L; $X_4$ is S or A; $X_5$ is S or T; $X_6$ is A or L; $X_7$ is V, P, or L; $X_8$ is D or E; $X_9$ is R or T; $X_{10}$ is V or A; $X_{11}$ is T or S; $X_{12}$ is I or L; and $X_{13}$ is T, S, or E; (b) an FR-L2 comprising the amino acid sequence of $WX_1QQKX_2GX_3X_4PX_5X_6LIY$ (SEQ ID NO: 14), wherein $X_1$ is Y or F; $X_2$ is P or S; $X_3$ is K or Q; $X_4$ is S or A; $X_5$ is K, R, or Q; and $X_6$ is L or S; (c) an FR-L3 comprising the amino acid sequence of $GX_1PX_2RFSGSGSGTX_3 FX_4LX_5ISX_6X_7X_8PEDX_9AX_{10}YX_{11}C$ (SEQ ID NO: 15), wherein $X_1$ is V or I; $X_2$ is S or A; $X_3$ is D or R; $X_4$ is T or S; $X_5$ is T or K; $X_6$ is S or G; $X_7$ is L or M; $X_8$ is Q or E; $X_9$ is F, V, or E; $X_{10}$ is T, V, or D; and $X_{11}$ is F or Y; and (d) an FR-L4 comprising the amino acid sequence of $FGX_1GTKX_2EIK$ (SEQ ID NO: 16), wherein $X_1$ is G or S and $X_2$ is V or L.

In some aspects, the VL domain comprises: (a) an FR-L1 comprising the amino acid sequence of DIQMTQSPSSL-SASVGDRVTITC (SEQ ID NO: 21); (b) an FR-L2 comprising the amino acid sequence of WYQQKPGKSPKLLIY (SEQ ID NO: 22); (c) an FR-L3 comprising the amino acid sequence of GVPSRFSGSGSGTDFTLTISSLQPEDFA-TYFC (SEQ ID NO: 23); and (d) an FR-L4 comprising the amino acid sequence of FGGGTKVEIK (SEQ ID NO: 24).

In some aspects, the VL domain comprises the amino acid sequence of SEQ ID NO: 8.

In another aspect, provided herein is an isolated antibody that specifically binds IL-33, or an antigen-binding fragment thereof, wherein the antibody comprises a binding domain comprising (a) a VH domain comprising an amino acid sequence of SEQ ID NO: 7 and (b) a VL domain comprising an amino acid sequence of SEQ ID NO: 8.

In another aspect, provided herein is an isolated antibody that specifically binds IL-33, or an antigen-binding fragment thereof, wherein the antibody comprises a binding domain comprising (a) a heavy chain (HC) comprising an amino acid sequence of SEQ ID NO: 25 and (b) a light chain (LC) comprising an amino acid sequence of SEQ ID NO: 26.

In some aspects, the VL domain comprises: (a) an FR-L1 comprising the amino acid sequence of DIQMTQSPSSL-SASVGDRVTITC (SEQ ID NO: 21); (b) an FR-L2 comprising the amino acid sequence of WFQQKPGKAPKSLIY (SEQ ID NO: 53); (c) an FR-L3 comprising the amino acid sequence of GVPSRFSGSGSGTDFTLTISSLQPEDFA-TYYC (SEQ ID NO: 54); and (d) an FR-L4 comprising the amino acid sequence of FGGGTKVEIK (SEQ ID NO: 24).

In some aspects, the VL domain comprises the amino acid sequence of SEQ ID NO: 55.

In some aspects, the VL domain comprises: (a) an FR-L1 comprising the amino acid sequence of DIQMTQSPSSL-SASVGDRVTITC (SEQ ID NO: 21); (b) an FR-L2 comprising the amino acid sequence of WYQQKPGKAPKSLIY (SEQ ID NO: 56); (c) an FR-L3 comprising the amino acid sequence of GVPSRFSGSGSGTDFTLTISSLQPEDFA-TYFC (SEQ ID NO: 23); and (d) an FR-L4 comprising the amino acid sequence of FGGGTKVEIK (SEQ ID NO: 24).

In some aspects, the VL domain comprises the amino acid sequence of SEQ ID NO: 57.

In some aspects, the VL domain comprises: (a) an FR-L1 comprising the amino acid sequence of DIQMTQSPSSL- SASVGDRVTITC (SEQ ID NO: 21); (b) an FR-L2 comprising the amino acid sequence of WFQQKPGKAPKSLIY (SEQ ID NO: 53); (c) an FR-L3 comprising the amino acid sequence of GVPSRFSGSGSGTDFTLTISSLQPEDFATYFC (SEQ ID NO: 23); and (d) an FR-L4 comprising the amino acid sequence of FGGGTKVEIK (SEQ ID NO: 24).

In some aspects, the VL domain comprises the amino acid sequence of SEQ ID NO: 58.

In some aspects, the VL domain comprises: (a) an FR-L1 comprising the amino acid sequence of DIQMTQSPSSLSASVGDRVTITC (SEQ ID NO: 21); (b) an FR-L2 comprising the amino acid sequence of WYQQKPGKAPKSLIY (SEQ ID NO: 56); (c) an FR-L3 comprising the amino acid sequence of GVPSRFSGSGSGTDFTLTISSLQPEDFATYYC (SEQ ID NO: 54); and (d) an FR-L4 comprising the amino acid sequence of FGGGTKVEIK (SEQ ID NO: 24).

In some aspects, the VL domain comprises the amino acid sequence of SEQ ID NO: 59.

In some aspects, the VL domain comprises: (a) an FR-L1 comprising the amino acid sequence of DIQMTQSPSSLSASVGDRVTITC (SEQ ID NO: 21); (b) an FR-L2 comprising the amino acid sequence of WYQQKPGKSPKLLIY (SEQ ID NO: 22); (c) an FR-L3 comprising the amino acid sequence of GVPSRFSGSGSGTDFTLTISSLQPEDVATYYC (SEQ ID NO: 60); and (d) an FR-L4 comprising the amino acid sequence of FGGGTKVEIK (SEQ ID NO: 24).

In some aspects, the VL domain comprises the amino acid sequence of SEQ ID NO: 61.

In another aspect, provided herein is an isolated antibody that specifically binds IL-33, or an antigen-binding fragment thereof, wherein the antibody comprises a binding domain comprising (a) a VH domain comprising an amino acid sequence of SEQ ID NO: 41 and (b) a VL domain comprising an amino acid sequence of SEQ ID NO: 55.

In another aspect, provided herein is an isolated antibody that specifically binds IL-33, or an antigen-binding fragment thereof, wherein the antibody comprises a binding domain comprising (a) a VH domain comprising an amino acid sequence of SEQ ID NO: 43 and (b) a VL domain comprising an amino acid sequence of SEQ ID NO: 55.

In another aspect, provided herein is an isolated antibody that specifically binds IL-33, or an antigen-binding fragment thereof, wherein the antibody comprises a binding domain comprising (a) a VH domain comprising an amino acid sequence of SEQ ID NO: 41 and (b) a VL domain comprising an amino acid sequence of SEQ ID NO: 8.

In another aspect, provided herein is an isolated antibody that specifically binds IL-33, or an antigen-binding fragment thereof, wherein the antibody comprises a binding domain comprising (a) a VH domain comprising an amino acid sequence of SEQ ID NO: 43 and (b) a VL domain comprising an amino acid sequence of SEQ ID NO: 8.

In another aspect, provided herein is an isolated antibody that specifically binds IL-33, or an antigen-binding fragment thereof, wherein the antibody comprises a binding domain comprising (a) a VH domain comprising an amino acid sequence of SEQ ID NO: 44 and (b) a VL domain comprising an amino acid sequence of SEQ ID NO: 8.

In another aspect, provided herein is an isolated antibody that specifically binds IL-33, or an antigen-binding fragment thereof, wherein the antibody comprises a binding domain comprising (a) a VH domain comprising an amino acid sequence of SEQ ID NO: 46 and (b) a VL domain comprising an amino acid sequence of SEQ ID NO: 8.

In another aspect, provided herein is an isolated antibody that specifically binds IL-33, or an antigen-binding fragment thereof, wherein the antibody comprises a binding domain comprising (a) a VH domain comprising an amino acid sequence of SEQ ID NO: 48 and (b) a VL domain comprising an amino acid sequence of SEQ ID NO: 8.

In another aspect, provided herein is an isolated antibody that specifically binds IL-33, or an antigen-binding fragment thereof, wherein the antibody comprises a binding domain comprising (a) a VH domain comprising an amino acid sequence of SEQ ID NO: 43 and (b) a VL domain comprising an amino acid sequence of SEQ ID NO: 57.

In another aspect, provided herein is an isolated antibody that specifically binds IL-33, or an antigen-binding fragment thereof, wherein the antibody comprises a binding domain comprising (a) a VH domain comprising an amino acid sequence of SEQ ID NO: 44 and (b) a VL domain comprising an amino acid sequence of SEQ ID NO: 57.

In another aspect, provided herein is an isolated antibody that specifically binds IL-33, or an antigen-binding fragment thereof, wherein the antibody comprises a binding domain comprising (a) a VH domain comprising an amino acid sequence of SEQ ID NO: 46 and (b) a VL domain comprising an amino acid sequence of SEQ ID NO: 57.

In another aspect, provided herein is an isolated antibody that specifically binds IL-33, or an antigen-binding fragment thereof, wherein the antibody comprises a binding domain comprising (a) a VH domain comprising an amino acid sequence of SEQ ID NO: 48 and (b) a VL domain comprising an amino acid sequence of SEQ ID NO: 57.

In another aspect, provided herein is an isolated antibody that specifically binds IL-33, or an antigen-binding fragment thereof, wherein the antibody comprises a binding domain comprising (a) a VH domain comprising an amino acid sequence of SEQ ID NO: 50 and (b) a VL domain comprising an amino acid sequence of SEQ ID NO: 57.

In another aspect, provided herein is an isolated antibody that specifically binds IL-33, or an antigen-binding fragment thereof, wherein the antibody comprises a binding domain comprising (a) a VH domain comprising an amino acid sequence of SEQ ID NO: 43 and (b) a VL domain comprising an amino acid sequence of SEQ ID NO: 58.

In another aspect, provided herein is an isolated antibody that specifically binds IL-33, or an antigen-binding fragment thereof, wherein the antibody comprises a binding domain comprising (a) a VH domain comprising an amino acid sequence of SEQ ID NO: 44 and (b) a VL domain comprising an amino acid sequence of SEQ ID NO: 58.

In another aspect, provided herein is an isolated antibody that specifically binds IL-33, or an antigen-binding fragment thereof, wherein the antibody comprises a binding domain comprising (a) a VH domain comprising an amino acid sequence of SEQ ID NO: 46 and (b) a VL domain comprising an amino acid sequence of SEQ ID NO: 58.

In another aspect, provided herein is an isolated antibody that specifically binds IL-33, or an antigen-binding fragment thereof, wherein the antibody comprises a binding domain comprising (a) a VH domain comprising an amino acid sequence of SEQ ID NO: 48 and (b) a VL domain comprising an amino acid sequence of SEQ ID NO: 58.

In another aspect, provided herein is an isolated antibody that specifically binds IL-33, or an antigen-binding fragment thereof, wherein the antibody comprises a binding domain comprising (a) a VH domain comprising an amino acid sequence of SEQ ID NO: 50 and (b) a VL domain comprising an amino acid sequence of SEQ ID NO: 58.

In another aspect, provided herein is an isolated antibody that specifically binds IL-33, or an antigen-binding fragment thereof, wherein the antibody comprises a binding domain comprising (a) a VH domain comprising an amino acid sequence of SEQ ID NO: 43 and (b) a VL domain comprising an amino acid sequence of SEQ ID NO: 59.

In another aspect, provided herein is an isolated antibody that specifically binds IL-33, or an antigen-binding fragment thereof, wherein the antibody comprises a binding domain comprising (a) a VH domain comprising an amino acid sequence of SEQ ID NO: 44 and (b) a VL domain comprising an amino acid sequence of SEQ ID NO: 59.

In another aspect, provided herein is an isolated antibody that specifically binds IL-33, or an antigen-binding fragment thereof, wherein the antibody comprises a binding domain comprising (a) a VH domain comprising an amino acid sequence of SEQ ID NO: 46 and (b) a VL domain comprising an amino acid sequence of SEQ ID NO: 59.

In another aspect, provided herein is an isolated antibody that specifically binds IL-33, or an antigen-binding fragment thereof, wherein the antibody comprises a binding domain comprising (a) a VH domain comprising an amino acid sequence of SEQ ID NO: 48 and (b) a VL domain comprising an amino acid sequence of SEQ ID NO: 59.

In another aspect, provided herein is an isolated antibody that specifically binds IL-33, or an antigen-binding fragment thereof, wherein the antibody comprises a binding domain comprising (a) a VH domain comprising an amino acid sequence of SEQ ID NO: 50 and (b) a VL domain comprising an amino acid sequence of SEQ ID NO: 59.

In another aspect, provided herein is an isolated antibody that specifically binds IL-33, or an antigen-binding fragment thereof, wherein the antibody comprises a binding domain comprising (a) a VH domain comprising an amino acid sequence of SEQ ID NO: 52 and (b) a VL domain comprising an amino acid sequence of SEQ ID NO: 61.

In another aspect, provided herein is an isolated antibody that specifically binds IL-33, or an antigen-binding fragment thereof, wherein the antibody comprises a binding domain comprising (a) a VH domain comprising an amino acid sequence having at least 95% sequence identity to the amino acid sequence of SEQ ID NO: 35; (b) a VL domain comprising an amino acid sequence having at least 95% sequence identity to the amino acid sequence of SEQ ID NO: 36; or (c) a VH domain as in (a) and a VL domain as in (b).

In some aspects, the VH domain comprises: (a) an FR-H1 comprising the amino acid sequence of EVQLVESGG-GLVQPGTSLKLSCLASGFTFN (SEQ ID NO: 27); (b) an FR-H2 comprising the amino acid sequence of WIRQAPGKGLEWIA (SEQ ID NO: 28); (c) an FR-H3 comprising the amino acid sequence of RFTISRDDAKST-LYLQMNSLRSEDTATYYCTR (SEQ ID NO: 29); and (d) an FR-H4 comprising the amino acid sequence of WGQGTLVTVSS (SEQ ID NO: 12).

In some aspects, the VH domain comprises the amino acid sequence of SEQ ID NO: 35.

In some aspects, the VL domain comprises: (a) an FR-L1 comprising the amino acid sequence of DIQMTQSPASL-SASLGETVSIEC (SEQ ID NO: 31); (b) an FR-L2 comprising the amino acid sequence of WYQQKSGKSPQLLIY (SEQ ID NO: 32); (a) an FR-L3 comprising the amino acid sequence of GVPSRFSGSGSGTRFSLKISGMQPEDEAD-YFC (SEQ ID NO: 33); and (d) an FR-L4 comprising the amino acid sequence of FGSGTKLEIK (SEQ ID NO: 34).

In some aspects, the VL domain comprises the amino acid sequence of SEQ ID NO: 36.

In another aspect, provided herein is an isolated antibody that specifically binds IL-33, or an antigen-binding fragment thereof, wherein the antibody comprises a binding domain comprising (a) a VH domain comprising an amino acid sequence of SEQ ID NO: 35 and (b) a VL domain comprising an amino acid sequence of SEQ ID NO: 36.

In another aspect, provided herein is an isolated antibody that specifically binds IL-33, wherein the antibody comprises a binding domain comprising (a) a heavy chain (HC) comprising an amino acid sequence of SEQ ID NO: 37 and (b) a light chain (LC) comprising an amino acid sequence of SEQ ID NO: 38.

In another aspect, provided herein is an isolated antibody that specifically binds IL-33, or an antigen-binding fragment thereof, wherein the antibody comprises a binding domain comprising (a) a VH domain comprising an amino acid sequence having at least 95% sequence identity to the amino acid sequence of SEQ ID NO: 65; (b) a VL domain comprising an amino acid sequence having at least 95% sequence identity to the amino acid sequence of SEQ ID NO: 69; or (c) a VH domain as in (a) and a VL domain as in (b).

In some aspects, the VH domain comprises: (a) an FR-H1 comprising the amino acid sequence of EVQLVQS-GAEVKKPGASVKVSCKASGFTFN (SEQ ID NO: 62); (b) an FR-H2 comprising the amino acid sequence of WVRQAPGQGLEWMG (SEQ ID NO: 63); (c) an FR-H3 comprising the amino acid sequence of RVTMTRDTST-STVYMELSSLRSEDTAVYYCTR (SEQ ID NO: 64); and (d) an FR-H4 comprising the amino acid sequence of WGQGTLVTVSS (SEQ ID NO: 12).

In some aspects, the VH domain comprises the amino acid sequence of SEQ ID NO: 65.

In some aspects, the VL domain comprises: (a) an FR-L1 comprising the amino acid sequence of EIVLTQSPATLSL-SPGERATLSC (SEQ ID NO: 66); (b) an FR-L2 comprising the amino acid sequence of WYQQKPGQAPRLLIY (SEQ ID NO: 67); (c) an FR-L3 comprising the amino acid sequence of GIPARFSGSGSGTDFTLTISSLEPED-FAVYYC (SEQ ID NO: 68); and (d) an FR-L4 comprising the amino acid sequence of FGGGTKVEIK (SEQ ID NO: 24).

In some aspects, the VL domain comprises the amino acid sequence of SEQ ID NO: 69.

In another aspect, provided herein is an isolated antibody that specifically binds IL-33, or an antigen-binding fragment thereof, wherein the antibody comprises a binding domain comprising (a) a VH domain comprising an amino acid sequence of SEQ ID NO: 65 and (b) a VL domain comprising an amino acid sequence of SEQ ID NO: 69.

In some aspects, the antibody specifically binds human or cyno IL-33.

In some aspects, the antibody specifically binds both human and cyno IL-33.

In some aspects, the antibody specifically binds both human and cyno IL-33 with a $K_D$ of about 1 nM or lower.

In some aspects, the antibody specifically binds human IL-33 with a $K_D$ between about 100 fM and about 1 nM.

In some aspects, the antibody specifically binds human IL-33 with a $K_D$ between about 750 fM and about 300 pM.

In some aspects, the antibody specifically binds human IL-33 with a $K_D$ between about 1 pM and about 200 pM.

In some aspects, the antibody specifically binds human IL-33 with a $K_D$ of about 118 pM.

In some aspects, the antibody specifically binds human IL-33 with a $K_D$ of about 15 pM.

In some aspects, the antibody specifically binds cyno IL-33 with a $K_D$ between about 100 fM and about 1 nM.

In some aspects, the antibody specifically binds cyno IL-33 with a $K_D$ between about 1 pM and about 500 pM.

In some aspects, the antibody specifically binds cyno IL-33 with a $K_D$ between about 20 pM and about 50 pM.

In some aspects, the antibody specifically binds cyno IL-33 with a $K_D$ of about 35 pM.

In some aspects, the antibody specifically binds both human and cyno IL-33 with a $K_D$ of between about 1 pM and about 500 pM.

In some aspects, the antibody specifically binds both human and cyno IL-33 with a $K_D$ of between about 10 pM and about 40 pM.

In some aspects, the antibody is capable of inhibiting the binding of IL-33 to an IL-33 receptor.

In some aspects, the inhibiting is measured using a cell-based blocking assay.

In some aspects, the antibody inhibits binding of human IL-33 to an IL-33 receptor with an IC50 of between about 800 fM and about 100 pM.

In some aspects, the IC50 is between about 1 pM and about 50 pM.

In some aspects, the IC50 is about 31 pM.

In some aspects, the antibody has a viscosity of less than about 5 centipoise (cP) at a concentration of about 180 mg/mL.

In some aspects, the antibody has a viscosity of between about 3 cP and about 5 cP at a concentration of about 180 mg/mL.

In some aspects, the antibody has a viscosity of about 4.6 cP at a concentration of about 180 mg/mL.

In some aspects, the antibody has a turbidity (optical density (OD)) of about 0.5 or lower at a concentration of about 150 mg/ml or higher in phosphate-buffered saline (PBS) pH 7.4.

In some aspects, the antibody has a turbidity (OD) of between about 0.25 and about 0.5 at a concentration of about 150 mg/ml to about 250 mg/ml.

In some aspects, the antibody has a turbidity (OD) of about 0.38 at a concentration of about 200 mg/ml.

In some aspects, the antibody is monoclonal, human, humanized, or chimeric.

In some aspects, the antibody is an antibody fragment that binds IL-33.

In some aspects, the antibody fragment is an Fab, Fab'-SH, Fv, scFv, or (Fab')$_2$ fragment.

In some aspects, the antibody fragment is an Fab.

In some aspects, the antibody is a full-length antibody.

In some aspects, the antibody is an IgG antibody.

In some aspects, the IgG antibody is an IgG1 antibody.

In some aspects, the IgG antibody is an IgG4 antibody.

In some aspects, the antibody is a monospecific antibody.

In some aspects, the antibody is a multispecific antibody.

In some aspects, the antibody is a bispecific antibody.

In some aspects, the bispecific antibody comprises a second binding domain that binds to a second biological molecule, wherein the second biological molecule is interleukin-13 (IL-13), interleukin-4 (IL-4), interleukin-5 (IL-5), interleukin-17 (IL-17), Factor D, HtrA1, VEGF, or a VEGF receptor.

In another aspect, provided herein is an isolated nucleic acid encoding any one of the antibodies disclosed herein or a set of isolated nucleic acids together encoding the antibody.

In another aspect, provided herein is a vector or a set of vectors comprising any of the isolated nucleic acids or set of isolated nucleic acids disclosed herein.

In another aspect, provided herein is a host cell comprising any one of the vectors or the set of vectors disclosed herein.

In some aspects, the host cell is a mammalian cell.

In some aspects, the mammalian cell is a Chinese hamster ovary (CHO) cell.

In some aspects, the host cell is a prokaryotic cell.

In some aspects, the prokaryotic cell is *E. coli*.

In another aspect, provided herein is a method of producing an antibody that specifically binds to IL-33, the method comprising culturing any one of the host cells disclosed herein in a culture medium.

In some aspects, the method further comprises recovering the antibody from the host cell or the culture medium.

In another aspect, provided herein is a composition comprising any one of the antibodies disclosed herein.

In some aspects, the composition further comprises a pharmaceutically acceptable carrier, excipient, or diluent.

In some aspects, the composition is a pharmaceutical composition.

In some aspects, the pharmaceutical composition further comprises an ST2 binding antagonist, a Factor D binding antagonist, an HtrA1 binding antagonist, a VEGF antagonist, a tryptase-beta binding antagonist, a chemoattractant receptor-homologous molecule expressed on Th2 cells (CRTH2) binding antagonist, an interleukin-13 (IL-13) binding antagonist, an interleukin-17 (IL-17) binding antagonist, a JAK1 antagonist, and/or an interleukin-5 (IL-5) binding antagonist.

In some aspects, the pharmaceutical composition comprises a Factor D binding antagonist.

In some aspects, the Factor D binding antagonist is an anti-Factor D antibody or an antigen-binding fragment thereof.

In some aspects, the pharmaceutical composition comprises an HtrA1 binding antagonist.

In some aspects, the HtrA1 binding antagonist is an anti-HtrA1 antibody or an antigen-binding fragment thereof.

In some aspects, the pharmaceutical composition comprises a VEGF antagonist.

In some aspects, the VEGF antagonist is an anti-VEGF antibody or an antigen-binding fragment thereof.

In some aspects, the antibody concentration is about 1 mg/mL to about 400 mg/mL.

In some aspects, the antibody concentration is about 150 mg/mL to about 250 mg/mL.

In some aspects, the antibody concentration is about 175 mg/mL to about 225 mg/mL.

In some aspects, the antibody concentration is about 200 mg/mL.

In another aspect, provided herein is any one of the antibodies disclosed herein or any one of the compositions disclosed herein for use as a medicament.

In another aspect, provided herein is any one of the antibodies disclosed herein or any one of the compositions disclosed herein for use in treating an IL-33-mediated disorder.

In some aspects, the IL-33-mediated disorder is an ocular disorder, an inflammatory condition, an immune disorder, a fibrotic disorder, an eosinophilic disorder, an infection, pain, a central nervous system disorder, or a solid tumor.

In some aspects, the ocular disorder is age-related macular degeneration (AMD), retinopathy of the eye, polypoidal choroidal vasculopathy (PCV), diabetic macular edema, dry eye disease, Behcet's disease, retina detachment, glaucoma, uveitis, retinitis pigmentosa, Leber Congenital Amaurosis, Stargardt's disease, traumatic eye injury, or conjunctivitis.

In some aspects, the AMD is geographic atrophy (GA), wet AMD, or dry AMD.

In some aspects, the AMD is GA.

In some aspects, the AMD is intermediate AMD or advanced AMD.

In some aspects, the retinopathy of the eye is diabetic retinopathy (DR) or retinopathy of prematurity (ROP).

In some aspects, the retinopathy of the eye is high-altitude DR.

In some aspects, the conjunctivitis is infectious conjunctivitis or non-infectious conjunctivitis.

In some aspects, the conjunctivitis is allergic conjunctivitis.

In some aspects, the inflammatory condition is asthma, sepsis, septic shock, atopic dermatitis, allergic rhinitis, rheumatoid arthritis, or chronic obstructive pulmonary disease (COPD).

In some aspects, the immune disorder is asthma, rheumatoid arthritis, allergy, anaphylaxis, anaphylactic shock, allergic rhinitis, psoriasis, inflammatory bowel disease (IBD), Crohn's disease, diabetes, or liver disease.

In some aspects, the fibrotic disease is idiopathic pulmonary fibrosis (IPF).

In some aspects, the eosinophilic disorder is an eosinophil-associated gastrointestinal disorder (EGID).

In some aspects, the EGID is eosinophilic esophagitis.

In some aspects, the infection is a helminth infection, a protozoan infection, or a viral infection.

In some aspects, the protozoan infection is a *Leishmania major* infection.

In some aspects, the viral infection is a respiratory syncytial virus (RSV) infection or an influenza infection.

In some aspects, the pain is inflammatory pain.

In some aspects, the central nervous system disorder is Alzheimer's disease.

In some aspects, the solid tumor is a breast tumor, a colon tumor, a prostate tumor, a lung tumor, a kidney tumor, a liver tumor, a pancreas tumor, a stomach tumor, an intestinal tumor, a brain tumor, a bone tumor, and a skin tumor.

In some aspects, the antibody or composition is used in combination with an ST2 binding antagonist, a Factor D binding antagonist, an HtrA1 binding antagonist, a VEGF antagonist, a tryptase-beta binding antagonist, a CRTH2 binding antagonist, an IL-13 binding antagonist, an IL-17 binding antagonist, a JAK1 antagonist, and/or an IL-5 binding antagonist.

In some aspects, the antibody or composition is used in in combination with a Factor D binding antagonist.

In some aspects, the Factor D binding antagonist is an anti-Factor D antibody or an antigen-binding fragment thereof.

In some aspects, the antibody or composition is used in in combination with an HtrA1 binding antagonist.

In some aspects, the HtrA1 binding antagonist is an anti-HtrA1 antibody or an antigen-binding fragment thereof.

In some aspects, the antibody or composition is used in in combination with a VEGF antagonist.

In some aspects, the VEGF antagonist is an anti-VEGF antibody or an antigen-binding fragment thereof.

In another aspect, provided herein is the use of any one of the antibodies disclosed herein or any one of the compositions disclosed herein in the manufacture of a medicament for treating an IL-33-mediated disorder.

In some aspects, the IL-33-mediated disorder is an ocular disorder, an inflammatory condition, an immune disorder, a fibrotic disorder, an eosinophilic disorder, an infection, pain, a central nervous system disorder, or a solid tumor.

In some aspects, the ocular disorder is AMD, retinopathy of the eye, PCV, diabetic macular edema, dry eye disease, Behcet's disease, retina detachment, glaucoma, uveitis, retinitis pigmentosa, Leber Congenital Amaurosis, Stargardt's disease, traumatic eye injury, or conjunctivitis.

In some aspects, the AMD is GA, wet AMD, or dry AMD.

In some aspects, the AMD is GA.

In some aspects, the AMD is intermediate AMD or advanced AMD.

In some aspects, the retinopathy of the eye is DR or ROP.

In some aspects, the retinopathy of the eye is high-altitude DR.

In some aspects, the conjunctivitis is infectious conjunctivitis or non-infectious conjunctivitis.

In some aspects, the conjunctivitis is allergic conjunctivitis.

In some aspects, the inflammatory condition is asthma, sepsis, septic shock, atopic dermatitis, allergic rhinitis, rheumatoid arthritis, or COPD.

In some aspects, the immune disorder is asthma, rheumatoid arthritis, allergy, anaphylaxis, anaphylactic shock, allergic rhinitis, psoriasis, IBD, Crohn's disease, diabetes, or liver disease.

In some aspects, the fibrotic disease is IPF.

In some aspects, the eosinophilic disorder is an EGID.

In some aspects, the EGID is eosinophilic esophagitis.

In some aspects, the infection is a helminth infection, a protozoan infection, or a viral infection.

In some aspects, the protozoan infection is a *Leishmania major* infection.

In some aspects, the viral infection is an RSV infection or an influenza infection.

In some aspects, the pain is inflammatory pain.

In some aspects, the central nervous system disorder is Alzheimer's disease.

In some aspects, the solid tumor is a breast tumor, a colon tumor, a prostate tumor, a lung tumor, a kidney tumor, a liver tumor, a pancreas tumor, a stomach tumor, an intestinal tumor, a brain tumor, a bone tumor, and a skin tumor.

In some aspects, the medicament is formulated for use in combination with an ST2 binding antagonist, a Factor D binding antagonist, an HtrA1 binding antagonist, a VEGF antagonist, a tryptase-beta binding antagonist, a CRTH2 binding antagonist, an IL-13 binding antagonist, an IL-17 binding antagonist, a JAK1 antagonist, and/or an IL-5 binding antagonist.

In some aspects, the medicament is formulated for use in combination with a Factor D binding antagonist.

In some aspects, the Factor D binding antagonist is an anti-Factor D antibody or an antigen-binding fragment thereof.

In some aspects, the medicament is formulated for use in combination with an HtrA1 binding antagonist.

In some aspects, the HtrA1 binding antagonist is an anti-HtrA1 antibody or an antigen-binding fragment thereof.

In some aspects, the medicament is formulated for use in combination with a VEGF antagonist.

In some aspects, the VEGF antagonist is an anti-VEGF antibody or an antigen-binding fragment thereof.

In another aspect, provided herein is a method of treating an IL-33-mediated disorder in a subject in need thereof, the method comprising administering to the subject a therapeutically effective amount of any one of the antibodies disclosed herein or any one of the compositions disclosed herein.

In some aspects, the IL-33-mediated disorder is an ocular disorder, an inflammatory condition, an immune disorder, a fibrotic disorder, an eosinophilic disorder, an infection, pain, a central nervous system disorder, or a solid tumor.

In some aspects, the ocular disorder is AMD, retinopathy of the eye, PCV, diabetic macular edema, dry eye disease, Behcet's disease, retina detachment, glaucoma, uveitis, retinitis pigmentosa, Leber Congenital Amaurosis, Stargardt's disease, traumatic eye injury, or conjunctivitis.

In some aspects, the AMD is GA, wet AMD, or dry AMD.

In some aspects, the AMD is GA.

In some aspects, the AMD is intermediate AMD or advanced AMD.

In some aspects, the retinopathy of the eye is DR or ROP.

In some aspects, the retinopathy of the eye is high-altitude DR.

In some aspects, the conjunctivitis is infectious conjunctivitis or non-infectious conjunctivitis.

In some aspects, the conjunctivitis is allergic conjunctivitis.

In some aspects, the inflammatory condition is asthma, sepsis, septic shock, atopic dermatitis, allergic rhinitis, rheumatoid arthritis, or COPD.

In some aspects, the immune disorder is asthma, rheumatoid arthritis, allergy, anaphylaxis, anaphylactic shock, allergic rhinitis, psoriasis, IBD, Crohn's disease, diabetes, and liver disease.

In some aspects, the fibrotic disease is IPF.

In some aspects, the eosinophilic disorder is an EGID.

In some aspects, the EGID is eosinophilic esophagitis.

In some aspects, the infection is a helminth infection, a protozoan infection, or a viral infection.

In some aspects, the protozoan infection is a *Leishmania major* infection.

In some aspects, the viral infection is an RSV infection or an influenza infection.

In some aspects, the pain is inflammatory pain.

In some aspects, the solid tumor is a breast tumor, a colon tumor, a prostate tumor, a lung tumor, a kidney tumor, a liver tumor, a pancreas tumor, a stomach tumor, an intestinal tumor, a brain tumor, a bone tumor, and a skin tumor.

In some aspects, the method further comprises administering to the subject an ST2 binding antagonist, a Factor D binding antagonist, an HtrA1 binding antagonist, a VEGF antagonist, a tryptase-beta binding antagonist, a CRTH2 binding antagonist, an IL-13 binding antagonist, an IL-17 binding antagonist, a JAK1 antagonist, and/or an IL-5 binding antagonist.

In some aspects, the method further comprises administering to the subject a Factor D binding antagonist.

In some aspects, the Factor D binding antagonist is anti-Factor D antibody or an antigen-binding fragment thereof.

In some aspects, the method further comprises administering to the subject an HtrA1 binding antagonist.

In some aspects, the HtrA1 binding antagonist is an anti-HtrA1 antibody or an antigen-binding fragment thereof.

In some aspects, the method further comprises administering to the subject a VEGF antagonist.

In some aspects, the VEGF antagonist is an anti-VEGF antibody or an antigen-binding fragment thereof.

In another aspect, provided herein is a method of treating GA in a subject in need thereof, the method comprising administering to the subject a therapeutically effective amount of any one of the antibodies disclosed herein or any one of the compositions disclosed herein.

In some aspects, the antibody is an Fab fragment.

In some aspects, the antibody or the composition is administered intravitreally, ocularly, intraocularly, juxtasclerally, subtenonly, superchoroidally, topically, intravenously, intramuscularly, intradermally, percutaneously, intraarterially, intraperitoneally, intralesionally, intracranially, intraarticularly, intraprostatically, intrapleurally, intratracheally, intrathecally, intranasally, intravaginally, intrarectally, topically, intratumorally, intraperitoneally, peritoneally, intraventricularly, subcutaneously, subconjunctivally, intravesicularly, mucosally, intrapericardially, intraumbilically, intraorbitally, orally, transdermally, by inhalation, by injection, by eye drop, by implantation, by infusion, by continuous infusion, by localized perfusion bathing target cells directly, by catheter, by lavage, in cremes, or in lipid compositions.

In some aspects, the antibody or the composition is administered intravitreally, ocularly, intraocularly, juxtasclerally, subtenonly, superchoroidally, or topically.

In some aspects, the antibody or the composition is administered intravitreally by injection.

In some aspects, the antibody or the composition is administered topically by eye drop or ointment.

In some aspects, the antibody or the composition is administered by a port delivery device.

In some aspects, the subject is a human.

BRIEF DESCRIPTION OF THE DRAWINGS

FIGS. 1A and 1B are sequence alignments of the heavy chain variable region (VH) and light chain variable region (VL) sequences of the 1E1 hybridoma and 1E1v8 anti-IL-33 antibody clones. Complementarity-determining region (CDR) sequences according to Kabat definition are underlined.

Figure 2A:
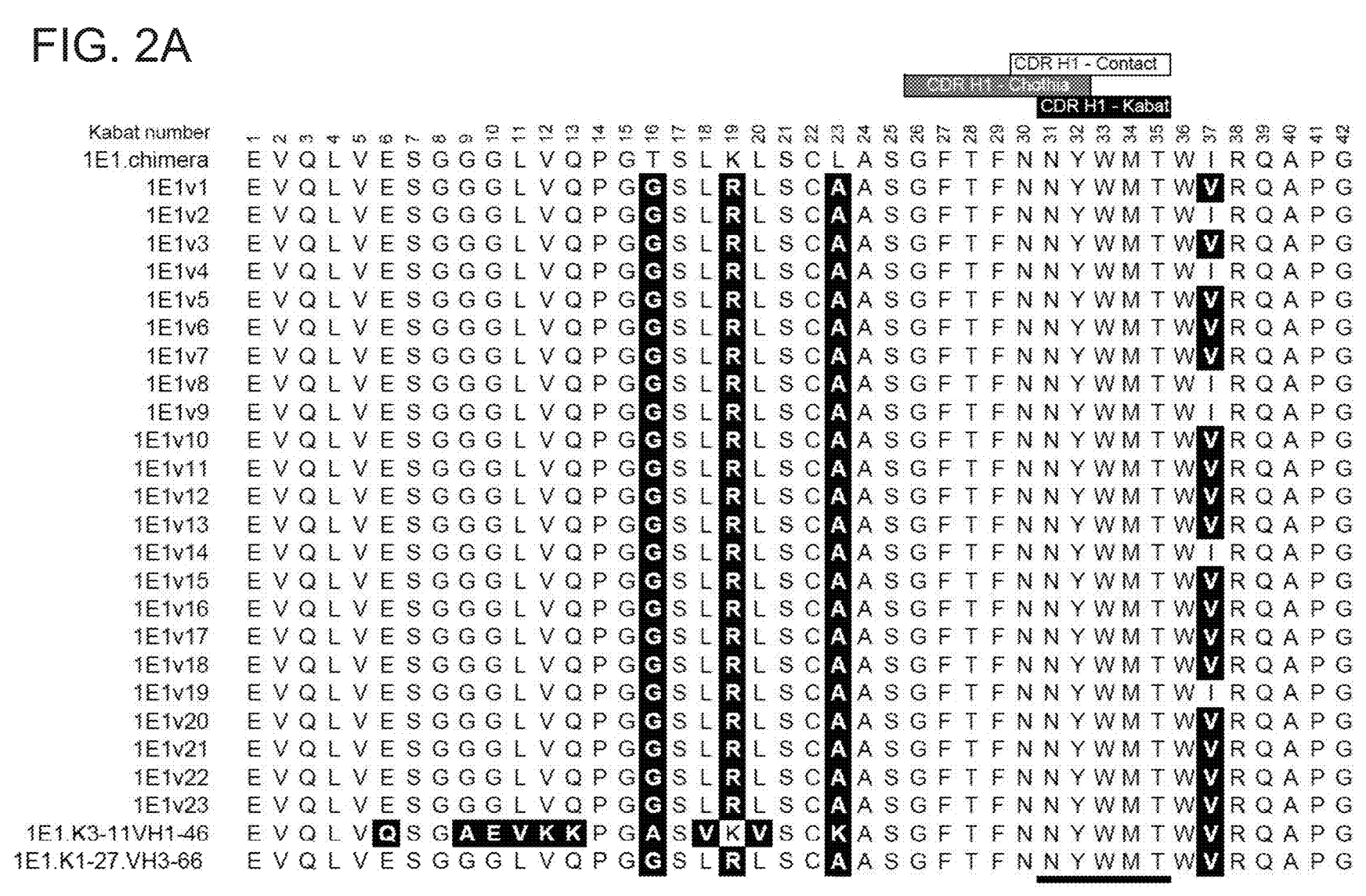
Figure 2A:
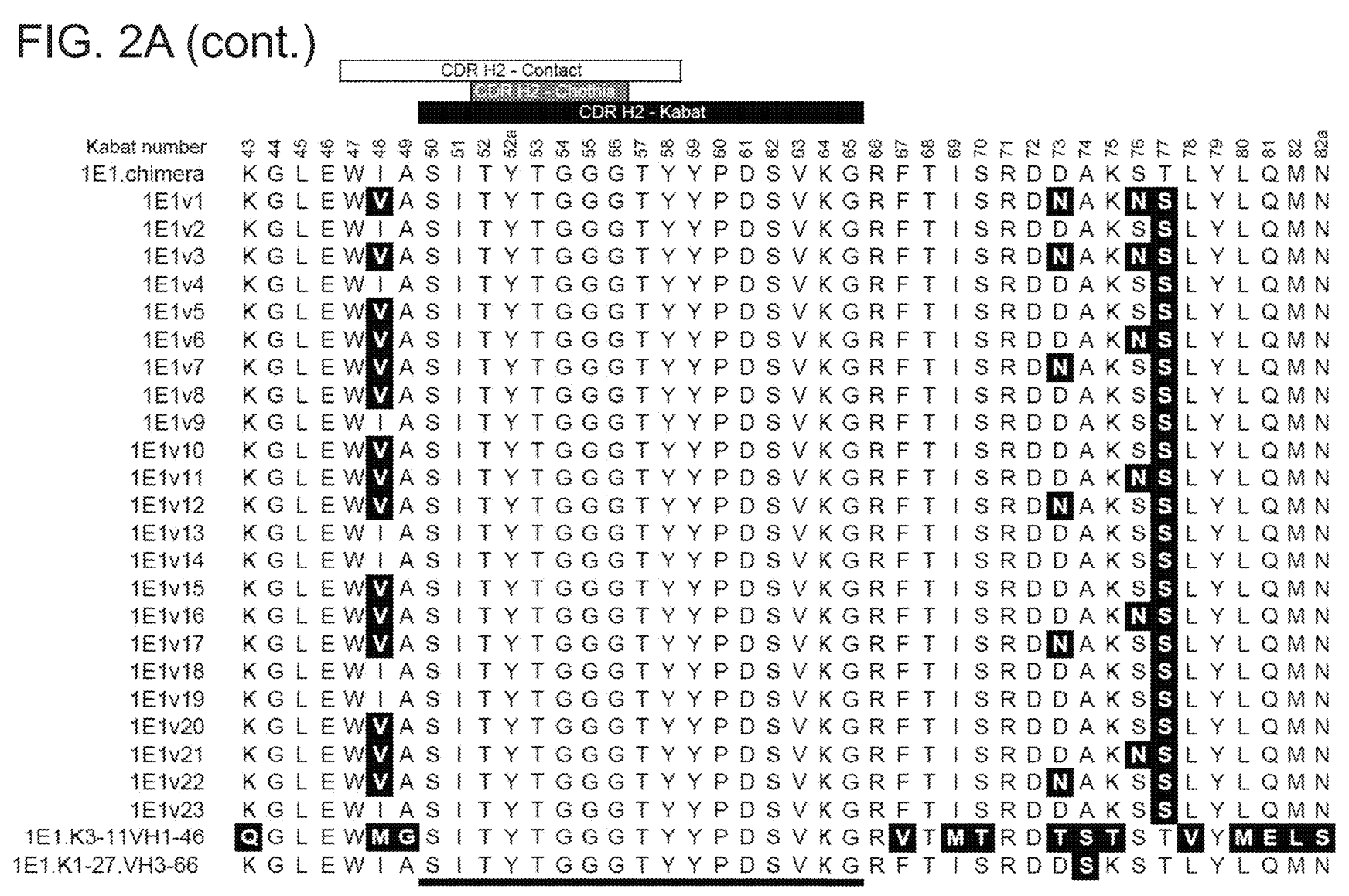

FIGS. 2A and 2B are sequence alignments of the VH and VL sequences of the indicated anti-IL-33 antibody clones. CDR sequences according to Kabat definition are underlined.

DETAILED DESCRIPTION OF EMBODIMENTS OF THE INVENTION

I. Definitions

Figure 2B:
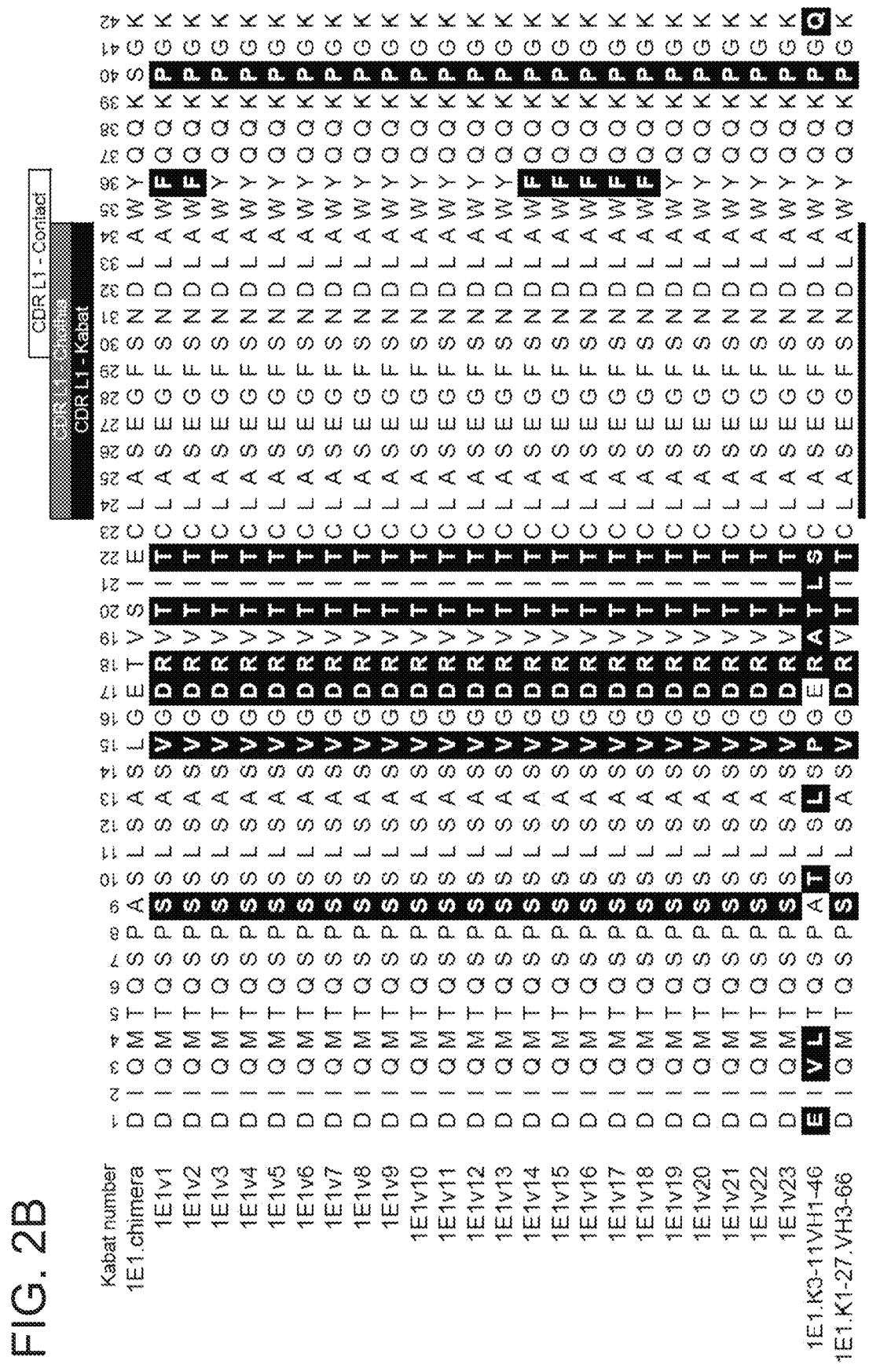

The term "about" as used herein refers to the usual error range for the respective value readily known to the skilled person in this technical field. Reference to "about" a value or parameter herein includes (and describes) embodiments that are directed to that value or parameter per se.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Specific illustrative and exemplary embodiments for measuring binding affinity are described in the following.

An "affinity-matured" antibody is one with one or more alterations in one or more HVRs and/or framework regions which result in an improvement in the affinity of the antibody for antigen, compared to a parent antibody which does not possess those alteration(s). Preferred affinity-matured antibodies will have nanomolar or even picomolar affinities for the target antigen. Affinity-matured antibodies are produced by procedures known in the art. For example, Marks et al. *Bio/Technology* 10:779-783, 1992 describes affinity maturation by VH and VL domain shuffling. Random mutagenesis of HVR and/or framework residues is described by: Barbas et al. *Proc. Nat. Acad. Sci. USA* 91:3809-3813, 1994; Schier et al. *Gene* 169:147-155, 1995; Yelton et al. *J. Immunol.* 155:1994-2004, 1995; Jackson et al. *J. Immunol.* 154(7):3310-3319, 1995; and Hawkins et al. *J. Mol. Biol.* 226:889-896, 1992.

The term "antibody" herein is used in the broadest sense and encompasses various antibody structures, including but not limited to monoclonal antibodies, polyclonal antibodies, multispecific antibodies (e.g., bispecific antibodies, including anti-IL-33/anti-IL-13 bispecific antibodies), and antibody fragments so long as they exhibit the desired antigen-binding activity.

The term "interleukin-33 (IL-33)," as used herein, refers to any native IL-33 from any vertebrate source, including mammals such as primates (e.g., humans and cynomolgus monkeys) and rodents (e.g., mice and rats), unless otherwise indicated. IL-33 is also referred to in the art as nuclear factor of high endothelial venules (NF-HEV; see, e.g., Baekkevold et al. *Am. J. Pathol.* 163(1): 69-79, 2003), DVS27, C9orf26, and interleukin-1 family member 11 (IL-1F11). The term encompasses "full-length," unprocessed IL-33, as well as any form of IL-33 that results from processing in the cell. Human full-length, unprocessed IL-33 contains 270 amino acids (a.a.) and may also be referred to as IL-33$_{1-270}$. Processed forms of human IL-33 include, for example, IL-33$_{95-270}$, IL-33$_{99-270}$, IL-33$_{109-270}$, IL-33$_{112-270}$, IL-33$_{1-178}$, and IL-33$_{179-270}$ (Lefrangais et al. *Proc. Natl. Acad. Sci.* 109(5):1673-1678, 2012 and Martin, *Semin. Immunol.* 25: 449-457, 2013). In some embodiments, processed forms of human IL-33, e.g., IL-3395-270, IL-33$_{99-270}$, IL-33$_{109-270}$, or other forms processed by proteases such as calpain, proteinase 3, neutrophil elastase, and cathepsin G may have increased biological activity compared to full-length IL-33. The term also encompasses naturally occurring variants of IL-33, for example, splice variants (e.g., the constitutively active splice variant spIL-33 which lacks exon 3, Hong et al. *J. Biol. Chem.* 286(22): 20078-20086, 2011) or allelic variants. IL-33 may be present within a cell (e.g., within the nucleus) or as a secreted cytokine form. Full-length IL-33 protein contains a helix-turn-helix DNA-binding motif including nuclear localization sequence (a.a.1-75 of human IL-33), which includes a chromatin binding motif (a.a. 40-58 of human IL-33). Forms of IL-33 that are processed and secreted lack these N-terminal motifs. The amino acid sequence of an exemplary human IL-33 can be found, for example, under UniProtKB accession number O95760.

By "IL-33 axis" is meant a nucleic acid (e.g., a gene or mRNA transcribed from the gene) or polypeptide that is involved in IL-33 signal transduction. For example, the IL-33 axis may include the ligand IL-33, a receptor (e.g., ST2 and/or IL-1RAcP), adaptor molecules (e.g., MyD88), or proteins that associate with receptor molecules and/or adaptor molecules (e.g., kinases, such as interleukin-1 receptor-associated kinase 1 (IRAK1) and interleukin-1 receptor-associated kinase 4 (IRAK4), or E3 ubiquitin ligases, such as TNF receptor associated factor 6 (TRAF6)).

The terms "interleukin 1 receptor-like 1 (IL1RL1)" and "ST2," used interchangeably herein, refer to any native ST2 from any vertebrate source, including mammals such as primates (e.g., humans) and rodents (e.g., mice and rats), unless otherwise indicated. ST2 is also referred to in the art as DER4, T1, and FIT-1. The term encompasses "full-length," unprocessed ST2, as well as any form of ST2 that results from processing in the cell. At least four isoforms of ST2 are known in the art, including soluble (sST2, also known as IL1RL1-a) and transmembrane (ST2L, also known as IL1RL1-b), which arise from differential mRNA expression from a dual promoter system, and ST2V and ST2LV, which arise from alternative splicing, as described below. The domain structure of ST2L includes three extracellular immunoglobulin-like C2 domains, a transmembrane domain, and a cytoplasmic Toll/Interleukin-1 receptor (TIR) domain. sST2 lacks the transmembrane and cytoplasmic domains contained within ST2L and includes a unique 9 amino acid (a.a.) C-terminal sequence (see, e.g., Kakkar et al. *Nat. Rev. Drug Disc.* 7: 827-840, 2008). sST2 can function as a decoy receptor to inhibit soluble IL-33. The term also encompasses naturally occurring variants of ST2, e.g., splice variants (e.g., ST2V, which lacks the third immunoglobulin motif and has a unique hydrophobic tail, and ST2LV, which lacks the transmembrane domain of ST2L) or allelic variants (e.g., variants that are protective against asthma risk or that confer asthma risk as described herein). The amino acid sequence of an exemplary human ST2 can be found, for example, under UniProtKB accession number Q01638. ST2 is a part of the IL-33 receptor along with the co-receptor protein IL-1RAcP. Binding of IL-33 to ST2 and the co-receptor interleukin-1 receptor accessory protein (IL-1RAcP) forms a 1:1:1 ternary signaling complex to promote downstream signal transduction, as depicted in FIG. 1A (see, e.g., Lingel et al. *Structure* 17(10): 1398-1410, 2009, and Liu et al. *Proc. Natl. Acad. Sci.* 110(37): 14918-14924, 2013).

The terms "anti-IL-33 antibody," an "antibody that binds to IL-33," and "antibody that specifically binds IL-33" refer to an antibody that is capable of binding IL-33 with sufficient affinity such that the antibody is useful as a therapeutic and/or diagnostic agent in targeting IL-33. In one embodiment, the extent of binding of an anti-IL-33 antibody to an unrelated, non-IL-33 protein is less than about 10% of the binding of the antibody to IL-33 as measured, e.g., by a radioimmunoassay (RIA). In certain embodiments, an antibody that binds to IL-33 has a dissociation constant ($K_D$) of ≤1 µM, ≤100 nM, ≤10 nM, ≤1 nM, ≤0.1 nM, ≤0.01 nM, or ≤0.001 nM (e.g., $10^{-8}$ M or less, e.g. from $10^{-8}$ M to $10^{-13}$ M, e.g., from $10^{-9}$ M to $10^{-13}$ M). In certain embodiments, an anti-IL-33 antibody binds to an epitope of IL-33 that is conserved among IL-33 from different species.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (see U.S. Pat. No. 5,641,870, Example 2; Zapata et al. *Protein Eng.* 8(10):1057-1062, 1995); single-chain antibody molecules; and multispecific antibodies formed from antibody fragments.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain (VH), and the first constant domain of one heavy chain ($C_H1$). Pepsin treatment of an antibody yields a single large F(ab')$_2$ fragment which roughly corresponds to two disulfide linked Fab fragments having divalent antigen-binding activity and is still capable of cross-linking antigen. Fab' fragments differ from Fab fragments by having an additional few residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al. *Sequences of Proteins of Immunological Interest*, 5th Ed. Public Health Service, National Institutes of Health, Bethesda, Md., 1991.

"Fv" consists of a dimer of one heavy- and one light-chain variable region domain in tight, noncovalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three Hs specific for an antigen) has the ability to recognize and bind antigen, although often at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the VH and VL domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315, 1994.

The term "diabodies" refers to small antibody fragments prepared by constructing sFv fragments (see preceding paragraph) with short linkers (about 5-10 residues) between the VH and VL domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the VH and VL domains of the two antibodies are present on different polypeptide chains. Diabodies are described more fully in, for example, EP 404,097; WO 93/11161; and Hollinger et al. *Proc. Natl. Acad. Sci. USA* 90:6444-6448, 1993.

By "binding domain" is meant a part of a compound or a molecule that specifically binds to a target epitope, antigen, ligand, or receptor. Binding domains include but are not limited to antibodies (e.g., monoclonal, polyclonal, recombinant, humanized, and chimeric antibodies), antibody fragments or portions thereof (e.g., Fab fragments, Fab'2, scFv antibodies, SMIP, domain antibodies, diabodies, minibodies, scFv-Fc, affibodies, nanobodies, and VH and/or VL domains of antibodies), receptors, ligands, aptamers, and other molecules having an identified binding partner.

A "blocking" antibody or an "antagonist" antibody is one which inhibits or reduces biological activity of the antigen it binds. Certain blocking antibodies or antagonist antibodies substantially or completely inhibit the biological activity of the antigen.

A "cell-based blocking assay" refers to an assay in which the ability of an antibody to inhibit or reduce the biological activity of the antigen it binds can be measured. For example, a cell-based assay can be used to measure the concentration of antibody required to inhibit a specific biological or biochemical function. In some embodiments, the half maximal inhibitory concentration (IC50) and/or 90% inhibitory concentration (IC90) of an antibody (e.g., an anti-IL-33 antibody disclosed herein) is measured using a cell-based blocking assay. In some embodiments, the cell-based blocking assay is used to determine whether an antibody blocks the interaction between a ligand (e.g., IL-33) and its receptor (e.g., ST2 and/or the coreceptor IL-1RAcP). An exemplary cell-based blocking assay for IL-33 is provided, e.g., in Example 2B of U.S. Pat. No. 10,093,730. Additional exemplary cell-based blocking assays for IL-33 are provided, for example, in Example 8 of U.S. Pat. No. 10,093,730, including primary natural killer (NK) cell assays and primary basophil cell assays.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch et al. *Annu. Rev. Immunol.* 9:457-492, 1991. To assess ADCC activity of a molecule of interest, an in vitro ADCC assay, such as that described in U.S. Pat. No. 5,500,362 or 5,821,337 can be performed. Useful effector cells for such assays include peripheral blood mononuclear cells (PBMC) and Natural Killer (NK) cells. Alternatively, or additionally, ADCC activity of the molecule of interest can be assessed in vivo, e.g., in an animal model such as that disclosed in Clynes et al. *Proc. Natl. Acad. Sci. USA* 95:652-656, 1998.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review M. in Daëron, *Annu. Rev. Immunol.* 15:203-234, 1997). FcRs are reviewed, for example, in Ravetch et al. *Annu. Rev. Immunol.* 9:457-492, 1991; Capel et al. *Immunomethods* 4:25-34, 1994; and de Haas et al. *J. Lab. Clin. Med.* 126:330-41, 1995. Other FcRs, including those to be identified in the future, are encompassed by the term "FcR" herein. The term also includes the neonatal receptor, FcRn, which is responsible for the transfer of maternal IgGs to the fetus (see, e.g., Guyer et al. *J. Immunol.* 117:587, 1976; and Kim et al. *J. Immunol.* 24:249, 1994).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells, and neutrophils; with PBMCs and NK cells being preferred. The effector cells can be isolated from a native source, e.g., from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al. *J. Immunol. Methods* 202:163, 1996, can be performed.

An "epitope" is the portion of the antigen to which the antibody selectively binds. For a polypeptide antigen, the epitope is generally a peptide portion of about 4-15 amino acid residues.

The terms "full-length antibody," "intact antibody," and "whole antibody" are used herein interchangeably to refer to an antibody having a structure substantially similar to a native antibody structure or having heavy chains that contain an Fc region as defined herein.

A "human antibody" is one which possesses an amino acid sequence which corresponds to that of an antibody produced by a human and/or has been made using any of the techniques for making human antibodies. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al. *Sequences of Proteins of Immunological Interest*, Fifth Edition, NIH Publication 91-3242, Bethesda Md., vols. 1-3, 1991. In one embodiment, for the VL, the subgroup is subgroup kappa III or kappa IV as in Kabat et al. supra. In one embodiment, for the VH, the subgroup is subgroup III as in Kabat et al. supra.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al. *Nature* 321:522-525, 1986; Riechmann et al. *Nature* 332:323-329, 1988; and Presta, *Curr. Op. Struct. Biol.* 2:593-596, 1992.

An "immunoconjugate" is an antibody conjugated to one or more heterologous molecule(s), including but not limited to a cytotoxic agent.

The term "isolated" when used to describe the various antibodies disclosed herein, means an antibody that has been identified and separated and/or recovered from a cell or cell culture from which it was expressed. Contaminant components of its natural environment are materials that would typically interfere with diagnostic or therapeutic uses for the polypeptide, and can include enzymes, hormones, and other proteinaceous or non-proteinaceous solutes. In some embodiments, an antibody is purified to greater than 95% or 99% purity as determined by, for example, electrophoretic (e.g., sodium dodecyl sulfate polyacrylamide gel electrophoresis (SDS-PAGE), isoelectric focusing (IEF), capillary electrophoresis) or chromatographic (e.g., ion exchange or reverse phase HPLC) methods. For a review of methods for assessment of antibody purity, see, for example, Flatman et al. *J. Chromatogr. B* 848:79-87, 2007. In preferred embodiments, the antibody will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated antibody includes antibodies in situ within recombinant cells, because at least one component of the polypeptide natural environment will not be present. Ordinarily, however, isolated polypeptide will be prepared by at least one purification step.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "multispecific antibody" is used in the broadest sense and specifically covers an antibody comprising a heavy chain variable domain (VH) and a light chain variable domain (VL), where the VHVL unit has polyepitopic specificity (i.e., is capable of binding to two different epitopes on one biological molecule or each epitope on a different biological molecule). Such multispecific antibodies include, but are not limited to, full-length antibodies, antibodies having two or more VL and VH domains, antibody fragments such as Fab, Fv, dsFv, scFv, diabodies, bispecific diabodies and triabodies, antibody fragments that have been linked covalently or non-covalently. "Polyepitopic specificity" refers to the ability to specifically bind to two or more different epitopes on the same or different target(s). "Dual specificity" or "bispecificity" refers to the ability to specifically bind to two different epitopes on the same or different target(s). However, in contrast to bispecific antibodies, dual-specific antibodies have two antigen-binding arms that are identical in amino acid sequence and each Fab arm is capable of recognizing two antigens. Dual-specificity allows the antibodies to interact with high affinity with two different antigens as a single Fab or IgG molecule. According to one embodiment, the multispecific antibody in an IgG1 form binds to each epitope with an affinity of 5 µM to 0.001 pM, 3 µM to 0.001 pM, 1 µM to 0.001 pM, 0.5 µM to 0.001 pM or 0.1 µM to 0.001 pM. "Monospecific" refers to the ability to bind only one epitope.

The term "knob-into-hole" or "KnH" technology as used herein refers to the technology directing the pairing of two polypeptides together in vitro or in vivo by introducing a protuberance (knob) into one polypeptide and a cavity (hole) into the other polypeptide at an interface in which they interact. For example, KnHs have been introduced in the Fc:Fc binding interfaces, CL:CH1 interfaces, or VH/VL interfaces of antibodies (see, e.g., US 2011/0287009, US2007/0178552, WO 96/027011, WO 98/050431, and Zhu et al. *Protein Science* 6:781-788, 1997). In some embodiments, KnHs drive the pairing of two different heavy chains together during the manufacture of multispecific antibodies. For example, multispecific antibodies having KnH in their Fc regions can further comprise single variable domains linked to each Fc region, or further comprise different heavy chain variable domains that pair with similar or different light chain variable domains. KnH technology can also be used to pair two different receptor extracellular domains together or any other polypeptide sequences that comprises different target recognition sequences (e.g., including affibodies, peptibodies, and other Fc fusions).

The term "knob mutation," as used herein, refers to a mutation that introduces a protuberance (knob) into a polypeptide at an interface in which the polypeptide interacts with another polypeptide. In some embodiments, the other polypeptide has a hole mutation (see e.g., U.S. Pat. Nos. 5,731,168; 5,807,706; 5,821,333; 7,695,936; and 8,216,805, which are each incorporated herein by reference in their entirety).

The term "hole mutation," as used herein, refers to a mutation that introduces a cavity (hole) into a polypeptide at an interface in which the polypeptide interacts with another polypeptide. In some embodiments, the other polypeptide has a knob mutation (see e.g., U.S. Pat. Nos. 5,731,168; 5,807,706; 5,821,333; 7,695,936; and 8,216,805, which are each incorporated herein by reference in their entirety).

A "naked antibody" refers to an antibody that is not conjugated to a heterologous moiety (e.g., a cytotoxic moiety) or radiolabel. The naked antibody may be present in a pharmaceutical composition.

With regard to the binding of an antibody to a target molecule, the term "specific binding" or "specifically binds" or is "specific for" a particular polypeptide or an epitope on a particular polypeptide target means binding that is measurably different from a non-specific interaction. Specific binding can be measured, for example, by determining binding of a molecule compared to binding of a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a $K_D$ for the target of $10^{-4}$ M or lower, alternatively $10^{-5}$ M or lower, alternatively $10^{-6}$ M or lower, alternatively $10^{-7}$ M or lower, alternatively $10^{-8}$ M or lower, alternatively $10^{-9}$ M or lower, alternatively $10^{-10}$ M or lower, alternatively $10^{-11}$ M or lower, alternatively $10^{-12}$ M or lower or a $K_D$ in the range of $10^{-4}$ M to $10^{-6}$ M or $10^{-6}$ M to $10^{-10}$ M or $10^{-7}$ M to $10^{-9}$ M. As will be appreciated by the skilled artisan, affinity and $K_D$ values are inversely related. A high affinity for an antigen is measured by a low $K_D$ value. In one embodiment, the term "specific binding" refers to binding where a molecule binds to a particular polypeptide or epitope on a particular polypeptide without substantially binding to any other polypeptide or polypeptide epitope.

The term "variable" refers to the fact that certain segments of the variable domains differ extensively in sequence among antibodies. The variable or "V" domain mediates antigen binding and defines specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al. supra). Accordingly, the HVR and FR sequences generally appear in the following sequence in VH (or VL): FR1-H1(L1)-FR2-H2(L2)-FR3-H3(L3)-FR4. The constant domains are not involved directly in binding an antibody to an antigen, but exhibit various effector functions, such as participation of the antibody in antibody dependent cellular cytotoxicity (ADCC).

The term "hypervariable region," "HVR," or "HV," when used herein refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu, in *Methods in Molecular Biology* 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., *Nature* 363:446-448 (1993); Sheriff et al., *Nature Struct. Biol.* 3:733-736 (1996).

A number of HVR delineations are in use and are encompassed herein. The Kabat Complementarity Determining Regions (CDRs) are based on sequence variability and are the most commonly used (Kabat et al., *Sequences of Proteins of Immunological Interest*, 5th Ed. Public Health Service, National Institutes of Health, Bethesda, Md. (1991)). Chothia refers instead to the location of the structural loops (Chothia and Lesk *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

| Loop | Kabat | AbM | Chothia | Contact | |
|---|---|---|---|---|---|
| L1 | L24-L34 | L24-L34 | L26-L32 | L30-L36 | |
| L2 | L50-L56 | L50-L56 | L50-L52 | L46-L55 | |
| L3 | L89-L97 | L89-L97 | L91-L96 | L89-L96 | |
| H1 | H31-H35B | H26-H35B | H26-H32 | H30-H35B | (Kabat Numbering) |
| H1 | H31-H35 | H26-H35 | H26-H32 | H30-H35 | (Chothia Numbering) |
| H2 | H50-H65 | H50-H58 | H53-H55 | H47-H58 | |
| H3 | H95-H102 | H95-H102 | H96-H101 | H93-H101 | |

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

"Framework" or "FR" residues are those variable domain residues other than the HVR residues as herein defined.

The term "variable domain residue numbering as in Kabat" or "amino acid position numbering as in Kabat," and variations thereof, refers to the numbering system used for heavy chain variable domains or light chain variable domains of the compilation of antibodies in Kabat et al. supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g., residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g., Kabat et al. supra). The "EU numbering system" or "EU index" is generally used when referring to a residue in an immunoglobulin heavy chain constant region (e.g., the EU index reported in Kabat et al. supra). The "EU index as in Kabat" refers to the residue numbering of the human IgG1 EU antibody. Unless stated otherwise herein, references to residue numbers in the variable domain of antibodies means residue numbering by the Kabat numbering system. Unless stated otherwise herein, references to residue numbers in the constant domain of antibodies means residue numbering by the EU numbering system (e.g., see U.S. Provisional Application No. 60/640,323, Figures for EU numbering).

As used herein, "administering" is meant a method of giving a dosage of a compound (e.g., an anti-IL-33 antibody provided herein or a nucleic acid encoding an anti-IL-33 antibody provided herein) or a composition (e.g., a pharmaceutical composition, e.g., a pharmaceutical composition including an anti-IL-33 antibody provided herein) to a subject. The compositions utilized in the methods described herein can be administered, for example, intravitreally, intramuscularly, intravenously, intradermally, percutaneously, intraarterially, intraperitoneally, intralesionally, intracranially, intraarticularly, intraprostatically, intrapleurally, intratracheally, intrathecally, intranasally, intravaginally, intrarectally, topically, intratumorally, peritoneally, subcutaneously, subconjunctivally, intravesicularly, mucosally, intrapericardially, intraumbilically, intraocularly, intraorbitally, orally, topically, transdermally, periocularly, conjunctivally, subtenonly, intracamerally, subretinally, retrobulbarly, intracanalicularly, by inhalation, by injection, by implantation, by infusion, by continuous infusion, by localized perfusion bathing target cells directly, by catheter, by lavage, in cremes, or in lipid compositions. The compositions utilized in the methods described herein can also be administered systemically or locally. The method of administration can vary depending on various factors (e.g., the compound or composition being administered, and the severity of the condition, disease, or disorder being treated).

The term "asthma" refers herein to a disorder characterized by variable and recurring symptoms, reversible airflow obstruction (e.g., by bronchodilator), and bronchial hyperresponsiveness, which may or may not be associated with underlying inflammation. Asthma may therefore be inflammatory/inflamed asthma or non-inflammatory/non-inflamed asthma. Examples of asthma include allergic asthma, exercise-induced asthma, aspirin sensitive/exacerbated asthma, atopic asthma, severe asthma, mild asthma, moderate to severe asthma, corticosteroid naïve asthma, chronic asthma, corticosteroid resistant asthma, corticosteroid refractory asthma, newly diagnosed and untreated asthma, asthma due to smoking, asthma uncontrolled on corticosteroids, and other asthmas as mentioned in Bousquet et al. *J. Allergy Clin. Immunol.* 126(5): 926-938, 2010.

A "disorder" or "disease" is any condition that would benefit from treatment with an antibody provided herein. For example, a disorder may be an IL-33-mediated disorder. This includes chronic and acute disorders or diseases including those pathological conditions which predispose the mammal to the disorder in question. Examples of disorders to be treated herein include IL-33-mediated disorders (e.g., asthma, allergic rhinitis, atopic dermatitis, and fibrosis (e.g., pulmonary fibrosis, e.g., idiopathic pulmonary fibrosis)).

The term "IL-33-mediated disorder," as used herein, refers to any disorder or condition mediated by, or associated with, the IL-33 axis. In some embodiments, IL-33-mediated disorders are associated with excess IL-33 levels or activity in which atypical symptoms may manifest due to the levels or activity of IL-33 locally and/or systemically in the body. Exemplary IL-33-mediated disorders include ocular disorders, inflammatory conditions, immune disorders, fibrotic disorders, eosinophilic disorders, infections, pain, central nervous system disorders, and solid tumors. IL-33-mediated disorders are described, for example, in Liew et al. *Nature Reviews Immunology* 10: 103-110, 2010, which is incorporated herein by reference in its entirety.

The term "ocular disorder," as used herein, includes any ocular disorder (also referred to interchangeably herein as "ocular condition") associated with pathological angiogenesis and/or atrophy. An ocular disorder may be characterized by altered or unregulated proliferation and/or invasion of new blood vessels into the structures of ocular tissues such as the retina or cornea. An ocular disorder may be characterized by atrophy of retinal tissue (photoreceptors and the underlying retinal pigment epithelium (RPE) and choriocapillaris). Non-limiting ocular disorders include, for example, AMD (e.g., wet AMD, dry AMD, intermediate AMD, advanced AMD, and geographic atrophy (GA)), macular degeneration, macular edema, diabetic macular edema (DME) (e.g., focal, non-center DME and diffuse, center-involved DME), retinopathy, diabetic retinopathy (DR) (e.g., proliferative DR (PDR), non-proliferative DR (NPDR), and high-altitude DR), other ischemia-related retinopathies, ROP, retinal vein occlusion (RVO) (e.g., central (CRVO) and branched (BRVO) forms), choroidal neovascularization (CNV) (e.g., myopic CNV), corneal neovascularization, diseases associated with corneal neovascularization, retinal neovascularization, diseases associated with retinal/choroidal neovascularization, central serous retinopathy (CSR), pathologic myopia, von Hippel-Lindau disease, histoplasmosis of the eye, familial exudative vitreoretinopathy (FEVR), Coats' disease, Norrie Disease, retinal abnormalities associated with osteoporosis-pseudoglioma syndrome (OPPG), subconjunctival hemorrhage, rubeosis, ocular neovascular disease, neovascular glaucoma, retinitis pigmentosa (RP), hypertensive retinopathy, retinal angiomatous proliferation, macular telangiectasia, iris neovascularization, intraocular neovascularization, retinal degeneration, cystoid macular edema (CME), vasculitis, papilloedema, retinitis, including but not limited to CMV retinitis, ocular melanoma, retinal blastoma, conjunctivitis (e.g., infectious conjunctivitis and non-infectious (e.g., allergic) conjunctivitis), Leber congenital amaurosis (also known as Leber's congenital amaurosis or LCA), uveitis (including infectious and non-infectious uveitis), choroiditis (e.g., multifocal choroiditis), ocular histoplasmosis, blepharitis, dry eye, traumatic eye injury, Sjëgren's disease, and other ophthalmic diseases wherein the disease or disorder is associated with ocular neovascularization, vascular leakage, and/or retinal edema or retinal atrophy. Additional exemplary ocular disorders include retinoschisis (abnormal splitting of the retina neurosensory layers), diseases associated with rubeosis (neovascularization of the angle) and diseases caused by the abnormal proliferation of fibrovascular or fibrous tissue, including all forms of proliferative vitreoretinopathy.

Exemplary diseases associated with corneal neovascularization include, but are not limited to, epidemic keratoconjunctivitis, vitamin A deficiency, contact lens overwear, atopic keratitis, superior limbic keratitis, terygium keratitis sicca, Sjögren's syndrome, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, marginal keratolysis, rheumatoid arthritis, systemic lupus, polyarteritis, trauma, Wegener's sarcoidosis, scleritis, Stevens-Johnson syndrome, periphigoid radial keratotomy, and corneal graph rejection.

Exemplary diseases associated with choroidal neovascularization and defects in the retina vasculature, including increased vascular leak, aneurisms and capillary drop-out include, but are not limited to, diabetic retinopathy, macular degeneration, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme's disease, systemic lupus erythematosis, retinopathy of prematurity, retina edema (including macular edema), Eales disease, Behcet's disease, infections causing retinitis or choroiditis (e.g., multifocal choroidits), presumed ocular histoplasmosis, Best's disease (vitelliform macular degeneration), myopia, optic pits, pars planitis, retinal detachment (e.g., chronic retinal detachment), hyperviscosity syndromes, toxoplasmosis, trauma, and post-laser complications.

Exemplary diseases associated with atrophy of retinal tissues (photoreceptors and the underlying RPE) include, but are not limited to, atrophic or nonexudative AMD (e.g., geographic atrophy or advanced dry AMD), macular atrophy (e.g., atrophy associated with neovascularization and/or geographic atrophy), diabetic retinopathy, Stargardt's disease, Sorsby Fundus Dystrophy, retinoschisis, and retinitis pigmentosa.

Exemplary inflammatory conditions include asthma (e.g., allergic asthma, exercise-induced asthma, aspirin sensitive/exacerbated asthma, atopic asthma, severe asthma, mild asthma, moderate to severe asthma, corticosteroid naïve asthma, chronic asthma, corticosteroid resistant asthma, corticosteroid refractory asthma, newly diagnosed and untreated asthma, asthma due to smoking, asthma uncontrolled on corticosteroids, etc.), airway inflammation, airway hyperreactivity, airway hyperresponsiveness, rhinosinusitis, rhinosinusitis with polyps, nasal polyposis, arthritis (e.g., osteoarthritis, rheumatoid arthritis, collagen-induced arthritis, arthritic joints as a result of injury, etc.), eosinophilic inflammation, mast cell-mediated inflammatory diseases, sepsis, septic shock, seronegative enthesopathy and arthropathy (SEA) syndrome, osteoporosis, eosinophilic esophagitis, scleroderma, dermatitis, atopic dermatitis, allergic rhinitis, bullous pemphigoid, chronic urticaria, cartilage inflammation, polymyalgia rheumatic, polyarteritis nodossa, Wegener's granulomatosis, Behcet's disease, myolitis, polymyolitis, dermatomyolitis, dermatomyositis, vasculitis, arteritis, diabetic nephropathy, interstitial cystitis, graft versus host disease (GVHD), gastrointestinal inflammatory conditions (e.g., inflammatory bowel disease (IBD), ulcerative colitis (UC), Crohn's disease (CD), colitis (e.g., colitis caused by environmental insults (e.g., caused by or associated with a therapeutic regimen, such as chemotherapy, radiation therapy, etc.), infectious colitis, ischemic colitis, collagenous or lymphocytic colitis, necrotizing enterocolitis, colitis in conditions such as chronic granulomatous disease or celiac disease, food allergies, gastritis, infectious gastritis or enterocolitis (e.g., Helicobacterpylori-infected chronic active gastritis), and other forms of gastrointestinal inflammation caused by an infectious agent), and inflammatory pulmonary conditions (e.g., chronic obstructive pulmonary disease (COPD), eosinophilic pulmonary inflammation, infection-induced pulmonary conditions (including those associated with viral (e.g., influenza, parainfluenza, rotavirus, human metapneumovirus, and respiratory syncytial virus), bacterial, fungal (e.g., *Aspergillus*), parasitic, or prion infection, allergen-induced pulmonary conditions, pollutant-induced pulmonary conditions (e.g., asbestosis, silicosis, or berylliosis), gastric aspiration-induced pulmonary conditions, immune dysregulation, inflammatory conditions with genetic predisposition such as cystic fibrosis, physical trauma-induced pulmonary conditions (e.g., ventilator injury), emphysema, bronchitis, sarcoidosis, histiocytosis, lymphangiomyomatosis, acute lung injury, acute respiratory distress syndrome, chronic lung disease, bronchopulmonary dysplasia, pneumonia (e.g., community-acquired pneumonia, nosocomial pneumonia, ventilator-associated pneumonia, viral pneumonia, bacterial pneumonia, and severe pneumonia), airway exacerbations, and acute respiratory distress syndrome (ARDS)).

Exemplary immune disorders include those mediated at least in part by mast cells, such as asthma (e.g., allergic asthma), eczema, itch, allergy, atopic allergy, anaphylaxis, anaphylactic shock, allergic bronchopulmonary aspergillosis, allergic rhinitis, allergic conjunctivitis, as well as autoimmune disorders including rheumatoid arthritis, juvenile rheumatoid arthritis, psoriatic arthritis, pancreatitis, psoriasis, plaque psoriasis, guttate psoriasis, inverse psoriasis, pustular psoriasis, erythrodermic psoriasis, paraneoplastic autoimmune diseases, autoimmune hepatitis, bullous pemphigoid, myasthenia gravis, inflammatory bowel disease, Crohn's disease, ulcerative colitis, celiac disease, thyroiditis (e.g., Graves' disease), Sjogren's syndrome, Guillain-Barre disease, Raynaud's phenomenon, Addison's disease, liver diseases (e.g., primary biliary cirrhosis, primary sclerosing cholangitis, non-alcoholic fatty liver disease, and non-alcoholic steatohepatitis), and diabetes (e.g., type I diabetes).

As used herein, the terms "fibrotic disorder" and "fibrosis" refer to conditions involving formation of excess fibrous connective tissue in an organ or tissue. Exemplary fibrotic disorders include lung fibrosis, liver fibrosis (e.g., fibrosis associated with cirrhosis (e.g., alcohol-induced cirrhosis, viral-induced cirrhosis, post-hepatitis C cirrhosis, and primary biliary cirrhosis), schistosomiasis, cholangitis (e.g., sclerosing cholangitis), and autoimmune-induced hepatitis), kidney fibrosis (e.g., tubulointerstitial fibrosis, scleroderma, diabetic nephritis, and glomerular nephritis), dermal fibrosis (e.g., scleroderma, hypertrophic and keloid scarring, nephrogenic fibrosing dermatopathy, and burns), myelofibrosis, neurofibromatosis, fibroma, intestinal fibrosis, and fibrotic adhesions resulting from surgical procedures), heart fibrosis (e.g., fibrosis associated with myocardial infarction), vascular fibrosis (e.g., fibrosis associated with postangioplasty arterial restenosis and atherosclerosis), eye fibrosis (e.g., fibrosis associated with post-cataract surgery, proliferative vitreoretinopathy, and retro-orbital fibrosis), and bone marrow fibrosis (e.g., idiopathic myelofibrosis and drug-induced myelofibrosis). The fibrosis can be organ-specific or systemic (e.g., systemic sclerosis and fibrosis associated with GVHD).

Examples of lung fibrosis include, for example, lung or pulmonary fibrosis associated with idiopathic pulmonary fibrosis, fibrosis with collagen vascular disease, Hermansky-Pudlak syndrome, adult respiratory distress syndrome, non-specific interstitial pneumonia, respiratory bronciolitis, sarcoidosis, histiocytosis X, bronchiolitis obliterans, and cryptogenic organizing pneumonia. In one embodiment, the lung fibrosis is idiopathic pulmonary fibrosis.

As used herein, an "eosinophilic disorder" is a disorder associated with excess eosinophil numbers in which atypical symptoms may manifest due to the levels or activity of eosinophils locally or systemically in the body. Eosinophilic disorders include but are not limited to, asthma (including aspirin sensitive asthma, atopic asthma, and severe asthma), eosinophilic inflammation, atopic dermatitis, allergic rhinitis (including seasonal allergic rhinitis), non-allergic rhinitis, chronic eosinophilic pneumonia, allergic bronchopulmonary aspergillosis, celiac disease, Churg-Strauss syndrome (periarteritis nodosa plus atopy), eosinophilic myalgia syndrome, hypereosinophilic syndrome, edematous reactions including episodic angiodema, helminth infections, where eosinophils may have a protective role, onchocercal dermatitis, eosinophil-associated gastrointestinal disorders (EGIDs), including but not limited to, eosinophilic esophagitis, eosinophilic gastritis, eosinophilic gastroenteritis, eosinophilic enteritis and eosinophilic colitis, nasal micropolyposis and polyposis, aspirin intolerance, and obstructive sleep apnea. Eosinophil-derived secretory products have also been associated with the promotion of angiogenesis and connective tissue formation in tumors and the fibrotic responses seen in conditions such as chronic asthma, Crohn's disease, scleroderma and endomyocardial fibrosis (Munitz et al. *Allergy* 59: 268-275, 2004; Adamko et al. *Allergy* 60: 13-22, 2005; Oldhoff et al. *Allergy* 60: 693-696, 2005). Other examples include cancer (e.g., glioblastoma (such as glioblastoma multiforme) and non-Hodgkin's lymphoma (NHL)), atopic dermatitis, allergic rhinitis, inflammatory bowel disease, fibrosis (e.g., pulmonary fibrosis (e.g., idiopathic pulmonary fibrosis (IPF) and pulmonary fibrosis secondary to sclerosis) and hepatic fibrosis), and COPD.

Examples of infection include helminth infection (e.g., nematode infection, such as *Trichuris muris* infection of mice, which is a model for infection by the human parasite *Trichuris trichiura*), protozoan infection (e.g., *Leishmania major* infection), and viral infection (e.g., respiratory syncytial virus infection and influenza virus infection).

Examples of pain include inflammatory pain, hyperalgesia (e.g., mechanical hyperalgesia), allodynia, and hypernociception (e.g., cutaneous and articular hypernociception, which may or may not be antigen-induced).

Examples of central nervous system disorders include subarachnoid hemorrhage, inflammatory diseases of the central nervous system, neurodegenerative diseases (e.g., Alzheimer's disease, experimental autoimmune encephalomyelitis, multiple sclerosis, Parkinson's disease, Huntington's disease), bipolar disorder, and infection of the central nervous system (e.g., viral infection).

Examples of solid tumors include tumors of the colon, breast, prostate, lung, kidney, liver, pancreas, ovary, head and neck, oral cavity, stomach, duodenum, small intestine, large intestine, gastrointestinal tract, anus, gall bladder, labium, nasopharynx, skin, uterus, male genital organ, urinary organs, bladder, and skin. Solid tumors of non-epithelial origin include sarcomas, brain tumors, and bone tumors.

The above list is not all-inclusive, and it will be understood by the skilled artisan that a disease or disorder may fall within various categories. For example, asthma can be categorized in some instances as both an inflammatory disorder and immune disorder and considered by some clinicians to be an autoimmune disorder.

An "IL-33 axis binding antagonist" refers to a molecule that inhibits the interaction of an IL-33 axis binding partner with one or more of its binding partners. As used herein, an IL-33 axis binding antagonist includes IL-33 binding antagonists, ST2 binding antagonists, and IL1RAcP binding antagonists. Exemplary IL-33 axis binding antagonists include anti-IL-33 antibodies and antigen-binding fragments thereof (e.g., anti-IL-33 antibodies such as ANB-020 (AnaptysBio, Inc.) or any of the antibodies described in U.S. Ser. No. 10/093,730, EP1725261, U.S. Pat. No. 8,187,596, WO2011031600, WO2014164959, WO2015099175 or WO2015106080, which are each incorporated herein by reference in their entirety); polypeptides that bind IL-33 and/or its receptor (ST2 and/or IL-1RAcP) and block ligand-receptor interaction (e.g., ST2-Fc proteins, such as those described in WO 2014/152195, which is herein incorporated by reference in its entirety; immunoadhesins, peptibodies, and soluble ST2, or derivatives thereof); anti-IL-33 receptor antibodies (e.g., anti-ST2 antibodies, for example, AMG-282 (Amgen) or STLM15 (Janssen) or any of the anti-ST2 antibodies described in WO 2013/173761 and WO 2013/165894, which are each incorporated herein by reference in their entirety; or ST2-Fc proteins, such as those described in WO 2013/173761; WO 2013/165894; or WO 2014/152195, which are each incorporated herein by reference in their entirety); and IL-33 receptor antagonists, such as small molecule inhibitors, aptamers that bind IL-33, and nucleic acids that hybridize under stringent conditions to IL-33 axis nucleic acid sequences (e.g., short interfering RNAs (siRNA) or clustered regularly interspaced short palindromic repeat RNAs (CRISPR-RNA or crRNA), including single guide RNAs (sgRNAs) having a crRNA and tracrRNA sequence as described in Mali et al. (*Science*. 339: 823-26, 2013), which is incorporated herein by reference in its entirety).

As used herein, "chemoattractant receptor-homologous molecule expressed on Th2 cells (CRTH2)" refers to any native CRTH2 from any vertebrate source, including mammals such as primates (e.g., humans) and rodents (e.g., mice and rats), unless otherwise indicated. CRTH2 is also referred to as G protein coupled receptor 44 (GPR44), cluster of differentiation 294 (CD294), DL1R, and DP2. The term encompasses "full-length," unprocessed CRTH2, as well as any form of CRTH2 that results from processing in the cell. The amino acid sequence of an exemplary human CRTH2 can be found, for example, under UniProtKB accession number Q9Y5Y4.

The term "CRTH2 binding antagonist" refers to a molecule that decreases, blocks, inhibits, abrogates or interferes with signal transduction resulting from the interaction of CRTH2 with one or more of its binding partners, such as prostaglandin D2. Exemplary CRTH2 binding antagonists known in the art include AMG-853, AP768, AP-761, MLN6095, and ACT129968.

The term "interleukin-5 (IL-5)," as used herein, refers to any native IL-5 from any vertebrate source, including mammals such as primates (e.g. humans) and rodents (e.g., mice and rats), unless otherwise indicated. The term encompasses "full-length," unprocessed IL-5, as well as any form of IL-5 that results from processing in the cell. The term also encompasses naturally occurring variants of IL-5, such as splice variants or allelic variants. The amino acid sequence of an exemplary IL-5 can be found, for example, under UniProtKB accession number P05113.

The term "IL-5 binding antagonist" refers to a molecule that decreases, blocks, inhibits, abrogates or interferes with signal transduction resulting from the interaction of IL-5 with one or more of its binding partners, such as IL-5 receptor, alpha (IL5RA). Exemplary IL-5 binding antagonists that can be used in the methods disclosed herein include, for example, anti-IL-5 antibodies (e.g., mepolizumab and reslizumab) and anti-IL-5R antibodies.

As used herein, "interleukin-13 (IL-13)" refers to any native IL-13 from any vertebrate source, including mammals such as primates (e.g., humans) and rodents (e.g., mice and rats), unless otherwise indicated. IL-13 is a cytokine secreted by many cell types, including T helper type 2 (Th2) cells. The term encompasses "full-length," unprocessed IL-13, as well as any form of IL-13 that results from processing in the cell. The amino acid sequence of an exemplary human IL-13 can be found, for example, under UniProtKB accession number P35225.

The term "IL-13 binding antagonist" refers to a molecule that decreases, blocks, inhibits, abrogates or interferes with signal transduction resulting from the interaction of IL-13 with one or more of its binding partners, such as IL-4 receptor alpha (IL4Ra), IL-13 receptor alpha1 (IL13RA1) and IL-13 receptor alpha2 (IL13RA2). IL-13 binding antagonists include anti-IL-13 antibodies, for example, lebrikizumab, 228B/C-1, 228A-4, 227-26, and 227-43 (see, for example, U.S. Pat. Nos. 7,674,459; 8,067,199; 8,088,618; 8,318,160; and 8,734,797).

As used herein, "interleukin-17 (IL-17)" refers to any native IL-17 from any vertebrate source, including mammals such as primates (e.g., humans) and rodents (e.g., mice and rats), unless otherwise indicated, and includes family members IL-17A, IL-17B, IL-17C, IL-17D, IL-17E, and IL-17F. The term encompasses "full-length," unprocessed IL-17, as well as any form of IL-17 that results from processing in the cell. The amino acid sequence of an exemplary human IL-17A can be found, for example, under UniProtKB accession number Q16552. The amino acid sequence of an exemplary human IL-17B can be found, for example, under UniProtKB accession number Q9UHF5. The amino acid sequence of an exemplary human IL-17C can be found, for example, under UniProtKB accession number Q9POM4. The amino acid sequence of an exemplary human IL-17D can be found, for example, under UniProtKB accession number Q8TAD2. The amino acid sequence of an exemplary human IL-17E can be found, for example, under UniProtKB accession number Q9H293. The amino acid sequence of an exemplary human IL-17F can be found, for example, under UniProtKB accession number Q96PD4.

The term "IL-17 binding antagonist" refers to a molecule that decreases, blocks, inhibits, abrogates or interferes with signal transduction resulting from the interaction of IL-17 with one or more of its binding partners, such as interleukin-17 receptor (IL-17R) family member proteins interleukin 17 receptor A (IL17RA), interleukin 17 receptor B (IL17RB), interleukin 17 receptor C (IL17RC), interleukin 17 receptor D (IL17RD), interleukin 17 receptor E (IL17RE), and interleukin 17 receptor E-like (IL17REL). Exemplary IL-17 binding antagonists include, for example, anti-IL-17 antibodies (e.g., ixekizumab (LY2439821) and anti-IL-17R antibodies (e.g., brodalumab (AMG-827)).

The term "Janus kinase 1 (JAK1)," as used herein, refers to any native JAK1 from any vertebrate source, including mammals such as primates (e.g. humans) and rodents (e.g., mice and rats), unless otherwise indicated. The term encompasses "full-length," unprocessed JAK1 as well as any form of JAK1 that results from processing in the cell. The term also encompasses naturally occurring variants of JAK1, e.g., splice variants or allelic variants. The amino acid sequence of an exemplary JAK1 can be found, for example, under UniProtKB accession number P23458.

The term "JAK1 antagonist," as used herein, refers to compounds or agents which inhibit or reduce the biological activity of JAK1. Exemplary JAK1 antagonists include small molecule inhibitors (e.g., ruxolitinib, GLPG0634, and GSK2586184).

The term "ST2 binding antagonist" refers to a molecule that inhibits the interaction of an ST2 with IL-33, IL1RAcP, and/or a second ST2 molecule. The ST2 binding antagonist may be a protein, such as an "ST2-Fc protein" that includes an IL-33-binding domain (e.g., all or a portion of an ST2 or IL1RAcP protein) and a multimerizing domain (e.g., an Fc portion of an immunoglobulin, e.g., an Fc domain of an IgG selected from the isotypes IgG1, IgG2, IgG3, and IgG4, as well as any allotype within each isotype group), which are attached to one another either directly or indirectly through a linker (e.g., a serine-glycine (SG) linker, glycine-glycine (GG) linker, or variant thereof (e.g., a SGG, a GGS, an SGS, or a GSG linker)), and includes, but is not limited to, ST2-Fc proteins and variants thereof described in WO 2013/173761, WO 2013/165894, and WO 2014/152195, which are each incorporated herein by reference in their entirety. In some embodiments, a ST2 binding antagonist may be an anti-ST2 antibody, for example, AMG-282 (Amgen) or STLM15 (Janssen) or any of the anti-ST2 antibodies described in WO 2013/173761 and WO 2013/165894.

As used herein, "tryptase-beta" refers to any native tryptase-beta from any vertebrate source, including mammals such as primates (e.g., humans) and rodents (e.g., mice and rats), unless otherwise indicated. As used herein, the term encompasses tryptase beta-1 (encoded by the TPSAB1 gene, which also encodes tryptase alpha-1) and tryptase beta-2 (encoded by the TPSB2 gene). The term encompasses "full-length," unprocessed tryptase-beta as well as any form of tryptase-beta that results from processing in the cell. The amino acid sequence of an exemplary human tryptase beta-2 can be found, for example, under UniProtKB accession number P20231.

The term "tryptase-beta antagonist," as used herein, refers to compounds or agents which inhibit or reduce the biological activity of tryptase beta.

As used herein, "Factor D" refers to any native Factor D from any vertebrate source, including mammals such as primates (e.g., humans) and rodents (e.g., mice and rats), unless otherwise indicated. Factor D is also referred to as C3 proactivator convertase, properdin factor D esterase, Factor D (complement), Complement Factor D, CFD, and adipsin. The term encompasses "full-length," unprocessed Factor D, as well as any form of Factor D that results from processing in the cell. The amino acid sequence of an exemplary human Factor D can be found, for example, under UniProtKB accession number P00746.

The term "Factor D binding antagonist," as used herein, refers to compounds or agents which inhibit or reduce the biological activity of Factor D. Exemplary Factor D binding antagonists include, for example, small molecule inhibitors and anti-Factor D antibodies, for example, any anti-Factor D antibody described in WO 2007/056227, WO 01/70818, and/or US 2002/0081293, which are each incorporated herein by reference in their entirety. In some embodiments, the anti-Factor D antibody is or is derived from monoclonal antibody 166-32, produced by the hybridoma deposited with the ATCC and designated HB 12476.

The term "High-temperature requirement A serine peptidase 1" or "HtrA1," as used herein, refers to any native HtrA1 from any vertebrate source, including mammals such as primates (e.g., humans) and rodents (e.g., mice and rats), unless otherwise indicated. HtrA1 is also known in the art as HtrA serine peptidase 1, L56, and Serine protease 11. The term encompasses "full-length," unprocessed HtrA1 as well as any form of HtrA1 that results from processing in the cell. The term also encompasses naturally occurring variants of HtrA1, e.g., splice variants or allelic variants. The amino acid sequence of an exemplary human HtrA1 can be found, for example, under UniProtKB accession number Q92743.

The term "HtrA1 binding antagonist" as used herein, refers to compounds or agents which inhibit or reduce the biological activity of HtrA1. Exemplary HtrA1 binding antagonists include, for example, small molecule inhibitors and anti-HtrA1 antibodies, for example, any anti-HtrA1 antibody described in U.S. Ser. No. 10/421,822 or U.S. Pat. No. 9,738,727, each of which is incorporated herein by reference in its entirety.

The term "vascular endothelial growth factor" or "VEGF" refers to vascular endothelial growth factor protein A, as exemplified by Swiss Prot Accession Number P15692. The term "VEGF" encompasses the protein having the amino acid sequence exemplified by Swiss Prot Accession Number P15692 as well as homologues and isoforms thereof. The term "VEGF" also encompasses the known isoforms, e.g., splice isoforms of VEGF, e.g., $VEGF_{111}$, $VEGF_{121}$, $VEGF_{145}$, $VEGF_{165}$, $VEGF_{189}$, and $VEGF_{206}$, together with the naturally-occurring allelic and processed forms thereof, including the 110-amino acid human vascular endothelial cell growth factor generated by plasmin cleavage of $VEGF_{165}$ as described in Ferrara *Mol. Biol. Cell.* 21:687 (2010), Leung et al., *Science,* 246:1306 (1989), and Houck et al., *Mol. Endocrin.,* 5:1806 (1991). The term "VEGF" also refers to VEGFs from non-human species such as mouse, rat or primate. Sometimes the VEGF from a specific species are indicated by terms such as hVEGF for human VEGF, mVEGF for murine VEGF, and the like. The term "VEGF" is also used to refer to truncated forms of the polypeptide comprising amino acids 8 to 109 or 1 to 109 of the 165-amino acid human vascular endothelial cell growth factor. Reference to any such forms of VEGF may be identified in the present application, e.g., by "$VEGF_{109}$," "VEGF (8-109)," "VEGF (1-109)" or "$VEGF_{165}$." The amino acid positions for a "truncated" native VEGF are numbered as indicated in the native VEGF sequence. For example, amino acid position 17 (methionine) in truncated native VEGF is also position 17 (methionine) in native VEGF. The truncated native VEGF has binding affinity for the KDR and Flt-1 receptors comparable to native VEGF. The term "VEGF variant" as used herein refers to a VEGF polypeptide which includes one or more amino acid mutations in the native VEGF sequence. Optionally, the one or more amino acid mutations include amino acid substitution(s). For purposes of shorthand designation of VEGF variants described herein, it is noted that numbers refer to the amino acid residue position along the amino acid sequence of the putative native VEGF (provided in Leung et al., supra and Houck et al., supra). Unless specified otherwise, the term "VEGF" as used herein indicates VEGF-A.

The term "VEGF antagonist," as used herein, refers to a molecule capable of binding to VEGF, reducing VEGF expression levels, or neutralizing, blocking, inhibiting, abrogating, reducing, or interfering with VEGF biological activities, including, but not limited to, VEGF binding to one or more VEGF receptors, VEGF signaling, and VEGF-mediated angiogenesis and endothelial cell survival or proliferation. For example, a molecule capable of neutralizing, blocking, inhibiting, abrogating, reducing, or interfering with VEGF biological activities can exert its effects by binding to one or more VEGF receptor (VEGFR) (e.g., VEGFR1, VEGFR2, VEGFR3, membrane-bound VEGF receptor (mbVEGFR), or soluble VEGF receptor (sVEGFR)). Included as VEGF antagonists useful in the methods disclosed herein are polypeptides that specifically bind to VEGF, anti-VEGF antibodies and antigen-binding fragments thereof, receptor molecules and derivatives which bind specifically to VEGF thereby sequestering its binding to one or more receptors, fusions proteins (e.g., VEGF-Trap (Regeneron)), and $VEGF_{121}$-gelonin (Peregrine). VEGF antagonists also include antagonist variants of VEGF polypeptides, antisense nucleobase oligomers complementary to at least a fragment of a nucleic acid molecule encoding a VEGF polypeptide; small RNAs complementary to at least a fragment of a nucleic acid molecule encoding a VEGF polypeptide; ribozymes that target VEGF; peptibodies to VEGF; and VEGF aptamers. VEGF antagonists also include polypeptides that bind to VEGFR, anti-VEGFR antibodies, and antigen-binding fragments thereof, and derivatives which bind to VEGFR thereby blocking, inhibiting, abrogating, reducing, or interfering with VEGF biological activities (e.g., VEGF signaling), or fusions proteins. VEGF antagonists also include nonpeptide small molecules that bind to VEGF or VEGFR and are capable of blocking, inhibiting, abrogating, reducing, or interfering with VEGF biological activities. Thus, the term "VEGF activities" specifically includes VEGF-mediated biological activities of VEGF. In certain embodiments, the VEGF antagonist reduces or inhibits, by at least 10%, 20%, 30%, 40%, 50%, 60%, 70%, 80%, 90% or more, the expression level or biological activity of VEGF. In some embodiments, the VEGF inhibited by the VEGF-specific antagonist is VEGF (8-109), VEGF (1-109), or $VEGF_{165}$.

As used herein VEGF antagonists can include, but are not limited to, anti-VEGFR2 antibodies and related molecules (e.g., ramucirumab, tanibirumab, aflibercept), anti-VEGFR1 antibodies and related molecules (e.g., icrucumab, aflibercept (VEGF Trap-Eye; EYLEA®), and ziv-aflibercept (VEGF Trap; ZALTRAP®)), bispecific VEGF antibodies (e.g., MP-0250, vanucizumab (VEGF-ANG2), and bispecific antibodies disclosed in US 2001/0236388), bispecific antibodies including combinations of two of anti-VEGF, anti-VEGFR1, and anti-VEGFR2 arms, anti-VEGF antibodies (e.g., bevacizumab, sevacizumab, and ranibizumab), and nonpeptide small molecule VEGF antagonists (e.g., pazopanib, axitinib, vandetanib, stivarga, cabozantinib, lenvatinib, nintedanib, orantinib, telatinib, dovitinig, cediranib, motesanib, sulfatinib, apatinib, foretinib, famitinib, and tivozanib).

The terms "anti-VEGF antibody," an "antibody that binds to VEGF," and "antibody that specifically binds VEGF" refer to an antibody that is capable of binding VEGF with sufficient affinity such that the antibody is useful as a diagnostic and/or therapeutic agent in targeting VEGF. In one embodiment, the extent of binding of an anti-VEGF antibody to an unrelated, non-VEGF protein is less than about 10% of the binding of the antibody to VEGF as measured, for example, by a radioimmunoassay (RIA). In certain embodiments, an antibody that binds to VEGF has a dissociation constant (Kd) of ≤1 μM, ≤100 nM, ≤10 nM, ≤1 nM, ≤0.1 nM, ≤0.01 nM, or ≤0.001 nM (e.g. $10^{-8}$ M or less, e.g., from $10^{-8}$ M to $10^{-13}$ M, e.g., from $10^{-9}$ M to $10^{-13}$ M). In certain embodiments, an anti-VEGF antibody binds to an epitope of VEGF that is conserved among VEGF from different species.

In certain embodiments, the anti-VEGF antibody can be used as a therapeutic agent in targeting and interfering with diseases or conditions wherein the VEGF activity is involved. Also, the antibody may be subjected to other biological activity assays, e.g., in order to evaluate its effectiveness as a therapeutic. Such assays are known in the art and depend on the target antigen and intended use for the antibody. Examples include the HUVEC inhibition assay; tumor cell growth inhibition assays (as described in WO 89/06692, for example); antibody-dependent cellular cytotoxicity (ADCC) and complement-mediated cytotoxicity (CDC) assays (U.S. Pat. No. 5,500,362); and agonistic activity or hematopoiesis assays (see WO 95/27062). An anti-VEGF antibody will usually not bind to other VEGF homologues such as VEGF-B or VEGF-C, nor other growth factors such as PIGF, PDGF, or bFGF. In one embodiment, anti-VEGF antibody is a monoclonal antibody that binds to the same epitope as the monoclonal anti-VEGF antibody A4.6.1 produced by hybridoma ATCC HB 10709. In another embodiment, the anti-VEGF antibody is a recombinant humanized anti-VEGF monoclonal antibody generated according to Presta et al. (1997) *Cancer Res.* 57:4593-4599, including but not limited to the antibody known as bevacizumab (BV; AVASTIN®).

The anti-VEGF antibody "bevacizumab (BV)," also known as "rhuMAb VEGF" or "AVASTIN®," is a recombinant humanized anti-VEGF monoclonal antibody generated according to Presta et al. (1997) *Cancer Res.* 57:4593-4599. It comprises mutated human IgG1 framework regions and antigen-binding complementarity-determining regions from the murine anti-hVEGF monoclonal antibody A.4.6.1 that blocks binding of human VEGF to its receptors. Approximately 93% of the amino acid sequence of bevacizumab, including most of the framework regions, is derived from human IgG1, and about 7% of the sequence is derived from the murine antibody A4.6.1. Bevacizumab has a molecular mass of about 149,000 daltons and is glycosylated. Bevacizumab and other humanized anti-VEGF antibodies are further described in U.S. Pat. No. 6,884,879 issued Feb. 26, 2005, the entire disclosure of which is expressly incorporated herein by reference. Additional preferred antibodies include the G6 or B20 series antibodies (e.g., G6-31, B20-4.1), as described in PCT Application Publication Nos. WO 2005/012359 and WO 2005/044853, which are each incorporated herein by reference in their entirety. For additional preferred antibodies see U.S. Pat. Nos. 7,060,269, 6,582,959, 6,703,020; 6,054,297; WO98/45332; WO 96/30046; WO94/10202; EP 0666868B1; U.S. Patent Application Publication Nos. 2006009360, 20050186208, 20030206899, 20030190317, 20030203409, and 20050112126; and Popkov et al., *Journal of Immunological Methods* 288:149-164 (2004). Other preferred antibodies include those that bind to a functional epitope on human VEGF comprising of residues F17, M18, D19, Y21, Y25, Q89, 191, K101, E103, and C104 or, alternatively, comprising residues F17, Y21, Q22, Y25, D63, 183, and Q89. Additional anti-VEGF antibodies include anti-VEGF antibodies described in PCT Application Publication No. WO 2009/155724.

The anti-VEGF antibody "ranibizumab" also known as "LUCENTIS®" or "rhuFab V2" is a humanized, affinity-matured anti-human VEGF Fab fragment. Ranibizumab is produced by standard recombinant technology methods in *Escherichia coli* expression vector and bacterial fermentation. Ranibizumab is not glycosylated and has a molecular mass of ~48,000 daltons. See WO 98/45331 and US 2003/0190317.

A "chemotherapeutic agent" is a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaII (see, e.g., Nicolaou et al. *Angew. Chem Intl. Ed. Engl.*, 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); combretastatin; folic acid analogues such as denopterin, methotrexate, pteropterin, trimetrexate; purine analogues such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products); razoxane; rhizoxin; sizofuran; spirogermanium; tenuazonic acid; triaziquone; 2,2',2'-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL), albumin-engineered nanoparticle formulation of paclitaxel (ABRAXANE™), and docetaxel (TAXOTERE®); chloranbucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylornithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGFR) (e.g., erlotinib (TARCEVA™)); and VEGF-A that reduce cell proliferation; vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g. celecoxib or etoricoxib), proteosome inhibitor (e.g. PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors; tyrosine kinase inhibitors; serine-threonine kinase inhibitors such as rapamycin (sirolimus, RAPAMUNE®); farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin, and pharmaceutically acceptable salts, acids or derivatives of any of the above; as well as combinations of two or more of the above.

Chemotherapeutic agents as defined herein include "antihormonal agents" or "endocrine therapeutics" which act to regulate, reduce, block, or inhibit the effects of hormones that can promote the growth of cancer. They may be hormones themselves, including, but not limited to: antiestrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and nonsteroidal aromatase inhibitors such as anastrazole (ARIMIDEX®), letrozole (FEMARA®) and aminoglutethimide, and other aromatase inhibitors include vorozole (RIVISOR®), megestrol acetate (MEGASE®), fadrozole, and 4(5)-imidazoles; luteinizing hormone-releaseing hormone agonists, including leuprolide (LUPRON® and ELIGARD®), goserelin, buserelin, and tripterelin; sex steroids, including progestines such as megestrol acetate and medroxyprogesterone acetate, estrogens such as diethylstilbestrol and premarin, and androgens/retinoids such as fluoxymesterone, all transretionic acid and fenretinide; onapristone; anti-progesterones; estrogen receptor downregulators (ERDs); anti-androgens such as flutamide, nilutamide and bicalutamide; and pharmaceutically acceptable salts, acids or derivatives of any of the above; as well as combinations of two or more of the above.

The term "cytotoxic agent" as used herein refers to a substance that inhibits or prevents a cellular function and/or causes cell death or destruction. Cytotoxic agents include, but are not limited to, radioactive isotopes (e.g., $At^{21}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (e.g., vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed herein.

A "growth inhibitory agent" when used herein refers to a compound or composition which inhibits growth of a cell either in vitro or in vivo. Thus, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (e.g., vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in Mendelsohn et al. eds., *The Molecular Basis of Cancer*, Chapter 1, entitled "Cell cycle regulation, oncogenes, and antineoplastic drugs" by Murakami et al. (W.B. Saunders, Philadelphia, 1995), e.g., p. 13. The taxanes (paclitaxel and docetaxel) are anticancer drugs both derived from the yew tree. Docetaxel (TAXOTERE®), derived from the European yew, is a semisynthetic analogue of paclitaxel (TAXOL®). Paclitaxel and docetaxel promote the assembly of microtubules from tubulin dimers and stabilize microtubules by preventing depolymerization, which results in the inhibition of mitosis in cells.

An "isolated nucleic acid" refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. The host cell may be an "isolated host cell," which refers to a host cell that has been separated from a component of its natural environment.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Percent (%) amino acid sequence identity" with respect to the polypeptide sequences identified herein is defined as the percentage of amino acid residues in a candidate sequence that are identical with the amino acid residues in the polypeptide being compared, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, or Megalign (DNASTAR) software. Those skilled in the art can determine appropriate parameters for measuring alignment, including any algorithms needed to achieve maximal alignment over the full-length of the sequences being compared. For purposes herein, however, % amino acid sequence identity values are generated using the sequence comparison computer program ALIGN-2. The ALIGN-2 sequence comparison computer program was authored by Genentech, Inc. and the source code has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction $X/Y$ where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The amino acid sequences described herein are contiguous amino acid sequences unless otherwise specified.

The term "package insert" is used to refer to instructions customarily included in commercial packages of therapeutic products, that contain information about the indications, usage, dosage, administration, combination therapy, contraindications and/or warnings concerning the use of such therapeutic products.

The term "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" *Biochemical Society Transactions*, 14, pp. 375-382, 615th Meeting Belfast (1986) and Stella et al. "Prodrugs: A Chemical Approach to Targeted Drug Delivery," *Directed Drug Delivery*, Borchardt et al. (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

By "reduce or inhibit" is meant the ability to cause an overall decrease preferably of 20% or greater, more preferably of 50% or greater, and most preferably of 75%, 85%, 90%, 95%, or greater. Reduce or inhibit can refer to the symptoms of the disorder being treated, the presence or size of metastases, and/or the size of the primary tumor.

A "subject" is a vertebrate, preferably a mammal, more preferably a human. Mammals include, but are not limited to, farm animals (such as cows, and sheep), sport animals, pets (such as cats, dogs and horses), primates (e.g., humans and non-human primates such as monkeys), and rodents (e.g., mice and rats).

The term "therapeutically effective amount" refers to an amount of a compound (e.g., an anti-IL-33 antibody provided herein (including an antibody fragment, such an Fab fragment) or a nucleic acid encoding an anti-IL-33 antibody provided herein) or a composition (e.g., a pharmaceutical composition, e.g., a pharmaceutical composition including an anti-IL-33 antibody provided herein) to treat a disease or disorder in a subject. In the case of an IL-33-mediated disorder, the therapeutically effective amount of the antibody or antibody fragment (e.g., an anti-IL-33 antibody, including bispecific anti-IL-33 antibodies that bind to IL-33 and a second biological molecule, e.g., IL-13, e.g., bispecific anti-IL-33/anti-IL-13 antibodies) may ameliorate or treat the disease, or prevent, reduce, ameliorate, or treat symptoms associated with the disease. In the case of a proliferative disease (e.g., a solid tumor), the therapeutically effective amount of the antibody or antibody fragment may reduce the number of cancer cells; reduce the primary tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the antibody or antibody fragment may prevent growth and/or kill existing cancer cells, it may be cytostatic and/or cytotoxic. For cancer therapy, efficacy in vivo can, for example, be measured by assessing the duration of survival, time to disease progression (TTP), duration of disease free survival (DFS), duration of progression free survival (PFS), the response rates (RR), duration of response, and/or quality of life.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies disclosed herein are used to delay development of a disease or to slow the progression of a disease. A patient may be successfully "treated" for asthma if, for example, after receiving an asthma therapy, the patient shows observable and/or measurable reduction in or absence of one or more of the following: recurrent wheezing, coughing, trouble breathing, chest tightness, symptoms that occur or worsen at night, symptoms that are triggered by cold air, exercise or exposure to allergens.

"Tumor", as used herein, refers to all neoplastic cell growth and proliferation, whether malignant or benign, and all pre-cancerous and cancerous cells and tissues.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors" or "expression vectors"). In general, expression vectors of utility in recombinant DNA techniques are often in the form of plasmids. In the present specification, "plasmid" and "vector" may be used interchangeably.

The term "turbidity," as used herein, refers to the cloudiness or haziness of a liquid due to suspended insoluble particles. Turbidity can be assessed by measuring the optical density (OD) of a liquid sample, e.g., using a spectrophotometer.

The term "viscosity," as used herein, refers to a measure of a fluid's resistance to deformation at a given rate. The SI unit of dynamic viscosity is the pascal-second (Pa·s), but is also commonly expressed as centipoise (cP), which is equal to one millipascal-second (mPa·s).

II. Compositions and Methods

In one aspect, the invention is based, at least in part, on improved antibodies that bind to IL-33. The antibodies provided herein have unexpectedly advantageous properties, including high stability (including under conditions of chemical and light stress) and reduced oxidation compared to existing anti-IL-33 antibodies. For example, the antibodies disclosed herein may lack a tryptophan residue in CDR-H3 that can result in decreased stability due to oxidation. Moreover, the antibodies provided herein also bind to human and cynomolgus monkey (cyno) IL-33 with high affinity and inhibitory activity, e.g., as assessed using surface plasmon resonance (SPR) and in cell-based blocking assays (e.g., using HEK-BLUE™ cells), respectively. Further, the antibodies provided herein have low viscosity at high protein concentrations and high solubility. Antibodies disclosed herein are useful, e.g., for the treatment of IL-33-mediated disorders. The unexpectedly favorable properties described above (including improved stability with reduced oxidation, high solubility, and the ability to be formulated at high concentration with low viscosity) are particularly advantageous in the context of ocular administration, e.g., for treatment of ocular disorders (e.g., AMD (e.g., GA)). For example, in the context of GA, without wishing to be bound by any theory, targeted inhibition of IL-33 signaling in the eye may protect photoreceptors and RPE in the area bordering GA lesions, e.g., by limiting the influx of inflammatory mononuclear phagocytes.

A. Exemplary Anti-IL-33 Antibodies

In one example, provided herein is an anti-IL-33 antibody that includes at least one, two, three, four, five, or six CDRs selected from: (a) CDR-H1 comprising the amino acid sequence of NYWMT (SEQ ID NO: 1); (b) CDR-H2 comprising the amino acid sequence of SITYTGGGTYYPDSVKG (SEQ ID NO: 2); (c) CDR-H3 comprising the amino acid sequence of ANYYYNTYGGFPY (SEQ ID NO: 3); (d) CDR-L1 comprising the amino acid sequence of LASEGFSNDLA (SEQ ID NO: 4); (e) CDR-L2 comprising the amino acid sequence of AASRLQD (SEQ ID NO: 5); and (f) CDR-L3 comprising the amino acid sequence of QQGSKYPLT (SEQ ID NO: 6), or a combination of one or more of the above CDRs and/or one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 1-6. For example, in some instances, the anti-IL-33 antibody includes at least one, two, three, four, five, or six CDRs selected from: (a) CDR-H1 comprising the amino acid sequence of NYWMT (SEQ ID NO: 1); (b) CDR-H2 comprising the amino acid sequence of SITYTGGGTYYPDSVKG (SEQ ID NO: 2); (c) CDR-H3 comprising the amino acid sequence of ANYYYNTYGGFPY (SEQ ID NO: 3); (d) CDR-L1 comprising the amino acid sequence of LASEGFSNDLA (SEQ ID NO: 4); (e) CDR-L2 comprising the amino acid sequence of AASRLQD (SEQ ID NO: 5); and (f) CDR-L3 comprising the amino acid sequence of QQGSKYPLT (SEQ ID NO: 6).

In another example, provided herein is an anti-IL-33 antibody that includes (a) a VH domain comprising an amino acid sequence having at least 90% sequence identity (e.g., at least 91%, 92%, 93%, 94%, 95%, 96%, 97%, 98%, or 99% sequence identity) to, or the sequence of, the amino acid sequence of SEQ ID NO: 7; (b) a VL domain comprising an amino acid sequence having at least 90% sequence identity (e.g., at least 91%, 92%, 93%, 94%, 95%, 96%, 97%, 98%, or 99% sequence identity) to, or the sequence of, the amino acid sequence of SEQ ID NO: 8; or (c) a VH domain as in (a) and a VL domain as in (b).

Any of the anti-IL-33 antibodies provided herein may include one, two, three, or four of the following heavy chain framework regions: an FR-H1 comprising the amino acid sequence of EVQLVX$_1$SGX$_2$X$_3$X$_4$X$_5$X$_6$PGX$_7$SX$_8$X$_9$X$_{10}$SCX$_{11}$ASGFTFN (SEQ ID NO: 9), wherein X$_1$ is E or Q; X$_2$ is G or A; X$_3$ is G or E; X$_4$ is L or V; X$_5$ is V or K; X$_6$ is Q or K; X$_7$ is G, A, or T; X$_8$ is L or V; X$_9$ is R or K; X$_{10}$ is L or V; and X$_{11}$ is A, K, or L; an FR-H2 comprising the amino acid sequence of WX$_1$RQAPGX$_2$GLEWX$_3$X$_4$ (SEQ ID NO: 10), wherein X$_1$ is I or V; X$_2$ is K or Q; X$_3$ is V, M, or I; and X$_4$ is A or G; an FR-H3 comprising the amino acid sequence of RX$_1$TX$_2$X$_3$RDX$_4$X$_5$X$_6$X$_7$X$_8$X$_9$YX$_{10}$X$_{11}$X$_{12}$X$_{13}$SLRX$_{14}$EDTAX$_{15}$YYCTR (SEQ ID NO: 11), wherein X$_1$ is F or V; X$_2$ is I or M; X$_3$ is S or T; X$_4$ is D, N, or T; X$_5$ is A or S; X$_6$ is K or T; X$_7$ is S or N; X$_8$ is S or T; X$_9$ is L or V; X$_{10}$ is L or M; X$_{11}$ is Q or E; X$_{12}$ is M or L; X$_{13}$ is N or S; X$_{14}$ is A or S; and X$_{15}$ is V or T; and an FR-H4 comprising the amino acid sequence of WGQGTLVTVSS (SEQ ID NO: 12), or a combination of one or more of the above FRs and/or one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 9-12.

For example, in some instances, the anti-IL-33 antibody may include one, two, three, or four of the following heavy chain framework regions: an FR-H1 comprising the amino acid sequence of EVQLVESGGGLVQPGGSLRLS-CAASGFTFN (SEQ ID NO: 17); an FR-H2 comprising the amino acid sequence of WIRQAPGKGLEWVA (SEQ ID NO: 18); an FR-H3 comprising the amino acid sequence of RFTISRDDAKSSLYLQMNSLRAEDTAVYYCTR (SEQ ID NO: 19); and an FR-H4 comprising the amino acid sequence of WGQGTLVTVSS (SEQ ID NO: 12), or a combination of one or more of the above FRs and/or one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 12 and 17-19. In some instances, the anti-IL-33 antibody may include one, two, three, or four of the following heavy chain framework regions: an FR-H1 comprising the amino acid sequence of EVQLVESGGGLVQPGGSLRLSCAASGFTFN (SEQ ID NO: 17); an FR-H2 comprising the amino acid sequence of WIRQAPGKGLEWVA (SEQ ID NO: 18); an FR-H3 comprising the amino acid sequence of RFTISRDDAKSS-LYLQMNSLRAEDTAVYYCTR (SEQ ID NO: 19); and an FR-H4 comprising the amino acid sequence of WGQGTLVTVSS (SEQ ID NO: 12). In some embodiments, the VH domain comprises the amino acid sequence of SEQ ID NO: 7.

In another example, in some instances, the anti-IL-33 antibody may include one, two, three, or four of the following heavy chain framework regions: an FR-H1 comprising the amino acid sequence of EVQLVESGG-GLVQPGGSLRLSCAASGFTFN (SEQ ID NO: 17); an FR-H2 comprising the amino acid sequence of WVRQAPGKGLEWVA (SEQ ID NO: 39); an FR-H3 comprising the amino acid sequence of RFTISRDNAKNS-LYLQMNSLRAEDTAVYYCTR (SEQ ID NO: 40); and an FR-H4 comprising the amino acid sequence of WGQGTLVTVSS (SEQ ID NO: 12), or a combination of one or more of the above FRs and/or one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 12, 17, 39, and 40. In some instances, the anti-IL-33 antibody may include one, two, three, or four of the following heavy chain framework regions: an FR-H1 comprising the amino acid sequence of EVQLVESGGGLVQPGGSLRLSCAASGFTFN (SEQ ID NO: 17); an FR-H2 comprising the amino acid sequence of WVRQAPGKGLEWVA (SEQ ID NO: 39); an FR-H3 comprising the amino acid sequence of RFTISRDNAKNS-LYLQMNSLRAEDTAVYYCTR (SEQ ID NO: 40); and an FR-H4 comprising the amino acid sequence of WGQGTLVTVSS (SEQ ID NO: 12). In some embodiments, the VH domain comprises the amino acid sequence of SEQ ID NO: 41.

In another example, in some instances, the anti-IL-33 antibody may include one, two, three, or four of the following heavy chain framework regions: an FR-H1 comprising the amino acid sequence of EVQLVESGG-GLVQPGGSLRLSCAASGFTFN (SEQ ID NO: 17); an FR-H2 comprising the amino acid sequence of WIRQAPGKGLEWIA (SEQ ID NO: 42); an FR-H3 comprising the amino acid sequence of RFTISRDDAKSS-LYLQMNSLRAEDTAVYYCTR (SEQ ID NO: 19); and an FR-H4 comprising the amino acid sequence of WGQGTLVTVSS (SEQ ID NO: 12), or a combination of one or more of the above FRs and/or one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 12, 17, 19, and 42. In some instances, the anti-IL-33 antibody may include one, two, three, or four of the following heavy chain framework regions: an FR-H1 comprising the amino acid sequence of EVQLVESGGGLVQPGGSLRLSCAASGFTFN (SEQ ID NO: 17); an FR-H2 comprising the amino acid sequence of WIRQAPGKGLEWIA (SEQ ID NO: 42); an FR-H3 comprising the amino acid sequence of RFTISRDDAKSS-LYLQMNSLRAEDTAVYYCTR (SEQ ID NO: 19); and an FR-H4 comprising the amino acid sequence of WGQGTLVTVSS (SEQ ID NO: 12). In some instances, the VH domain comprises the amino acid sequence of SEQ ID NO: 43.

In another example, in some instances, the anti-IL-33 antibody may include one, two, three, or four of the following heavy chain framework regions: an FR-H1 comprising the amino acid sequence of EVQLVESGG-GLVQPGGSLRLSCAASGFTFN (SEQ ID NO: 17); an FR-H2 comprising the amino acid sequence of WVRQAPGKGLEWVA (SEQ ID NO: 39); an FR-H3 comprising the amino acid sequence of RFTISRDDAKSS-LYLQMNSLRAEDTAVYYCTR (SEQ ID NO: 19); and an FR-H4 comprising the amino acid sequence of WGQGTLVTVSS (SEQ ID NO: 12), or a combination of one or more of the above FRs and/or one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 12, 17, 19, and 39. In some instances, the anti-IL-33 antibody may include one, two, three, or four of the following heavy chain framework regions: an FR-H1 comprising the amino acid sequence of EVQLVESGGGLVQPGGSLRLSCAASGFTFN (SEQ ID NO: 17); an FR-H2 comprising the amino acid sequence of WVRQAPGKGLEWVA (SEQ ID NO: 39); an FR-H3 comprising the amino acid sequence of RFTISRDDAKSS-LYLQMNSLRAEDTAVYYCTR (SEQ ID NO: 19); and an FR-H4 comprising the amino acid sequence of WGQGTLVTVSS (SEQ ID NO: 12). In some instances, the VH domain comprises the amino acid sequence of SEQ ID NO: 44.

In another example, in some instances, the anti-IL-33 antibody may include one, two, three, or four of the following heavy chain framework regions: an FR-H1 comprising the amino acid sequence of EVQLVESGG-GLVQPGGSLRLSCAASGFTFN (SEQ ID NO: 17); an FR-H2 comprising the amino acid sequence of WVRQAPGKGLEWVA (SEQ ID NO: 39); an FR-H3 comprising the amino acid sequence of RFTISRDDAKNS-LYLQMNSLRAEDTAVYYCTR (SEQ ID NO: 45); and an FR-H4 comprising the amino acid sequence of WGQGTLVTVSS (SEQ ID NO: 12), or a combination of one or more of the above FRs and/or one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 12, 17, 39, and 45. In some instances, the anti-IL-33 antibody may include one, two, three, or four of the following heavy chain framework regions: an FR-H1 comprising the amino acid sequence of EVQLVESGGGLVQPGGSLRLSCAASGFTFN (SEQ ID NO: 17); an FR-H2 comprising the amino acid sequence of WVRQAPGKGLEWVA (SEQ ID NO: 39); an FR-H3 comprising the amino acid sequence of RFTISRDDAKNS- LYLQMNSLRAEDTAVYYCTR (SEQ ID NO: 45); and an FR-H4 comprising the amino acid sequence of WGQGTLVTVSS (SEQ ID NO: 12). In some embodiments, the VH domain comprises the amino acid sequence of SEQ ID NO: 46.

In another example, in some instances, the anti-IL-33 antibody may include one, two, three, or four of the following heavy chain framework regions: an FR-H1 comprising the amino acid sequence of EVQLVESGGGLVQPGGSLRLSCAASGFTFN (SEQ ID NO: 17); an FR-H2 comprising the amino acid sequence of WVRQAPGKGLEWVA (SEQ ID NO: 39); an FR-H3 comprising the amino acid sequence of RFTISRDNAKSSLYLQMNSLRAEDTAVYYCTR (SEQ ID NO: 47); and an FR-H4 comprising the amino acid sequence of WGQGTLVTVSS (SEQ ID NO: 12), or a combination of one or more of the above FRs and/or one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 12, 17, 39, and 47. In some instances, the anti-IL-33 antibody may include one, two, three, or four of the following heavy chain framework regions: an FR-H1 comprising the amino acid sequence of EVQLVESGGGLVQPGGSLRLSCAASGFTFN (SEQ ID NO: 17); an FR-H2 comprising the amino acid sequence of WVRQAPGKGLEWVA (SEQ ID NO: 39); an FR-H3 comprising the amino acid sequence of RFTISRDNAKSSLYLQMNSLRAEDTAVYYCTR (SEQ ID NO: 47); and an FR-H4 comprising the amino acid sequence of WGQGTLVTVSS (SEQ ID NO: 12). In some embodiments, the VH domain comprises the amino acid sequence of SEQ ID NO: 48.

In another example, in some instances, the anti-IL-33 antibody may include one, two, three, or four of the following heavy chain framework regions: an FR-H1 comprising the amino acid sequence of EVQLVESGGGLVQPGGSLRLSCAASGFTFN (SEQ ID NO: 17); an FR-H2 comprising the amino acid sequence of WVRQAPGKGLEWIA (SEQ ID NO: 49); an FR-H3 comprising the amino acid sequence of RFTISRDDAKSSLYLQMNSLRAEDTAVYYCTR (SEQ ID NO: 19); and an FR-H4 comprising the amino acid sequence of WGQGTLVTVSS (SEQ ID NO: 12), or a combination of one or more of the above FRs and/or one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 12, 17, 19 and 49. In some instances, the anti-IL-33 antibody may include one, two, three, or four of the following heavy chain framework regions: an FR-H1 comprising the amino acid sequence of EVQLVESGGGLVQPGGSLRLSCAASGFTFN (SEQ ID NO: 17); an FR-H2 comprising the amino acid sequence of WVRQAPGKGLEWIA (SEQ ID NO: 49); an FR-H3 comprising the amino acid sequence of RFTISRDDAKSSLYLQMNSLRAEDTAVYYCTR (SEQ ID NO: 19); and an FR-H4 comprising the amino acid sequence of WGQGTLVTVSS (SEQ ID NO: 12). In some instances, the VH domain comprises the amino acid sequence of SEQ ID NO: 50.

In another example, in some instances, the anti-IL-33 antibody may include one, two, three, or four of the following heavy chain framework regions: an FR-H1 comprising the amino acid sequence of EVQLVESGGGLVQPGGSLRLSCAASGFTFN (SEQ ID NO: 17); an FR-H2 comprising the amino acid sequence of WVRQAPGKGLEWIA (SEQ ID NO: 49); an FR-H3 comprising the amino acid sequence of RFTISRDDSKSTLYLQMNSLRAEDTAVYYCTR (SEQ ID NO: 51); and an FR-H4 comprising the amino acid sequence of WGQGTLVTVSS (SEQ ID NO: 12), or a combination of one or more of the above FRs and/or one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 12, 17, 49, and 51. In some instances, the anti-IL-33 antibody may include one, two, three, or four of the following heavy chain framework regions: an FR-H1 comprising the amino acid sequence of EVQLVESGGGLVQPGGSLRLSCAASGFTFN (SEQ ID NO: 17); an FR-H2 comprising the amino acid sequence of WVRQAPGKGLEWIA (SEQ ID NO: 49); an FR-H3 comprising the amino acid sequence of RFTISRDDSKSTLYLQMNSLRAEDTAVYYCTR (SEQ ID NO: 51); and an FR-H4 comprising the amino acid sequence of WGQGTLVTVSS (SEQ ID NO: 12). In some instances, the VH domain comprises the amino acid sequence of SEQ ID NO: 52.

Any of the anti-IL-33 antibodies provided herein may include one, two, three, or four of the following light chain framework regions: an FR-L1 comprising the amino acid sequence of $X_1IX_2X_3TQSPX_4X_5LSX_6SX_7GX_8X_9X_{10}X_{11}X_{12}X_{13}C$ (SEQ ID NO: 13), wherein $X_1$ is D or E; $X_2$ is Q or V; $X_3$ is M or L; $X_4$ is S or A; $X_5$ is S or T; $X_6$ is A or L; $X_7$ is V, P, or L; $X_8$ is D or E; $X_9$ is R or T; $X_{10}$ is V or A; $X_{11}$ is T or S; $X_{12}$ is I or L; and $X_{13}$ is T, S, or E; an FR-L2 comprising the amino acid sequence of $WX_1QQKX_2GX_3X_4PX_5X_6LIY$ (SEQ ID NO: 14), wherein $X_1$ is Y or F; $X_2$ is P or S; $X_3$ is K or Q; $X_4$ is S or A; $X_5$ is K, R, or Q; and $X_6$ is L or S; an FR-L3 comprising the amino acid sequence of $GX_1PX_2RFSGSGSGTX_3FX_4LX_5ISX_6X_7X_8PEDX_9AX_{10}YX_{11}C$ (SEQ ID NO: 15), wherein $X_1$ is V or I; $X_2$ is S or A; $X_3$ is D or R; $X_4$ is T or S; $X_5$ is T or K; $X_6$ is S or G; $X_7$ is L or M; $X_8$ is Q or E; $X_9$ is F, V, or E; $X_{10}$ is T, V, or D; and $X_{11}$ is F or Y; and an FR-L4 comprising the amino acid sequence of $FGX_1GTKX_2EIK$ (SEQ ID NO: 16), wherein $X_1$ is G or S and $X_2$ is V or L, or a combination of one or more of the above FRs and/or one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 13-16. In some instances, the anti-IL-33 antibody may include one, two, three, or four of the following light chain framework regions: an FR-L1 comprising the amino acid sequence of $X_1IX_2X_3TQSPX_4X_5LSX_6SX_7GX_8X_9X_{10}X_{11}X_{12}X_{13}C$ (SEQ ID NO: 13), wherein $X_1$ is D or E; $X_2$ is Q or V; $X_3$ is M or L; $X_4$ is S or A; $X_5$ is S or T; $X_6$ is A or L; $X_7$ is V, P, or L; $X_8$ is D or E; $X_9$ is R or T; $X_{10}$ is V or A; $X_{11}$ is T or S; $X_{12}$ is I or L; and $X_{13}$ is T, S, or E; an FR-L2 comprising the amino acid sequence of $WX_1QQKX_2GX_3X_4PX_5X_6LIY$ (SEQ ID NO: 14), wherein $X_1$ is Y or F; $X_2$ is P or S; $X_3$ is K or Q; $X_4$ is S or A; $X_5$ is K, R, or Q; and $X_6$ is L or S; an FR-L3 comprising the amino acid sequence of $GX_1PX_2RFSGSGSGTX_3FX_4LX_5ISX_6X_7X_8PEDX_9AX_{10}YX_{11}C$ (SEQ ID NO: 15), wherein $X_1$ is V or I; $X_2$ is S or A; $X_3$ is D or R; $X_4$ is T or S; $X_5$ is T or K; $X_6$ is S or G; $X_7$ is L or M; $X_8$ is Q or E; $X_9$ is F, V, or E; $X_{10}$ is T, V, or D; and $X_{11}$ is F or Y; and an FR-L4 comprising the amino acid sequence of $FGX_1GTKX_2EIK$ (SEQ ID NO: 16), wherein $X_1$ is G or S and $X_2$ is V or L.

For example, in some instances, the anti-IL-33 antibody may include one, two, three, or four of the following light chain framework regions: an FR-L1 comprising the amino acid sequence of DIQMTQSPSSLSASVGDRVTITC (SEQ ID NO: 21); an FR-L2 comprising the amino acid sequence of WYQQKPGKSPKLLIY (SEQ ID NO: 22); an FR-L3 comprising the amino acid sequence of GVPSRFSGSGSGTDFTLTISSLQPEDFATYFC (SEQ ID NO: 23); and an FR-L4 comprising the amino acid sequence of FGGGTKVEIK (SEQ ID NO: 24), or a combination of one or more of the above FRs and/or one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 21-24. In some instances, the anti-IL-33 antibody may include one, two, three, or four of the following light chain framework regions: an FR-L1 comprising the amino acid sequence of DIQMTQSPSSLSASVGDRVTITC (SEQ ID NO: 21); an FR-L2 comprising the amino acid sequence of WYQQKPGKSPKLLIY (SEQ ID NO: 22); an FR-L3 comprising the amino acid sequence of GVPSRFSGSGSGTDFTLTISSLQPEDFATYFC (SEQ ID NO: 23); and an FR-L4 comprising the amino acid sequence of FGGGTKVEIK (SEQ ID NO: 24). In some instances, the VL domain comprises the amino acid sequence of SEQ ID NO: 8.

For instance, the anti-IL-33 antibody may include (a) CDR-H1 comprising the amino acid sequence of NYWMT (SEQ ID NO: 1); (b) CDR-H2 comprising the amino acid sequence of SITYTGGGTYYPDSVKG (SEQ ID NO: 2); (c) CDR-H3 comprising the amino acid sequence of ANYYYNTYGGFPY (SEQ ID NO: 3); (d) CDR-L1 comprising the amino acid sequence of LASEGFSNDLA (SEQ ID NO: 4); (e) CDR-L2 comprising the amino acid sequence of AASRLQD (SEQ ID NO: 5); and (f) CDR-L3 comprising the amino acid sequence of QQGSKYPLT (SEQ ID NO: 6). In some instances, the anti-IL-33 antibody comprises (a) a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 7; (b) a light chain variable (VL) domain comprising an amino acid sequence having at least 90% sequence (e.g., at least 91%, 92%, 93%, 94%, 95%, 96%, 97%, 98%, or 99% sequence identity) to, or the sequence of, SEQ ID NO: 8; or (c) a VH domain as in (a) and a VL domain as in (b). In some instances, the anti-IL-33 antibody includes the following heavy chain framework regions: FR-H1 comprising the amino acid sequence of EVQLVESGGGLVQPGGSLRLSCAASGFTFN (SEQ ID NO: 17); FR-H2 comprising the amino acid sequence of WIRQAPGKGLEWVA (SEQ ID NO: 18); FR-H3 comprising the amino acid sequence of RFTISRDDAKSSLYLQMNSLRAEDTAVYYCTR (SEQ ID NO: 19); and FR-H4 comprising the amino acid sequence of WGQGTLVTVSS (SEQ ID NO: 12). In some instances, the anti-IL-33 antibody includes the following light chain framework regions: FR-L1 comprising the amino acid sequence of DIQMTQSPSSLSASVGDRVTITC (SEQ ID NO: 21); FR-L2 comprising the amino acid sequence of WYQQKPGKSPKLLIY (SEQ ID NO: 22); FR-L3 comprising the amino acid sequence of GVPSRFSGSGSGTDFTLTISSLQPEDFATYFC (SEQ ID NO: 23); and FR-L4 comprising the amino acid sequence of FGGGTKVEIK (SEQ ID NO: 24). In some instances, the anti-IL-33 antibody includes a binding domain comprising (a) a VH domain comprising an amino acid sequence of SEQ ID NO: 7 and (b) a VL domain comprising an amino acid sequence of SEQ ID NO: 8. In some instances, the exemplary anti-IL-33 antibody is 1E1v8.

For example, provided herein is an isolated antibody that specifically binds IL-33, or an antigen-binding fragment thereof, wherein the antibody comprises (a) a VH domain comprising an amino acid sequence of SEQ ID NO: 7 and (b) a VL domain comprising an amino acid sequence of SEQ ID NO: 8.

In another example, provided herein is an isolated antibody that specifically binds IL-33, or an antigen-binding fragment thereof, wherein the antibody comprises (a) a heavy chain (HC) comprising an amino acid sequence of SEQ ID NO: 25 and (b) a light chain (LC) comprising an amino acid sequence of SEQ ID NO: 26.

In another example, in some instances, the anti-IL-33 antibody may include one, two, three, or four of the following light chain framework regions: an FR-L1 comprising the amino acid sequence of DIQMTQSPSSLSASVGDRVTITC (SEQ ID NO: 21); an FR-L2 comprising the amino acid sequence of WFQQKPGKAPKSLIY (SEQ ID NO: 53); an FR-L3 comprising the amino acid sequence of GVPSRFSGSGSGTDFTLTISSLQPEDFATYYC (SEQ ID NO: 54); and an FR-L4 comprising the amino acid sequence of FGGGTKVEIK (SEQ ID NO: 24), or a combination of one or more of the above FRs and/or one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 21, 24, 53, and 54. In some instances, the anti-IL-33 antibody may include one, two, three, or four of the following light chain framework regions: an FR-L1 comprising the amino acid sequence of DIQMTQSPSSLSASVGDRVTITC (SEQ ID NO: 21); an FR-L2 comprising the amino acid sequence of WFQQKPGKAPKSLIY (SEQ ID NO: 53); an FR-L3 comprising the amino acid sequence of GVPSRFSGSGSGTDFTLTISSLQPEDFATYYC (SEQ ID NO: 54); and an FR-L4 comprising the amino acid sequence of FGGGTKVEIK (SEQ ID NO: 24). In some instances, the VL domain comprises the amino acid sequence of SEQ ID NO: 55.

In another example, in some instances, the anti-IL-33 antibody may include one, two, three, or four of the following light chain framework regions: an FR-L1 comprising the amino acid sequence of DIQMTQSPSSLSASVGDRVTITC (SEQ ID NO: 21); an FR-L2 comprising the amino acid sequence of WYQQKPGKAPKSLIY (SEQ ID NO: 56); an FR-L3 comprising the amino acid sequence of GVPSRFSGSGSGTDFTLTISSLQPEDFATYFC (SEQ ID NO: 23); and an FR-L4 comprising the amino acid sequence of FGGGTKVEIK (SEQ ID NO: 24), or a combination of one or more of the above FRs and/or one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 21, 23, 24 and 56. In some instances, the anti-IL-33 antibody may include one, two, three, or four of the following light chain framework regions: an FR-L1 comprising the amino acid sequence of DIQMTQSPSSLSASVGDRVTITC (SEQ ID NO: 21); an FR-L2 comprising the amino acid sequence of WYQQKPGKAPKSLIY (SEQ ID NO: 56); an FR-L3 comprising the amino acid sequence of GVPSRFSGSGSGTDFTLTISSLQPEDFATYFC (SEQ ID NO: 23); and an FR-L4 comprising the amino acid sequence of FGGGTKVEIK (SEQ ID NO: 24). In some instances, the VL domain comprises the amino acid sequence of SEQ ID NO: 57.

In another example, in some instances, the anti-IL-33 antibody may include one, two, three, or four of the following light chain framework regions: an FR-L1 comprising the amino acid sequence of DIQMTQSPSSLSASVGDRVTITC (SEQ ID NO: 21); an FR-L2 comprising the amino acid sequence of WFQQKPGKAPKSLIY (SEQ ID NO: 53); an FR-L3 comprising the amino acid sequence of GVPSRFSGSGSGTDFTLTISSLQPEDFATYFC (SEQ ID NO: 23); and an FR-L4 comprising the amino acid sequence of FGGGTKVEIK (SEQ ID NO: 24), or a combination of one or more of the above FRs and/or one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 21, 23, 24, and 53. In some instances, the anti-IL-33 antibody may include one, two, three, or four of the following light chain framework regions: an FR-L1 comprising the amino acid sequence of DIQMTQSPSSLSASVGDRVTITC (SEQ ID NO: 21); an FR-L2 comprising the amino acid sequence of WFQQKPGKAPKSLIY (SEQ ID NO: 53); an FR-L3 comprising the amino acid sequence of GVPSRFSGSGSGTDFTLTISSLQPEDFATYFC (SEQ ID NO: 23); and an FR-L4 comprising the amino acid sequence of FGGGTKVEIK (SEQ ID NO: 24). In some instances, the VL domain comprises the amino acid sequence of SEQ ID NO: 58.

In another example, in some instances, the anti-IL-33 antibody may include one, two, three, or four of the following light chain framework regions: an FR-L1 comprising the amino acid sequence of DIQMTQSPSSLSASVGDRVTITC (SEQ ID NO: 21); an FR-L2 comprising the amino acid sequence of WYQQKPGKAPKSLIY (SEQ ID NO: 56); an FR-L3 comprising the amino acid sequence of GVPSRFSGSGSGTDFTLTISSLQPEDFATYYC (SEQ ID NO: 54); and an FR-L4 comprising the amino acid sequence of FGGGTKVEIK (SEQ ID NO: 24), or a combination of one or more of the above FRs and/or one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 21, 24, 54 and 56. In some instances, the anti-IL-33 antibody may include one, two, three, or four of the following light chain framework regions: an FR-L1 comprising the amino acid sequence of DIQMTQSPSSLSASVGDRVTITC (SEQ ID NO: 21); an FR-L2 comprising the amino acid sequence of WYQQKPGKAPKSLIY (SEQ ID NO: 56); an FR-L3 comprising the amino acid sequence of GVPSRFSGSGSGTDFTLTISSLQPEDFATYYC (SEQ ID NO: 54); and an FR-L4 comprising the amino acid sequence of FGGGTKVEIK (SEQ ID NO: 24). In some instances, the VL domain comprises the amino acid sequence of SEQ ID NO: 59.

In another example, in some instances, the anti-IL-33 antibody may include one, two, three, or four of the following light chain framework regions: an FR-L1 comprising the amino acid sequence of DIQMTQSPSSLSASVGDRVTITC (SEQ ID NO: 21); an FR-L2 comprising the amino acid sequence of WYQQKPGKSPKLLIY (SEQ ID NO: 22); an FR-L3 comprising the amino acid sequence of GVPSRFSGSGSGTDFTLTISSLQPEDVATYYC (SEQ ID NO: 60); and an FR-L4 comprising the amino acid sequence of FGGGTKVEIK (SEQ ID NO: 24), or a combination of one or more of the above FRs and/or one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 21, 22, 24, and 60. In some instances, the anti-IL-33 antibody may include one, two, three, or four of the following light chain framework regions: an FR-L1 comprising the amino acid sequence of DIQMTQSPSSLSASVGDRVTITC (SEQ ID NO: 21); an FR-L2 comprising the amino acid sequence of WYQQKPGKSPKLLIY (SEQ ID NO: 22); an FR-L3 comprising the amino acid sequence of GVPSRFSGSGSGTDFTLTISSLQPEDVATYYC (SEQ ID NO: 60); and an FR-L4 comprising the amino acid sequence of FGGGTKVEIK (SEQ ID NO: 24). In some instances, the VL domain comprises the amino acid sequence of SEQ ID NO: 61.

For example, provided herein is an isolated antibody that specifically binds IL-33, or an antigen-binding fragment thereof, wherein the antibody comprises (a) a VH domain comprising an amino acid sequence of SEQ ID NO: 41 and (b) a VL domain comprising an amino acid sequence of SEQ ID NO: 55.

In another example, provided herein is an isolated antibody that specifically binds IL-33, or an antigen-binding fragment thereof, wherein the antibody comprises (a) a VH domain comprising an amino acid sequence of SEQ ID NO: 43 and (b) a VL domain comprising an amino acid sequence of SEQ ID NO: 55.

In another example, provided herein is an isolated antibody that specifically binds IL-33, or an antigen-binding fragment thereof, wherein the antibody comprises (a) a VH domain comprising an amino acid sequence of SEQ ID NO: 41 and (b) a VL domain comprising an amino acid sequence of SEQ ID NO: 8.

In another example, provided herein is an isolated antibody that specifically binds IL-33, or an antigen-binding fragment thereof, wherein the antibody comprises (a) a VH domain comprising an amino acid sequence of SEQ ID NO: 43 and (b) a VL domain comprising an amino acid sequence of SEQ ID NO: 8.

In another example, provided herein is an isolated antibody that specifically binds IL-33, or an antigen-binding fragment thereof, wherein the antibody comprises (a) a VH domain comprising an amino acid sequence of SEQ ID NO: 44 and (b) a VL domain comprising an amino acid sequence of SEQ ID NO: 8.

In another example, provided herein is an isolated antibody that specifically binds IL-33, or an antigen-binding fragment thereof, wherein the antibody comprises (a) a VH domain comprising an amino acid sequence of SEQ ID NO: 46 and (b) a VL domain comprising an amino acid sequence of SEQ ID NO: 8.

In another example, provided herein is an isolated antibody that specifically binds IL-33, or an antigen-binding fragment thereof, wherein the antibody comprises (a) a VH domain comprising an amino acid sequence of SEQ ID NO: 48 and (b) a VL domain comprising an amino acid sequence of SEQ ID NO: 8.

In another example, provided herein is an isolated antibody that specifically binds IL-33, or an antigen-binding fragment thereof, wherein the antibody comprises (a) a VH domain comprising an amino acid sequence of SEQ ID NO: 43 and (b) a VL domain comprising an amino acid sequence of SEQ ID NO: 57.

In another example, provided herein is an isolated antibody that specifically binds IL-33, or an antigen-binding fragment thereof, wherein the antibody comprises (a) a VH domain comprising an amino acid sequence of SEQ ID NO: 44 and (b) a VL domain comprising an amino acid sequence of SEQ ID NO: 57.

In another example, provided herein is an isolated antibody that specifically binds IL-33, or an antigen-binding fragment thereof, wherein the antibody comprises (a) a VH domain comprising an amino acid sequence of SEQ ID NO: 46 and (b) a VL domain comprising an amino acid sequence of SEQ ID NO: 57.

In another example, provided herein is an isolated antibody that specifically binds IL-33, or an antigen-binding fragment thereof, wherein the antibody comprises (a) a VH domain comprising an amino acid sequence of SEQ ID NO: 48 and (b) a VL domain comprising an amino acid sequence of SEQ ID NO: 57.

In another example, provided herein is an isolated antibody that specifically binds IL-33, or an antigen-binding fragment thereof, wherein the antibody comprises (a) a VH domain comprising an amino acid sequence of SEQ ID NO: 50 and (b) a VL domain comprising an amino acid sequence of SEQ ID NO: 57.

In another example, provided herein is an isolated antibody that specifically binds IL-33, or an antigen-binding fragment thereof, wherein the antibody comprises (a) a VH domain comprising an amino acid sequence of SEQ ID NO: 43 and (b) a VL domain comprising an amino acid sequence of SEQ ID NO: 58.

In another example, provided herein is an isolated antibody that specifically binds IL-33, or an antigen-binding fragment thereof, wherein the antibody comprises (a) a VH domain comprising an amino acid sequence of SEQ ID NO: 44 and (b) a VL domain comprising an amino acid sequence of SEQ ID NO: 58.

In another example, provided herein is an isolated antibody that specifically binds IL-33, or an antigen-binding fragment thereof, wherein the antibody comprises (a) a VH domain comprising an amino acid sequence of SEQ ID NO: 46 and (b) a VL domain comprising an amino acid sequence of SEQ ID NO: 58.

In another example, provided herein is an isolated antibody that specifically binds IL-33, or an antigen-binding fragment thereof, wherein the antibody comprises (a) a VH domain comprising an amino acid sequence of SEQ ID NO: 48 and (b) a VL domain comprising an amino acid sequence of SEQ ID NO: 58.

In another example, provided herein is an isolated antibody that specifically binds IL-33, or an antigen-binding fragment thereof, wherein the antibody comprises (a) a VH domain comprising an amino acid sequence of SEQ ID NO: 50 and (b) a VL domain comprising an amino acid sequence of SEQ ID NO: 58.

In another example, provided herein is an isolated antibody that specifically binds IL-33, or an antigen-binding fragment thereof, wherein the antibody comprises (a) a VH domain comprising an amino acid sequence of SEQ ID NO: 43 and (b) a VL domain comprising an amino acid sequence of SEQ ID NO: 59.

In another example, provided herein is an isolated antibody that specifically binds IL-33, or an antigen-binding fragment thereof, wherein the antibody comprises (a) a VH domain comprising an amino acid sequence of SEQ ID NO: 44 and (b) a VL domain comprising an amino acid sequence of SEQ ID NO: 59.

In another example, provided herein is an isolated antibody that specifically binds IL-33, or an antigen-binding fragment thereof, wherein the antibody comprises (a) a VH domain comprising an amino acid sequence of SEQ ID NO: 46 and (b) a VL domain comprising an amino acid sequence of SEQ ID NO: 59.

In another example, provided herein is an isolated antibody that specifically binds IL-33, or an antigen-binding fragment thereof, wherein the antibody comprises (a) a VH domain comprising an amino acid sequence of SEQ ID NO: 48 and (b) a VL domain comprising an amino acid sequence of SEQ ID NO: 59.

In another example, provided herein is an isolated antibody that specifically binds IL-33, or an antigen-binding fragment thereof, wherein the antibody comprises (a) a VH domain comprising an amino acid sequence of SEQ ID NO: 50 and (b) a VL domain comprising an amino acid sequence of SEQ ID NO: 59.

In another example, provided herein is an isolated antibody that specifically binds IL-33, or an antigen-binding fragment thereof, wherein the antibody comprises (a) a VH domain comprising an amino acid sequence of SEQ ID NO: 52 and (b) a VL domain comprising an amino acid sequence of SEQ ID NO: 61.

In another example, provided herein is an anti-IL-33 antibody that includes (a) a VH domain comprising an amino acid sequence having at least 90% sequence identity (e.g., at least 91%, 92%, 93%, 94%, 95%, 96%, 97%, 98%, or 99% sequence identity) to, or the sequence of, the amino acid sequence of SEQ ID NO: 35; (b) a VL domain comprising an amino acid sequence having at least 90% sequence identity (e.g., at least 91%, 92%, 93%, 94%, 95%, 96%, 97%, 98%, or 99% sequence identity) to, or the sequence of, the amino acid sequence of SEQ ID NO: 36; or (c) a VH domain as in (a) and a VL domain as in (b).

In another example, in some instances, the anti-IL-33 antibody may include one, two, three, or four of the following heavy chain framework regions: an FR-H1 comprising the amino acid sequence of EVQLVESGGGLVQPGT-SLKLSCLASGFTFN (SEQ ID NO: 27); an FR-H2 comprising the amino acid sequence of WIRQAPGKGLEWIA (SEQ ID NO: 28); an FR-H3 comprising the amino acid sequence of RFTISRDDAKSTLYLQMNSLRSED-TATYYCTR (SEQ ID NO: 29); and an FR-H4 comprising the amino acid sequence of WGQGTLVTVSS (SEQ ID NO: 12), or a combination of one or more of the above FRs and/or one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 12, 27, 28, and 29. In some instances, the anti-IL-33 antibody may include one, two, three, or four of the following heavy chain framework regions: an FR-H1 comprising the amino acid sequence of EVQLVESGGGLVQPGT-SLKLSCLASGFTFN (SEQ ID NO: 27); an FR-H2 comprising the amino acid sequence of WIRQAPGKGLEWIA (SEQ ID NO: 28); an FR-H3 comprising the amino acid sequence of RFTISRDDAKSTLYLQMNSLRSED-TATYYCTR (SEQ ID NO: 29); and an FR-H4 comprising the amino acid sequence of WGQGTLVTVSS (SEQ ID NO: 12). In some instances, the VH domain comprises the amino acid sequence of SEQ ID NO: 35.

In another example, in some instances, the anti-IL-33 antibody may include one, two, three, or four of the following light chain framework regions: an FR-L1 comprising the amino acid sequence of DIQMTQSPASLSASLGETVSIEC (SEQ ID NO: 31); an FR-L2 comprising the amino acid sequence of WYQQKSGKSPQLLIY (SEQ ID NO: 32); an FR-L3 comprising the amino acid sequence of GVPSRFSGSGSGTRFSLKISGMQPEDEADYFC (SEQ ID NO: 33); and an FR-L4 comprising the amino acid sequence of FGSGTKLEIK (SEQ ID NO: 34), or a combination of one or more of the above FRs and/or one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 31-34. In some instances, the anti-IL-33 antibody may include one, two, three, or four of the following light chain framework regions: an FR-L1 comprising the amino acid sequence of DIQMTQSPASLSASLGETVSIEC (SEQ ID NO: 31); an FR-L2 comprising the amino acid sequence of WYQQKSGKSPQLLIY (SEQ ID NO: 32); an FR-L3 comprising the amino acid sequence of GVPSRFSGSGSGTRFSLKISGMQPEDEADYFC (SEQ ID NO: 33); and an FR-L4 comprising the amino acid sequence of FGSGTKLEIK (SEQ ID NO: 34). In some instances, the VL domain comprises the amino acid sequence of SEQ ID NO: 36.

For example, provided herein is an isolated antibody that specifically binds IL-33, or an antigen-binding fragment thereof, wherein the antibody comprises (a) a VH domain comprising an amino acid sequence of SEQ ID NO: 35 and (b) a VL domain comprising an amino acid sequence of SEQ ID NO: 36.

For example, provided herein is an isolated antibody that specifically binds IL-33, wherein the antibody comprises (a) a heavy chain (HC) comprising an amino acid sequence of SEQ ID NO: 37 and (b) a light chain (LC) comprising an amino acid sequence of SEQ ID NO: 38.

In another example, provided herein is an anti-IL-33 antibody that includes (a) a VH domain comprising an amino acid sequence having at least 90% sequence identity (e.g., at least 91%, 92%, 93%, 94%, 95%, 96%, 97%, 98%, or 99% sequence identity) to, or the sequence of, the amino acid sequence of SEQ ID NO: 65; (b) a VL domain comprising an amino acid sequence having at least 90% sequence identity (e.g., at least 91%, 92%, 93%, 94%, 95%, 96%, 97%, 98%, or 99% sequence identity) to, or the sequence of, the amino acid sequence of SEQ ID NO: 69; or (c) a VH domain as in (a) and a VL domain as in (b).

In another example, in some instances, the anti-IL-33 antibody may include one, two, three, or four of the following heavy chain framework regions: an FR-H1 comprising the amino acid sequence of EVQLVQSGAEVKKPGASVKVSCKASGFTFN (SEQ ID NO: 62); an FR-H2 comprising the amino acid sequence of WVRQAPGQGLEWMG (SEQ ID NO: 63); an FR-H3 comprising the amino acid sequence of RVTMTRDTSTSTVYMELSSLRSEDTAVYYCTR (SEQ ID NO: 64); and an FR-H4 comprising the amino acid sequence of WGQGTLVTVSS (SEQ ID NO: 12), or a combination of one or more of the above FRs and/or one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 12 and 62-64. In some instances, the anti-IL-33 antibody may include one, two, three, or four of the following heavy chain framework regions: an FR-H1 comprising the amino acid sequence of EVQLVQSGAEVKKPGASVKVSCKASGFTFN (SEQ ID NO: 62); an FR-H2 comprising the amino acid sequence of WVRQAPGQGLEWMG (SEQ ID NO: 63); an FR-H3 comprising the amino acid sequence of RVTMTRDTSTSTVYMELSSLRSEDTAVYYCTR (SEQ ID NO: 64); and an FR-H4 comprising the amino acid sequence of WGQGTLVTVSS (SEQ ID NO: 12). In some instances, the VH domain comprises the amino acid sequence of SEQ ID NO: 65.

In another example, in some instances, the anti-IL-33 antibody may include one, two, three, or four of the following light chain framework regions: an FR-L1 comprising the amino acid sequence of EIVLTQSPATLSLSPGERATLSC (SEQ ID NO: 66); an FR-L2 comprising the amino acid sequence of WYQQKPGQAPRLLIY (SEQ ID NO: 67); an FR-L3 comprising the amino acid sequence of GIPARFSGSGSGTDFTLTISSLEPEDFAVYYC (SEQ ID NO: 68); and an FR-L4 comprising the amino acid sequence of FGGGTKVEIK (SEQ ID NO: 24), or a combination of one or more of the above FRs and/or one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 24 and 66-68. In some instances, the anti-IL-33 antibody may include one, two, three, or four of the following light chain framework regions: an FR-L1 comprising the amino acid sequence of EIVLTQSPATLSLSPGERATLSC (SEQ ID NO: 66); an FR-L2 comprising the amino acid sequence of WYQQKPGQAPRLLIY (SEQ ID NO: 67); an FR-L3 comprising the amino acid sequence of GIPARFSGSGSGTDFTLTISSLEPEDFAVYYC (SEQ ID NO: 68); and an FR-L4 comprising the amino acid sequence of FGGGTKVEIK (SEQ ID NO: 24). In some instances, the VL domain comprises the amino acid sequence of SEQ ID NO: 69.

For example, provided herein is an isolated antibody that specifically binds IL-33, or an antigen-binding fragment thereof, wherein the antibody comprises (a) a VH domain comprising an amino acid sequence of SEQ ID NO: 65 and (b) a VL domain comprising an amino acid sequence of SEQ ID NO: 69.

Any of the antibodies provided herein may specifically bind human or cynomolgus monkey (cyno) IL-33. In some instances, the antibody specifically binds both human and cyno IL-33. In certain instances, an anti-IL-33 antibody provided herein specifically binds both human and cyno IL-33 with a $K_D$ of 100 nM or lower (e.g., 100 nM or lower, 10 nM or lower, 1 nM or lower, 100 pM or lower, 10 pM or lower, 1 pM or lower, or 0.1 pM or lower).

In some instances, the antibody specifically binds human IL-33 with a $K_D$ of 1 nM or lower (e.g., 1 nm or lower, 100 pM or lower, 10 pM or lower, 1 pM or lower, or 0.1 pM or lower). For example, in some instances, the antibody specifically binds human IL-33 with a $K_D$ between 100 fM and 1 nM. For example, in some instances, the antibody specifically binds human IL-33 with a $K_D$ between 100 fM and 1 nM. In another example, in some instances, the antibody specifically binds human IL-33 with a $K_D$ between 750 fM and 300 pM. In another example, in some instances, the antibody specifically binds human IL-33 with a $K_D$ between 1 pM and 200 pM. In some instances, the antibody specifically binds human IL-33 with a $K_D$ of 118 pM. In other instances, the antibody specifically binds human IL-33 with a $K_D$ of 15 pM.

In some instances, the antibody specifically binds cyno IL-33 with a $K_D$ of 1 nM or lower (e.g., 1 nm or lower, 100 pM or lower, 10 pM or lower, 1 pM or lower, or 0.1 pM or lower). For example, in some instances, the antibody specifically binds cyno IL-33 with a $K_D$ between 100 fM and 1 nM. In another example, in some instances, the antibody specifically binds cyno IL-33 with a $K_D$ between 1 pM and 500 pM. In another example, in some instances, the antibody specifically binds cyno IL-33 with a $K_D$ between 20 pM and 50 pM. In some instances, the antibody specifically binds cyno IL-33 with a $K_D$ of 35 pM.

In certain instances, the antibody specifically binds both human and cyno IL-33 with a $K_D$ of 1 nM or lower (e.g., 1 nm or lower, 100 pM or lower, 10 pM or lower, 1 pM or lower, or 0.1 pM or lower). For example, in some instances, the antibody specifically binds both human and cyno IL-33 with a $K_D$ of between 1 pM and 500 pM. In some instances, the antibody specifically binds both human and cyno IL-33 with a $K_D$ of between 10 pM and 40 pM.

For example, in some instances, the antibody specifically binds human IL-33 with a $K_D$ of between about 1 pM and about 1 nM (e.g., between about 1 pM and about 900 pM, between about 1 pM and about 800 pM, between about 1 pM and about 700 pM, between about 1 pM and about 600 pM, between about 1 pM and about 500 pM, between about 1 pM and about 400 pM, between about 1 pM and about 300 pM, between about 1 pM and about 200 pM, between about 1 pM and about 190 pM, between about 1 pM and about 180 pM, between about 1 pM and about 170 pM, between about 1 pM and about 160 pM, between about 1 pM and about 150 pM, between about 1 pM and about 140 pM, between about 1 pM and about 130 pM, between about 1 pM and about 120 pM, between about 1 pM and about 110 pM, between about 1 pM and about 100 pM, between about 1 pM and about 90 pM, between about 1 pM and about 80 pM, between about 1 pM and about 70 pM, between about 1 pM and about 60 pM, between about 1 pM and about 50 pM, between about 1 pM and about 40 pM, between about 1 pM and about 30 pM, between about 1 pM and about 20 pM, or between about 1 pM and about 10 pM). In some instances, the antibody specifically binds human IL-33 with a $K_D$ of between about 1 pM and about 250 pM (e.g., between about 1 pM and about 250 pM, between about 1 pM and about 225 pM, between about 1 pM and about 200 pM, between about 1 pM and about 190 pM, between about 1 pM and about 180 pM, between about 1 pM and about 170 pM, between about 1 pM and about 160 pM, between about 1 pM and about 150 pM, between about 1 pM and about 140 pM, between about 1 pM and about 130 pM, between about 1 pM and about 120 pM, between about 1 pM and about 110 pM, between about 1 pM and about 100 pM, between about 1 pM and about 90 pM, between about 1 pM and about 80 pM, between about 1 pM and about 70 pM, between about 1 pM and about 60 pM, between about 1 pM and about 50 pM, between about 1 pM and about 40 pM, between about 1 pM and about 30 pM, between about 1 pM and about 20 pM, or between about 1 pM and about 10 pM). In some instances, the antibody specifically binds human IL-33 with a $K_D$ of between about 50 pM and about 180 pM (e.g., about 50 pM, about 60 pM, about 70 pM, about 80 pM, about 90 pM, about 100 pM, about 110 pM, about 120 pM, about 130 pM, about 140 pM, about 150 pM, about 160 pM, or about 180 pM). In some instances, the antibody specifically binds human IL-33 with a $K_D$ of 118 pM. In other instances, the antibody specifically binds human IL-33 with a $K_D$ of 15 pM. Any of the preceding $K_D$ values may be determined by surface plasmon resonance, for example, as described herein (see, e.g., the Examples, including Examples 4, 6, and 7).

In some instances, the antibody specifically binds human IL-33 with a $K_D$ of about 400 pM or lower at 25° C. For example, in some instances, the antibody specifically binds human IL-33 with a $K_D$ of about 390 pM or lower, about 380 pM or lower, about 375 pM or lower, about 350 pM or lower, about 325 pM or lower, about 300 pM or lower, about 275 pM or lower, about 250 pM or lower, about 250 pM or lower, about 225 pM or lower, about 200 pM or lower, about 175 pM or lower, about 150 pM or lower, about 130 pM or lower, about 125 pM or lower, about 100 pM or lower, about 75 pM or lower, about 50 pM or lower, about 25 pM or lower, about 20 pM or lower at 25° C., about 15 pM or lower at 25° C., about 10 pM or lower at 25° C., or about 5 pM or lower at 25° C. In some instances, the antibody specifically binds human IL-33 with a $K_D$ of about 1 pM to about 150 pM (e.g., about 1 pM, about 5 pM, about 10 pM, about 15 pM, about 20 pM, about 30 pM, about 40 pM, about 50 pM, about 60 pM, about 70 pM, about 80 pM, about 90 pM, about 100 pM, about 110 pM, about 120 pM, about 130 pM, about 140 pM, or about 150 pM) at 25° C. In some instances, the antibody specifically binds human IL-33 with a $K_D$ of about 15 pM at 25° C. The antibody may be a Fab fragment. In some instances, any of the preceding $K_D$ values may be determined by surface plasmon resonance, for example, as described herein (see, e.g., the Examples, including Examples 4, 6, and 7).

In some instances, the antibody specifically binds human IL-33 with a $K_D$ of about 400 pM or lower at 37° C. For example, in some instances, the antibody specifically binds human IL-33 with a $K_D$ of about 390 pM or lower, about 380 pM or lower, about 375 pM or lower, about 350 pM or lower, about 325 pM or lower, about 300 pM or lower, about 275 pM or lower, about 250 pM or lower, about 250 pM or lower, about 225 pM or lower, about 200 pM or lower, about 175 pM or lower, about 150 pM or lower, about 130 pM or lower, about 125 pM or lower, about 100 pM or lower, about 75 pM or lower, about 50 pM or lower, about 25 pM or lower, about 20 pM or lower, about 15 pM or lower, about 10 pM or lower, or about 5 pM or lower at 37° C. In some instances, the antibody specifically binds human IL-33 with a $K_D$ of about 1 pM to about 150 pM (e.g., about 1 pM, about 5 pM, about 10 pM, about 15 pM, about 20 pM, about 30 pM, about 40 pM, about 50 pM, about 60 pM, about 70 pM, about 80 pM, about 90 pM, about 100 pM, about 110 pM, about 120 pM, about 130 pM, about 140 pM, or about 150 pM) at 37° C. In some instances, the antibody specifically binds human IL-33 with a $K_D$ of about 15 pM at 37° C. The antibody may be a Fab fragment. In some instances, any of the preceding $K_D$ values may be determined by surface plasmon resonance, for example, as described herein (see, e.g., the Examples, including Examples 4, 6, and 7).

In some instances, the antibody specifically binds cyno IL-33 with a $K_D$ of between about 1 pM and about 1 nM (e.g., between about 1 pM and about 900 pM, between about 1 pM and about 800 pM, between about 1 pM and about 700 pM, between about 1 pM and about 600 pM, between about 1 pM and about 500 pM, between about 1 pM and about 400 pM, between about 1 pM and about 300 pM, between about 1 pM and about 200 pM, between about 1 pM and about 190 pM, between about 1 pM and about 180 pM, between about 1 pM and about 170 pM, between about 1 pM and about 160 pM, between about 1 pM and about 150 pM, between about 1 pM and about 140 pM, between about 1 pM and about 130 pM, between about 1 pM and about 120 pM, between about 1 pM and about 110 pM, between about 1 pM and about 100 pM, between about 1 pM and about 90 pM, between about 1 pM and about 80 pM, between about 1 pM and about 70 pM, between about 1 pM and about 60 pM, between about 1 pM and about 50 pM, between about 1 pM and about 40 pM, between about 1 pM and about 30 pM, between about 1 pM and about 20 pM, or between about 1 pM and about 10 pM). In some instances, the antibody specifically binds cyno IL-33 with a $K_D$ of between about 100 pM and about 750 pM (e.g., between about 100 pM and about 750 pM, between about 200 pM and about 750 pM, between about 225 pM and about 750 pM, between about 250 pM and about 750 pM, between about 265 pM and about 750 pM, between about 275 pM and about 750 pM, between about 300 pM and about 750 pM, between about 325 pM and about 750 pM, between about 350 pM and about 750 pM, between about 375 pM and about 750 pM, between about 400 pM and about 750 pM, between about 425 pM and about 750 pM, between about 450 pM and about 750 pM, between about 475 pM and about 750 pM, between about 500 pM and about 750 pM, between about 525 pM and about 750 pM, between about 550 pM and about 750 pM, between about 575 pM and about 750 pM, between about 600 pM and about 750 pM, between about 650 pM and about 750 pM, or between about 250 pM and about 650 pM). In some instances, any of the preceding $K_D$ values may be determined by surface plasmon resonance, for example, as described herein (see, e.g., the Examples, including Examples 4, 6, and 7).

In some instances, the antibody specifically binds cyno IL-33 with a $K_D$ of about 400 pM or lower at 25° C. For example, in some instances, the antibody specifically binds cyno IL-33 with a $K_D$ of about 390 pM or lower, about 380 pM or lower, about 375 pM or lower, about 350 pM or lower, about 325 pM or lower, about 300 pM or lower, about 275 pM or lower, about 250 pM or lower, about 250 pM or lower, about 225 pM or lower, about 200 pM or lower, about 175 pM or lower, about 150 pM or lower, about 130 pM or lower, about 125 pM or lower, about 100 pM or lower, about 75 pM or lower, about 50 pM or lower, about 25 pM or lower, about 20 pM or lower at 25° C., about 15 pM or lower at 25° C., about 10 pM or lower at 25° C., or about 5 pM or lower at 25° C. In some instances, the antibody specifically binds cyno IL-33 with a $K_D$ of about 1 pM to about 150 pM (e.g., about 1 pM, about 5 pM, about 10 pM, about 15 pM, about 20 pM, about 30 pM, about 40 pM, about 50 pM, about 60 pM, about 70 pM, about 80 pM, about 90 pM, about 100 pM, about 110 pM, about 120 pM, about 130 pM, about 140 pM, or about 150 pM) at 25° C. In some instances, the antibody specifically binds cyno IL-33 with a $K_D$ of about 22 pM at 25° C. The antibody may be a Fab fragment. In some instances, any of the preceding $K_D$ values may be determined by surface plasmon resonance, for example, as described herein (see, e.g., the Examples, including Examples 4, 6, and 7).

In some instances, the antibody specifically binds cyno IL-33 with a $K_D$ of about 400 pM or lower at 37° C. For example, in some instances, the antibody specifically binds cyno IL-33 with a $K_D$ of about 390 pM or lower, about 380 pM or lower, about 375 pM or lower, about 350 pM or lower, about 325 pM or lower, about 300 pM or lower, about 275 pM or lower, about 250 pM or lower, about 250 pM or lower, about 225 pM or lower, about 200 pM or lower, about 175 pM or lower, about 150 pM or lower, about 130 pM or lower, about 125 pM or lower, about 100 pM or lower, about 75 pM or lower, about 50 pM or lower, about 25 pM or lower, about 20 pM or lower, about 15 pM or lower, about 10 pM or lower, or about 5 pM or lower at 37° C. In some instances, the antibody specifically binds cyno IL-33 with a $K_D$ of about 1 pM to about 150 pM (e.g., about 1 pM, about 5 pM, about 10 pM, about 15 pM, about 20 pM, about 30 pM, about 40 pM, about 50 pM, about 60 pM, about 70 pM, about 80 pM, about 90 pM, about 100 pM, about 110 pM, about 120 pM, about 130 pM, about 140 pM, or about 150 pM) at 37° C. In some instances, the antibody specifically binds cyno IL-33 with a $K_D$ of about 34 pM at 37° C. The antibody may be a Fab fragment. In some instances, any of the preceding $K_D$ values may be determined by surface plasmon resonance, for example, as described herein (see, e.g., the Examples, including Examples 4, 6, and 7).

In some instances, an anti-IL-33 antibody provided herein is capable of inhibiting the binding of IL-33 to an IL-33 receptor. In some instances, the inhibiting is measured using a cell-based blocking assay. In some instances, the antibody inhibits the binding of human IL-33 to an IL-33 receptor with a half-maximal inhibitory concentration (IC50) of between about 750 fM and about 250 pM (e.g., between about 750 fM and about 250 pM, between about 1 pM and about 250 pM, between about 1 pM and about 100 pM, between about 1 pM and about 50 pM, between about 1 pM and about 10 pM, or between about 1 pM and about 5 pM). In some instances, the antibody inhibits the binding of human IL-33 to an IL-33 receptor with an IC50 of about 50 pM or below (e.g., about 50 pM or below, about 40 pM or below, about 30 pM or below, about 20 pM or below, about 15 pM or below, about 10 pM or below, about 9 pM or below, about 8 pM or below, about 7 pM or below, about 6 pM or below, about 5 pM or below, about 4 pM or below, about 3 pM or below, about 2.5 pM or below, about 2 pM or below, about 1 pM or below, about 900 fM or below, about 800 fM or below, or about 750 fM or below). In some instances, the antibody inhibits the binding of human IL-33 to an IL-33 receptor with an IC50 of between about 1 pM and about 50 pM. In some instances, the antibody inhibits the binding of human IL-33 to an IL-33 receptor with an IC50 of about 31 pM. In some instances, the inhibiting is measured using a cell-based blocking assay using HEK-BLUE™ cells, for example, as described herein (see, e.g., the Examples, including Examples 3 and 6).

In some instances, the antibody inhibits the binding of cyno IL-33 to an IL-33 receptor with an IC50 of between about 1 nM and about 10 nM (e.g., between about 1 nM and about 10 nM, between about 1 nM and about 9 nM, between about 1 nM and about 8 nM, between about 1 nM and about 7 nM, between about 1 nM and about 6 nM, between about 1 nM and about 5 nM, between about 1 nM and about 4 nM, or between about 1 nM and about 3 nM). In some instances, the inhibiting is measured using a cell-based blocking assay using HEK-BLUE™ cells, for example, as described herein (see, e.g., the Examples, including Examples 3 and 6).

Any of the antibodies provided herein may have a viscosity of less than about 10 centipoise (cP), e.g., at a concentration of about 100 mg/mL, about 110 mg/mL, about 120 mg/mL, about 130 mg/mL, about 140 mg/mL, about 150 mg/mL, about 160 mg/mL, about 170 mg/mL, about 180 mg/mL, about 190 mg/mL, about 200 mg/mL, about 210 mg/mL, about 220 mg/mL, about 230 mg/mL, about 240 mg/mL, about 250 mg/mL, about 260 mg/mL, about 270 mg/mL, about 280 mg/mL, about 290 mg/mL, about 300 mg/mL, about 310 mg/mL, about 320 mg/mL, about 330 mg/mL, about 340 mg/mL, about 350 mg/mL, about 360 mg/mL, about 370 mg/mL, about 380 mg/mL, about 390 mg/mL, or about 400 mg/mL.

For example, in some instances, the antibody has a viscosity of less than about 10 cP, less than about 9.5 cP, less than about 9 cP, less than about 8.5 cP, less than about 8 cP, less than about 7.5 cP, less than about 7 cP, less than about 6.5 cP, less than about 6 cP, less than about 5.5 cP, less than about 5 cP, less than about 4.5 cP, less than about 4 cP, less than about 3.5 cP, less than about 3 cP, less than about 2.5 cP, less than about 2 cP, less than about 1.5 cP, less than about 1 cP, or less than about 0.5 cP, e.g., at a concentration of about 100 mg/mL, about 110 mg/mL, about 120 mg/mL, about 130 mg/mL, about 140 mg/mL, about 150 mg/mL, about 160 mg/mL, about 170 mg/mL, about 180 mg/mL, about 190 mg/mL, about 200 mg/mL, about 210 mg/mL, about 220 mg/mL, about 230 mg/mL, about 240 mg/mL, about 250 mg/mL, about 260 mg/mL, about 270 mg/mL, about 280 mg/mL, about 290 mg/mL, about 300 mg/mL, about 310 mg/mL, about 320 mg/mL, about 330 mg/mL, about 340 mg/mL, about 350 mg/mL, about 360 mg/mL, about 370 mg/mL, about 380 mg/mL, about 390 mg/mL, or about 400 mg/mL. In some instances, the antibody has a viscosity of less than about 10 cP, less than about 9.5 cP, less than about 9 cP, less than about 8.5 cP, less than about 8 cP, less than about 7.5 cP, less than about 7 cP, less than about 6.5 cP, less than about 6 cP, less than about 5.5 cP, less than about 5 cP, less than about 4.5 cP, less than about 4 cP, less than about 3.5 cP, less than about 3 cP, less than about 2.5 cP, less than about 2 cP, less than about 1.5 cP, less than about 1 cP, or less than about 0.5 cP, e.g., at a concentration of about 180 mg/mL.

For example, in some instances, an antibody provided herein may have a viscosity of less than about 5 cP, e.g., at a concentration of about 100 mg/mL or higher (e.g., about 100 mg/mL, about 110 mg/mL, about 120 mg/mL, about 130 mg/mL, about 140 mg/mL, about 150 mg/mL, about 160 mg/mL, about 170 mg/mL, about 180 mg/mL, about 190 mg/mL, about 200 mg/mL, about 210 mg/mL, about 220 mg/mL, about 230 mg/mL, about 240 mg/mL, about 250 mg/mL, about 260 mg/mL, about 270 mg/mL, about 280 mg/mL, about 290 mg/mL, about 300 mg/mL, about 310 mg/mL, about 320 mg/mL, about 330 mg/mL, about 340 mg/mL, about 350 mg/mL, about 360 mg/mL, about 370 mg/mL, about 380 mg/mL, about 390 mg/mL, or about 400 mg/mL). In some instances, the antibody has a viscosity of between about 0.5 cP and about 5 cP, between about 0.5 cP and about 4.5 cP, between about 0.5 cP and about 4 cP, between about 0.5 cP and about 3.5 cP, between about 0.5 cP and about 3 cP, between about 0.5 cP and about 2.5 cP, between about 0.5 cP and about 2 cP, between about 0.5 cP and about 1.5 cP, between about 0.5 cP and about 1 cP, between about 1 cP and about 5 cP, between about 1 cP and about 4.5 cP, between about 1 cP and about 4 cP, between about 1 cP and about 3.5 cP, between about 1 cP and about 3 cP, between about 1 cP and about 2.5 cP, between about 1 cP and about 2 cP, between about 1 cP and about 1.5 cP, between about 1.5 cP and about 5 cP, between about 1.5 cP and about 4.5 cP, between about 1.5 cP and about 4 cP, between about 1.5 cP and about 3.5 cP, between about 1.5 cP and about 3 cP, between about 1.5 cP and about 2.5 cP, between about 1.5 cP and about 2 cP, between about 2 cP and about 5 cP, between about 2 cP and about 4.5 cP, between about 2 cP and about 4 cP, between about 2 cP and about 3.5 cP, between about 2 cP and about 3 cP, between about 2 cP and about 2.5 cP, between about 2.5 cP and about 5 cP, between about 2.5 cP and about 4.5 cP, between about 2.5 cP and about 4 cP, between about 2.5 cP and about 3.5 cP, between about 2.5 cP and about 3 cP, between about 3 cP and about 5 cP, between about 3 cP and about 4.5 cP, between about 3 cP and about 4 cP, between about 3 cP and about 3.5 cP, between about 3.5 cP and about 5 cP, between about 3.5 cP and about 4.5 cP, between about 3.5 cP and about 4 cP, between about 4 cP and about 5 cP, between about 4 cP and about 4.5 cP, or between about 4.5 cP and about 5 cP, e.g., at a concentration of about 180 mg/mL.

about 300 mg/mL, about 310 mg/mL, about 320 mg/mL, about 330 mg/mL, about 340 mg/mL, about 350 mg/mL, about 360 mg/mL, about 370 mg/mL, about 380 mg/mL, about 390 mg/mL, or about 400 mg/mL.

In some instances, the antibody has a viscosity of between about 0.5 cP and about 5 cP, between about 0.5 cP and about 4.5 cP, between about 0.5 cP and about 4 cP, between about 0.5 cP and about 3.5 cP, between about 0.5 cP and about 3 cP, between about 0.5 cP and about 2.5 cP, between about 0.5 cP and about 2 cP, between about 0.5 cP and about 1.5 cP, between about 0.5 cP and about 1 cP, between about 1 cP and about 5 cP, between about 1 cP and about 4.5 cP, between about 1 cP and about 4 cP, between about 1 cP and about 3.5 cP, between about 1 cP and about 3 cP, between about 1 cP and about 2.5 cP, between about 1 cP and about 2 cP, between about 1 cP and about 1.5 cP, between about 1.5 cP and about 5 cP, between about 1.5 cP and about 4.5 cP, between about 1.5 cP and about 4 cP, between about 1.5 cP and about 3.5 cP, between about 1.5 cP and about 3 cP, between about 1.5 cP and about 2.5 cP, between about 1.5 cP and about 2 cP, between about 2 cP and about 5 cP, between about 2 cP and about 4.5 cP, between about 2 cP and about 4 cP, between about 2 cP and about 3.5 cP, between about 2 cP and about 3 cP, between about 2 cP and about 2.5 cP, between about 2.5 cP and about 5 cP, between about 2.5 cP and about 4.5 cP, between about 2.5 cP and about 4 cP, between about 2.5 cP and about 3.5 cP, between about 2.5 cP and about 3 cP, between about 3 cP and about 5 cP, between about 3 cP and about 4.5 cP, between about 3 cP and about 4 cP, between about 3 cP and about 3.5 cP, between about 3.5 cP and about 5 cP, between about 3.5 cP and about 4.5 cP, between about 3.5 cP and about 4 cP, between about 4 cP and about 5 cP, between about 4 cP and about 4.5 cP, or between about 4.5 cP and about 5 cP, e.g., at a concentration of about 180 mg/mL.

In particular instances, the antibody may have a viscosity of about 4.6 cP at a concentration of about 180 mg/mL.

Any of the antibodies provided herein may have a turbidity (OD) of about 1 or lower, e.g., at a concentration of about 100 mg/mL or higher (e.g., about 100 mg/mL or higher, about 110 mg/mL or higher, about 120 mg/mL or higher, about 130 mg/mL or higher, about 140 mg/mL or higher, about 140 mg/mL or higher, about 150 mg/mL or higher, about 160 mg/mL or higher, about 170 mg/mL or higher, about 180 mg/mL or higher, about 190 mg/mL or higher, about 200 mg/mL or higher, about 210 mg/mL or higher, about 220 mg/mL or higher, about 230 mg/mL or higher, about 240 mg/mL or higher, about 250 mg/mL or higher, about 260 mg/mL or higher, about 270 mg/mL or higher, about 280 mg/mL or higher, about 290 mg/mL or higher, about 300 mg/mL or higher, about 310 mg/mL or higher, about 320 mg/mL or higher, about 330 mg/mL or higher, about 340 mg/mL or higher, about 350 mg/mL or higher, about 360 mg/mL or higher, about 370 mg/mL or higher, about 380 mg/mL or higher, about 390 mg/mL or higher, or about 400 mg/mL or higher), e.g., in any suitable buffer (e.g., phosphate-buffered saline (PBS) pH 7.4). For example, any of the antibodies provided herein may have a turbidity (optical density (OD)) of about 0.5 or lower, about 0.45 or lower, about 0.4 or lower, about 0.35 or lower, about 0.3 or lower, about 0.25 or lower, about 0.2 or lower, about 0.15 or lower, about 0.1 or lower, or about 0.05 or lower, e.g., at a concentration of about 100 mg/mL or higher (e.g., about 100 mg/mL or higher, about 110 mg/mL or higher, about 120 mg/mL or higher, about 130 mg/mL or higher, about 140 mg/mL or higher, about 140 mg/mL or higher, about 150 mg/mL or higher, about 160 mg/mL or higher, about 170 mg/mL or higher, about 180 mg/mL or higher, about 190 mg/mL or higher, about 200 mg/mL or higher, about 210 mg/mL or higher, about 220 mg/mL or higher, about 230 mg/mL or higher, about 240 mg/mL or higher, about 250 mg/mL or higher, about 260 mg/mL or higher, about 270 mg/mL or higher, about 280 mg/mL or higher, about 290 mg/mL or higher, about 300 mg/mL or higher, about 310 mg/mL or higher, about 320 mg/mL or higher, about 330 mg/mL or higher, about 340 mg/mL or higher, about 350 mg/mL or higher, about 360 mg/mL or higher, about 370 mg/mL or higher, about 380 mg/mL or higher, about 390 mg/mL or higher, or about 400 mg/mL or higher), e.g., in any suitable buffer (e.g., phosphate-buffered saline (PBS) pH 7.4).

In some instances, any of the antibodies provided herein may have a turbidity (OD) of between about 0.05 and about 0.5, between about 0.1 and about 0.5, between about 0.15 and about 0.5, between about 0.2 and about 0.5, between about 0.25 and about 0.5, between about 0.3 and about 0.5, between about 0.35 and about 0.5, between about 0.4 and about 0.5, between about 0.45 and about 0.5, between about 0.05 and about 0.45, between about 0.1 and about 0.45, between about 0.15 and about 0.45, between about 0.2 and about 0.45, between about 0.25 and about 0.45, between about 0.3 and about 0.45, between about 0.35 and about 0.45, between about 0.4 and about 0.45, between about 0.05 and about 0.4, between about 0.1 and about 0.4, between about 0.15 and about 0.4, between about 0.2 and about 0.4, between about 0.25 and about 0.4, between about 0.3 and about 0.4, between about 0.35 and about 0.4, between about 0.05 and about 0.35, between about 0.1 and about 0.35, between about 0.15 and about 0.35, between about 0.2 and about 0.35, between about 0.25 and about 0.35, between about 0.3 and about 0.35, between about 0.05 and about 0.3, between about 0.1 and about 0.3, between about 0.15 and about 0.3, between about 0.2 and about 0.3, between about 0.25 and about 0.3, between about 0.05 and about 0.25, between about 0.1 and about 0.25, between about 0.15 and about 0.25, between about 0.2 and about 0.25, between about 0.05 and about 0.2, between about 0.1 and about 0.2, between about 0.15 and about 0.2, between about 0.05 and about 0.15, between about 0.1 and about 0.15, or between about 0.05 and about 0.1, e.g., at a concentration of about 100 mg/mL or higher (e.g., about 100 mg/mL or higher, about 110 mg/mL or higher, about 120 mg/mL or higher, about 130 mg/mL or higher, about 140 mg/mL or higher, about 140 mg/mL or higher, about 150 mg/mL or higher, about 160 mg/mL or higher, about 170 mg/mL or higher, about 180 mg/mL or higher, about 190 mg/mL or higher, about 200 mg/mL or higher, about 210 mg/mL or higher, about 220 mg/mL or higher, about 230 mg/mL or higher, about 240 mg/mL or higher, about 250 mg/mL or higher, about 260 mg/mL or higher, about 270 mg/mL or higher, about 280 mg/mL or higher, about 290 mg/mL or higher, about 300 mg/mL or higher, about 310 mg/mL or higher, about 320 mg/mL or higher, about 330 mg/mL or higher, about 340 mg/mL or higher, about 350 mg/mL or higher, about 360 mg/mL or higher, about 370 mg/mL or higher, about 380 mg/mL or higher, about 390 mg/mL or higher, or about 400 mg/mL or higher), e.g., in any suitable buffer (e.g., phosphate-buffered saline (PBS) pH 7.4).

In some instances, any of the antibodies provided herein may have a turbidity (OD) of between about 0.05 and about 0.5, between about 0.1 and about 0.5, between about 0.15 and about 0.5, between about 0.2 and about 0.5, between about 0.25 and about 0.5, between about 0.3 and about 0.5, between about 0.35 and about 0.5, between about 0.4 and about 0.5, between about 0.45 and about 0.5, between about 0.05 and about 0.45, between about 0.1 and about 0.45, between about 0.15 and about 0.45, between about 0.2 and about 0.45, between about 0.25 and about 0.45, between about 0.3 and about 0.45, between about 0.35 and about 0.45, between about 0.4 and about 0.45, between about 0.05 and about 0.4, between about 0.1 and about 0.4, between about 0.15 and about 0.4, between about 0.2 and about 0.4, between about 0.25 and about 0.4, between about 0.3 and about 0.4, between about 0.35 and about 0.4, between about 0.05 and about 0.35, between about 0.1 and about 0.35, between about 0.15 and about 0.35, between about 0.2 and about 0.35, between about 0.25 and about 0.35, between about 0.3 and about 0.35, between about 0.05 and about 0.3, between about 0.1 and about 0.3, between about 0.15 and about 0.3, between about 0.2 and about 0.3, between about 0.25 and about 0.3, between about 0.05 and about 0.25, between about 0.1 and about 0.25, between about 0.15 and about 0.25, between about 0.2 and about 0.25, between about 0.05 and about 0.2, between about 0.1 and about 0.2, between about 0.15 and about 0.2, between about 0.05 and about 0.15, between about 0.1 and about 0.15, or between about 0.05 and about 0.1, e.g., at a concentration of about 150 mg/mL or higher, e.g., in any suitable buffer (e.g., phosphate-buffered saline (PBS) pH 7.4).

In some instances, any of the antibodies provided herein may have a turbidity (OD) of between about 0.25 and about 0.5 at a concentration of about 150 mg/mL to about 250 mg/mL.

In particular instances, the antibody has a turbidity (OD) of about 0.38 at a concentration of about 200 mg/mL.

In some instances, any of the anti-IL-33 antibodies described herein (e.g., described above or below) may have one or more (e.g., 1, 2, 3, 4, or 5) of the following features: (i) the antibody specifically binds human IL-33 with a $K_D$ of between about 1 pM and about 200 pM; (ii) the antibody specifically binds cyno IL-33 with a $K_D$ of between about 1 pM and about 200 pM; (iii) the antibody inhibits the binding of human IL-33 to an IL-33 receptor (e.g., ST2 and/or IL-1RAcP) with an IC50 of between about 1 pM and about 250 pM, for example, in a cell-based blocking assay using HEK-BLUE™ cells; (iv) the antibody has a viscosity of between about 3 cP and about 5 cP at a concentration of about 180 mg/mL; and/or (v) the antibody has a turbidity (OD) of between about 0.25 and about 0.5 at a concentration of about 150 mg/ml to about 250 mg/ml. In some instances, any of the anti-IL-33 antibodies described herein may have one of the preceding features. In some instances, any of the anti-IL-33 antibodies described herein may have two of the preceding features. In some instances, any of the anti-IL-33 antibodies described herein may have three of the preceding features. In some instances, any of the anti-IL-33 antibodies described herein may have four of the preceding features. In some instances, any of the anti-IL-33 antibodies described herein may have all five of the preceding features.

Any of the anti-IL-33 antibodies provided herein may be a monoclonal antibody, including a chimeric, humanized, or human antibody.

Any of the anti-IL-33 antibodies provided herein may be an antibody fragment, e.g., a Fv, Fab, Fab', scFv, diabody, or F(ab')$_2$ fragment. In particular instances, the antibody fragment is an Fab fragment.

In other instances, any of the anti-IL-33 antibodies provided herein may be a full-length antibody, e.g., an intact IgG1 antibody, an intact IgG4 antibody, or other antibody class or isotype as defined herein. In some instances, the antibody is an IgG4 antibody that comprises a mutation in the hinge region. In some instances, the mutation is a substitution mutation. In some instances, the substitution mutation is at amino acid residue S228 (EU numbering). In some instances, the substitution mutation is an S228P mutation.

Any of the anti-IL-33 antibodies provided herein may be a monospecific antibody. In other instances, any of the anti-IL-33 antibodies provided herein may be a multispecific antibody (e.g., a bispecific antibody). In some instances, the bispecific antibody comprises a second binding domain that binds to a second biological molecule, wherein the second biological molecule is interleukin-13 (IL-13), interleukin-4 (IL-4), interleukin-5 (IL-5), interleukin-17 (IL-17), Factor D, HtrA1, VEGF, or a VEGF receptor.

In a further aspect, any of the anti-IL-33 antibodies disclosed herein may incorporate any of the features, singly or in combination, as described in Sections 1-7 below:

1. Antibody Affinity

In certain embodiments, an antibody provided herein has a dissociation constant ($K_D$) of ≤1 µM, ≤100 nM, ≤10 nM, ≤1 nM, ≤0.1 nM, ≤0.01 nM, ≤1 pM, or ≤0.1 pM (e.g., $10^{-6}$ M or less, e.g., from $10^{-6}$ M to $10^{-9}$ M or less, e.g., from $10^{-9}$ M to $10^{-13}$ M or less).

In one embodiment, $K_D$ is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al. *J. Mol. Biol.* 293:865-881, 1999). To establish conditions for the assay, MICROTITER® multi-well plates (Thermo Scientific) are coated overnight with 5 pg/mL of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (NUNC™ #269620), 100 pM or 26 pM [$^{125}$I]-antigen are mixed with serial dilutions of a Fab of interest (e.g., consistent with assessment of the anti-VEGF antibody, Fab-12, in Presta et al. *Cancer Res.* 57:4593-4599, 1997). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN®-20) in PBS. When the plates have dried, 150 µL/well of scintillant (MICROS-CINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, $K_D$ is measured using a BIACORE® surface plasmon resonance assay. For example, an assay using a BIACORE®-2000 or a BIACORE®-3000 (BIAcore, Inc.) is performed at 25° C. with immobilized antigen CM5 chips at ~10 response units (RU). In one embodiment, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µL/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in phosphate buffered saline (PBS) with 0.05% polysorbate 20 (TWEEN®-20) surfactant (PBST) at 25° C. at a flow rate of approximately 25 µL/min. Association rates ($k_{on}$) and dissociation rates ($k_{off}$) are calculated using a simple one-to-one *Langmuir* binding model (BIACORE® Evaluation Software version 3.2) by simultaneously fitting the association and dissociation sensorgrams. The equilibrium dissociation constant ($K_D$) is calculated as the ratio $k_{off}/k_{on}$. See, for example, Chen et al. (*J. Mol. Biol.* 293:865-881, 1999). If the on-rate exceeds $10^6$ $M^{-1}s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ Spectrophotometer (ThermoSpectronic) with a stirred cuvette.

2. Antibody Fragments

Any of the antibodies provided herein may be an antibody fragment (e.g., an antigen-binding (e.g., IL-33-binding) antibody fragment). Antibody fragments include, but are not limited to, Fab, Fab', Fab'-SH, F(ab')$_2$, Fv, and scFv fragments, and other fragments described below. In certain instances, the antibody fragment is an Fab. For a review of certain antibody fragments, see Hudson et al. *Nat. Med.* 9:129-134 (2003). For a review of scFv fragments, see, e.g., Pluckthun, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al. *Nat. Med.* 9:129-134, 2003; and Hollinger et al. *Proc. Nat. Acad. Sci. USA* 90: 6444-6448, 1993. Triabodies and tetrabodies are also described in Hudson et al. *Nat. Med.* 9:129-134, 2003.

Single-domain antibodies are antibody fragments comprising all or a portion of the heavy chain variable domain or all or a portion of the light chain variable domain of an antibody. In certain embodiments, a single-domain antibody is a human single-domain antibody (see, e.g., U.S. Pat. No. 6,248,516 B1).

Antibody fragments can be made by various techniques, including but not limited to proteolytic digestion of an intact antibody as well as production by recombinant host cells (e.g., *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al. *Proc. Nat. Acad. Sci. USA*, 81:6851-6855, 1984). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), for example, to restore or improve antibody specificity or affinity.

Humanized antibodies and methods of making them are reviewed, for example, in Almagro et al. *Front. Biosci.* 13:1619-1633, 2008, and are further described, e.g., in Riechmann et al. *Nature* 332:323-329, 1988; Queen et al. *Proc. Natl. Acad. Sci. USA* 86:10029-10033, 1989; U.S. Pat. Nos. 5,821,337, 7,527,791, 6,982,321, and 7,087,409; Kashmiri et al. *Methods* 36:25-34, 2005 (describing specificity determining region (SDR) grafting); Padlan, *Mol. Immunol.* 28:489-498, 1991 (describing "resurfacing"); Dall'Acqua et al. *Methods* 36:43-60, 2005 (describing "FR shuffling"); and Osbourn et al. *Methods* 36:61-68, 2005 and Klimka et al. *Br. J. Cancer,* 83:252-260, 2000 (describing the "guided selection" approach to FR shuffling).

Human framework regions that may be used for humanization include but are not limited to: framework regions selected using the "best-fit" method (see, e.g., Sims et al. *J. Immunol.* 151:2296, 1993); framework regions derived from the consensus sequence of human antibodies of a particular subgroup of light or heavy chain variable regions (see, e.g., Carter et al. *Proc. Nat. Acad. Sci. USA,* 89:4285, 1992; and Presta et al. *J. Immunol.,* 151:2623, 1993); human mature (somatically mutated) framework regions or human germline framework regions (see, e.g., Almagro et al. *Front. Biosci.* 13:1619-1633, 2008); and framework regions derived from screening FR libraries (see, e.g., Baca et al. *J. Biol. Chem.* 272:10678-10684, 1997 and Rosok et al. *J. Biol. Chem.* 271:22611-22618, 1996).

4. Human Antibodies

In certain embodiments, an antibody provided herein is a human antibody. Human antibodies can be produced using various techniques known in the art. Human antibodies are described generally in van Dijk et al. *Curr. Opin. Pharmacol.* 5:368-74, 2001 and Lonberg, *Curr. Opin. Immunol.* 20:450-459, 2008.

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125, 2005. See also, for example, U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCIMOUSE® technology. Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.* 133:3001, 1984; Brodeur et al. *Monoclonal Antibody Production Techniques and Applications,* pp. 51-63 (Marcel Dekker, Inc., New York, 1987); and Boerner et al. *J. Immunol.* 147: 86, 1991). Human antibodies generated via human B-cell hybridoma technology are also described in Li et al. *Proc. Natl. Acad. Sci. USA,* 103:3557-3562, 2006. Additional methods include those described, for example, in U.S. Pat. No. 7,189,826 (describing production of monoclonal human IgM antibodies from hybridoma cell lines) and Ni, *Xiandai Mianyixue,* 26(4):265-268, 2006 (describing human-human hybridomas). Human hybridoma technology (Trioma technology) is also described in Vollmers et al. *Histology and Histopathology* 20(3):927-937, 2005 and Vollmers et al. *Methods and Findings in Experimental and Clinical Pharmacology* 27(3):185-91, 2005.

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies disclosed herein may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al. *Nature* 348:552-554, 1990; Clackson et al. *Nature* 352: 624-628, 1991; Marks et al. *J. Mol. Biol.* 222: 581-597, 1992; Marks et al. in *Methods in Molecular Biology* 248:161-175 (Lo, ed., Human Press, Totowa, N.J., 2003); Sidhu et al. *J. Mol. Biol.* 338(2): 299-310, 2004; Lee et al. *J. Mol. Biol.* 340(5): 1073-1093, 2004; Fellouse, *Proc. Natl. Acad. Sci. USA* 101(34):12467-12472, 2004; and Lee et al. *J. Immunol.* Methods 284(1-2): 119-132, 2004.

In certain phage display methods, repertoires of VH and VL genes are separately cloned by polymerase chain reaction (PCR) and recombined randomly in phage libraries, which can then be screened for antigen-binding phage as described in Winter et al. *Ann. Rev. Immunol.,* 12: 433-455, 1994. Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al. *EMBO J.* 12: 725-734, 1993. Finally, naive libraries can also be made synthetically by cloning unrearranged V-gene segments from stem cells, and using PCR primers containing random sequence to encode the highly variable HVR3 regions and to accomplish rearrangement in vitro, as described by Hoogenboom et al. *J. Mol. Biol.*, 227: 381-388, 1992. Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, for example, a bispecific antibody. Multispecific antibodies are monoclonal antibodies that have binding specificities for at least two different sites. In certain embodiments, bispecific antibodies may bind to two different epitopes of IL-33. In certain embodiments, one of the binding specificities is for IL-33 and the other is for any other antigen (e.g., a second biological molecule, e.g., IL-13, IL-4, IL-5, IL-17, Factor D, HtrA1, VEGF, or a VEGF receptor). Accordingly, the bispecific antibody may have binding specificity for IL-33 and IL-13; IL-33 and IL-4; IL-33 and IL-5; IL-33 and IL-17; IL-33 and Factor D; IL-33 and HtrA1; IL-33 and VEGF; or IL-33 and a VEGF receptor (e.g., VEGFR1, VEGFR2, VEGFR3, membrane-bound VEGF receptor (mbVEGFR), or soluble VEGF receptor (sVEGFR)). In some instances, the bispecific antibody may have binding specificity for IL-33 and Factor D. In other instances, the bispecific antibody may have binding specificity for IL-33 and HtrA1. In yet other instances, the bispecific antibody may have binding specificity for IL-33 and VEGF. In other instances, the bispecific antibody may have binding specificity for IL-33 and a VEGF receptor. In particular, the bispecific antibody may have binding specificity for IL-33 and IL-13. Bispecific antibodies can be prepared as full-length antibodies or antibody fragments.

Techniques for making multispecific antibodies include, but are not limited to, recombinant co-expression of two immunoglobulin heavy chain-light chain pairs having different specificities (see Milstein et al. *Nature* 305: 537, 1983; WO 93/08829; and Traunecker et al. *EMBO J.* 10: 3655, 1991), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al. *Science,* 229: 81, 1985); using leucine zippers to produce bispecific antibodies (see, e.g., Kostelny et al. *J. Immunol.,* 148(5):1547-1553, 1992); using "diabody" technology for making bispecific antibody fragments (see, e.g., Hollinger et al. *Proc. Natl. Acad. Sci. USA* 90:6444-6448, 1993); and using single-chain Fv (scFv) dimers (see, e.g. Gruber et al. *J. Immunol.* 152:5368, 1994); and preparing trispecific antibodies as described, e.g., in Tutt et al. *J. Immunol.* 147: 60, 1991.

Engineered antibodies with three or more functional antigen binding sites, including "Octopus antibodies," are also included herein (see, e.g. US 2006/0025576A1).

The antibody or fragment herein also includes a "Dual Acting Fab" or "DAF" comprising an antigen binding site that binds to IL-33 as well as another, different antigen (see, US 2008/0069820, for example).

Knobs-into-Holes

The use of knobs-into-holes as a method of producing multispecific antibodies is described, e.g., in U.S. Pat. No. 5,731,168, WO2009/089004, US2009/0182127, US2011/0287009, Marvin and Zhu, *Acta Pharmacol. Sin.* (2005) 26(6):649-658, and Kontermann (2005) *Acta Pharmacol. Sin.,* 26:1-9. A brief nonlimiting discussion is provided below.

A "protuberance" refers to at least one amino acid side chain which projects from the interface of a first polypeptide and is therefore positionable in a compensatory cavity in the adjacent interface (i.e., the interface of a second polypeptide) so as to stabilize the heteromultimer, and thereby favor heteromultimer formation over homomultimer formation, for example. The protuberance may exist in the original interface or may be introduced synthetically (e.g., by altering nucleic acid encoding the interface). In some embodiments, a nucleic acid encoding the interface of the first polypeptide is altered to encode the protuberance. To achieve this, the nucleic acid encoding at least one "original" amino acid residue in the interface of the first polypeptide is replaced with nucleic acid encoding at least one "import" amino acid residue which has a larger side chain volume than the original amino acid residue. It will be appreciated that there can be more than one original and corresponding import residue. The side chain volumes of the various amino residues are shown, for example, in Table 1 of US 2011/0287009 or Table 1 of U.S. Pat. No. 7,642,228.

In some embodiments, import residues for the formation of a protuberance are naturally occurring amino acid residues selected from arginine (R), phenylalanine (F), tyrosine (Y) and tryptophan (W). In some embodiments, an import residue is tryptophan or tyrosine. In some embodiments, the original residue for the formation of the protuberance has a small side chain volume, such as alanine, asparagine, aspartic acid, glycine, serine, threonine, or valine. See, for example, U.S. Pat. No. 7,642,228.

A "cavity" refers to at least one amino acid side chain which is recessed from the interface of a second polypeptide and therefore accommodates a corresponding protuberance on the adjacent interface of a first polypeptide. The cavity may exist in the original interface or may be introduced synthetically (e.g., by altering nucleic acid encoding the interface). In some embodiments, nucleic acid encoding the interface of the second polypeptide is altered to encode the cavity. To achieve this, the nucleic acid encoding at least one "original" amino acid residue in the interface of the second polypeptide is replaced with DNA encoding at least one "import" amino acid residue which has a smaller side chain volume than the original amino acid residue. It will be appreciated that there can be more than one original and corresponding import residue. In some embodiments, import residues for the formation of a cavity are naturally occurring amino acid residues selected from alanine (A), serine (S), threonine (T), and valine (V). In some embodiments, an import residue is serine, alanine, or threonine. In some embodiments, the original residue for the formation of the cavity has a large side chain volume, such as tyrosine, arginine, phenylalanine, or tryptophan.

The protuberance is "positionable" in the cavity which means that the spatial location of the protuberance and cavity on the interface of a first polypeptide and second polypeptide respectively and the sizes of the protuberance and cavity are such that the protuberance can be located in the cavity without significantly perturbing the normal association of the first and second polypeptides at the interface. Since protuberances such as Tyr, Phe, and Trp do not typically extend perpendicularly from the axis of the interface and have preferred conformations, the alignment of a protuberance with a corresponding cavity may, in some instances, rely on modeling the protuberance/cavity pair based upon a three-dimensional structure such as that obtained by X-ray crystallography or nuclear magnetic resonance (NMR). This can be achieved using widely accepted techniques in the art.

In some embodiments, a knob mutation in an IgG1 constant region is T366W. In some embodiments, a hole mutation in an IgG1 constant region comprises one or more mutations selected from T366S, L368A, and Y407V. In some embodiments, a hole mutation in an IgG1 constant region comprises T366S, L368A, and Y407V.

In some embodiments, a knob mutation in an IgG4 constant region is T366W. In some embodiments, a hole mutation in an IgG4 constant region comprises one or more mutations selected from T366S, L368A, and Y407V. In some embodiments, a hole mutation in an IgG4 constant region comprises T366S, L368A, and Y407V.

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, for example, antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table A under the heading of "preferred substitutions." More substantial changes are provided in Table A under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE A

| Original Residue | Exemplary Substitutions | Preferred Substitutions |
|---|---|---|
| Ala (A) | Val; Leu; Ile | Val |
| Arg (R) | Lys; Gin; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gin;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more HVR (e.g., CDR) residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, for example, using phage display-based affinity maturation techniques such as those described herein. Briefly, one or more HVR residues are mutated and the variant antibodies displayed on phage and screened for a particular biological activity (e.g., binding affinity).

Alterations (e.g., substitutions) may be made in HVRs (e.g., CDRs), e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196, 2008), and/or residues that contact antigen, with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al. ed., Human Press, Totowa, N.J., 2001). In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. HVR-H3 and HVR-L3 in particular are often targeted.

In certain embodiments, substitutions, insertions, or deletions may occur within one or more HVRs (e.g., CDRs) so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham et al. *Science* 244:1081-1085, 1989. In this method, a residue or group of target residues (e.g., charged residues such as Arg, Asp, His, Lys, and Glu) are identified and replaced by a neutral or negatively charged amino acid (e.g., Ala or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, for example, Wright et al. *TIBTECH* 15:26-32, 1997. The oligosaccharide may include various carbohydrates, for example, mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody disclosed herein may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. 2003/0157108 and 2004/0093621. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO 2005/053742; WO 2002/031140; Okazaki et al. *J. Mol. Biol.* 336:1239-1249, 2004; Yamane-Ohnuki et al. *Biotech. Bioeng.* 87: 614, 2004. Examples of cell lines capable of producing defucosylated antibodies include Lec13 CHO cells deficient in protein fucosylation (Ripka et al. *Arch. Biochem.* Biophys. 249:533-545, 1986; US 2003/0157108; and WO 2004/056312 A1, especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614, 2004; Kanda et al. *Biotechnol. Bioeng.* 94(4):680-688, 2006; and WO 2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546. Antibody variants with at least one galactose residue in the oligosaccharide attached to the Fc region are also provided. Such antibody variants may have improved CDC function. Such antibody variants are described, e.g., in WO 1997/30087; WO 1998/58964; and WO 1999/22764.

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch et al. *Annu. Rev. Immunol.* 9:457-492, 1991. Non-limiting examples of in vitro assays to assess ADCC activity of a molecule of interest is described in U.S. Pat. No. 5,500,362 (see, e.g. Hellstrom et al. *Proc. Natl. Acad. Sci. USA* 83:7059-7063, 1986 and Hellstrom et al. *Proc. Natl. Acad. Sci. USA* 82:1499-1502, 1985; U.S. Pat. No. 5,821,337 (see Bruggemann et al. *J. Exp. Med.* 166:1351-1361, 1987). Alternatively, non-radioactive assays methods may be employed (see, for example, ACTI™ non-radioactive cytotoxicity assay for flow cytometry (CellTechnology, Inc. Mountain View, Calif.; and CYTOTOX 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, for example, in an animal model such as that disclosed in Clynes et al. *Proc. Natl. Acad. Sci. USA* 95:652-656, 1998. C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, e.g., Gazzano-Santoro et al. *J. Immunol. Methods* 202:163, 1996; Cragg et al. *Blood* 101:1045-1052, 2003; and Cragg et al. *Blood* 103:2738-2743, 2004). FcRn binding and in vivo clearance/half-life determinations can also be performed using methods known in the art (see, e.g., Petkova et al. *Intl. Immunol.* 18(12):1759-1769, 2006).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312; and Shields et al. *J. Biol. Chem.* 9(2): 6591-6604, 2001).

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), for example, as described in U.S. Pat. No. 6,194,551, WO 99/51642, and Idusogie et al. *J. Immunol.* 164: 4178-4184, 2000.

Antibodies with increased half-lives and improved binding to the neonatal Fc receptor (FcRn), which is responsible for the transfer of maternal IgGs to the fetus (Guyer et al. *J. Immunol.* 117:587, 1976 and Kim et al. *J. Immunol.* 24:249, 1994), are described in US2005/0014934. Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan et al. *Nature* 322:738-40, 1988; U.S. Pat. Nos. 5,648,260 and 5,624,821; and WO 94/29351 concerning other examples of Fc region variants.

d) Cysteine Engineered Antibody Variants

In certain embodiments, it may be desirable to create cysteine engineered antibodies, for example, "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al. *Proc. Natl. Acad. Sci. USA* 102: 11600-11605, 2005). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, for example, as described in U.S. Pat. No. 4,816,567. In one embodiment, isolated nucleic acid encoding an anti-IL-33 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, for example, a Chinese Hamster Ovary (CHO) cell, 293 cell, or lymphoid cell (e.g., Y0, NS0, Sp20 cell). In one embodiment, a method of making an anti-IL-33 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-IL-33 antibody, nucleic acid encoding an antibody, for example, as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, for example, U.S. Pat. Nos. 5,648,237, 5,789,199, and 5,840,523. (See also Charlton, *Methods in Molecular Biology, Vol.* 248 (B. K. C. Lo, ed., Humana Press, Totowa, N.J., 2003), pp. 245-254, describing expression of antibody fragments in *E. coli.*) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross *Nat. Biotech.* 22:1409-1414, 2004 and Li et al. *Nat. Biotech.* 24:210-215, 2006.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, for example, U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al. *J. Gen Virol.* 36:59, 1977); baby hamster kidney cells (BHK); mouse sertoli cells (TM4 cells as described, e.g., in *Mather Biol. Reprod.* 23:243-251, 1980); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68, 1982; MRC 5 cells; and FS4 cells. Other useful mammalian host cell lines include Chinese hamster ovary (CHO) cells, including DHFR⁻ CHO cells (Urlaub et al. *Proc. Natl. Acad. Sci. USA* 77:4216, 1980); and myeloma cell lines such as Y0, NS0 and Sp2/0. For a review of certain mammalian host cell lines suitable for antibody production, see, e.g., Yazaki et al. *Methods in Molecular Biology*, Vol. 248 (B. K. C. Lo, ed., Humana Press, Totowa, N.J.), pp. 255-268, 2003.

C. Assays

Anti-IL-33 antibodies provided herein may be identified, screened for, or characterized for their physical/chemical properties and/or biological activities by various assays known in the art.

1. Binding Assays and Other Assays

In one aspect, an anti-IL-33 antibody disclosed herein is tested for its antigen-binding activity, for example, by known methods such as ELISA, Western blot, and the like.

In another aspect, competition assays may be used to identify an antibody that competes with an anti-IL-33 antibody disclosed herein for binding to IL-33. In certain embodiments, such a competing antibody binds to the same epitope (e.g., a linear or a conformational epitope) that is bound by an anti-IL-33 antibody disclosed herein. Detailed exemplary methods for mapping an epitope to which an antibody binds are provided in Morris "Epitope Mapping Protocols," in Methods in Molecular Biology Vol. 66 (Humana Press, Totowa, N.J.), 1996.

In an exemplary competition assay, immobilized IL-33 is incubated in a solution comprising a first labeled antibody that binds to IL-33 and a second unlabeled antibody that is being tested for its ability to compete with the first antibody for binding to IL-33. The second antibody may be present in a hybridoma supernatant. As a control, immobilized IL-33 is incubated in a solution comprising the first labeled antibody but not the second unlabeled antibody. After incubation under conditions permissive for binding of the first antibody to IL-33, excess unbound antibody is removed, and the amount of label associated with immobilized IL-33 is measured. If the amount of label associated with immobilized IL-33 is substantially reduced in the test sample relative to the control sample, then that indicates that the second antibody is competing with the first antibody for binding to IL-33. See Harlow et al. *Antibodies: A Laboratory Manual* Ch. 14 (Cold Spring Harbor Laboratory, Cold Spring Harbor, N.Y.), 1988.

2. Activity Assays

In one aspect, assays are provided for identifying anti-IL-33 antibodies thereof having biological activity. Biological activity may include, for example, binding to IL-33 (e.g., IL-33 in the blood stream), or a peptide fragment thereof, either in vivo, in vitro, or ex vivo. In other embodiments, biological activity may include blocking or neutralizing IL-33, or preventing IL-33 from binding to a ligand, for example, a receptor (e.g., the IL-33 receptor ST2 and/or IL-1RAcP). In some embodiments, biological activity may include binding to site 1 on IL-33 and blocking of binding to the IL-33 receptor (i.e., ST2 and/or IL-1RAcP). Antibodies having such biological activity in vivo and/or in vitro are also provided. In certain embodiments, an antibody disclosed herein is tested for such biological activity. In some embodiments, an anti-IL-33 antibody disclosed herein is tested for inhibition in a cell-based IL-33 blocking assay. In some embodiments, an anti-IL-33 antibody disclosed herein is tested for inhibition of IL-33-induced reporter activity in a cell-based blocking assay (e.g., an IL-33 HEK-BLUE™ cell-based assay as described herein (see, e.g., Examples 3 and 6)). In some embodiments, an antibody disclosed herein is tested for inhibition of an IL-33 activity in primary cells, for example, in a primary NK cell assay (see, e.g., Example 8, Section C of WO 2016/077381) or a primary basophil assay (see, e.g., Example 8, Section D of WO 2016/077381). In some embodiments, an antibody disclosed herein is tested for inhibiting the binding of IL-33 to an IL-33 receptor in a competitive binding ELISA (see, e.g., Example 8, Section F of WO 2016/077381).

D. Immunoconjugates

The invention also provides immunoconjugates comprising an anti-IL-33 antibody provided herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498, 298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al. *Cancer Res.* 53:3336-3342, 1993; and Lode et al. *Cancer Res.* 58:2925-2928, 1998); an anthracycline such daunomycin or doxorubicin (see Kratz et al. *Current Med. Chem.* 13:477-523, 2006; Jeffrey et al. *Bioorganic & Med. Chem. Letters* 16:358-362, 2006; Torgov et al. *Bioconj. Chem.* 16:717-721, 2005; Nagy et al. *Proc. Natl. Acad. Sci. USA* 97:829-834, 2000; Dubowchik et al. *Bioorg. & Med. Chem. Letters* 12:1529-1532, 2002; King et al. *J. Med. Chem.* 45:4336-4343, 2002; and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example technetium-99m (tc99m) or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al. *Science* 238:1098, 1987. Carbon-14-labeled 1-isothiocyanatobenzyl-3-methyldiethylene triaminepentaacetic acid (MX-DTPA) is an exemplary chelating agent for conjugation of radionucleotide to the antibody. See WO 94/11026. The linker may be a "cleavable linker" facilitating release of a cytotoxic drug in the cell. For example, an acid-labile linker, peptidase-sensitive linker, photolabile linker, dimethyl linker or disulfide-containing linker (see, e.g., Chari et al. *Cancer Res.* 52:127-131, 1992; U.S. Pat. No. 5,208,020) may be used.

The immunoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A.).

E. Methods and Compositions for Diagnostics and Detection

In certain embodiments, any of the anti-IL-33 antibodies provided herein is useful for detecting the presence of IL-33 in a biological sample. The term "detecting" as used herein encompasses quantitative or qualitative detection. In certain embodiments, a biological sample comprises a cell or tissue, such as smooth muscle, epithelial cells, endothelial cells, blood, blood cells (e.g., macrophages, innate type II (ILC2) cells, mast cells, basophils, eosinophils, and dendritic cells), central nervous system cells (e.g., glia cells), or eye cells (e.g., retinal cells (e.g., Muller cells or retinal pigment epithelium (RPE) cells) and vascular endothelial cells of the eye).

In one embodiment, an anti-IL-33 antibody for use in a method of diagnosis or detection is provided. In a further aspect, a method of detecting the presence of IL-33 in a biological sample is provided. In certain embodiments, the method comprises contacting the biological sample with an anti-IL-33 antibody as described herein under conditions permissive for binding of the anti-IL-33 antibody to IL-33, and detecting whether a complex is formed between the anti-IL-33 antibody and IL-33. Such method may be an in vitro or in vivo method. In one embodiment, an anti-IL-33 antibody is used to select subjects eligible for therapy with an anti-IL-33 antibody, for example, where IL-33 is a biomarker for selection of patients.

Exemplary disorders that may be diagnosed using an antibody disclosed herein include IL-33-mediated disorders, including, for example, ocular disorders (e.g., age-related macular degeneration (AMD) or retinopathy of the eye), inflammatory conditions (e.g., asthma, sepsis, septic shock, atopic dermatitis, allergic rhinitis, rheumatoid arthritis, and chronic obstructive pulmonary disease (COPD)), immune disorders (e.g., asthma, rheumatoid arthritis, allergy, atopic allergy, anaphylaxis, anaphylactic shock, allergic rhinitis, psoriasis, inflammatory bowel disease (IBD), Crohn's disease, diabetes, and liver disease), fibrotic disorders (e.g., pulmonary fibrosis (e.g., idiopathic pulmonary fibrosis), eosinophilic disorders (e.g., eosinophil-associated gastrointestinal disorders (EGIDs) including eosinophilic esophagitis), infections (e.g., helminth infections, protozoan infections, and viral infections), pain (e.g., inflammatory pain), central nervous system disorders (e.g., Alzheimer's disease), and solid tumors (e.g., breast, colon, prostate, lung, kidney, liver, pancreas, stomach, intestinal, brain, bone, and skin tumors). In some instances, the ocular disorder that may be diagnosed using an antibody disclosed herein includes AMD (e.g., wet AMD, dry AMD, intermediate AMD, advanced AMD, and geographic atrophy (GA)), retinopathy (e.g., diabetic retinopathy (DR), retinopathy of prematurity (ROP), and high-altitude DR), polypoidal choroidal vasculopathy (PCV), diabetic macular edema, dry eye disease, Behcet's disease, retina detachment, glaucoma, uveitis (e.g., infectious and non-infectious uveitis), retinitis pigmentosa, Leber Congenital Amaurosis, Stargardt's disease, traumatic eye injury, and conjunctivitis (e.g., infectious conjunctivitis, non-infectious conjunctivitis, and allergic conjunctivitis).

In some instances, the ocular disorder includes AMD (including wet AMD, dry AMD, and GA), retinopathy (e.g., DR and ROP), PCV, diabetic macular edema, dry eye disease, Behcet's disease, allergic conjunctivitis, and retina detachment.

In other instances, the ocular disorder includes intermediate AMD, advanced AMD, glaucoma, uveitis (e.g., infectious and non-infectious uveitis), retinitis pigmentosa, Leber Congenital Amaurosis, Stargardt's disease, high-altitude diabetic retinopathy, traumatic eye injury, and conjunctivitis (e.g., infectious conjunctivitis and non-infectious conjunctivitis).

In certain embodiments, labeled anti-IL-33 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an anti-IL-33 antibody disclosed herein are prepared by mixing such antibody having the desired degree of purity with one or more optional pharmaceutically acceptable carriers (see, e.g., *Remington's Pharmaceutical Sciences* 16th edition, Osol, A. Ed., 1980), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO 2006/044908, the latter formulations including a histidine-acetate buffer.

The formulation herein may also contain more than one active ingredients as necessary for the particular indication being treated, preferably those with complementary activities that do not adversely affect each other. For example, it may be desirable to further provide an ST2 binding antagonist, a complement pathway inhibitor (e.g., a Factor D binding antagonist), an HtrA1 binding antagonist, a VEGF antagonist, a tryptase-beta binding antagonist, a chemoattractant receptor-homologous molecule expressed on Th2 cells (CRTH2) binding antagonist, an interleukin-13 (IL-13) binding antagonist, an interleukin-17 (IL-17) binding antagonist, a JAK1 antagonist, and/or an interleukin-5 (IL-5) binding antagonist. In some instances, the complement pathway inhibitor is a Factor D binding antagonist. In some instances, the Factor D binding antagonist is an anti-Factor D antibody or an antigen-binding fragment thereof, for example, as described below in Section G, "Therapeutic Methods and Compositions." In some instances, the HtrA1 binding antagonist is an anti-HtrA1 antibody or an antigen-binding fragment thereof, for example, as described below in Section G, "Therapeutic Methods and Compositions." In some instances, the anti-HtrA1 antibody fragment is an Fab, Fab'-SH, Fv, scFv, or an (Fab')$_2$ fragment. In some instances, the anti-Factor D antibody fragment is an Fab, Fab'-SH, Fv, scFv, or an (Fab')$_2$ fragment. In some instances, the VEGF antagonist is an anti-VEGF antibody or an antigen-binding fragment thereof, for example, as described below in Section G, "Therapeutic Methods and Compositions." In some instances, the anti-VEGF antibody fragment is an Fab, Fab'-SH, Fv, scFv, or an (Fab')$_2$ fragment. In some instances, the VEGF antagonist is an anti-VEGF receptor antibody or an antigen-binding fragment thereof. In some instances, the anti-VEGF receptor antibody fragment is an Fab, Fab'-SH, Fv, scFv, or an (Fab')$_2$ fragment. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed., 1980.

Sustained-release preparations may be prepared. Suitable examples of sustained-release preparations include semipermeable matrices of solid hydrophobic polymers containing the antibody, which matrices are in the form of shaped articles, e.g., films, or microcapsules.

For delivery to the eye (ophthalmic delivery), an antibody disclosed herein may be combined, for example, with ophthalmologically acceptable preservatives, co-solvents, surfactants, viscosity enhancers, penetration enhancers, buffers, sodium chloride, and/or water. Preservatives may be included, for example, to inhibit microbial contamination during use. Suitable preservatives include: edetate disodium, methyl paraben, propyl paraben, sorbic acid, phenylethyl alcohol, chlorobutanol, polyquaternium-1, or other agents known in the art. Such preservatives are typically employed at a level of from 0.001 to 1.0% w/v. In some instances, a pharmaceutical formulation disclosed herein does not include a preservative. In certain instances, compositions intended to be administered topically to the eye may be formulated as eye drops or eye ointments. In some instances, the total amount of antibody will be about 0.001 to 1.0% (w/w), for example, about 0.01 to about 1.0% (w/w), of such a formulation.

The formulations to be used for in vivo administration are generally sterile. Sterility may be readily accomplished, for example, by filtration through sterile filtration membranes.

An anti-IL-33 antibody (e.g., any anti-IL-33 antibody disclosed herein) can be formulated in a polymeric formulation.

Any suitable concentration of any of the antibodies disclosed herein may be used in the compositions (e.g., pharmaceutical compositions). For example, the concentration of an antibody in a composition disclosed herein may range, for example, from about 1 mg/mL to about 400 mg/mL (e.g., about 1 mg/mL to about 400 mg/mL, about 1 mg/mL to about 375 mg/mL, about 1 mg/mL to about 350 mg/mL, about 1 mg/mL to about 325 mg/mL, about 1 mg/mL to about 300 mg/mL, about 1 mg/mL to about 275 mg/mL, about 1 mg/mL to about 250 mg/mL, about 1 mg/mL to about 225 mg/mL, about 1 mg/mL to about 200 mg/mL, about 1 mg/mL to about 175 mg/mL, about 1 mg/mL to about 150 mg/mL, about 1 mg/mL to about 125 mg/mL, about 1 mg/mL to about 100 mg/mL, about 1 mg/mL to about 75 mg/mL, about 1 mg/mL to about 50 mg/mL, about 1 mg/mL to about 25 mg/mL, about 25 mg/mL to about 350 mg/mL, about 25 mg/mL to about 325 mg/mL, about 25 mg/mL to about 300 mg/mL, about 25 mg/mL to about 275 mg/mL, about 25 mg/mL to about 250 mg/mL, about 25 mg/mL to about 225 mg/mL, about 25 mg/mL to about 200 mg/mL, about 25 mg/mL to about 175 mg/mL, about 25 mg/mL to about 150 mg/mL, about 25 mg/mL to about 125 mg/mL, about 25 mg/mL to about 100 mg/mL, about 25 mg/mL to about 75 mg/mL, about 25 mg/mL to about 50 mg/mL, about 50 mg/mL to about 350 mg/mL, about 50 mg/mL to about 325 mg/mL, about 50 mg/mL to about 300 mg/mL, about 50 mg/mL to about 275 mg/mL, about 50 mg/mL to about 250 mg/mL, about 50 mg/mL to about 225 mg/mL, about 50 mg/mL to about 200 mg/mL, about 50 mg/mL to about 175 mg/mL, about 50 mg/mL to about 150 mg/mL, about 50 mg/mL to about 125 mg/mL, about 50 mg/mL to about 100 mg/mL, about 50 mg/mL to about 75 mg/mL, about 75 mg/mL to about 350 mg/mL, about 75 mg/mL to about 325 mg/mL, about 75 mg/mL to about 300 mg/mL, about 75 mg/mL to about 275 mg/mL, about 75 mg/mL to about 250 mg/mL, about 75 mg/mL to about 225 mg/mL, about 75 mg/mL to about 200 mg/mL, about 75 mg/mL to about 175 mg/mL, about 75 mg/mL to about 150 mg/mL, about 75 mg/mL to about 125 mg/mL, about 75 mg/mL to about 100 mg/mL, about 100 mg/mL to about 350 mg/mL, about 100 mg/mL to about 325 mg/mL, about 100 mg/mL to about 300 mg/mL, about 100 mg/mL to about 275 mg/mL, about 100 mg/mL to about 250 mg/mL, about 100 mg/mL to about 225 mg/mL, about 100 mg/mL to about 200 mg/mL, about 100 mg/mL to about 175 mg/mL, about 100 mg/mL to about 150 mg/mL, about 100 mg/mL to about 125 mg/mL, or about 150 mg/mL to about 175 mg/mL. In some instances, the antibody is at a concentration of about 50 mg/mL to about 300 mg/mL (e.g., about 50 mg/mL, about 60 mg/mL, about 70 mg/mL, about 80 mg/mL, about 90 mg/mL, about 100 mg/mL, about 110 mg/mL, about 120 mg/mL, about 130 mg/mL, about 140 mg/mL, about 150 mg/mL, about 160 mg/mL, about 170 mg/mL, about 180 mg/mL, about 190 mg/mL, about 200 mg/mL, about 210 mg/mL, about 220 mg/mL, about 230 mg/mL, about 240 mg/mL, about 250 mg/mL, about 260 mg/mL, about 270 mg/mL, about 280 mg/mL, about 290 mg/mL, or about 300 mg/mL. In some instances, the antibody is at a concentration of about 175 mg/mL to about 225 mg/mL (e.g., about 175 mg/mL, about 176 mg/mL, about 177 mg/mL, about 178 mg/mL about 179 mg/mL, about 180 mg/mL, about 181 mg/mL, about 182 mg/mL, about 183 mg/mL, about 184 mg/mL, about 185 mg/mL, about 186 mg/mL, about 187 mg/mL, about 188 mg/mL, about 189 mg/mL, about 190 mg/mL, about 191 mg/mL, about 192 mg/mL, about 193 mg/mL, about 194 mg/mL, about 195 mg/mL, about 196 mg/mL, about 197 mg/mL, about 198 mg/mL, about 199 mg/mL, about 200 mg/mL, about 201 mg/mL, about 202 mg/mL, about 203 mg/mL, about 204 mg/mL, about 205 mg/mL, about 206 mg/mL, about 207 mg/mL, about 208 mg/mL, about 209 mg/mL, about 210 mg/mL, about 211 mg/mL, about 212 mg/mL, about 213 mg/mL, about 214 mg/mL, about 215 mg/mL, about 216 mg/mL, about 217 mg/mL, about 218 mg/mL, about 219 mg/mL, about 220 mg/mL, about 221 mg/mL, about 222 mg/mL, about 223 mg/mL, about 224 mg/mL, or about 225 mg/mL. In particular instances, the antibody concentration is about 200 mg/mL.

G. Therapeutic Methods and Compositions

Any of the anti-IL-33 antibodies disclosed herein may be used in therapeutic methods.

The invention provides an IL-33 axis binding antagonist for use as a medicament. In one aspect, an anti-IL-33 antibody for use as a medicament is provided. In further aspects, an anti-IL-33 antibody for use in treating IL-33-mediated disorders is provided. In certain embodiments, an anti-IL-33 antibody for use in a method of treatment is provided. In certain embodiments, the invention provides an anti-IL-33 antibody for use in a method of treating an individual having an IL-33-mediated disorder comprising administering to the individual an effective amount of the anti-IL-33 antibody. In one such embodiment, the method further comprises administering to the individual an effective amount of at least one additional therapeutic agent, for example, as described below. An "individual" according to any of the above embodiments is preferably a human.

The invention provides an IL-33 axis binding antagonist in the manufacture or preparation of a medicament. In a further aspect, the invention provides for the use of an anti-IL-33 antibody in the manufacture or preparation of a medicament. In one embodiment, the medicament is for treatment of an IL-33-mediated disorder. In a further embodiment, the medicament is for use in a method of treating IL-33-mediated disorder comprising administering to an individual having IL-33-mediated disorder an effective amount of the medicament. In one such embodiment, the method further comprises administering to the individual an effective amount of at least one additional therapeutic agent, e.g., as described below. An "individual" according to any of the above embodiments may be a human.

In a further aspect, the invention provides a method for treating an IL-33-mediated disorder. In some instances, the method comprises administering the individual having such an IL-33-mediated disorder an effective amount of an IL-33 axis binding antagonist. In one embodiment, the method comprises administering to an individual having such IL-33-mediated disorder an effective amount of an anti-IL-33 antibody (e.g., any anti-IL-33 antibody disclosed herein). In one such embodiment, the method further comprises administering to the individual an effective amount of at least one additional therapeutic agent, as described below. An "individual" according to any of the above embodiments may be a human.

In a further aspect, the invention provides pharmaceutical formulations comprising any of the anti-IL-33 antibodies provided herein, e.g., for use in any of the above therapeutic methods. In one embodiment, a pharmaceutical formulation comprises any of the anti-IL-33 antibodies provided herein and a pharmaceutically acceptable carrier. In another embodiment, a pharmaceutical formulation comprises any of the anti-IL-33 antibodies provided herein and at least one additional therapeutic agent, for example, as described below.

In any of the preceding aspects, the IL-33 mediated disorder may be an ocular disorder, an inflammatory condition, an immune disorder, a fibrotic disorder, an eosinophilic disorder, an infection, pain, a central nervous system disorder, or a solid tumor. For example, in some instances, an inflammatory condition may be asthma, airway hyperresponsiveness, airway inflammation, sepsis, septic shock, atopic dermatitis, allergic rhinitis, rheumatoid arthritis, or chronic obstructive pulmonary disease (COPD). In some instances, an immune disorder may be asthma, rheumatoid arthritis, allergy, atopic allergy, anaphylaxis, anaphylactic shock, allergic rhinitis, psoriasis, inflammatory bowel disease (IBD), Crohn's disease, diabetes, or liver disease. In some instances, the fibrotic disease may be idiopathic pulmonary fibrosis (IPF). In some instances, the eosinophilic disorder may be an eosinophil-associated gastrointestinal disorder (EGID). In some instances, the EGID may be eosinophilic esophagitis. In some instances, the infection may be a helminth infection, a protozoan infection, or a viral infection. In some instances, the protozoan infection may be *Leishmania major* infection. In some instances, the viral infection may be respiratory syncytial virus (RSV) infection or influenza infection. In some instances, the pain may be inflammatory pain. In some instances, the central nervous system disorder may be Alzheimer's disease. In some instances, the solid tumor may be a breast tumor, colon tumor, prostate tumor, lung tumor, kidney tumor, liver tumor, pancreas tumor, stomach tumor, intestinal tumor, brain tumor, bone tumor, or skin tumor. In particular instances, the IL-33-mediated disorder may be asthma, allergic rhinitis, atopic dermatitis, COPD, eosinophilic esophagitis, or pulmonary fibrosis (e.g., IPF). For example, in some instances, the IL-33-mediated disorder is asthma. In other instances, the IL-33-mediated disorder is pulmonary fibrosis (e.g., IPF).

In some instances of any of the preceding aspects, the IL-33-mediated disorder may be an ocular disorder (e.g., any ocular disorder disclosed herein). Non-limiting ocular disorders include, for example, AMD (e.g., wet AMD, dry AMD, intermediate AMD, advanced AMD, and geographic atrophy (GA)), macular degeneration, macular edema, DME (e.g., focal, non-center DME and diffuse, center-involved DME), retinopathy, diabetic retinopathy (DR) (e.g., proliferative DR (PDR), non-proliferative DR (NPDR), and high-altitude DR), other ischemia-related retinopathies, ROP, retinal vein occlusion (RVO) (e.g., central (CRVO) and branched (BRVO) forms), CNV (e.g., myopic CNV), corneal neovascularization, diseases associated with corneal neovascularization, retinal neovascularization, diseases associated with retinal/choroidal neovascularization, central serous retinopathy (CSR), pathologic myopia, von Hippel-Lindau disease, histoplasmosis of the eye, FEVR, Coats' disease, Norrie Disease, retinal abnormalities associated with osteoporosis-pseudoglioma syndrome (OPPG), subconjunctival hemorrhage, rubeosis, ocular neovascular disease, neovascular glaucoma, retinitis pigmentosa (RP), hypertensive retinopathy, retinal angiomatous proliferation, macular telangiectasia, iris neovascularization, intraocular neovascularization, retinal degeneration, cystoid macular edema (CME), vasculitis, papilloedema, retinitis, including but not limited to CMV retinitis, ocular melanoma, retinal blastoma, conjunctivitis (e.g., infectious conjunctivitis and non-infectious (e.g., allergic) conjunctivitis), Leber congenital amaurosis (also known as Leber's congenital amaurosis or LCA), uveitis (including infectious and non-infectious uveitis), choroiditis (e.g., multifocal choroiditis), ocular histoplasmosis, blepharitis, dry eye, traumatic eye injury, Sjögren's disease, and other ophthalmic diseases wherein the disease or disorder is associated with ocular neovascularization, vascular leakage, and/or retinal edema or retinal atrophy. Additional exemplary ocular disorders include retinoschisis (abnormal splitting of the retina neurosensory layers), diseases associated with rubeosis (neovascularization of the angle) and diseases caused by the abnormal proliferation of fibrovascular or fibrous tissue, including all forms of proliferative vitreoretinopathy.

Exemplary diseases associated with corneal neovascularization include, but are not limited to, epidemic keratoconjunctivitis, vitamin A deficiency, contact lens overwear, atopic keratitis, superior limbic keratitis, terygium keratitis sicca, Sjëgren's syndrome, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, marginal keratolysis, rheumatoid arthritis, systemic lupus, polyarteritis, trauma, Wegener's sarcoidosis, scleritis, Stevens-Johnson syndrome, periphigoid radial keratotomy, and corneal graph rejection.

Exemplary diseases associated with choroidal neovascularization and defects in the retina vasculature, including increased vascular leak, aneurisms and capillary drop-out include, but are not limited to, diabetic retinopathy, macular degeneration, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme's disease, systemic lupus erythematosis, retinopathy of prematurity, retina edema (including macular edema), Eales disease, Behcet's disease, infections causing retinitis or choroiditis (e.g., multifocal choroidits), presumed ocular histoplasmosis, Best's disease (vitelliform macular degeneration), myopia, optic pits, pars planitis, retinal detachment (e.g., chronic retinal detachment), hyperviscosity syndromes, toxoplasmosis, trauma, and post-laser complications.

Exemplary diseases associated with atrophy of retinal tissues (photoreceptors and the underlying RPE) include, but are not limited to, atrophic or nonexudative AMD (e.g., geographic atrophy or advanced dry AMD), macular atrophy (e.g., atrophy associated with neovascularization and/or geographic atrophy), diabetic retinopathy, Stargardt's disease, Sorsby Fundus Dystrophy, retinoschisis and retinitis pigmentosa.

In some instances, the ocular disorder includes AMD (including wet AMD, dry AMD, and GA), retinopathy (e.g., DR and ROP), PCV, diabetic macular edema, dry eye disease, Behcet's disease, allergic conjunctivitis, and retina detachment.

In other instances, the ocular disorder includes intermediate AMD, advanced AMD, glaucoma, uveitis (e.g., infectious and non-infectious uveitis), retinitis pigmentosa, Leber Congenital Amaurosis, Stargardt's disease, high-altitude diabetic retinopathy, traumatic eye injury, and conjunctivitis (e.g., infectious conjunctivitis and non-infectious conjunctivitis).

For example, the invention provides a method of treating an ocular disorder in a subject in need thereof, the method comprising administering to the subject a therapeutically effective amount of an anti-IL-33 antibody, for example, an anti-IL-33 antibody disclosed herein. In some instances, the ocular disorder may be selected from the group consisting of age-related macular degeneration (AMD), including wet AMD, dry AMD, intermediate AMD, advanced AMD, and geographic atrophy (GA)), retinopathy (e.g., diabetic retinopathy (DR), retinopathy of prematurity (ROP), and high-altitude DR), polypoidal choroidal vasculopathy (PCV), diabetic macular edema, dry eye disease, Behcet's disease, retina detachment, glaucoma, uveitis (e.g., infectious and non-infectious uveitis), retinitis pigmentosa, Leber Congenital Amaurosis (also known as Leber's congenital amaurosis), Stargardt's disease, traumatic eye injury, and conjunctivitis (e.g., infectious conjunctivitis, non-infectious conjunctivitis, and allergic conjunctivitis). In some instances, the ophthalmologic disorder includes AMD (including wet AMD, dry AMD, and GA), retinopathy (e.g., DR and ROP), PCV, diabetic macular edema, dry eye disease, Behcet's disease, allergic conjunctivitis, and retina detachment. In other instances, the ocular disorder includes intermediate AMD, advanced AMD, glaucoma, uveitis (e.g., infectious and non-infectious uveitis), retinitis pigmentosa, Leber Congenital Amaurosis, Stargardt's disease, high-altitude diabetic retinopathy, traumatic eye injury, and conjunctivitis (e.g., infectious conjunctivitis and non-infectious conjunctivitis).

An anti-IL-33 antibody (e.g., any anti-IL-33 antibody disclosed herein) can be used either alone or in combination with other agents in a therapy. For instance, an anti-IL-33 antibody (e.g., any anti-IL-33 antibody disclosed herein) may be co-administered with at least one additional therapeutic agent. In certain embodiments, an additional therapeutic agent is an ST2 binding antagonist, a complement pathway inhibitor (e.g., a Factor D binding antagonist), an HtrA1 binding antagonist, a VEGF antagonist, a tryptase-beta binding antagonist, a chemoattractant receptor-homologous molecule expressed on Th2 cells (CRTH2) binding antagonist, an interleukin-13 (IL-13) binding antagonist, an interleukin-17 (IL-17) binding antagonist, a JAK1 antagonist, and/or an interleukin-5 (IL-5) binding antagonist. In some embodiments, an additional therapeutic agent is a chemotherapeutic agent, an anti-hormonal agent, a cytotoxic agent, a growth inhibitory agent, or combinations thereof.

An anti-IL-33 antibody (e.g., any anti-IL-33 antibody disclosed herein) for use in any of the methods described herein can be formulated in a polymeric formulation.

For example, in certain embodiments, any of the preceding methods further comprises administering one or more additional compounds. In certain embodiments, the anti-IL-33 antibody or polymeric formulation is administered simultaneously with the additional compound(s). In certain embodiments, the anti-IL33 antibody or polymeric formulation is administered before or after the additional compound(s). In certain embodiments, the additional compound binds to a second biological molecule selected from the group consisting of IL-1β; IL-6; IL-6R; IL-13; IL-13R; PDGF; angiopoietin; Ang2; Tie2; S1P; integrins αvβ3, αvβ5, and α5β1; betacellulin; apelin/APJ; erythropoietin; complement factor D; TNFα; HtrA1; a VEGF receptor; ST-2 receptor; and proteins genetically linked to AMD risk, such as complement pathway components C2, factor B, factor H, CFHR3, C3b, C5, C5a, and C3a; HtrA1; ARMS2; TIMP3; HLA; interleukin-8 (IL-8); CX3CR1; TLR3; TLR4; CETP; LIPC; COL10A1; and TNFRSF10A. In certain embodiments, the additional compound is an antibody or antigen-binding fragment thereof. In certain embodiments according to (or as applied to) any of the embodiments above, the ocular disorder is an intraocular neovascular disease selected from the group consisting of proliferative retinopathies, choroidal neovascularization (CNV), age-related macular degeneration (AMD), diabetic and other ischemia-related retinopathies, diabetic macular edema, pathological myopia, von Hippel-Lindau disease, histoplasmosis of the eye, retinal vein occlusion (RVO), including CRVO and BRVO, corneal neovascularization, retinal neovascularization, and retinopathy of prematurity (ROP). For example, in some instances, the additional compound is a bispecific antibody (e.g., an anti-VEGF/anti-Ang2 bispecific antibody, such as RG-7716 or any bispecific anti-VEGF/anti-Ang2 bispecific antibody disclosed in WO 2010/069532 or WO 2016/073157 or a variant thereof. In another example, in some instances, the additional compound is an anti-IL-6 antibody, for example, EBI-031 (Eleven Biotherapeutics; see, e.g., WO 2016/073890), siltuximab (SYLVANT®), olokizumab, clazakizumab, sirukumab, elsilimomab, OPR-003, MEDI5117, PF-04236921, or a variant thereof. In a still further example, in some instances, the additional compound is an anti-IL-6R antibody, for example, tocilizumab (ACTEMRA®) (see, e.g., WO 1992/019579), sarilumab, ALX-0061, SA237, or a variant thereof.

In some instances, an antibody of the invention, and/or polymeric formulation thereof, may be administered in combination with at least one additional therapeutic agent for treatment of an ocular disorder, for example, an ocular disorder described herein (e.g., AMD (e.g., wet AMD), DME, DR, RVO, or GA). Exemplary additional therapeutic agents for combination therapy for treatment of ocular disorders include, without limitation, anti-angiogenic agents, such as VEGF antagonists, including, for example, anti-VEGF antibodies (e.g., the anti-VEGF Fab LUCENTIS® (ranibizumab)), soluble receptor fusion proteins (e.g., the recombinant soluble receptor fusion protein EYLEA® (aflibercept, also known as VEGF Trap Eye; Regeneron/Aventis)), aptamers (e.g., the anti-VEGF pegylated aptamer MACUGEN® (pegaptanib sodium; NeXstar Pharmaceuticals/OSI Pharmaceuticals)), and VEGFR tyrosine kinase inhibitors (e.g., 4-(4-bromo-2-fluoroanilino)-6-methoxy-7-(1-methylpiperidin-4-ylmethoxy)quinazoline (ZD6474), 4-(4-fluoro-2-methylindol-5-yloxy)-6-methoxy-7-(3-pyrrolidin-1-ylpropoxy)quinazoline (AZD2171), vatalanib (PTK787), semaxaminib (SU5416; SUGEN), and SUTENT® (sunitinib)); Tryptophanyl-tRNA synthetase (TrpRS); squalamine; RETAANE® (anecortave acetate for depot suspension; Alcon, Inc.); Combretastatin A4 Prodrug (CA4P); MIFEPREX® (mifepristone-ru486); subtenon triamcinolone acetonide; intravitreal crystalline triamcinolone acetonide; matrix metalloproteinase inhibitors (e.g., Prinomastat (AG3340; Pfizer)); fluocinolone acetonide (including fluocinolone intraocular implant; Bausch & Lomb/Control Delivery Systems); linomide; inhibitors of integrin β3 function; angiostatin, and combinations thereof. These and other therapeutic agents that can be administered in combination with an antibody of the invention are described, for example, in U.S. Patent Application No. US 2014/0017244, which is incorporated herein by reference in its entirety.

Further examples of additional therapeutic agents that can be used in combination with an antibody of the invention, and/or polymeric formulation thereof, for treatment of an ocular disorder (e.g., AMD, DME, DR, RVO, or GA), include, but are not limited to, VISUDYNE® (verteporfin; a light-activated drug that is typically used in conjunction with photodynamic therapy with a non-thermal laser), PKC412, Endovion (NS 3728; NeuroSearch A/S), neurotrophic factors (e.g., glial derived neurotrophic factor (GDNF) and ciliary neurotrophic factor (CNTF)), diltiazem, dorzolamide, PHOTOTROP®, 9-cis-retinal, eye medication (e.g., phospholine iodide, echothiophate, or carbonic anhydrase inhibitors), veovastat (AE-941; AEterna Laboratories, Inc.), Sirna-027 (AGF-745; Sima Therapeutics, Inc.), neurotrophins (including, by way of example only, NT-4/5, Genentech), Cand5 (Acuity Pharmaceuticals), INS-37217 (Inspire Pharmaceuticals), integrin antagonists (including those from Jerini AG and Abbott Laboratories), EG-3306 (Ark Therapeutics Ltd.), BDM-E (BioDiem Ltd.), thalidomide (as used, for example, by EntreMed, Inc.), cardiotrophin-1 (Genentech), 2-methoxyestradiol (Allergan/Oculex), DL-8234 (Toray Industries), NTC-200 (Neurotech), tetrathiomolybdate (University of Michigan), LYN-002 (Lynkeus Biotech), microalgal compound (Aquasearch/Albany, Mera Pharmaceuticals), D-9120 (Celltech Group plc), ATX-S10 (Hamamatsu Photonics), TGF-beta 2 (Genzyme/Celtrix), tyrosine kinase inhibitors (e.g., those from Allergan, SUGEN, or Pfizer), NX-278-L (NeXstar Pharmaceuticals/Gilead Sciences), Opt-24 (OPTIS France SA), retinal cell ganglion neuroprotectants (Cogent Neurosciences), N-nitropyrazole derivatives (Texas A&M University System), KP-102 (Krenitsky Pharmaceuticals), cyclosporin A, therapeutic agents used in photodynamic therapy (e.g., VISUDYNE®; receptor-targeted PDT, Bristol-Myers Squibb, Co.; porfimer sodium for injection with PDT; verteporfin, QLT Inc.; rostaporfin with PDT, Miravent Medical Technologies; talaporfin sodium with PDT, Nippon Petroleum; and motexafin lutetium, Pharmacyclics, Inc.), antisense oligonucleotides (including, by way of example, products tested by Novagali Pharma SA and ISIS-13650, Ionis Pharmaceuticals), and combinations thereof.

An antibody of the invention, and/or polymeric formulation thereof, may be administered in combination with a therapy or surgical procedure for treatment of an ocular disorder (e.g., AMD, DME, DR, RVO, or GA), including, for example, laser photocoagulation (e.g., panretinal photocoagulation (PRP)), drusen lasering, macular hole surgery, macular translocation surgery, implantable miniature telescopes, PHI-motion angiography (also known as micro-laser therapy and feeder vessel treatment), proton beam therapy, microstimulation therapy, retinal detachment and vitreous surgery, scleral buckle, submacular surgery, transpupillary thermotherapy, photosystem I therapy, use of RNA interference (RNAi), extracorporeal rheopheresis (also known as membrane differential filtration and rheotherapy), microchip implantation, stem cell therapy, gene replacement therapy, ribozyme gene therapy (including gene therapy for hypoxia response element, Oxford Biomedica; Lentipak, Genetix; and PDEF gene therapy, GenVec), photoreceptor/retinal cells transplantation (including transplantable retinal epithelial cells, Diacrin, Inc.; retinal cell transplant, e.g., Astellas Pharma US, Inc., ReNeuron, CHA Biotech), acupuncture, and combinations thereof.

In some instances, an antibody of the invention, and/or polymeric formulation thereof, can be administered in combination with an anti-angiogenic agent for treatment of an ocular disorder (e.g., AMD, DME, DR, RVO, or GA). Any suitable anti-angiogenic agent can be used in combination with an antibody of the invention, including, but not limited to, those listed by Carmeliet et al. Nature 407:249-257, 2000. In some embodiments, the anti-angiogenic agent is a VEGF antagonist, including, but not limited to, an anti-VEGF antibody (e.g., the anti-VEGF Fab LUCENTIS® (ranibizumab), RTH-258 (formerly ESBA-1008, an anti-VEGF single-chain antibody fragment; Novartis), or a bispecific anti-VEGF antibody (e.g., an anti-VEGF/anti-angiopoeitin 2 bispecific antibody such as RG-7716; Roche)), a soluble recombinant receptor fusion protein (e.g., EYLEA® (aflibercept)), a VEGF variant, a soluble VEGFR fragment, an aptamer capable of blocking VEGF (e.g., pegaptanib) or VEGFR, a neutralizing anti-VEGFR antibody, a small molecule inhibitor of VEGFR tyrosine kinases, an anti-VEGF DARPin® (e.g., abicipar pegol, Molecular Partners AG/Allergan), a small interfering RNAs which inhibits expression of VEGF or VEGFR, a VEGFR tyrosine kinase inhibitor (e.g., 4-(4-bromo-2-fluoroanilino)-6-methoxy-7-(1-methylpiperidin-4-ylmethoxy)quinazoline (ZD6474), 4-(4-fluoro-2-methylindol-5-yloxy)-6-methoxy-7-(3-pyrrolidin-1-ylpropoxy)quinazoline (AZD2171), vatalanib (PTK787), semaxaminib (SU5416; SUGEN), and SUTENT® (sunitinib)), and combinations thereof. In some instances, the bispecific anti-IL-33 antibody binds to a therapeutic agent targeting a second biological molecule, including but not limited to IL-1β; IL-6; IL-6R; PDGF (e.g., PDGF-BB); angiopoietin; angiopoietin 2; Tie2; S1P; integrins αvβ3, αvβ5, and α5β1; betacellulin; apelin/APJ; erythropoietin; complement factor D; TNFα; HtrA1; a VEGF receptor (e.g., VEGFR1, VEGFR2, VEGFR3, mbVEGFR, or sVEGFR); ST-2 receptor; and proteins genetically linked to age-related macular degeneration (AMD) risk, such as complement pathway components C2, factor B, factor H, CFHR3, C3b, C5, C5a, and C3a; HtrA1; ARMS2; TIMP3; HLA; IL-8; CX3CR1; TLR3; TLR4; CETP; LIPC; COL10A1; and TNFRSF10A. For example, in some instances, the additional compound is a bispecific antibody (e.g., an anti-VEGF/anti-Ang2 bispecific antibody, such as RG-7716 or any bispecific anti-VEGF/anti-Ang2 bispecific antibody disclosed in WO 2010/069532 or WO 2016/073157 or a variant thereof).

Other suitable anti-angiogenic agents that may be administered in combination with an antibody of the invention, and/or polymeric formulation thereof, for treatment of an ocular disorder (e.g., AMD, DME, DR, RVO, or GA) include corticosteroids, angiostatic steroids, anecortave acetate, angiostatin, endostatin, tyrosine kinase inhibitors, matrix metalloproteinase (MMP) inhibitors, insulin-like growth factor-binding protein 3 (IGFBP3), stromal derived factor (SDF-1) antagonists (e.g., anti-SDF-1 antibodies), pigment epithelium-derived factor (PEDF), gamma-secretase, Delta-like ligand 4, integrin antagonists, hypoxia-inducible factor (HIF)-1α antagonists, protein kinase CK2 antagonists, agents that inhibit stem cell (e.g., endothelial progenitor cell) homing to the site of neovascularization (e.g., an anti-vascular endothelial cadherin (CD-144) antibody and/or an anti-SDF-1 antibody), and combinations thereof.

In a further example, in some instances, an antibody of the invention, and/or polymeric formulation thereof, can be administered in combination with an agent that has activity against neovascularization for treatment of an ocular disorder (e.g., AMD, DME, DR, RVO, or GA), such as an anti-inflammatory drug, a mammalian target of rapamycin (mTOR) inhibitor (e.g., rapamycin, AFINITOR® (everolimus), and TORISEL® (temsirolimus)), cyclosporine, a tumor necrosis factor (TNF) antagonist (e.g., an anti-TNFα antibody or antigen-binding fragment thereof (e.g., infliximab, adalimumab, certolizumab pegol, and golimumab) or a soluble receptor fusion protein (e.g., etanercept)), an anti-complement agent, a nonsteroidal anti-inflammatory agent (NSAID), or combinations thereof.

In a still further example, in some instances, an antibody of the invention, and/or polymeric formulation thereof, can be administered in combination with an agent that is neuroprotective and can potentially reduce the progression of dry AMD to wet AMD, such as the class of drugs called the "neurosteroids," which include drugs such as dehydroepiandrosterone (DHEA) (brand names: PRASTERA™ and FIDELIN®), dehydroepiandrosterone sulfate, and pregnenolone sulfate.

Any suitable AMD therapeutic agent can be administered as an additional therapeutic agent in combination with an antibody of the invention, and/or polymeric formulation thereof, for treatment of an ocular disorder (e.g., AMD, DME, DR, RVO, or GA), including, but not limited to, a VEGF antagonist, for example, an anti-VEGF antibody (e.g., LUCENTIS® (ranibizumab), RTH-258 (formerly ESBA-1008, an anti-VEGF single-chain antibody fragment; Novartis), or a bispecific anti-VEGF antibody (e.g., an anti-VEGF/anti-angiopoeitin 2 bispecific antibody such as RG-7716; Roche)), a soluble VEGF receptor fusion protein (e.g., EYLEA® (aflibercept)), an anti-VEGF DARPin® (e.g., abicipar pegol; Molecular Partners AG/Allergan), or an anti-VEGF aptamer (e.g., MACUGEN® (pegaptanib sodium)); a platelet-derived growth factor (PDGF) antagonist, for example, an anti-PDGF antibody, an anti-PDGFR antibody (e.g., REGN2176-3), an anti-PDGF-BB pegylated aptamer (e.g., FOVISTA®; Ophthotech/Novartis), a soluble PDGFR receptor fusion protein, or a dual PDGF/VEGF antagonist (e.g., a small molecule inhibitor (e.g., DE-120 (Santen) or X-82 (TyrogeneX)) or a bispecific anti-PDGF/anti-VEGF antibody)); VISUDYNE® (verteporfin) in combination with photodynamic therapy; an antioxidant; a complement system antagonist, for example, a complement factor C5 antagonist (e.g., a small molecule inhibitor (e.g., ARC-1905; Opthotech) or an anti-C5 antibody (e.g., LFG-316; Novartis), a properdin antagonist (e.g., an anti-properdin antibody, e.g., CLG-561; Alcon), or a complement factor D antagonist (e.g., an anti-complement factor D antibody, e.g., lampalizumab; Roche)); a C3 blocking peptide (e.g., APL-2, Appellis); a visual cycle modifier (e.g., emixustat hydrochloride); squalamine (e.g., OHR-102; Ohr Pharmaceutical); vitamin and mineral supplements (e.g., those described in the Age-Related Eye Disease Study 1 (AREDS1; zinc and/or antioxidants) and Study 2 (AREDS2; zinc, antioxidants, lutein, zeaxanthin, and/or omega-3 fatty acids)); a cell-based therapy, for example, NT-501 (Renexus); PH-05206388 (Pfizer), huCNS-SC cell transplantation (StemCells), CNTO-2476 (umbilical cord stem cell line; Janssen), OpRegen (suspension of RPE cells; Cell Cure Neurosciences), or MA09-hRPE cell transplantation (Ocata Therapeutics); a tissue factor antagonist (e.g., hI-con1; Iconic Therapeutics); an alpha-adrenergic receptor agonist (e.g., brimonidine tartrate; Allergan); a peptide vaccine (e.g., S-646240; Shionogi); an amyloid beta antagonist (e.g., an anti-beta amyloid monoclonal antibody, e.g., GSK-933776); an S1P antagonist (e.g., an anti-S1P antibody, e.g., iSONEP™; Lpath Inc); a ROBO4 antagonist (e.g., an anti-ROBO4 antibody, e.g., DS-7080a; Daiichi Sankyo); a lentiviral vector expressing endostatin and angiostatin (e.g., RetinoStat); and any combination thereof. In some instances, AMD therapeutic agents (including any of the preceding AMD therapeutic agents) can be co-formulated. For example, the anti-PDGFR antibody REGN2176-3 can be co-formulated with aflibercept (EYLEA®). In some instances, such a co-formulation can be administered in combination with an antibody of the invention. In some instances, the ocular disorder is AMD (e.g., wet AMD).

An antibody of the invention, and/or polymeric formulation thereof, can be administered in combination with LUCENTIS® (ranibizumab) for treatment of an ocular disorder (e.g., AMD, DME, DR, RVO, or GA). In some instances, the ocular disorder is AMD (e.g., wet AMD). In some instances, the ocular disorder is GA.

An antibody of the invention, and/or polymeric formulation thereof, can be administered in combination with EYLEA® (aflibercept) for treatment of an ocular disorder (e.g., AMD, DME, DR, RVO, or GA). In some instances, the ocular disorder is AMD (e.g., wet AMD). In some instances, the ocular disorder is GA.

An antibody of the invention, and/or polymeric formulation thereof, can be administered in combination with MACUGEN® (pegaptanib sodium) for treatment of an ocular disorder (e.g., AMD, DME, DR, RVO, or GA). In some instances, the ocular disorder is AMD (e.g., wet AMD). In some instances, the ocular disorder is GA.

An antibody of the invention, and/or polymeric formulation thereof, can be administered in combination with VISUDYNE® (verteporfin) in combination with photodynamic therapy for treatment of an ocular disorder (e.g., AMD, DME, DR, RVO, or GA). In some instances, the ocular disorder is AMD (e.g., wet AMD). In some instances, the ocular disorder is GA.

An antibody of the invention, and/or polymeric formulation thereof, can be administered in combination with a PDGF antagonist for treatment of an ocular disorder (e.g., AMD, DME, DR, RVO, or GA). Exemplary PDGF antagonists which may be used in combination with an antibody of the invention include an anti-PDGF antibody, an anti-PDGFR antibody, a small molecule inhibitor (e.g., squalamine), an anti-PDGF-B pegylated aptamer such as FOVISTA® (E10030; Ophthotech/Novartis), or a dual PDGF/VEGF antagonist (e.g., a small molecule inhibitor (e.g., DE-120 (Santen) or X-82 (TyrogeneX)) or a bispecific anti-PDGF/anti-VEGF antibody). For example, FOVISTA® can be administered as an adjunct therapy to an antibody of the invention. OHR-102 can be administered in combination with VEGF antagonists such as LUCENTIS® or EYLEA®. In some embodiments, an antibody of the invention can be administered in combination with OHR-102, LUCENTIS®, and/or EYLEA®. In some instances, the ocular disorder is AMD (e.g., wet AMD). In some instances, the ocular disorder is GA.

An antibody of the invention, and/or polymeric formulation thereof, can be administered in combination with RTH-258 for treatment of an ocular disorder (e.g., AMD, DME, DR, RVO, or GA). RTH-258 can be administered, for example, by intravitreal injection or eye infusion. In some instances, the ocular disorder is AMD (e.g., wet AMD). In some instances, the ocular disorder is GA.

An antibody of the invention, and/or polymeric formulation thereof, can be administered in combination with RTH-258 for treatment of an ocular disorder (e.g., AMD, DME, DR, RVO, or GA). RTH-258 can be administered, for example, by intravitreal injection or eye infusion. In some instances, the ocular disorder is AMD (e.g., wet AMD). In some instances, the ocular disorder is GA.

An antibody of the invention, and/or polymeric formulation thereof, can be administered in combination with abicipar pegol for treatment of an ocular disorder (e.g., AMD, DME, DR, RVO, or GA). In some instances, the ocular disorder is AMD (e.g., wet AMD). In some instances, the ocular disorder is GA.

Any suitable DME and/or DR therapeutic agent can be administered in combination with an antibody of the invention, and/or polymeric formulation thereof, for treatment of an ocular disorder (e.g., AMD, DME, DR, RVO, or GA), including, but not limited, to a VEGF antagonist (e.g., LUCENTIS® or EYLEA®), a corticosteroid (e.g., a corticosteroid implant (e.g., OZURDEX® (dexamethasone intravitreal implant) or ILUVIEN® (fluocinolone acetonide intravitreal implant)) or a corticosteroid formulated for administration by intravitreal injection (e.g., triamcinolone acetonide)), or combinations thereof. In some instances, the ocular disorder is DME and/or DR.

An antibody of the invention, and/or polymeric formulation thereof, can be administered in combination with LUCENTIS® (ranibizumab) for treatment of DME and/or DR (e.g., NPDR or PDR).

An antibody of the invention, and/or polymeric formulation thereof, can be administered in combination with EYLEA® (aflibercept) for treatment of DME and/or DR (e.g., NPDR or PDR).

An antibody of the invention, and/or polymeric formulation thereof, can be administered in combination with OZURDEX® (dexamethasone intravitreal implant) for treatment of DME and/or DR.

An antibody of the invention, and/or polymeric formulation thereof, can be administered in combination with ILUVIEN® (dexamethasone intravitreal implant) for treatment of DME and/or DR.

In some cases, the TAO/PRN treatment regimen or TAE treatment regimen may be used to administer an AMD therapeutic agent (e.g., ranibizumab or aflibercept) in combination with an antibody of the invention, and/or polymeric formulation thereof. In some instances, the ocular disorder is AMD (e.g., wet AMD). In some instances, the ocular disorder is GA.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent or agents. In one embodiment, administration of the anti-IL33 antibody, or polymeric formulation and administration of an additional therapeutic agent occur within about one, two, three, four, or five months, or within about one, two or three weeks, or within about one, two, three, four, five, or six days, of each other.

In other examples, an anti-IL-33 antibody (e.g., any anti-IL-33 antibody disclosed herein) may be co-administered with an anti-IL-13 antibody, e.g., for the treatment of an inflammatory disorder, such as, for example, asthma, airway hyperresponsiveness, airway inflammation, sepsis, septic shock, atopic dermatitis, allergic rhinitis, rheumatoid arthritis, or chronic obstructive pulmonary disease (COPD), or a fibrotic disorder, such as, for example, idiopathic pulmonary fibrosis (IPF). In an exemplary embodiment, anti-IL-33 antibody (e.g., any anti-IL-33 antibody disclosed herein) may be co-administered with an anti-IL-13 antibody for treatment of asthma.

Any of the anti-IL-33 antibodies described herein may be administered in combination with an additional IL-33 axis binding antagonist. In some instances, the additional IL-33 axis binding antagonist is anti-IL-33 antibody such as ANB-020 (AnaptyxBio Inc.) or any of the antibodies described in WO2014164959, EP1725261, U.S. Pat. No. 8,187,569, WO2011031600, WO2015099175 or WO2015106080 (which are each incorporated herein by reference in their entirety); an anti-ST2 antibody such as AMG-282 (Amgen) or STLM15 (Janssen), or any of the antibodies described in WO2013173761 or WO2013165894 (which are each incorporated herein by reference in their entirety); or a ST2-Fc protein and variants thereof such as those described in WO 2013/173761, WO 2013/165894, or WO 2014/152195 (which are each incorporated herein by reference in their entirety).

In another example, an anti-IL-33 antibody (e.g., any anti-IL-33 antibody disclosed herein) may be co-administered with a complement pathway inhibitor. In some instances, a complement pathway inhibitor may be an inhibitor of the alternative complement pathway (e.g., Factor D, properdin, Factor B, Factor Ba, and Factor Bb) or the classical complement pathway (e.g., C3a, C5, C5a, C5b, C6, C7, C8, C9, and C5b-9). In some instances, the complement pathway inhibitor may be any complement pathway inhibitor described in WO 2007/056227, which is incorporated herein by reference in its entirety. In some instances, the complement pathway inhibitor may be a Factor D binding antagonist. In particular instances, a Factor D binding antagonist may an anti-Factor D antibody or an antigen-binding fragment thereof, for example, any Factor D antibody described in WO 2007/056227, WO 01/70818, and/or US 2002/0081293, which are each incorporated herein by reference in their entirety. As a non-limiting example, in some instances, the anti-Factor D antibody may comprise an amino acid sequence having at least 70% sequence identity (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, the monoclonal antibody 166-32 produced from the hybridoma deposited with the American Type Culture Collection (ATCC) and designated HB12476. In some instances, the anti-Factor D antibody is a humanized derivative of monoclonal antibody 166-32. In some embodiments, the anti-Factor D antibody binds to the same epitope as monoclonal antibody 166-32. In some instances, the anti-Factor D antibody is an antibody fragment derived from monoclonal antibody 166-32. In some instances, the antibody fragment derived from monoclonal antibody 166-32 is an Fab, Fab'-SH, Fv, scFv, or an (Fab')$_2$ fragment. In some embodiments, the antibody fragment derived from monoclonal antibody 166-32 is an Fab.

In another example, an anti-IL-33 antibody (e.g., any anti-IL-33 antibody disclosed herein) may be co-administered with an HtrA1 binding antagonist. In some instances, the HtrA1 binding antagonist may be an anti-HtrA1 antibody or an antigen-binding fragment thereof. Any of the anti-HtrA1 antibodies or antigen-binding fragments thereof known in the art and/or described herein may be used. For example, in some instances, the anti-HtrA1 antibody is an anti-HtrA1 antibody described in U.S. Ser. No. 10/421,822 or U.S. Pat. No. 9,738,727. In some instances, the anti-HtrA1 antibody fragment is an Fab, Fab'-SH, Fv, scFv, or an (Fab')$_2$ fragment. In some embodiments, the anti-HtrA1 antibody fragment is an Fab.

In another example, an anti-IL-33 antibody (e.g., any anti-IL-33 antibody disclosed herein) may be co-administered with a VEGF antagonist. In some instances, the VEGF antagonist may be an anti-VEGF antibody or an antigen-binding fragment thereof. Any of the anti-VEGF antibodies or antigen-binding fragments thereof known in the art and/or described herein may be used. For example, in some instances, the anti-VEGF antibody is bevacizumab (AVASTIN®) or ranibizumab (LUCENTIS®). In some instances, the anti-VEGF antibody fragment is an Fab, Fab'-SH, Fv, scFv, or an (Fab')$_2$ fragment. In some embodiments, the anti-VEGF antibody fragment is an Fab.

In some instances, the anti-VEGF antibody or antigen-binding fragment thereof is or is derived from any anti-VEGF antibody described in WO 2005/044853, which is incorporated herein by reference in its entirety. For example, in some instances, the anti-VEGF antibody is or is derived from a G6 series antibody (e.g., G6, G6-8, G6-23, G6-23.1, G6-23.2, or G6-31) or a B20 series antibody (e.g., B20, B20-4, or B20-4.1). In some embodiments, the anti-VEGF antibody is a humanized derivative of any of the preceding antibodies. In some embodiments, the anti-VEGF antibody is an antibody fragment derived from any of the preceding antibodies. In some embodiments, the antibody fragment is an Fab, Fab'-SH, Fv, scFv, or an (Fab')$_2$ fragment. In some embodiments, the antibody fragment is an Fab.

In another aspect, the invention provides a method of treating geographic atrophy in a subject in need thereof, the method comprising administering to the subject a therapeutically effective amount of an anti-IL-33 antibody (e.g., any anti-IL-33 antibody disclosed herein) and a therapeutically effective amount of a Factor D binding antagonist. In some instances, the Factor D binding antagonist may be an anti-Factor D antibody or an antigen-binding fragment thereof, for example, any Factor D antibody described in WO 2007/056227, WO 01/70818, and/or US 2002/0081293. For example, in some instances, the anti-Factor D antibody may comprise an amino acid sequence having at least 70% sequence identity (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, the monoclonal antibody 166-32 produced from the hybridoma deposited with the American Type Culture Collection (ATCC) and designated HB12476. In some instances, the anti-Factor D antibody is a humanized derivative of monoclonal antibody 166-32. In some embodiments, the anti-Factor D antibody binds to the same epitope as monoclonal antibody 166-32. In some instances, the anti-Factor D antibody is an antibody fragment derived from monoclonal antibody 166-32. In some instances, the antibody fragment derived from monoclonal antibody 166-32 is an Fab, Fab'-SH, Fv, scFv, or an (Fab')$_2$ fragment. In some embodiments, the antibody fragment derived from monoclonal antibody 166-32 is an Fab.

In another aspect, the invention provides a method of treating GA, AMD (wet or dry), DR, PCV, or ROP in a subject in need thereof, the method comprising administering to the subject a therapeutically effective amount of an anti-IL-33 antibody (e.g., any anti-IL-33 antibody disclosed herein) and a therapeutically effective amount of a HtrA1 binding antagonist. In some instances, the HtrA1 binding antagonist may be an anti-HtrA1 antibody or an antigen-binding fragment thereof, for example, any HtrA1 antibody described in U.S. Ser. No. 10/421,822 or U.S. Pat. No. 9,738,727. In some instances, the anti-HtrA1 antibody is an antibody fragment. In some instances, the antibody fragment is an Fab, Fab'-SH, Fv, scFv, or an (Fab')$_2$ fragment. In some embodiments, the antibody fragment derived is an Fab.

In some embodiments, an additional therapeutic agent is an asthma therapy, as described below. Moderate asthma is currently treated with a daily inhaled anti-inflammatory-corticosteroid or mast cell inhibitor such as cromolyn sodium or nedocromil plus an inhaled beta2-agonist as needed (3-4 times per day) to relieve breakthrough symptoms or allergen- or exercise-induced asthma. Exemplary inhaled corticosteroids include QVAR®, PULMICORT®, SYMBICORT®, AEROBID®, FLOVENT®, FLONASE®, ADVAIR®, and AZMACORT®. Additional asthma therapies include long acting bronchial dilators (LABD). In certain embodiments, the LABD is a long-acting beta-2 agonist (LABA), leukotriene receptor antagonist (LTRA), long-acting muscarinic antagonist (LAMA), theophylline, or oral corticosteroids (OCS). Exemplary LABDs include SYMBICORT®, ADVAIR®, BROVANA®, FORADIL®, PERFOROMIST™ and SEREVENT®.

Such combination therapies noted above encompass combined administration (where two or more therapeutic agents are included in the same or separate formulations), and separate administration, in which case, administration of the antibody disclosed herein can occur prior to, simultaneously, and/or following, administration of the additional therapeutic agent or agents. In one embodiment, administration of the anti-IL-33 antibody and administration of an additional therapeutic agent occur within about one month, or within about one, two or three weeks, or within about one, two, three, four, five, or six days, of each other. Antibodies disclosed herein can also be used in combination with radiation therapy.

An anti-IL-33 antibody (e.g., any anti-IL-33 antibody disclosed herein) (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. In some instances, an anti-IL-33 antibody (e.g., any anti-IL-33 antibody disclosed herein) may be administered intravitreally, intramuscularly, intravenously, intradermally, percutaneously, intraarterially, intraperitoneally, intralesionally, intracranially, intraarticularly, intraprostatically, intrapleurally, intratracheally, intrathecally, intranasally, intravaginally, intrarectally, topically, intratumorally, peritoneally, subcutaneously, subconjunctivally, intravesicularly, mucosally, intrapericardially, intraumbilically, intraocularly, intraorbitally, orally, topically, transdermally, periocularly, conjunctivally, subtenonly, intracamerally, subretinally, retrobulbarly, intracanalicularly, by inhalation, by injection, by implantation, by infusion, by continuous infusion, by localized perfusion bathing target cells directly, by catheter, by lavage, in cremes, or in lipid compositions. The compositions utilized in the methods described herein can also be administered systemically or locally. Dosing can be by any suitable route, for example, by injections, such as intravenous or subcutaneous injections, depending in part on whether the administration is brief or chronic. Various dosing schedules including but not limited to single or multiple administrations over various time-points, bolus administration, and pulse infusion are contemplated herein.

In some instances, an anti-IL-33 antibody (e.g., any anti-IL-33 antibody disclosed herein) may be administered directly to the eye by ocular tissue injection, for example, using intravitreal, intraocular, periocular, conjunctival, subconjunctival, subtenon, intracameral, subretinal, retrobulbar, or intracanalicular injections; by direct application to the eye, for example, using a catheter or other placement device (e.g., a retinal pellet, intraocular insert, suppository or an implant comprising a porous, non-porous, or gelatinous material); by topical ocular drops or ointments; or by a slow-release device in the cul-de-sac or implanted adjacent to the sclera (transscleral) or in the sclera (intrascleral) or within the eye. Intracameral injection may be through the cornea into the anterior chamber to allow the agent to reach the trabecular meshwork. Intracanalicular injection may be into the venous collector channels draining Schlemm's canal or into Schlemm's canal.

Antibodies disclosed herein would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody disclosed herein (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g., 0.1 mg/kg to 10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week, every two weeks, every three weeks, or every four weeks (e.g., such that the patient receives from about two to about twenty, or e.g., about six doses of the antibody). For example, a dose may be administered once per month, (e.g., by subcutaneous injection). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using an immunoconjugate disclosed herein in place of or in addition to an anti-IL-33 antibody (e.g., any anti-IL-33 antibody disclosed herein).

H. Articles of Manufacture

In another aspect, an article of manufacture containing materials useful for the treatment, prevention and/or diagnosis of the disorders described above is provided. The article of manufacture may include an anti-IL-33 antibody (e.g., any anti-IL-33 antibody disclosed herein). The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody disclosed herein. The label or package insert indicates that the composition is used for treating the condition of choice. Moreover, the article of manufacture may comprise (a) a first container with a composition contained therein, wherein the composition comprises an antibody disclosed herein; and (b) a second container with a composition contained therein, wherein the composition comprises a further cytotoxic or otherwise therapeutic agent. The article of manufacture in this embodiment disclosed herein may further comprise a package insert indicating that the compositions can be used to treat a particular condition. Alternatively, or additionally, the article of manufacture may further comprise a second (or third) container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate disclosed herein in place of or in addition to an anti-IL-33 antibody (e.g., any anti-IL-33 antibody disclosed herein).

III. EXAMPLES

The following are examples of methods and compositions of the invention. It is understood that various other embodiments may be practiced, given the general description provided above.

Example 1: Development and Characterization of Rat Anti-Human IL-33 Hybridoma Antibody 1E1

Sprague Dawley rats (Charles River, Hollister, Calif.) were immunized with 100 ag/animal for the first dose and 50 µg/animal for rest of the boosts with human IL-33 divided among sites: intraperitoneal (i.p.), subcutaneous (s.c.) at base of tail, s.c. at nape of neck, and s.c. in both hocks, with Toll-like receptor cocktail adjuvant including monophosphoryl lipid A (MPL) (Sigma-Aldrich, St. Louis, Mo.), polyinosinic:polycytidylic acid (Poly (I:C)), R848, and CpG oligodeoxynucleotide (CpG) (InvivoGen, San Diego, Calif.) for the first dose. Multiple lymph nodes were harvested from each rat two days after the last immunization and pooled. The lymphocytes were enriched for B cells using biotinylated anti-rat CD4 (Clone OX-35), biotinylated anti-rat CD8a (Clone OX-8), biotinylated anti-rat 11 b/c (Clone OX42), biotinylated anti-rat CD161 (Clone 10/78), and biotinylated anti-rat granulocyte marker (Clone HIS48) antibodies (BD Biosciences), followed by magnetic separation (Miltenyi Biotec, San Diego, Calif.) using streptavidin beads. The B cells were further enriched by using anti-rat IgM (Clone G53-238, BD Biosciences) and followed by magnetic separation (Miltenyi Biotec, San Diego, Calif.) using streptavidin beads. IgM depleted B-cells were fused with Sp2ab mouse myeloma cells (Abeome, Athens, Ga.) via electrofusion (Harvard Apparatus, Holliston, Mass.). Fused cells were incubated at 37° C., 7% $CO_2$, overnight in CLONACELL™-HY Medium C (StemCell Technologies, Vancouver, BC, Canada), before centrifugation and resuspension in CLONACELL™-HY Medium E (StemCell Technologies) supplemented with hypoxanthine and thymidine (HAT) (Sigma-Aldrich) and plating into 6-well plates and incubation to allow growth at 37° C., 7% $CO_2$. Four days after plating, hybridomas were stained with anti-rat IgG (goat polyclonal, Jackson ImmunoResearch) conjugated to ALEXA FLUOR® 488 dye, cynomolgus monkey (cyno) IL-33 conjugated to ALEXA FLUOR® 643 dye (Novus Biological) and human IL-33 conjugated to phycoerythrin (PE) (Novus Biological) and sorted for IgG$^+$/human IL-33$^+$ cells/cyno IL-33$^+$ hybridoma cells using a FACSARIA™ III sorter (BD, Franklin Lakes, N.J.). These cells were individually deposited into 96-well plates containing CLONACELL™-HY Medium E (StemCell Technologies). After culturing the cells for 7 days, supernatant was screened by enzyme-linked immunosorbent assay (ELISA) against IL-33. IgG+ hybridomas demonstrating binding to human IL-33 and cyno IL-33 by ELISA were scaled-up and supernatants were harvested and purified by protein G (GAMMABIND™ Plus, GE Healthcare, Pittsburgh, Pa.) for functional testing and further characterization.

Rat hybridoma derived anti-IL-33 antibodies of interest were cloned using standard molecular cloning techniques. Clones were formatted into human IgG vectors for transient expression in CHO cells using standard protocols and purified using MABSELECT SURE™ (GE).

Example 2: ELISA Screening for Anti-Human/Cyno IL-33 Antibodies

Hybridoma clones generated as described above were tested for binding to human IL-33 in an ELISA format. 384 well NUNC MAXISORB® plates (Thermo Scientific Nunc 384-well MAXISORB®, Cat. No. 464718) were coated with 50 μl of IL-33 at 1 μg/ml in coating buffer (50 mM carbonate, pH 9.6) overnight at 4° C. Plates were then blocked with ELISA diluent buffer (100 μl/well for 1 h). Hybridoma supernatants or purified hybridoma antibody diluted in ELISA diluent buffer were added to blocked plates (50 μl/well) and allowed to incubate at room temperature for 30 min. Plates were washed 3 times with wash buffer (phosphate-buffered saline (PBS), 0.05% TWEEN®20, 20× stock HYCLONE™ SH3A649-01) before adding secondary antibody, goat-anti-rat IgG-HRP (Bethyl A110-236P, diluted 1:5000). Following a 30 min incubation, plates were washed again three times with wash buffer before being developed with BIOFX™ 3,3',5,5'-tetramethylbenzidine (TMB) substrate (TMBW-1000-01) for 5 min. Reactions were stopped using BIOFX™ Stop reagent (LBSP-1000-01). Plates were read at 650 nm for absorbance.

Example 3: Cell-Based IL-33 Neutralization Assay

The IL-33 neutralization activity of anti-IL-33 antibodies as obtained from methods described above were determined by a cell-based assay. HEK-BLUE™ IL-33 cells (InvivoGen, Cat. No. hkb-hIL-33) were grown and treated according to manufacturer's supplied protocol. Serial dilutions of anti-IL-33 purified hybridoma antibodies were preincubated for 1 h at 37° C. with human IL-33 (160 pM), cyno IL-33 (300 pM) or mutant human IL-33 (14 pM) in test medium. Premixed antibody and IL-33 was added to the cells and incubated at 37° C. in a $CO_2$ incubator for 20-24 h. QUANTI-BLUE™ alkaline phosphatase detection medium (Invivogen, Cat. No. rep-qb2) was prepared according to manufacturer's protocol. QUANTI-BLUE™ (40 μl) was added to a flat9 bottom 384 well plate (Thermo Scientific NUNC™ 384-well MAXISORB™, Cat. No. 464718) and 10 μl of cell supernatant was added. After 1 h incubation at 37° C., secreted embryonic alkaline phosphatase (SEAP) levels were determined using a spectrophotometer at 620-655 nm. $IC_{50}$ values generated by GENEDATA SCREENER® software are shown in Table 1 below. The amino acid sequences of the heavy chain variable region and light chain variable region of 1E1 are shown in FIGS. 1A and 1B, respectively.

TABLE 1

| IL-33 neutralization activity of hybridoma derived clone 1E1 | |
|---|---|
| | $IC_{50}$ (M) |
| Human IL-33 | 3.6E−11 |
| Cyno IL-33 | 1.6E−10 |

Example 4: Characterization of Anti-IL-33 Hybridoma-Derived Clones by Surface Plasmon Resonance (SPR)

An array-based SPR imaging system (CFM/IBIS, CARTERRA® USA) was used to analyze binding kinetics and epitope bin a panel of anti-IL-33 monoclonal antibodies. Purified hybridoma antibodies were diluted at 10 μg/mi in 10 mM sodium acetate buffer pH 4.5. Using amine coupling, antibodies were directly immobilized onto a SPR sensor-prism CMD 200M chip (XanTec Bioanalytics, Germany) using a Continuous Flow Microspotter (CARTERRA®, USA) to create an array of antibodies. For both kinetics and binning experiments, the IBIS MX96 SPR imager (SPRi) (CARTERRA®, USA) was used to evaluate binding to the immobilized antibodies and the experiments were performed at 25° C. in a running buffer of 10 mM 4-(2-hydroxyethyl)-1-piperazineethanesulfonic acid (HEPES), pH 7.4, 150 mM NaCl, 3 mM EDTA, and 0.005% TWEEN®20 (HBS-TE). For kinetics analysis, IL-33 was injected for a time of 3 min and allowed to disassociate for a time of 10 min. The surface was regenerated between cycles with 10 mM glycine pH 1.7. Concentration series starting at 300 nM with a 1:3 dilution of human, cyno, rat, murine and oxidized human IL-33 were used for the study. The binding data was processed using Scrubber (BioLogic Software). For antibody binning, human IL-33 was first injected for 4 min at 100 nM and was followed by a second 4 min injection of purified antibody at 10 µg/ml in a running buffer of HBS-TE. The surface was regenerated between cycles with 10 mM glycine pH 1.7. The binding data was processed using Epitope Binning software tool (CARTERRA®, USA).

The binding kinetics of top anti-IL-33 antibodies were measured using SPR on a BIACORE® T200 instrument (GE Healthcare). A CM5 Series S sensorchip was coated with anti-rat Fc (Jackson) to create a capture surface. Antibody binding was measured to human, cyno, rat, mouse and oxidized IL-33 (His-tagged) using a concentration series starting with 50 nM with 1:3 dilutions. Sensorgrams for binding of cytokine were recorded using an injection time of 2 min with a flow rate of 30 µl/min, at a temperature of 25° C., and with a running buffer of 10 mM HEPES, pH 7.4, 150 mM NaCl, 3 mM EDTA, and 0.005% TWEEN®20. After injection, disassociation of the IL-33 from the antibody was monitored for 10 min in running buffer. The surface was regenerated between binding cycles with a 30µ injection of 10 mM glycine HCl pH 1.7. After subtraction of a blank which contained running buffer only, sensorgrams observed for cytokine binding to anti-IL-33 antibody were analyzed using a 1:1 Langmuir binding model with software supplied by the manufacturer to calculate the kinetics and binding constants. Kinetic constants from clone 1E1 are provided in Table 2 below.

TABLE 2

Kinetic constants for clone 1E1 binding to different forms of IL-33

|  | ka (1/Ms) | kd (1/s) | $K_D$ (M) |
|---|---|---|---|
| Human IL-33 | 1.08E6 | 2.28E−5 | 2.1E−11 |
| Cyno IL-33 | 0.57E6 | 2.24E−5 | 3.92E−11 |
| Rat IL-33 | 0.14E6 | 2.19E−4 | 1.6E−9 |
| Mouse IL-33 | 5.68E4 | 2.13E−3 | 37.4E−9 |
| Oxidized Human IL-33 | — | — | No binding |

Example 5: Humanization of Anti-IL-33 Antibodies

Humanization variants were generated by grafting the light chain and heavy chain CDRs from rat anti-IL-33 clone 1E1 into the closest matching human frameworks. Residues at Vernier positions were allowed to toggle between rat and human. A matrix of light chain and heavy chain variants in a human IgG1 backbone were transiently expressed small scale in EXPI293F™ cells and purified using MABSELECT SURE™ antibody purification resin (GE). Variants 1E1v1-1E1v23 (see Table 3 below) were analyzed for binding to cytokine and functional activity. The amino acid sequences of the heavy chain variable region and light chain variable region of these variants are shown in FIGS. 2A and 2B, respectively.

Example 6: Characterization of Humanized Anti-IL-33 Antibodies

A protein A sensorchip (GE Healthcare) was used following manufacturer provided protocols to capture humanized anti-IL-33 antibodies using a BIACORE® T200 instrument (GE). Antibody binding was measured to human IL-33 (His-tagged) using multi-cycle kinetics. Sensorgrams for binding of IL-33 were recorded using an injection time of 2 min with a flow rate of 30 µl/min, at a temperature of 25° C., and with a running buffer of 10 mM HEPES, pH 7.4, 150 mM NaCl, 3 mM EDTA, and 0.005% TWEEN620. After injection, disassociation of IL-33 from the antibody was monitored for 10 min in running buffer. The surface was regenerated between binding cycles with a 30 µl injection of 10 mM Glycine HCl pH 1.5. After subtraction of a blank which contained running buffer only, sensorgrams observed for cytokine binding to anti-IL-33 antibody were analyzed using a 1:1 Langmuir binding model with software supplied by the manufacturer to calculate the kinetics and binding constants. Kinetic constants from these data (n=2) are provided in Table 3 below.

The IL-33 neutralization activity of selected anti-IL-33 1E1 humanization variants were determined by a HEK-BLUE™ IL-33 cell-based assay (InvivoGen, Cat. No. hkb-hIL-33). The assay was performed as described above using human IL-33 (160 pM). $IC_{50}$ values generated by GENEDATA SCREENER® software are shown in Table 3 below.

TABLE 3

Kinetic constants and neutralization activity for 1E1 variants

|  | $K_D$ (nM) | $IC_{50}$ (M) |
|---|---|---|
| ch1E1 | 1.485E−10 ± 0.02 | 2.90E−11 |
| 1E1v1 | 2.955E−10 ± 0.12 |  |
| 1E1v2 | 2.025E−10 ± 0.26 |  |
| 1E1v3 | 1.49E−10 ± 0.14 |  |
| 1E1v4 | 1.54E−10 ± 0.17 | 3.11E−11 |
| 1E1v5 | 1.44E−10 ± 0.18 |  |
| 1E1v6 | 1.32E−10 ± 0.18 |  |
| 1E1v7 | 1.445E−10 ± 0.15 |  |
| 1E1v8 | 1.185E−10 ± 0.18 | 3.11E−11 |
| 1E1v9 | 1.29E−10 ± 0.14 | 3.05E−11 |
| 1E1v10 | 1.21E−10 ± 0.14 |  |
| 1E1v11 | 1.23E−10 ± 0.13 |  |
| 1E1v12 | 1.625E−10 ± 0.21 | 2.44E−11 |
| 1E1v13 | 1.395E−10 ± 0.23 | 2.98E−11 |
| 1E1v14 | 1.63E−10 ± 0.31 |  |
| 1E1v15 | 1.95E−10 ± 0.23 |  |
| 1E1v16 | 1.79E−10 ± 0.20 |  |
| 1E1v17 | 2.855E−10 ± 0.43 |  |
| 1E1v18 | 1.725E−10 ± 0.06 |  |
| 1E1v19 | 1.315E−10 ± 0.16 | 3.19E−11 |
| 1E1v20 | 1.275E−10 ± 0.05 | 3.44E−11 |
| 1E1v21 | 1.555E−10 ± 0.22 | 3.10E−11 |
| 1E1v22 | 1.465E−10 ± 0.16 |  |
| 1E1v23 | 1.51E−10 ± 0.13 |  |

The 1E1v8 variant was reformatted into a human IgG1 Fab construct and expressed in *E. coli*. Bacteria were lysed following expression and Fab was purified using GAMMA-BIND™ Plus sepharose (GE) following standard methods. A secondary purification step was performed using a HITRAP® sepharose high performance (SP HP) column (GE) to obtain final protein.

Example 7: Characterization of Anti-IL-33 1E1v8 Fab by SPR

The binding kinetics of the 1E1v8 Fab were measured using SPR on a BIACORE® 8k instrument (GE Healthcare). 1E1v8 Fab was directly immobilized on 4 different flow cells of a CM5 Series S sensorchip at low density using amine coupling. Antibody fragment binding was measured to human and cyno IL-33 (His-tagged) using a concentration series starting with 50 nM with 1:3 dilutions. Sensorgrams for binding of IL-33 were recorded using an injection time of 2 min with a flow rate of 100 µl/min, at a temperature of 25° C. or 35° C., and with a running buffer of 10 mM HEPES, pH 7.4, 150 mM NaCl, 3 mM EDTA, and 0.005% TWEEN®20. After injection, the disassociation of the IL-33 from the antibody was monitored for 30 min in running buffer. The surface was regenerated between binding cycles with a 30 μl injection of 10 mM glycine HCl pH 1.7. After subtraction of a blank which contained running buffer only, sensorgrams observed for cytokine binding to anti-IL-33 antibody were analyzed using a 1:1 Langmuir binding model with software supplied by the manufacturer to calculate the kinetics and binding constants. Kinetic constants from these data are provided in Table 4 below.

TABLE 4

Kinetic constants for 1E1v8 human Fab binding to human and cyno IL-33

| Cytokine | Temperature (° C.) | ka (1/Ms) | kd (1/s) | $K_D$ (M) |
|---|---|---|---|---|
| Human IL-33 | 25 | 6.84E+05 ± 0.34 | 9.99E-06 ± 1.25 | 1.47E-11 ± 0.25 |
| Human IL-33 | 35 | 8.58E+05 ± 0.80 | 1.26E-05 ± 0.17 | 1.48E-11 ± 0.28 |
| Cyno IL-33 | 25 | 3.54E+05 ± 0.22 | 7.85E-06 ± 0.34 | 2.23E-11 ± 0.22 |
| Cyno IL-33 | 35 | 5.27E+05 ± 0.22 | 1.82E-05 ± 0.34 | 3.45E-11 ± 0.22 |

Example 8: Molecular Assessment of 1E1v8 (and 10C12)

Molecular assessment (MA) analysis was performed on 1E1v8 (Fab) for stability properties. Briefly, the 1E1v8 Fab was tested for stress under chemical conditions with AAPH (2,2-azobis(2-amidinopropane) dihydrochloride), a small molecule known to generate free radicals (see, e.g., Ji et al., *J. Pharm. Sci.* 98(12):4485-4500, 2009), as well as under thermal conditions at varying pH (a two-week thermal stress test at 40° C., pH 5.5) (see, e.g., Zhang et al., *J. Chromatography A* 1272:56-64, 2013). Additional details regarding the MA stress conditions and analysis for these experiments are described below in the materials and methods section.

Table 5 shows results of MA analysis for 1E1v8 Fab.

TABLE 5

MA Properties of 1E1v8 Fab

| Stress | 1E1v8 Fab |
|---|---|
| Thermal Stress (Low Con His-Acetate, pH 5.5) | $D^{56}G^{57}$ in CDR-L2 is stable (no change in isomerization was observed (1.9% in t = 0 and 1.9% in t = 2 wk)) $N^{30}N^{31}$ in CDR-H1 is stable (no change in deamidation was observed (0.1% in t = 0 and 0.1% in t = 2 wk)) $N^{31}Y^{32}$ in CDR-H1 is stable (no observable deamidation at t = 2 wk) $D^{61}S^{62}$ in CDR-H2 is stable (no change in isomerization was observed (0.9% in t = 0 and 0.9% in t = 2 wk)) $N^{96}Y^{97}$ in CDR-H3 is stable (no observable deamidation at t = 2 wk) $N^{100}T^{100a}$ in CDR-H3 is stable (no observable deamidation at t = 2 wk) |
| AAPH Stress (20 mM His acetate pH 5.5) | $M^{34}$ in CDR-H1 is stable $W^{33}$ in CDR-H1 is stable (−2.3% decrease in $M^{34}$ and $W^{33}$ oxidation was observed (7.6% in control and 5.3% in AAPH stressed) |
| Size | Monomer loss (0.8%) is acceptable (loss of monomer is likely buffer related) |
| Charge | Main peak loss (9.4%) is acceptable |
| LC/MS | Masses are as expected with no change upon stress |

It is noted that the prior art antibody 10C12 (10C12.38.H6.87Y.581, Fab) had similarly been analyzed for stability and shown to exhibit extensive oxidation of the CDR-H3 $W^{100}$ residue as shown in Table 6. Efforts to solve the instability due to oxidation of the CDR-H3 W1100 residue by substitution of this residue with other amino acids were unsuccessful as such substitutions resulted in significantly decreases in binding to IL-33. Accordingly, a new and separate antibody generation was needed and resulted in the design and generation of the 1E1v8 Fab.

TABLE 6

MA Properties of 10C12.38.H6.87Y.581 Fab

| Stress | 10C12.38.H6.87Y.581 Fab |
|---|---|
| Thermal Stress (Low Con His-Acetate, pH 5.5) | $D^{58}Y^{59}$ in CDR-H2 is stable (no change in isomerization was observed (0.1% in t = 0 and 0.1% in t = 2 wk)) $D^{61}S^{62}$ in CDR-H2 is stable (no observable isomerization) $N^{96}Y^{97}$ in CDR-H3 is stable (no observable deamidation) |
| AAPH Stress (20 mM His acetate pH 5.5) | $M^{34}$ in CDR-H1 is stable (0.8% increase in oxidation was observed (0.5% in control and 1.3% in AAPH stressed) $W^{100}$ in CDR-H3 is unstable (73.4% increase in oxidation (0.8% in control and 74.2% in AAPH stressed) |
| Size | Monomer loss (0.0%) is acceptable at t = 2 wk |
| Charge | Main peak loss (0.5%) is acceptable at t = 2 wk |
| LC/MS | Masses are as expected with no change upon stress |

Materials and Methods

To test the chemical stability of CDR sequence motifs, both oxidative and accelerated thermal stress were performed. Oxidatively stressed samples were prepared by incubating 1 mM 2,2'-azobis (2-amidinopropane) dihydrochloride (AAPH) with 1.25 mg of antibody in low-ionic histidine-acetate, pH 5.5, for 16 h at 40° C. After 16 h, AAPH was quenched by adding to the solution a 20:1 excess of methionine (Met) to AAPH. Control samples were spiked with water instead of AAPH. Control and stress samples were buffer-exchanged prior to analysis. For thermal stress, antibody samples were incubated at 1 mg/mL and 150 mg/mL in low-ionic buffer, pH 5.5, for 2 weeks at 40° C. or PBS, pH 7.4, for 2 weeks at 37° C. Control samples were stored at −70° C.

Ultra-high-performance liquid chromatography-high resolution mass spectrometry (UHPLC-HRMS) analysis was performed as follows. Tryptic digests were analyzed using an ACQUITY® H-Class UHPLC (Waters) coupled to a Q EXACTIVE™ (Thermo Fisher) mass spectrometer (MS). Separation of a 10 μg injection was performed on an ACQUITY® UPLC Peptide CSH C18 column (Waters) with 1.7 μm, 130 Å particles running a flow rate of 0.2 mL/min at 77° C. Mobile phase A was water, and mobile phase B was acetonitrile, each containing 0.1% formic acid. The gradient was as follows: 2 min of 1% mobile phase B, 5 min of 1-13% mobile phase B, 35 min of 13-35% mobile phase B, 2 min of 35-95% mobile phase B, 2 min of 95% mobile phase B. MS data were collected in positive ion mode using a Top 8 data-dependent scan mode with resolution set to 35 000 for MS scans and 17 500 for MS2 scans. Dynamic exclusion was turned off, and the precursor scan range was set at 200-2000 m/z. External calibration of the instrument was conducted prior to sample analysis. Data were processed using instrument vendor software specific for biopharmaceutical characterization.

Relative quantitation of the chemical sequence motif was generated by integrating the extracted ion chromatograms of the monoisotopic m/z using the two most abundant charge states for the native tryptic peptide and its modified counterpart. The modified peptide peak area was divided by the sum of the modified and native peak areas and multiplied by 100 to obtain the percent modification for each chemical sequence motif. The percent change in deamidation of asparagine (N) residues, isomerization of aspartic acid (D) residues, and hydrolysis at asparagine-proline/aspartic acid-proline (NP/DP) bonds was measured following accelerated thermal stress in histidine-acetate and PBS buffers. The percent change in oxidation of methionine (M) and tryptophan (W) residues was measured following oxidative stress.

Example 9: Viscosity/Solubility Method

Viscosity measurements of the 1E1v8 Fab were performed on a Anton Paar Modular Compact Rheometer MCR502 using a CP20-0.3 measuring cone with a 20 mm diameter and 0.3 angle and a P-PTD 200/56/AIR lower plate with a 56 mm diameter. Samples went through shear-rate sweeps ramping from 10 to 10,000 $s^{-1}$. The reported value is the average of 2-3 shear rate sweeps of a sample at 1,000 $s^{-1}$ at 25° C. with increasing protein concentration ranging from 4-177 mg/ml in 20 mM histidine acetate, 150 mM NaCl, 240 mM sucrose at pH 5.5. Table 7 shows viscosity results of the 1E1v8 Fab, and Table 8 shows solubility results of the 1E1v8 Fab.

TABLE 7

Viscosity results of 1E1v8 Fab

| Concentration (mg/mL) | Viscosity (cP) |
| --- | --- |
| 0 | 1 |
| 108.52 | 3.5 |
| 154.88 | 3.74 |
| 180.24 | 4.6 |

The sample appeared clear; no visible particulates were observed.

TABLE 8

Solubility results of 1E1v8 Fab

| Sample | Turbidity (OD) |
| --- | --- |
| PBS pH 7.4 | 0.021 |
| 1E1v8 Fab | 0.192 |

Again, the 1E1v8 Fab proved to have properties superior to those of the prior 10C12 antibody, which had lower viscosity at 188 mg/mL and had higher turbidity as compared to 1E1v8, as shown in Tables 9 and 10.

TABLE 9

Viscosity results of 10C12 Fab

| Concentration (mg/mL) | Viscosity (cP) |
| --- | --- |
| 0 | 1 |
| 102 | 1.61 |
| 155 | 3.16 |
| 188 | 5.56 |

TABLE 10

Solubility results of 1E1v8 Fab

| Sample | Turbidity (OD) |
| --- | --- |
| PBS pH 7.4 | 0.017 |
| 10C12 Fab | 0.383 |

Example 10: Generation and Expression of Anti-IL-33 Antibodies and Fabs

Anti-IL-33 antibodies obtained from available sequences were reformatted into a human IgG1 Fab and human IgG1 constructs. The huIgG1 Fabs were expressed in *E. coli*. Bacteria were lysed following expression and Fab was purified using GAMMABIND® Plus Sepharose (GE) following standard methods. A secondary purification step was performed using a HITRAP® SP HP column (GE) to obtain final protein. The human IgG1s were expressed transiently in EXPI293F® cells and purified using MABSELECT SURE™ (GE).

Example 11: Antibody Binning Using SPR

An array-based SPR imaging system (CFM/IBIS, CARTERRA®, USA) was used to epitope bin a panel of anti-IL-33 monoclonal antibodies (see Table 11). Anti-IL-33 antibodies 10C12 and 4G12 are described in U.S. Pat. No. 10,093,730. Purified monoclonal antibodies were diluted at 10 µg/ml in 10 mM sodium acetate buffer pH 4.5. Using amine coupling, antibodies were directly immobilized onto a SPR sensorprism CMD 200M chip (XanTec Bioanalytics, Germany) using a Continuous Flow Microspotter (CARTERRA®, USA) to create an array of antibodies. For binning experiments, the IBIS MX96 SPRi (CARTERRA®, USA) was used to evaluate binding to the immobilized antibodies and the experiments were performed at 25'C in a running buffer of 10 mM HEPES, pH 7.4, 150 mM NaCl, 3 mM EDTA, and 0.005% TWEEN®20 (HBS-TE). For antibody binning, human IL-33 was first injected for 4 min at 100 nM and was followed by a second 4 min injection of purified antibody at 10 µg/ml in a running buffer of HBS-TE. The surface was regenerated between cycles with 10 mM glycine pH 1.7. The binding data was processed using Epitope Binning software tool (CARTERRA®, USA) and the results are shown in FIGS. 3A-3E.

Example 12: Results of Antibody Binning Using SPR

Figure 3B:
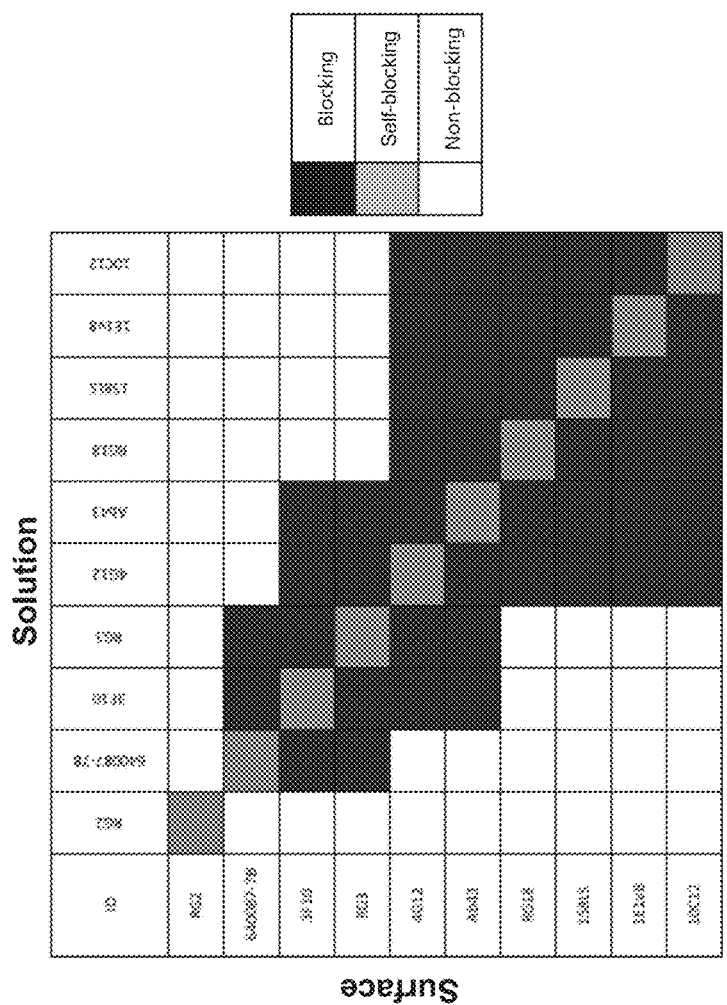
FIG. 3B is a heatmap showing relationships between clones or bins of anti-IL-33 antibody clones based on blocking activity.
Figure 3A:
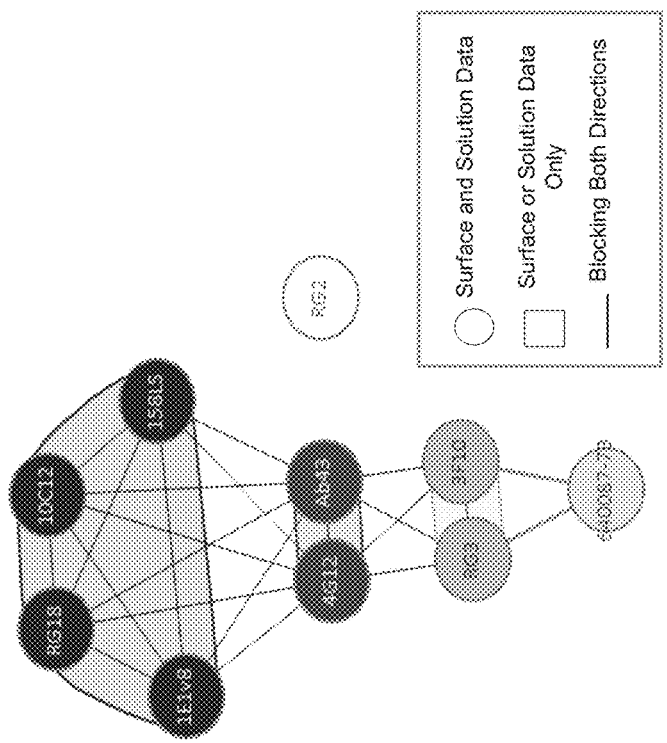
FIG. 3A is a network plot showing relationships between clones or bins of anti-IL-33 antibody clones based on blocking activity.
Figure 3C:
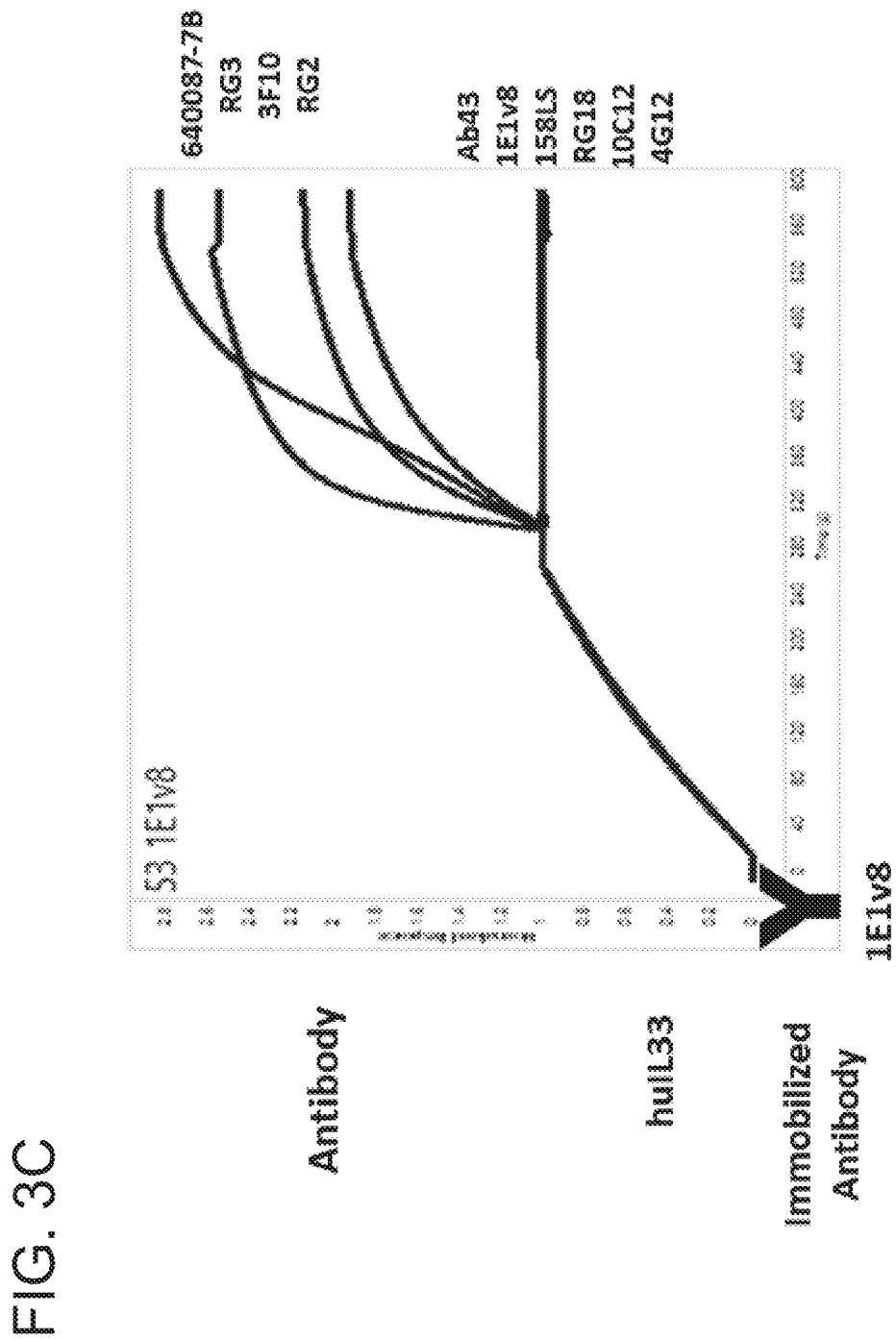
FIGS. 3C-3E are a series of graphs showing results of epitope binning using surface plasmon resonance (SPR). The graphs show normalized response as a function of time.
Figure 3D:
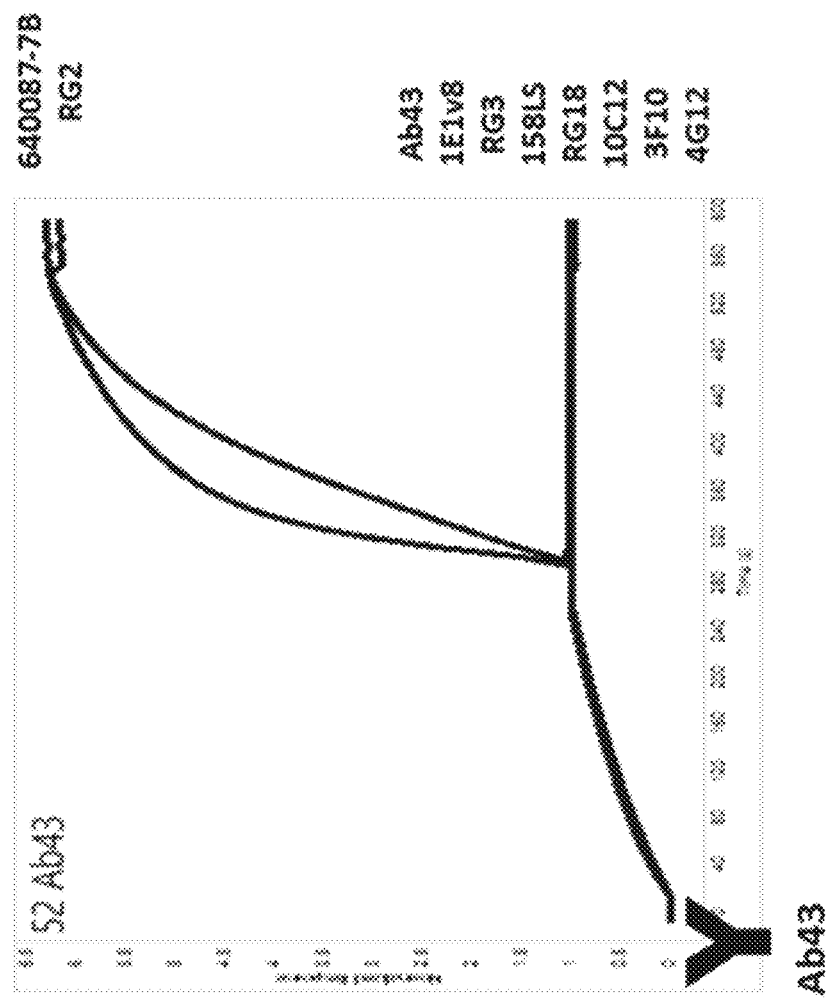
Figure 3E:
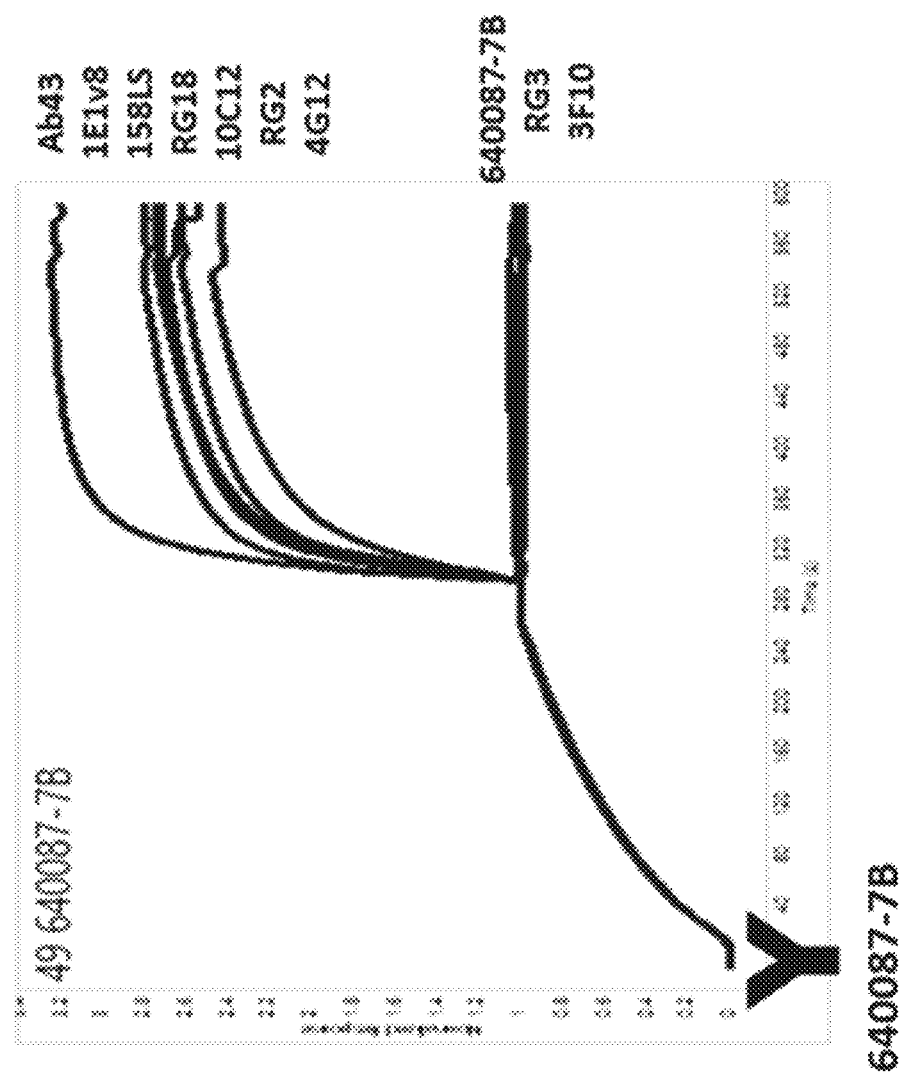

Anti-IL-33 monoclonal antibodies that were directly immobilized onto a sensorprism chip via amine coupling were binned against each other to assess overlapping epitopes. After human IL-33 was allowed to bind to the immobilized antibodies, each antibody was injected in solution one at a time to evaluate whether it was able to still bind to antigen or if it was blocked by antigen bound to the immobilized antibodies. For all antibodies, binding/binning data was collected from immobilization on the chip surface and also when injected in solution. Relationships between clones or bins of clones based on blocking activity and shown in the form of network plots and a heatmap (FIGS. 3A and 3B). Clones 1E1v8, 10C12, RG18, and 158LS all directly blocked each other and showed similar blocking activity when compared to other antibodies (FIG. 3C). Additionally, they blocked and were blocked by clones 4G12 and Ab43. Clones 4G12 and Ab43 showed different blocking activity because they also block RG3 and 3F110 (FIG. 3D). Clone 640087-7B only blocked and is blocked by clones RG3 and 3F110 (FIG. 3E).

TABLE 11

Antibody Clones used in Epitope Binning Analysis

| Antibody Name (reference) | HC or VH SEQ ID NO | LC or VL SEQ ID NO |
|---|---|---|
| 1E1v8 | 25 | 26 |
| RG18 (WO 2014/164959) | 76 | 77 |
| 158LS (WO 2017/187307) | 70 | 71 |
| Ab43 (WO 2018/081075) | 72 | 73 |
| RG3 (WO 2014/164959) | 74 | 75 |
| 3F10 | 80 | 81 |
| 640087-7B (WO 2016/156440) | 78 | 79 |

Example 13: Clinical Study of Anti-IL-33

The following Phase 1a, multicenter, open label, single dose, dose escalation study investigates the ocular and systemic safety, tolerability, pharmacokinetics (PK), and immunogenicity of intravitreal (IVT) injections of anti-IL-33 antibody in patients with GA secondary to AMD.

Patients, male or female, who are at least 50 years of age, have a best corrected visual acuity (BCVA) in the range of Snellen 20/125-20/400, and have a GA lesion area of at least 0.5 disc area, inclusive, are eligible. Site investigators are qualified ophthalmologists. Only one eye may be chosen as the study eye. If both eyes are eligible, the eye with the worse vision (i.e., worse visual acuity (VA) and/or least function as determined by the investigator and patient) will be selected for the study treatment (study eye). Each patient must satisfy all eligibility criteria at both the screening and the Day 1 visit (i.e., when the patient is enrolled into the study and when study drug is administered). In addition, images taken at the screening visit (i.e., color fundus photographs, fluorescein angiogram, and spectral domain optical coherence tomography) must be received by the central reading center for evaluation by the Day 1 visit.

Eligible patients are sequentially enrolled into cohorts. Each cohort is administered at gradually ascending dose levels with 1 sentinel patient at each level to ensure only 1 active patient is dosed initially at any dose level. Use of a sentinel patient at each level is to ensure that at most, 1 active patient is dosed for the first time at any dose level. Eligible patients are dosed with the study drug on Day 1, which will occur within 28 days of screening.

This study consists of two stages: a single-ascending dose stage with 4 planned ITV doses (1 mg, 3 mg, 10 mg, and 20 mg) to evaluate single-dose safety and tolerability of anti-IL-33 antibody with 3-6 patients in each cohort and an expansion cohort stage consisting of approximately 9-12 patients (for a maximum total of 15 patients) at the maximum tolerated dose (MTD) or maximum tested dose (MTeD) to obtain a minimum of 10 evaluable patients to further characterize safety, tolerability, and pharmacokinetics; and modulation of downstream IL-33 pathway activity.

The study is divided into three periods: a screening period lasting up to 28 days, a treatment period consisting of a single day (Day 1) during which anti-IL-33 antibody is administered, and a 12 week follow up period. The duration of study for each patient is 12 weeks, excluding the screening period. The end of the study is defined as the date when the last patient, last visit (LPLV) occurs.

This study allows graded exposure to anti-IL-33 antibody with escalation to the next higher dose cohort based on safety and tolerability data for at least 3 patients from the preceding dose cohort(s) after 14 days of follow up has elapsed from the last patient in the cohort. In the last cohort (i.e., Cohort D or cohort determined to be MTD) after safety and tolerability has been assessed in at least 3 patients, an additional expansion cohort of 9-12 patients for a total of 15 patients are enrolled to obtain a minimum 10 evaluable patients for further safety, PK, and PD evaluation. Evaluable patients are defined as patients who have received study drug injection, have completed the Week 12 visit, have not taken any prohibited therapy, and have not received any surgical or interventional procedures during the study.

This study is initially conducted in approximately 24-33 patients (one study eye per patient). Up to two additional optional cohorts of 15 patients each may be added for a potential total of 63 patients enrolled in the study.

The primary objective of this study is to characterize the safety profile associated with anti-IL-33 antibody administration. Statistical summaries are descriptive in nature (e.g., incidence rates, means, and percentiles). Patients are grouped according to treatment received, and any patients who receive any amount of anti-IL-33 antibody is included in the analyses. The primary analysis is safety analyses which include all patients who receive at least 1 dose of study drug, with patients grouped according to treatment received. Ocular and non-ocular adverse events, serious adverse events, and death are summarized separately. Abnormal ocular findings, laboratory test results and vital signs are listed. DLAEs are listed and summarized by study drug dose level and frequency cohorts.

Another safety objective is to determine the maximum tolerated dose administered as a single dose on the basis of the following endpoints: (1) frequency, severity, and timing of ocular and non-ocular adverse events including dose-limiting adverse events (DLAEs), serious adverse events, adverse events leading to study discontinuation and adverse events of special interest; (2) frequency, severity, and timing of notable findings in ocular examinations and ocular imaging following anti-IL-33 antibody administration; and (3) frequency, severity, and timing of notable findings in vital signs, physical findings, and clinical laboratory results following anti-IL-33 antibody administration.

Another objective is to characterize the PK of anti-IL-33 antibodies in patients with GA secondary to AMD on the basis of the following endpoints: (1) serum concentration of anti-IL-33 at specified timepoints; and (2) aqueous humor concentration of anti-IL-33 antibodies at specified timepoints Another objective for this study is to evaluate the immune response to anti-IL-33 on the basis of the following endpoint: prevalence of anti-drug antibodies (ADAs) at baseline and incidence of ADAs during the study. The immunogenicity of anti-IL-33 antibodies will be assessed by the detection of serum ADAs.

The PK objectives for this study are to evaluate potential relationships between drug exposure and safety, and drug exposure and exploratory biomarker response following single ITV doses on the basis of the following endpoint: PK exposure (e.g., serum and/or aqueous humor anti-IL-33 antibody concentrations) and safety and/or exploratory biomarker endpoints.

The immunogenicity objective for this study is to evaluate potential effects of ADAs on the basis of the following endpoint: relationship between ADA status and safety, PK, or activity endpoints.

Other Embodiments

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. An isolated antibody that specifically binds IL-33, or an antigen-binding fragment thereof, wherein the antibody comprises a binding domain comprising a heavy chain variable (VH) domain and a light chain variable (VL) domain, the binding domain comprising the following six complementarity-determining regions (CDRs):
   (a) a CDR-H1 comprising the amino acid sequence of NYWMT (SEQ ID NO: 1);
   (b) a CDR-H2 comprising the amino acid sequence of SITYTGGGTYYPDSVKG (SEQ ID NO: 2);
   (c) a CDR-H3 comprising the amino acid sequence of ANYYYNTYGGFPY (SEQ ID NO: 3);
   (d) a CDR-L1 comprising the amino acid sequence of LASEGFSNDLA (SEQ ID NO: 4);
   (e) a CDR-L2 comprising the amino acid sequence of AASRLQD (SEQ ID NO: 5); and
   (f) a CDR-L3 comprising the amino acid sequence of QQGSKYPLT (SEQ ID NO: 6).

2. The antibody of claim 1, wherein the antibody comprises a binding domain comprising (a) a VH domain comprising an amino acid sequence having at least 95% sequence identity to the amino acid sequence of SEQ ID NO: 7; (b) a VL domain comprising an amino acid sequence having at least 95% sequence identity to the amino acid sequence of SEQ ID NO: 8; or (c) a VH domain as in (a) and a VL domain as in (b).

3. The antibody of claim 1, wherein the VH domain comprises:
   (a) an FR-H1 comprising the amino acid sequence of EVQLVX$_1$SGX$_2$X$_3$X$_4$X$_5$X$_6$PGX$_7$SX$_8$X$_9$X$_{10}$SCX$_{11}$ASGFTFN (SEQ ID NO: 9), wherein X$_1$ is E or Q; X$_2$ is G or A; X$_3$ is G or E; X$_4$ is L or V; X$_5$ is V or K; X$_6$ is Q or K; X$_7$ is G, A, or T; X$_8$ is L or V; X$_9$ is R or K; X$_{10}$ is L or V; and X$_{11}$ is A, K, or L;
   (b) an FR-H2 comprising the amino acid sequence of WX$_1$RQAPGX$_2$GLEWX$_3$X$_4$ (SEQ ID NO: 10), wherein X$_1$ is I or V; X$_2$ is K or Q; X$_3$ is V, M, or I; and X$_4$ is A or G;
   (c) an FR-H3 comprising the amino acid sequence of RX$_1$TX$_2$X$_3$RDX$_4$X$_5$X$_6$X$_7$X$_8$X$_9$YX$_{10}$X$_{11}$X$_{12}$X$_{13}$SLRX$_{14}$EDTAX$_{15}$YYCTR (SEQ ID NO: 11), wherein X$_1$ is F or V; X$_2$ is I or M; X$_3$ is S or T; X$_4$ is D, N, or T; X$_5$ is A or S; X$_6$ is K or T; X$_7$ is S or N; X$_8$ is S or T; $X_9$ is L or V; $X_{10}$ is L or M; $X_{11}$ is Q or E; $X_{12}$ is M or L; $X_{13}$ is N or S; $X_{14}$ is A or S; and $X_{15}$ is V or T; and (d) an FR-H4 comprising the amino acid sequence of WGQGTLVTVSS (SEQ ID NO: 12).

4. The antibody of claim 1, wherein the VH domain comprises:
   (a) an FR-H1 comprising the amino acid sequence of EVQLVESGGGLVQPGGSLRLSCAASGFTFN (SEQ ID NO: 17);
   (b) an FR-H2 comprising the amino acid sequence of WIRQAPGKGLEWVA (SEQ ID NO: 18);
   (c) an FR-H3 comprising the amino acid sequence of RFTISRDDAKSSLYLQMNSLRAEDTAVYYCTR (SEQ ID NO: 19); and
   (d) an FR-H4 comprising the amino acid sequence of WGQGTLVTVSS (SEQ ID NO: 12).

5. The antibody of claim 1, wherein the VH domain comprises the amino acid sequence of SEQ ID NO: 7.

6. The antibody of claim 1, wherein the VL domain comprises:
   (a) an FR-L1 comprising the amino acid sequence of $X_1IX_2X_3TQSPX_4X_5LSX_6SX_7GX_8X_9X_{10}X_{11}X_{12}X_{13}C$ (SEQ ID NO: 13), wherein $X_1$ is D or E; $X_2$ is Q or V; $X_3$ is M or L; $X_4$ is S or A; $X_5$ is S or T; $X_6$ is A or L; $X_7$ is V, P, or L; $X_8$ is D or E; $X_9$ is R or T; $X_{10}$ is V or A; $X_{11}$ is T or S; $X_{12}$ is I or L; and $X_{13}$ is T, S, or E;
   (b) an FR-L2 comprising the amino acid sequence of $WX_1QQKX_2GX_3X_4PX_5X_6LIY$ (SEQ ID NO: 14), wherein $X_1$ is Y or F; $X_2$ is P or S; $X_3$ is K or Q; $X_4$ is S or A; $X_5$ is K, R, or Q; and $X_6$ is L or S;
   (c) an FR-L3 comprising the amino acid sequence of $GX_1PX_2RFSGSGSGTX_3FX_4LX_5ISX_6X_7X_8PEDX_9AX_{10}YX_{11}C$ (SEQ ID NO: 15), wherein $X_1$ is V or I; $X_2$ is S or A; $X_3$ is D or R; $X_4$ is T or S; $X_5$ is T or K; $X_6$ is S or G; $X_7$ is L or M; $X_8$ is Q or E; $X_9$ is F, V, or E; $X_{10}$ is T, V, or D; and $X_{11}$ is F or Y; and
   (d) an FR-L4 comprising the amino acid sequence of $FGX_1GTKX_2EIK$ (SEQ ID NO: 16), wherein $X_1$ is G or S and $X_2$ is V or L.

7. The antibody of claim 1, wherein the VL domain comprises:
   (a) an FR-L1 comprising the amino acid sequence of DIQMTQSPSSLSASVGDRVTITC (SEQ ID NO: 21);
   (b) an FR-L2 comprising the amino acid sequence of WYQQKPGKSPKLLIY (SEQ ID NO: 22);
   (c) an FR-L3 comprising the amino acid sequence of GVPSRFSGSGSGTDFTLTISSLQPEDFATYFC (SEQ ID NO: 23); and
   (d) an FR-L4 comprising the amino acid sequence of FGGGTKVEIK (SEQ ID NO: 24).

8. The antibody of claim 1, wherein the VL domain comprises the amino acid sequence of SEQ ID NO: 8.

9. The antibody of claim 1, wherein the antibody comprises:
   (i) a binding domain comprising (a) a VH domain comprising an amino acid sequence having at least 95% sequence identity to the amino acid sequence of SEQ ID NO: 35; (b) a VL domain comprising an amino acid sequence having at least 95% sequence identity to the amino acid sequence of SEQ ID NO: 36; or (c) a VH domain as in (a) and a VL domain as in (b);
   (ii) a binding domain comprising (a) a heavy chain (HC) comprising the amino acid sequence of SEQ ID NO: 37 and (b) a light chain (LC) comprising the amino acid sequence of SEQ ID NO: 38; or
   (iii) a binding domain comprising (a) a VH domain comprising an amino acid sequence having at least 95% sequence identity to the amino acid sequence of SEQ ID NO: 65; (b) a VL domain comprising an amino acid sequence having at least 95% sequence identity to the amino acid sequence of SEQ ID NO: 69; or (c) a VH domain as in (a) and a VL domain as in (b).

10. The antibody of claim 1, wherein:
    (i) the antibody specifically binds both human and cynomolgus monkey (cyno) interleukin-33 (IL-33) with a $K_D$ of about 1 nM or lower;
    (ii) the antibody inhibits the binding of human IL-33 to an IL-33 receptor with a 50% inhibitory concentration (IC50) of between about 800 fM and about 100 pM; or
    (iii) the antibody specifically binds both human and cyno IL-33 with a $K_D$ of about 1 nM or lower and inhibits the binding of human IL-33 to an IL-33 receptor with an IC50 of between about 800 fM and about 100 pM.

11. The antibody of claim 1, wherein:
    (i) the antibody has a viscosity of less than about 5 centipoise (cP) at a concentration of about 180 mg/mL in phosphate-buffered saline (PBS) pH 7.4;
    (ii) the antibody has an optical density (OD) of about 0.5 or lower at a concentration of about 150 mg/mL or higher in phosphate-buffered saline (PBS) pH 7.4; or
    (iii) the antibody has a viscosity of less than about 5 cP at a concentration of about 180 mg/mL and an OD of about 0.5 or lower at a concentration of about 150 mg/mL or higher in PBS pH 7.4.

12. The antibody of claim 1, wherein the antibody is monoclonal, human, humanized, or chimeric.

13. The antibody of claim 1, wherein the antibody is an antibody fragment that binds IL-33.

14. The antibody of claim 13, wherein the antibody fragment is an Fab, Fab'-SH, Fv, scFv, or (Fab')$_2$ fragment.

15. The antibody of claim 1, wherein the antibody is a monospecific antibody.

16. The antibody of claim 1, wherein the antibody is a multispecific antibody.

17. The antibody of claim 16, wherein the antibody is a bispecific antibody.

18. A pharmaceutical composition comprising the antibody of claim 1 and a pharmaceutically acceptable carrier, excipient, or diluent.

19. The antibody of claim 1, wherein the antibody is an Fab.

20. The antibody of claim 1, wherein the antibody is an IgG1 antibody.

21. An isolated antibody that specifically binds IL-33, or an antigen-binding fragment thereof, wherein the antibody comprises a binding domain comprising (a) a VH domain comprising the amino acid sequence of SEQ ID NO: 7 and (b) a VL domain comprising the amino acid sequence of SEQ ID NO: 8.

22. The antibody of claim 21, wherein the antibody is an Fab.

23. The antibody of claim 21, wherein the antibody is an IgG1 antibody.

24. A pharmaceutical composition comprising the antibody of claim 21 and a pharmaceutically acceptable carrier, excipient, or diluent.

25. An isolated antibody that specifically binds IL-33, or an antigen-binding fragment thereof, wherein the antibody comprises a binding domain comprising (a) a heavy chain (HC) comprising the amino acid sequence of SEQ ID NO: 25 and (b) a light chain (LC) comprising the amino acid sequence of SEQ ID NO: 26.

26. A pharmaceutical composition comprising the antibody of claim 25 and a pharmaceutically acceptable carrier, excipient, or diluent.

27. An isolated antibody that specifically binds IL-33, or an antigen-binding fragment thereof, wherein the antibody comprises:
- (i) a binding domain comprising (a) a VH domain comprising the amino acid sequence of SEQ ID NO: 41 and (b) a VL domain comprising the amino acid sequence of SEQ ID NO: 55;
- (ii) a binding domain comprising (a) a VH domain comprising the amino acid sequence of SEQ ID NO: 43 and (b) a VL domain comprising the amino acid sequence of SEQ ID NO: 55;
- (iii) a binding domain comprising (a) a VH domain comprising the amino acid sequence of SEQ ID NO: 41 and (b) a VL domain comprising the amino acid sequence of SEQ ID NO: 8;
- (iv) a binding domain comprising (a) a VH domain comprising the amino acid sequence of SEQ ID NO: 43 and (b) a VL domain comprising the amino acid sequence of SEQ ID NO: 8;
- (v) a binding domain comprising (a) a VH domain comprising the amino acid sequence of SEQ ID NO: 44 and (b) a VL domain comprising the amino acid sequence of SEQ ID NO: 8;
- (vi) a binding domain comprising (a) a VH domain comprising the amino acid sequence of SEQ ID NO: 46 and (b) a VL domain comprising the amino acid sequence of SEQ ID NO: 8;
- (vii) a binding domain comprising (a) a VH domain comprising the amino acid sequence of SEQ ID NO: 48 and (b) a VL domain comprising the amino acid sequence of SEQ ID NO: 8;
- (viii) a binding domain comprising (a) a VH domain comprising the amino acid sequence of SEQ ID NO: 43 and (b) a VL domain comprising the amino acid sequence of SEQ ID NO: 57;
- (ix) a binding domain comprising (a) a VH domain comprising the amino acid sequence of SEQ ID NO: 44 and (b) a VL domain comprising the amino acid sequence of SEQ ID NO: 57;
- (x) a binding domain comprising (a) a VH domain comprising the amino acid sequence of SEQ ID NO: 46 and (b) a VL domain comprising the amino acid sequence of SEQ ID NO: 57;
- (xi) a binding domain comprising (a) a VH domain comprising the amino acid sequence of SEQ ID NO: 48 and (b) a VL domain comprising the amino acid sequence of SEQ ID NO: 57;
- (xii) a binding domain comprising (a) a VH domain comprising the amino acid sequence of SEQ ID NO: 50 and (b) a VL domain comprising the amino acid sequence of SEQ ID NO: 57;
- (xiii) a binding domain comprising (a) a VH domain comprising the amino acid sequence of SEQ ID NO: 43 and (b) a VL domain comprising the amino acid sequence of SEQ ID NO: 58;
- (xiv) a binding domain comprising (a) a VH domain comprising the amino acid sequence of SEQ ID NO: 44 and (b) a VL domain comprising the amino acid sequence of SEQ ID NO: 58;
- (xv) a binding domain comprising (a) a VH domain comprising the amino acid sequence of SEQ ID NO: 46 and (b) a VL domain comprising the amino acid sequence of SEQ ID NO: 58;
- (xvi) a binding domain comprising (a) a VH domain comprising the amino acid sequence of SEQ ID NO: 48 and (b) a VL domain comprising the amino acid sequence of SEQ ID NO: 58;
- (xvii) a binding domain comprising (a) a VH domain comprising the amino acid sequence of SEQ ID NO: 50 and (b) a VL domain comprising the amino acid sequence of SEQ ID NO: 58;
- (xviii) a binding domain comprising (a) a VH domain comprising the amino acid sequence of SEQ ID NO: 43 and (b) a VL domain comprising the amino acid sequence of SEQ ID NO: 59;
- (xix) a binding domain comprising (a) a VH domain comprising the amino acid sequence of SEQ ID NO: 44 and (b) a VL domain comprising the amino acid sequence of SEQ ID NO: 59;
- (xx) a binding domain comprising (a) a VH domain comprising the amino acid sequence of SEQ ID NO: 46 and (b) a VL domain comprising the amino acid sequence of SEQ ID NO: 59;
- (xxi) a binding domain comprising (a) a VH domain comprising the amino acid sequence of SEQ ID NO: 48 and (b) a VL domain comprising the amino acid sequence of SEQ ID NO: 59;
- (xxii) a binding domain comprising (a) a VH domain comprising the amino acid sequence of SEQ ID NO: 50 and (b) a VL domain comprising the amino acid sequence of SEQ ID NO: 59; or
- (xxiii) a binding domain comprising (a) a VH domain comprising the amino acid sequence of SEQ ID NO: 52 and (b) a VL domain comprising the amino acid sequence of SEQ ID NO: 61.

* * * * *